United States Patent [19]

Ikawa et al.

[11] Patent Number: 5,120,738

[45] Date of Patent: Jun. 9, 1992

[54] PANTOTHENIC ACID DERIVATIVES

[75] Inventors: Hiroshi Ikawa, Tokyo; Hajime Matsumoto, Hino; Nobuo Kobayashi, Tama; Jun Kusunoki, Tokyo, all of Japan

[73] Assignee: Fujirebio Inc., Tokyo, Japan

[21] Appl. No.: 598,900

[22] Filed: Oct. 5, 1990

[51] Int. Cl.$^5$ .............. A61K 31/495; A61K 31/445; C07D 295/00; C07D 211/30

[52] U.S. Cl. .................... 514/255; 514/210; 514/212; 514/315; 514/423; 514/452; 514/548; 540/575; 540/610; 544/387; 544/388; 546/247; 548/530; 548/537; 548/950; 549/333; 549/372; 500/155

[58] Field of Search .............. 540/575, 610; 544/387, 544/388; 546/247; 548/530, 537, 950; 514/210, 212, 255, 315, 423, 426, 452, 548; 549/333, 372; 560/155

[30] Foreign Application Priority Data

Oct. 6, 1990 [JP] Japan .................. 2-261610
Nov. 2, 1990 [JP] Japan .................. 2-286758
Nov. 2, 1990 [JP] Japan .................. 2-286759

[56] References Cited

U.S. PATENT DOCUMENTS 2,807,644  9/1957  Moore et al. .................. 260/561

FOREIGN PATENT DOCUMENTS 1080301  5/1954  France .
1228806  3/1960  France .
  39983  4/1961  Luxembourg .
 315885  9/1956  Switzerland .

OTHER PUBLICATIONS

Turakhin et al., J. Org. Chem., 1986, vol. 51, pp. 1955-1960.
Davis et al., J. Biol. Chem., vol. 262, No. 1 (1987) pp. 90-96.
Romussi et al., Liebigs Annalen Des Chemie, 1981, No. 5 pp. 828-841.
Kopelevich et al., Chemical Abstracts, vol. 98 (1983) p. 704, Abstract No. 198716C.
Yoshioka et al., Chemical Abstracts, vol. 106 (1987), p. 516 Abstract No. 32710e.
Marieva et al. CA94-11490b (1981).

*Primary Examiner*—Cecilia Shen
*Attorney, Agent, or Firm*—Wenderoth, Lind & Ponack

[57] ABSTRACT

Compounds represented by general formula (I) below $$\begin{array}{c} R^1O \quad\quad OR^2 \\ | \quad\quad\quad | \\ H_2C \quad\quad *CH-CONH-(CH_2)_n-CO-Q-CO-R^3 \\ \diagdown \; \diagup \\ C \\ \diagup \; \diagdown \\ H_3C \quad\quad CH_3 \end{array} \quad (I)$$

wherein
$R^1$ and $R^2$, which are the same or different, each represent a hydrogen atom or a protective group for a hydroxyl group;
$R^3$ represents a saturated or unsaturated, linear, branched or cyclic, monovalent $C_5\sim C_{25}$-aliphatic hydrocarbon group which may be substituted with an aromatic group, or a group of formula $$-N\begin{cases}R^4 \\ R^5\end{cases}$$

where
$R^4$ represents a saturated or unsaturated, linear, branched or cyclic, monovalent $C_5\sim C_{25}$-aliphatic hydrocarbon group which may be substituted with an aromatic group, and
$R^5$ represents a hydrogen atom, or a saturated or unsaturated, linear, branched or cyclic, monovalent hydrovarbon group which may be substituted with an aromatic group;

Q represents
(a) a group of formula $-X^1-A-Y^1-$, where A represents a saturated or unsaturated, linear, branched or cyclic divalent $C_2\sim C_{16}$-aliphatic hydrocarbon group which may be substituted with an aromativ group, a divalent aromatic hydrocarbon group or a divalent aromatic heterocyclic group; one of $X^1$ and $Y^1$ represents $$\begin{array}{c} R^6 \\ | \\ -N-, \end{array}$$

and the other represents $-O-$, $-S-$ or $$\begin{array}{c} R^7 \\ | \\ -N-, \end{array}$$

in which $R^6$ and $R^7$ each represent a hydrogen atom or a lower alkyl group;
(b) a group of formula $-X^2-(CH_2)_l-Y^2-$, where one of $X^2$ and $Y^2$ represents a group of formula $$\begin{array}{c} \bigcirc \\ N \\ | \end{array}$$

and the other represents $-O-$, $-S-$ or $$\begin{array}{c} R^6 \\ | \\ -N- \end{array}$$

represents a 4~7-membered, divalent nitrogen-containing aromatic heterocyclic group, and $R^6$ has the same meaning as defined above, and l is 0, 1 or 2; or
(c) a group of formula (Abstract continued on next page.)

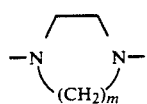
where m is 2 or 3;
n is an integer of from 1 to 4.
The compounds have excellent inhibitory activity against acyl Co A-cholesterol-acyltransferase.
17 Claims, No Drawings

PANTOTHENIC ACID DERIVATIVES

The present invention relates to pantothenic acid derivatives which have excellent inhibitory activity against acyl CoA-cholesterol-acyltransferase (hereafter, abbreviated as ("ACAT").

Recently, it revealed that in artherosclerosis, a popular artheriosclerosis, lipophagy in which fat is accumulated is observed to begin at the earliest stage of artheriosclerotic crisis. Main component of the fat accumulated is cholesterols. Further, many pathohistological and biochemical investigations revealed that the cholesterols are derived from plasma lipid. On the other hand, various epidemic researches showed that hyperlipemia is a major critical factor of artheriosclerotic diseases particularly premature coronary heart disease. Therefore, therapy of hyperlipemia is increasingly important in order to alleviate risks of arteriosclerotic diseases. As for remedies for the therapy of the diseases, development of a drug is strongly desired which can not only decrease level of serum lipid but also improve serum lipid balance or positively prevent crisis of artheriosclerosis.

Many drugs have already been provided as hypolipidemics which exhibit clinical effects to some extent relative to decrease of total serum cholesterol. However, they are insufficient in the effect of decreasing mortality due to artheriosclerotic diseases. Recently, based on elucidation of lipid metabolism, there have been developed drugs which can control serum lipid balance, that is, drugs which are effective for increasing serum high density lipoprotein (HDL) level and decreasing serum low density lipoprotein (LDL) level, drugs which can inhibit biosynthesis of cholesterol and as a result decrease serum lipid level (HMG CoA reductase inhibitors) and the like. While they are effective for improving blood lipid level, these drugs have almost no effect on the control of absorption of alimentary cholesterol through intestinal walls. In addition, they have no activity for positively prevent crisis or development of artheriosclerosis; it requires further investigation to find whether they can alleviate risks of artheriosclerotic diseases or not.

On the other hand, ACAT known as an intramembranous enzyme is present mostly in intracellular microsomes in lever and small intestines and catalyze the intracellular esterification of cholesterol. At present, it is known that there are two isozymes for this enzyme. The structures, physiological roles and the like of the ACAT have not been clarified yet because the isolation and purification of the enzyme are difficult. However, in view of the fact that it is known that ACAT play erucial role in the absorption of cholesterols through intestinal walls and accumulation of cholesterols within cells in a form of cholesterol esters and that the activity of the enzyme is increased in artheriosclerotic lesions. Thus, inhibition of intestinal ACAT would be expected to lead to decrease cholesterol esterification resulting in diminished intestinal absorption. Additional reduction in intracellular accumulation of cholesterol esters might be expected. Therefore, ACAT inhibitors offer potential for exhibiting both hypocholesterolemia and antiartheriosclerotic activity.

As a result of extensive investigations with view to synthesizing substances which have excellent ACAT inhibitory activities, the present invention has been completed.

Accordingly, the present invention provides a compound represented by general formula (I) below

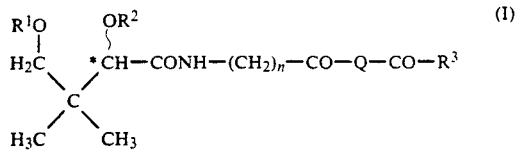

wherein
$R^1$ and $R^2$, which are the same or different, each represent a hydrogen atom or a protective group for a hydroxyl group;
$R^3$ represents a saturated or unsaturated, linear, branched or cyclic, monovalent $C_5 \sim C_{25}$-aliphatic hydrocarbon group which may be substituted with an aromatic group, or a group of formula

where
$R^4$ represents a saturated or unsaturated, linear, branched or cyclic, monovalent $C_5 \sim C_{25}$-aliphatic hydrocarbon group which may be substituted with an aromatic group, and
$R^5$ represents a hydrogen atom, or a saturated or unsaturated, linear, branched or cyclic, monovalent hydrocarbon group which may be substituted with an aromatic group;
Q represents
(a) a group of formula $-X^1-A-Y^1-$, where A represents a saturated or unsaturated, linear, branched or cyclic divalent $C_2 \sim C_{16}$-aliphatic hydrocarbon group which may be substituted with an aromatic group, a divalent aromatic hydrocarbon group or a divalent aromatic heterocyclic group; one of $X^1$ and $Y^1$ represents

and the other represents $-O-$, $-S-$ or

in which $R^6$ and $R^7$ each represent a hydrogen atom or a lower alkyl group;
(b) a group of formula $-X^2-(CH_2)$, $-Y^2-$, where one of $X^2$ and $Y^2$ represents a group of formula

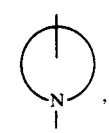

and the other represents $-O-$, $-S-$ or

in which

represents a 4~7-membered, divalent nitrogen-containing aromatic heterocyclic group, and $R^6$ has the same meaning as defined above, and l is 0, 1 or 2; or (c) a group of formula

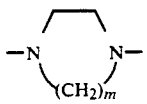

where m is 2 or 3;
n is an integer of from 1 to 4.

The term "lower" used herein indicates that elemental groups or compounds referred to together with this term have no more than 6 carbon atoms, preferably no more than 4 carbon atoms.

The term "a protective group of a hydroxyl group" used herein refers to any protective groups for hydroxyl groups usually used which can easily release as a result of usual protecting group elimination reaction, for example, hydrolysis or hydrogenolysis.

Specific examples of the protective group for a hydroxyl group include the following groups:

substituted or unsubstituted alkyl or alkenyl groups such as methyl, methoxyethyl, methylthiomethyl, benzyloxymethyl, t-butoxymethyl, 2-methoxyethoxymethyl, 2,2,2-trichloroethoxymethyl, bis(2-chloroethoxy)methyl, -ethoxyethyl, 1-methyl-1-methoxyethyl, 1-(isopropoxy)ethyl, 2,2,2-trichloroethyl, t-butyl, allyl, cinnamyl, benzyl, p-methoxybenzyl, o-nitrobenzyl, p-nitrobenzyl, p-chlorobenzyl, o-chlorobenzyl, p-cyanobenzyl, diphenylmethyl, α-naphthyldiphenylmethyl, triphenylmethyl, and di(p-methoxyphenyl)methyl groups;

heterocyclic groups such as tetrahydropyranyl, tetrahydrothiopyranyl, 4-methoxytetrahydropyranyl, 4-methoxytetrahydrothiopyranyl, tetrahydrofuranyl and tetrahydrothiofuranyl;

substituted silyl groups such as trimethylsilyl, triethylsilyl, isopropyldimethylsilyl, t-butyldimethylsilyl, t-butyldiphenylsilyl, methyldiisopropylsilyl, methyldi-t-butylsilyl, tribenzylsilyl, triphenylsilyl, and triisopropylsilyl groups;

acyl groups such as formyl, acetyl, propionyl, chloroacetyl, dichloroacetyl, trichloroacetyl, trifluoroacetyl, methoxyacetyl, triphenylmethoxyacetyl, phenoxyacetyl, p-chlorophenoxyacetyl, 2,6-dichloro-4-methylphenoxyacetyl, phenylacetyl, chlorodiphenylacetyl, 3-phenylpropionyl, 3-benzoylpropionyl, isobutyroyl, monosuccinoyl, 4-oxopentanoyl, pivaloyl, 2-butenoyl, (E)-2-methyl-2-butenoyl, benzoyl, 2-chlorobenzoyl, 3-nitrobenzoyl, 2-fluorobenzoyl, 3-trifluorobenzoyl, 3-trichlorobenzoyl, 4-phenylbenzoyl, 2,4,6-trimethylbenzoyl, and α-naphthoyl groups;

substituted oxycarbonyl groups such as methoxycarbonyl, ethoxycarbonyl, 2,2,2-triethoxycarbonyl, isobutoxycarbonyl, vinyloxycarbonyl, aryloxycarbonyl, cinnamyloxycarbonyl, p-nitrophenoxycarbonyl, benzyloxycarbonyl, p-methoxybenzyloxycarbonyl, 3,4-dimethoxybenzyloxycarbonyl, and p-nitrobenzyloxycarbonyl groups;

substituted carbamoyl groups such as phenylcarbamoyl, naphthylcarbamoyl, toluylcarbamoyl, fluorophenylcarbamoyl, difluorophenylcarbamoyl, nitrophenylcarbamoyl, cyanophenylcarbamoyl, benzylcarbamoyl, methylcarbamoyl, ethylcarbamoyl, isopropylcarbamoyl, butylcarbamoyl, cyclohexylcarbamoyl, cyclopropylmethylcarbamoyl, phenylthiocarbamoyl, naphthylthiocarbamoyl, toluylthiocarbamoyl, fluorophenylthiocarbamoyl, difluorophenylthiocarbamoyl, nitrophenylthiocarbamoyl, cyanophenylthiocarbamoyl, benzylthiocarbamoyl, propylthiocarbamoyl, butylthiocarbamoyl groups.

In the case where $R^1$ and $R^2$ in formula (I) above each represent a protective group, $R^1$ and $R^2$ may combine to form an ylidene group such as methylene, ethylidene, 1-t-butylethylidene, 1-phenylethylidene, 2,2,2-trichloroethylidene, isopropylidene, butylidene, cyclopentylidene, cyclohexylidene, cyclobutylidene, benzylidene, p-methoxybenzylidene, 2,4-dimethoxybenzylidene, p-dimethylaminobenzylidene, o-nitrobenzylidene, methoxymethylene, ethoxymethylene, dimethoxymethylene, 1-methoxyethylidene, 1,2-dimethoxyethylidene, α-methoxybenzylidene groups.

In formula (I) above, preferably $R^1$ and $R^2$, which are the same or different, each represent a hydrogen atom; a lower alkyl group, particularly a t-butyl group; a benzyl group which may optionally be substituted with a halogen atom, a lower alkoxy group, a nitro group or a cyano group, particularly, benzyl, p-methoxybenzyl, o-nitrobenzyl, p-nitrobenzyl, p-chlorobenzyl, o-chlorobenzyl, p-cyanobenzyl group; a 5- or 6-membered saturated heterocyclic group containing as hetero atoms N, S or O selected from tetrahydropyranyl, tetrahydrothiopyranyl, 4-methoxytetrahydropyranyl, 4-methoxytetrahydrothiopyranyl, tetrahydrofuranyl and tetrahydrothiofuranyl groups; or an acyl group, particularly acetyl, propionyl, phenylacetyl, chlorodiphenylacetyl, 3-phenylpropionyl, 3-benzoylpropionyl, isobutyroyl, pivaloyl, 2-butenoyl, (E)-2-methyl-2-butenoyl, benzoyl, 2-chlorobenzoyl, 3-nitrobenzoyl, 2-fluorobenzoyl, 3-trifuluoromethylbenzoyl, 3-trichloromethylbenzoyl, 4-phenylbenzoyl, 2,4,6-trimethylbenzoyl, and α-naphthoyl groups; or $R^1$ and $R^2$ may combine to form a ylidene group selected from 1-t-butylethylidene, 1-phenylethylidene, isopropylidene, butylidene, cyclopentylidene, cyclohexylidene, cycloheptylidene, benzylidene, p-methoxybenzylidene, 2,4-dimethoxybenzylidene, p-dimethylaminobenzylidene, and o-nitrobenzylidene groups.

As for the "saturated or unsaturated, linear, branched or cyclic monovalent aliphatic hydrocarbon group", there can be cited, for example, the following groups:

(1) an alkyl group, for example, methyl, ethyl, propyl, isopropyl, butyl, isobutyl, t-butyl, pentyl, neopentyl, isopentyl, t-pentyl, 1-ethylpentyl, 1-isopropylpentyl, 1-t-butylpentyl, 2-ethylpentyl, 2-isopropylpentyl, 2-t- butylpentyl, 3-ethylpentyl, 3-isopropylpentyl, 3-t-butylpentyl, hexyl, 1-ethylhexyl, 1-isopropylhexyl, 1-t-butylhexyl, 2-ethylhexyl, 2-isopropylhexyl, 2-t-butylhexyl, 3-ethylhexyl, 3-isopropylhexyl, 3-t-butylhexyl, heptyl, 1-ethylheptyl, 1-isopropylheptyl, 1-neopentylheptyl, 2-ethylheptyl, 2-isopropylheptyl, 2-neopentylheptyl, 3-ethylheptyl, 3-isopropylheptyl, 3-neopentylheptyl, octyl, 1-ethyloctyl, 1-isopropyloctyl, 1-t-butyloctyl, 2-ethyloctyl, 3-isopropyloctyl, 4-t-butyloctyl, nonyl, 1-methylnonyl, 1-ethylnonyl, 1-isopropylnonyl, 1-isobutylnonyl, 2-methylnonyl, 2-ethylnonyl, 3-isopropylnonyl, 4-isobutylnonyl, decyl, 1-ethyldecyl, 1,1-diethyldecyl, 1-t-butyldencyl, 3-ethyldecyl, 1,3-diethyldecyl, 2-t-butyldencyl, undecyl, 1-isopropylundecyl, 1,1-diethylundecyl, 2-isopropylundecyl, 1,2-diethylundecyl, dodecyl, 1-t-butyldodecyl, 1-isopropyldodecyl, 1,1-diethyldodecyl, 2-t-butyldodecyl, 3-isopropyldodecyl, 2,4-diethyldodecyl, tridecyl, 1,1-diethyltridecyl, 1-t-butyltridecyl, 1,5-diethyltridecyl, 3-t-butyltridecyl, tetradecyl, 1-isobutyltetradecyl, pentadecyl, 1-methylpentadecyl, 1,1-dimethylpentadecyl, 1-ethylpentadecyl, 1,1-diethylpentadecyl, 1-isopropylpentadecyl, 1-t-butylpentadecyl, -isobutyltetradecyl, 3-methylpentadecyl, 2,6-dimethylpentadecyl, 2-ethylpentadecyl, 1,4-diethylpentadecyl, 3-isopropylpentadecyl, 2-t-butylpentadecyl, hexadecyl, 1,1-dimethylhexadecyl, 1-methylhexadecyl, 1-ethylhexadecyl, 1-isopropylhexadecyl, 1-t-butylhexadecyl, 1,3-dimethylhexadecyl, 2-methylhexadecyl, 4-ethylhexadecyl, 3-isopropylhexadecyl, 4-t-butylhexadecyl, heptadecyl, 1-methylheptadecyl, 1,1-dimethylheptadecyl, 1-ethylheptadecyl, 1-isopropylheptadecyl, 1-t-butylheptadecyl, 2-methylheptadecyl, 3,5-dimethylheptadecyl, 2-ethylheptadecyl, 5-isopropylheptadecyl, 3-t-butyheptadecyl, octadecyl, 1-methyloctadecyl, 1,1-dimethyloctadecyl, 2,3-dimethyloctadecyl, 5-ethyloctadecyl, 1,2-diethyloctadecyl, nonadecyl, 1-methylnonadecyl, 1,1-dimethylnonadecyl, 1-t-butylnonadecyl, 2-methylnonadecyl, 2,3-dimethylnonadecyl, 3-butylnonadecyl, eicosyl, 1-methyleicosyl, 1,1-dimethyleicosyl, 1-ethyleicosyl, 1-t-butyleicosyl, 4-methyleicosyl, 2,2-dimethyleicosyl, 3-ethyleicosyl, 2,2-dimethyleicosyl, 3-ethyleicosyl, and 2-t-butyleicosyl groups;

(2) an alkenyl group, for example, vinyl, 1-propenyl, 1-methyl-2-propenyl, 1-methyl-1-butenyl, 2-butenyl, 1-methyl-3-butenyl, 1-pentenyl, 1-methyl-2-pentenyl, 1 ethyl-3-pentenyl, 4-pentenyl, 1,3-pentadienyl, 2,4-pentadienyl, 1 hexenyl, 1-methyl-2-hexenyl, 3-hexenyl, 4-hexenyl, 1-butyl-5-hexenyl, 1,3-hexadienyl, 2,4-haxedienyl, 1-heptenyl, 2-heptenyl, 3-heptenyl, 3-heptenyl, 5-heptenyl, 6-heptenyl, 1,3-heptadienyl, 2,4-heptadienyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 9-decenyl, 1-methyl-9-decenyl, 1,1-dimethyl-9-decenyl, 1-ethyl-9-decenyl, 6-undecenyl, 1-methyl-6-undecenyl, 1,1-dimethyl-6-undecenyl, 6-tridecenyl, 1-methyl-6-tridecenyl, 1,1-dimethyl-6 tridecenyl, 8-tridecenyl, 1-methyl-8-tridecenyl, 1,1-dimethyl-8-tridecenyl, 10-tridecenyl, 1-methyl-10-tridecenyl, 1,1-dimethyl-10-tridecenyl, 10-pentadecenyl, 1-methyl-10-pentadecenyl, 1,1-dimethyl-10-pentadecenyl, 8-pentadecenyl, 1-methyl-8-pentadecenyl, 1,1-dimethyl-8-pentadecenyl, 12-heptadecenyl, 1-methyl-12-heptadecenyl, 1,1-dimethyl-12-heptadecenyl, 10-heptadecenyl, 1-methyl-1-heptadecenyl, 1,1-dimethyl-10-heptadecenyl, 8-heptadecenyl, 1-methyl-8-heptadecenyl, 1,1-dimethyl-8-heptadecenyl, 1-ethyl-8-heptadecenyl, 8,11-heptadecadienyl, 1-methyl-8,11-heptadecadienyl, and 8,11,14-heptadecatrienyl groups.

(3) an alkynyl group, for example, propargyl, 2-butynyl, 1-methyl-3-butynyl, 2-pentynyl, 1-ethyl-3-pentynyl, 1-isopropyl-4-pentynyl, 1,3-pentadiynyl, 2,4-pentadiynyl, 1-hexylnyl, 1-methyl-2-hexynyl, 2-methyl-3-hexynyl, 1-ethyl-4-hexynyl, 5-hexynyl, 1,3-hexadiynyl, 2,4-hexadiynyl, 1-heptynyl, 1-methyl-2-heptynyl, 3-heptynyl, 1-ethyl-4-heptynyl, 2-propyl-5-heptynyl, 2-ethyl-6-heptynyl, 1,3-heptadiynyl, 2,4-heptadiynyl, 1-octynyl, 1-methyl-2-octynyl, 3-methyl-1-octynyl, 4-methyl-1-octynyl, 1-methyl-5-octynyl, 6-methyl-1-octynyl, 7-octynyl, 1-nonynyl, 2-methyl-1-nonynyl, 3-methyl-1-nonynyl, 1-methyl-4-nonynyl, 5-nonynyl, 6-methyl-1-nonynyl, 1-methyl-7-nonynyl, 8-nonynyl, 9-decynyl, 1-methyl-9-decynyl, 1,1-dimethyl-9-decynyl, 1-ethyl-9-decynyl, 6-undecynyl, 1-methyl-6-undecynyl, 1-methyl-6-tridecynyl, 1-methyl-6-tridecynyl, 1,1-dimethyl-6-tridecynyl, 8-tridecynyl, 1-methyl-8-tridecynyl, 1,1-dimethyl-8-tridecynyl, 10-tridecynyl, 1-methyl-10-tridecynyl, 1,1-dimethyl-10-tridecynyl, 10-pentadecynyl, 1-methyl-10-pentadecynyl, 1,1-dimethyl-10-entadecynyl, 8-pentadecynyl, 1-methyl-8-pentadecynyl, 1,1-dimethyl-8-pentadecynyl, 12-hetadecynyl, 1-methyl-12-heptadecynyl, 1,1-dimethyl-12-heptadecynyl, 10-heptadecynyl, 1-methyl-10-heptadecynyl, 1,1-dimethyl-10-heptadecynyl, 8-heptadecynyl, 1-methyl-8-heptadecynyl, 1,1-dimethyl-8-heptadecynyl, 1-ethyl-8-heptadecynyl, 8,11-heptadecadiynyl, 1-methyl-8,11-heptadecadiynyl, 1-methyl-8,11-heptadecadiynyl, and 8,11,14-heptadecatriynyl groups;

(4) a cycloalkyl group, for example, cyclopropyl, cyclobutyl, cyclopentyl, cyclohexyl, cycloheptyl, cyclooctyl, and perhydronaphthyl groups;

(5) a cycloalkenyl group, for example, cyclopentenyl, cyclohexenyl, cycloheptenyl, cyclooctenyl, cyclopentadienyl, cyclohexadienyl, cycloheptadienyl, and cyclooctadienyl groups;

(6) a cycloalkylalkyl group, for example, cyclohexylmethyl, cyclopentylmethyl, (4-isopropylcyclohexyl)methyl, (4-t-butylcyclohexyl)methyl, (4-neopentylcyclohexyl)methyl, 2-cyclopentylethyl, 2-cyclohexylethyl, 3-cyclopentylpropyl, 3-cyclohexylpropyl, 1-cyclopentylpentyl, 1-cyclohexylpentyl, 1-cyclohexylmethylpentyl, 3-cyclopentylpentyl, 2-cyclohexylpentyl, 2-cyclohexylmethylpentyl, 1-(4-t-butylcyclohexyl)methylpentyl, 1-cyclopentylhexyl, 1-cyclohexylhexyl, 1-cyclopentylmethylhexyl, 2-cyclopentylhexyl, 2-cyclohexylhexyl, 3-cyclopentylmethylhexyl, 1-(4-neopentylcyclohexyl)methylhexyl, 1-cyclopentylheptyl, 1-cyclohexylmethylheptyl, 1-(4-isopropylcyclohexyl)methylheptyl, 3-cyclopentylheptyl, 2-cyclohexylmethylheptyl, 4-(4-isopropylcyclohexyl)methylheptyl, 1-cyclopentyloctyl, 1-cyclohexyloctyl, 1-cyclopentylmethyloctyl, 2-cyclopentyloctyl, 3-cyclohexyloctyl, 2-cyclopentylmethyloctyl, 1-cyclopentylnonyl, 1-cyclohexylnonyl, 1-cyclohexylmethylnonyl, 3-cyclopentylnonyl, 2-cyclohexylnonyl, 2-cyclohexylmethylnonyl, 1-cyclopentyldencyl, 1-cyclopentylundecyl, 1-cyclohexylundecyl, 1-cyclopentyldodecyl, 1-cyclopentyltridecyl, 2-cyclopentyldecyl, 3-cyclopentylundecyl, 3-cyclohexylundecyl, 2-cyclopentyldodecyl, 2-cyclopentyltridecyl, 1-cyclopentyltetradecyl, 1-cyclohexyltetradecyl, 2-cyclopentyltetradecyl, and 3-cyclohexyltetradecyl groups;

(7) a cycloalkenylalkyl group, for example, 2-cyclohexen-1-ylmethyl, 1-cyclopenten-1-ylmethyl, 2-(2-cyclopenten-1-yl)ethyl, 2-(1-cyclohexen-1-yl)ethyl, 3-(1-cyclopenten-1-yl)propyl, 3-(1-cyclohexen-1-yl)propyl, 4-(1-cyclohexen-1-yl)butyl, 1-(1-cyclopenten-1-yl)pentyl, 1-(1-cyclohexen-1-yl)pentyl, 5-(1-cyclohexen-1-yl)pentyl, 1-(1-cyclohexen-1-ylmethyl)pentyl, 1-(1-cyclopenten-1-yl)hexyl, 6-(1-cyclopenten-1-yl)hexyl, 1-(1-cyclohexen-1-yl)hexyl, 6-(1-cyclohexen-1-yl)hexyl, 1-(2-cyclopenten-1-ylmethyl)hexyl, 1-(1-cyclopenten-1-yl)heptyl, 7-(1-cyclopenten-1-yl)heptyl, 1-(1-cyclohexen-1-ylmethyl)heptyl, 1-(1-cyclopenten-1-yl)octyl, 1-(2-cyclopenten-1-yl)octyl, 1-(2-cyclopenten-1-yl)octyl, 1-(2-cyclohexen-1-yl)octyl, 8-(2-cyclohexen-1-yl)octyl, 1-(1-cyclopenten-1-ylmethyl)octyl, 1-(1-cyclopenten-1-yl)nonyl, 9-(1-cyclopenten-1-yl)nonyl, 1-(1-cyclohexen-1-yl)nonyl, 9-(1-cyclohexen-1-yl)nonyl, 1-(1-cyclohexen-1-ylmethyl)nonyl, 1-(1-cyclopenten-1-yl)decyl, 10-(1-cyclopenten-1-yl)decyl, 1-(2-cyclopenten-1-yl)undecyl, 1-(2-cyclohexen-1-yl)undecyl, 1-(1-cyclopenten-1-yl)dodecyl, 1-(1-cyclopenten-1-yl)tridecyl, 1-(2-cyclopenten-1-yl)tetradecyl, and 1-(3-cyclohexen-1-yl)tetradecyl groups;

(8) an alkylcycloalkyl group and an alkenylcycloalkyl group, for example, 1-methylcyclobutyl, 2-ethylcyclobutyl, 2-propylcyclobutyl, 1-butylcyclobutyl, 1-pentylcyclobutyl, 1-hexylcyclobutyl, 1-heptylcyclobutyl, 1-octylcyclobutyl, 1-nonylcyclobutyl, 2-pentylcyclobutyl, 2-hexylcyclobutyl, 2-heptylcyclobutyl, 2-octylcyclobutyl, 2-nonylcyclobutyl, 1-decylcyclobutyl, 1-undecylcyclobutyl, 1-dodecylcyclobutyl, 1-pentadecylcyclobutyl, 1-(9-octadecynyl)cyclobutyl, 1-methylcyclopentyl, 2-methylcyclopentyl, 1-ethylcyclopentyl, 1-propylcyclopentyl, 1-butylcyclopentyl, 2-butylcyclopentyl, 1-pentylcyclopentyl, 1-hexylcyclopentyl, 3-hexylcyclopentyl, 1-heptylcyclopentyl, 1-octylcyclopentyl, 2-octylcyclopentyl, 1-decylcyclopentyl, 1-dodecylcyclopentyl, 1-tridecylcyclopentyl, 1-tetradecylcyclopentyl, 1-(9-octadecenyl)cyclopentyl, 1-methylcyclohexyl, 1-ethylcyclohexyl, 1-propylcyclohexyl, 2-methylcyclohexyl, 3-ethylcyclohexyl, 4-propylcyclohexyl, 1-butylcyclohexyl, 1-pentylcyclohexyl, 1-hexylcyclohexyl, 4-butylcyclohexyl, 4-pentylcyclohexyl, 4-hexylcyclohexyl, 1-heptylcyclohexyl, 1-octylcyclohexyl, 1-nonylcyclohexyl, 1-undecylcyclohexyl, 1-hexadecylcyclohexyl, and 1-(9-octadecenyl)cyclohexyl groups;

(9) alkycycloalkenyl group and alkenylcycloalkyenyl group, for example, 1-methyl-2-cyclopentenyl, 1-ethyl-2-cyclopentenyl, 1-propyl-2-cyclopentenyl, 1-butyl-2-cyclopentenyl, 1-pentyl-2-cyclopentenyl, 1-hexyl-2-cyclopentenyl, 1-heptyl-2-cyclopentenyl, 1-octyl-2-cyclopentenyl, 2-methyl-2-cyclopentenyl, 3-ethyl-2-cyclopentenyl, 2-propyl-3-cyclopentenyl, 3-butyl-2-cyclopentenyl, 2-pentyl-2-cyclopentenyl, 3-hexyl-3-cyclopentenyl, 2-heptyl-2-cyclopentenyl, 2-octyl-3-cyclopentenyl, 1-decyl-2-cyclopentenyl, 1-dodecyl-2-cyclopentenyl, 1-tridecyl-2-cyclopentenyl, 1-tetradecyl-2-cyclopentenyl, 1-(9-octadecenyl)-2-cyclopentenyl, 1-methyl-2-cyclopentenyl, 1-ethyl-2-cyclohexenyl, 1-propyl-2-cyclohexenyl, 1-butyl-2-cyclohexenyl, 1-pentyl-2-cyclohexenyl, 1-hexyl-2-cyclohexenyl, 1-heptyl-2-cyclohexenyl, 4-methyl-2-cyclohexenyl, 2-ethyl-2-cyclohexenyl, 3-propyl-2-cyclohexenyl, 4-butyl-3-cyclohexenyl, 3-pentyl-3-cyclohexenyl, 4-hexyl-3-cyclohexenyl, 4-heptyl-3-cyclohexenyl, 1-octyl-2-cyclohexenyl, 2-nonyl-2-cyclohexenyl, 1-undecyl-2-cyclohexenyl, 1-hexadecyl-2-cyclohexenyl, and 1-(9-octadecenyl)-2-cyclohexenyl groups; and the like.

The saturated or unsaturated, linear, branched or cyclic monovalent aliphatic hydrocarbon groups may optionally be substituted with an aromatic group selected from an aromatic hydrocarbon group and an aromatic heterocyclic group. Examples of the aromatic hydrocarbon group include phenyl and naphthyl groups. Examples of the aromatic heterocyclic group include furyl, thienyl, pyridyl, quinolyl, isoquinolyl, pyridazinyl, pyrazinyl, indolyl, benzoxadiazolyl, imidazolyl, benzothiadiazolyl, triazolyl and tetrazolyl groups.

Furthermore, these aromatic groups may have one or more substituent groups. Specific examples of the substituent groups include a halogen atom such as chlorine, bromine and fluorine, a lower alkyl group, a lower alkoxy group, a lower alkylthio group, a cyano group, a nitro group, a trichloromethyl group, a trifluoromethyl group, a hydroxyl group, a phenyl group, a phenoxy group, and the like.

As for the saturated or unsaturated, linear, branched or cyclic monovalent aliphatic hydrocarbon group which may be substituted with an aromatic group, represented by $R^3$ and $R^4$ in formula (I) above, those groups are used which are of a relatively long chain, i.e., have from 5 to 25 carbon atoms, preferably from 8 to 22 carbon atoms. On the other hand, the saturated or unsaturated, linear, branched or cyclic monovalent aliphatic hydrocarbon group which may be substituted with an aromatic group, represented by $R^5$ in formula (I) above, may be of either short chain or long chain but generally those groups are preferred which are of a short chain, preferably having from 1 to 10 carbon atoms, more preferably from 1 to 8 carbon atoms. It is desirable that total carbon atom number of $R^4$ and $R^5$ is in a range of from 5 to 25, preferably form 8 to 22.

Specific examples of the group of formula

include monosubstituted amino groups such as 2-cyclopentylethyl-amino, 2-cyclohexylethylamino, 3-cyclopentylpropylamino, 3-cyclohexylpropylamino, 2-cyclopentyl-1-methylethylamino, 2-cyclopentyl-1,1-dimethylethylamino, 2-cyclohexyl-1-methylethylamino, 3-cyclopentylpropylamino, 3-cyclohexylpropylamino, 4-cyclohexyl-1,1-dimethylbutylamino, 1-methylpentylamino, 1,1-dimethylpentylamino, 1-ethylpentylamino, 1-cyclohexyl-4-methylpentylamino, 1-cyclopentyl-4-methylpentylamino, 2-methylpentylamino, 1,2-dimethylpentylamino, 2-ethylpentylaminio, 2-cyclohexyl-4-methylpentylamino, 2-cyclopentyl-4-methylpentylamino, 3-methylpentylamino, 1,3-dimethylpentylamino, 3-ethylpentylamino, 1-cyclohexyl-3-methylpentylamino, 1-cyclopentyl-3-methylpentylamino, hexylamino, 1-methylhexylamino, 1,1-dimethylhexylamino, 1-ethylhexylamino, 1,1-diethylhexylamino, 1-propylhexylamino, 1-butylhexylamino, 1-cyclopentylhexylamino, 2-methylhexylamino, 1,2-dimethylhexylamino, 2-ethylhexylamino, 1,2-diethylhexylamino, 2-propylhexylamino, 2-butylhexylamino, 6-cyclopentylhexylamino, 6-cyclohexylhexylamino, heptylamino, 1-ethylheptylamino, 1,1-dimethylheptylamino, 1-cyclohexylheptylamino, 1-cyclopentylheptylamino, 1-cyclohexylmethylheptylamino, 1-cyclopentylmethylheptylamino, octylamino, 1,1-dimethyloctylamino, 1-methyloctylamino, 1-ethyloctylamino, 1,1- diethyloctylamino, 1-propyloctylamino, 1-butyloctylamino, 1-cyclopentyloctylamino, 1-cyclohexyloctylamino, 1-cyclopentylmethyloctylamino, 1-cyclohexylmethyloctylamino, nonylamino, 1-methylnonylamino, 1,1-dimethylnonylamino, 1-ethylnonylamino, 1,1-diethylnonylamino, decylamino, 1-methyldecylamino, 1,1-dimethyldecylamino, 1-ethyldecylamino, 1,1-diethyldecylamino, 1-cyclopentyldecylamino, 1-cyclohexyldecylamino, 1-cyclopentylmethyldecylamino, 1-cyclohexylmethyldecylamino, undecylamino, 1-methylundecylamino, 1,1-dimethylundecylamino, dodecylamino, 1-methyldodecylamino, 1,1-dimethyldodecylamino, tetradecylamino, 1-methyltetradecylamino, 1,1-dimethyltetradecylamino, pentadecylamino, 1-methylpentadecylamino, 1,1-dimethylpentadecylamino, hexadecylamino, 1-methylhexadecylamino, 1,1-dimethylhexadecylamino, heptadecylamino, 1-methylheptadecylamino, 1,1-dimethylheptadecylamino, octadecylamino, 1-methyloctadecylamino, 1,1-dimethyloctadecylamino, 3-cyclopentyl-2-propenylamino, 3-cyclohexyl-2-propenylamino, 1,1-dimethyl-3-butenylamino, 1-ethyl-3-butenylamino, 1-cyclopropyl-3-butenylamino, 1-methyl-2-pentenylamino, 1,1-dimethyl-2-pentenylamino, 1-ethyl-2-pentenylamino, 1-cyclopropyl-2-pentenylamino, 2-hexenylamino, 1-methyl-2-hexenylamino, 1,1-dimethyl-2-hexenyl-amino, 1,1-dimethyl-2-hexenylamino, 3-hexenylamino, 1-methyl-3-hexenylamino, 1,1-dimethyl-3-hexenylamino, 2-heptenylamino, 1-methyl-2-heptenylamino, 2-octenylamino, 1-methyl-2-octenylamino, 3-nonenylamino, 1-methyl-3-nonenylamino, 1,1-dimethyl-3-nonenylamino, 1-ethyl-3-nonenylamino, 1-propyl-3-nonenylamino, 8-nonenylamino, 1-methyl-8-nonenylamino, 1,1-dimethyl-8-nonenylamino, 1-ethyl-8-nonenylamino, 9-decenylamino, 1-methyl-9-decenylamino, 1,1 dimethyl-9-decenylamino, 1-ethyl-9-decenylamino, 6-undecenylamino, 1-methyl-6-undecenylamino, 1,1-dimethyl-6-undecenylamino, 6-tridecenylamino, 1-methyl-6-tridecenylamino, 1,1-dimethyl-6-tridecenylamino, 8-tridecenylamino, 1-methyl-8-tridecenylamino, 1,1-dimethyl-8-tridecenylamino, 10-tridecenylamino, 1-methyl-10-tridecenylamino, 1,1-dimethyl-10-tridecenylamino, 10-pentadecenylamino, 1-methyl-10-pentadecenylamino, 1,1-dimethyl-10-pentadecenylamino, 8-pentadecenylamino, 1-methyl-8-pentadecenylamino, 1,1-dimethyl-8-pentadecenylamino, 12-heptadecenylamino, 1,1-dimethyl-12-heptadecenylamino, 10-heptadecenylamino, 1-methyl-10-heptadecenylamino, 1,1-dimethyl-10-heptadecenylamino, 8-heptadecenylamino, 1-methyl-8-heptadecenylamino, 1,1-dimethyl-8-heptadecenylamino, 1-ethyl-8-heptadecenylamino, 8,11-heptadecadienylamino, 1-methyl-8,11-heptadecadienylamino, 8,11,14-heptadecatrienylamino, 1-ethylcyclobutylamino, 1-propylcyclobutylamino, 1-butylcyclobutylamino, 1-pentylcyclobutylamino, 1-hexycyclobutylamino, 1-pentylcyclobutylamino, 1-octylcyclobutylamino, 1-nonylcyclobutylamino, 1-decylcyclobutylamino, 1-undecylcyclobutylamino, 1-dodecylcyclobutylamino, 1-pentadecylcyclobutylamino, 1-(9-octadecenyl)cyclobutylamino, 1-methylcyclopentylamino, 1-ethylcyclopentylamino, 1-butylcyclopentylamino, 1-hexylcyclopentylamino, 1-octylcyclopentylamino, 1-decylcyclopentylamino, 1-dodecylcyclopentylamino, 1-tridecylcyclopentylamino, 1-tetradecylcyclopentylamino, 1-(9-octadecenyl)cyclopentylamino, cyclohexylamino, 1-methylcyclohexylamino, 1-propylcyclohexylamino, 1-pentylcyclohexylamino, 1-heptylcyclohexylamino, 1-nonylcyclohexylamino, 1-undecylcyclohexylamino, 1-hexadecylcyclohexylamino, and 1-(9-octadecenyl)cyclohexylamino groups; disubstituted amino groups such as (2-cyclopentylethyl)ethylamino, (2-cyclopentylbutyl)ethylamino, (2-cyclopentylethyl)octylamino, (2-cyclohexylethyl)propylamino, (2-cyclohexylethyl)pentylamino, (2-cyclohexylethyl)decylamino, (3-cyclopentylpropyl)hexylamino, (3-cyclohexylpropyl)octylamino, (2-cyclopentyl-1-methylethyl)butylamino, (2-cyclopentyl-1,1-dimethylethyl)hexylamino, (2-cyclohexyl-1-methylethyl)decylamino, (3-cyclopentylpropyl)heptylamino, (3-cyclohexylpropyl)octylamino, (4-cyclohexyl-1,1-dimethylbutyl)pentylamino, hexyl(1-methylpentyl)amino, (1,1-dimethylpentyl)heptylamino, (1-ethylpentyl)decylamino, (1-cyclohexyl-4-methylpentyl)butylamino, (1-cyclopentyl-4-methylpentyl)pentylamino, (2-methylpentyl)decylamino, (1,2-dimethylpentyl)heptylamino, (2-ethylpentyl)dodecylamino, (2-cyclohexyl-4-methylpentyl)butylamino, (2-cyclopentyl-4-methylpentyl)propylamino, (3-methylpentyl)octylamino, (1,3-dimethylpentyl)heptylamino, (3-ethylpentyl)nonylamino, (1-cyclohexyl-3-methylpentyl)butylamino, (1-cyclopentyl-3-methylpentyl)propylamino, dihexylamino, butylhexylamino, hexyloctylamino, decylhexylamino, (1-methylhexyl)pentylamino, (1,1-dimethylhexyl)decylamino, (1-ethylhexyl)undecylamino, (1,1-diethylhexyl)octylamino, heptyl(1-propylhexyl)amino, (1-butylhexyl)propylamino, (1-cyclopentylhexyl)butylamino, (2-methylhexyl)octylamino decyl(1,2-dimethylhexyl)amino, (2-ethylhexyl)tetradecylamino, (1,2-diethylhexyl)octylamino, (2-propylhexyl)dodecylamino, (2-butylhexyl)octylamino, (6-cyclopentylhexyl)butylamino, (6-cyclohexylhexyl)propylamino, diheptylamino, (1-ethylheptyl)tridecylamino, (1,1-dimethylheptyl)pentylamino, (1-cyclohexylheptyl)pentylamino, (1-cyclopentylheptyl)hexylamino, (1-cyclohexylmethylheptyl)butylamino, (1-cyclopentylmethylheptyl)propylamino, octylpropylamino, hexyloctylamino, (1,1-dimethyloctyl)pentylamino, hexyl(1-methyloctyl)amino, (1-ethyloctyl)pentylamino, (1,1-diethyloctyl)butylamino, octyl(1-propyloctyl)amino, (1-butyloctyl)hexylamino, (1-cyclopentyloctyl)pentylamino, (1-cyclohexyloctyl)butylamino, (1-cyclopentylmethyloctyl)propylamino, (1-cyclohexylmethyloctyl)propylamino, nonylpropylamino, (1-methylnonyl)heptylamino, (1,1-dimethylnonyl)hexylamino, (1-ethylnonyl)butylamino, (1,1-diethylnonyl)propylamino, hexyldecylamino, (1-methyldecyl)pentylamino, (1,1-dimethyldecyl)hexylamino, (1-ethyldecyl)butylamino, (1,1-diethyldecyl)pentylamino, (1-cyclopentyldecyl)butylamino, (1-cyclopentylmethylcyclohexyldecyl)propylamino, (1-cyclopentylmethyldecyl)ethylamino, (1-cyclohexylmethyldecyl)methylamino, butylundecylamino, (1-methylundecyl)propylamino, (1,1-dimethylundecyl)propylamino, butyldodecylamino, (1-methyldodecyl)propylamino, (1,1-dimethyldodecyl)propylamino, propyltetradecylamino, (1-methyltetradecyl)butylamino, (1,1-dimethyltetradecyl)propylamino, butylpentadecylamino, (1-methylpentadecyl)butylamino, (1,1-dimethylpentadecyl)propylamino, ethylhexadecylamino, ethyl(1-methylhexadecyl)amino, (1,1-dimethylhexadecyl)methyamino, heptadecylamethylamino, (1-methylheptadecyl)methylamino, (1,1-dimethylheptadecyl)methylamino, methyloctadecylamino, ethyl(1-methyloctadecyl)amino, ethyl(1,1-dimethyloctadecyl)amino, (3-cyclopentyl-2-propenyl)hexylamino, (3-cyclohexyl-2-propenyl)heptylamino, (1,1-dimethyl-3-butenyl)octylamino, (1-ethyl-3-butenyl)nonylamino, (1-cyclopropyl-3-butenyl)decylamino, (1-methyl-2-pentenyl)decylamino, (1,1-dimethyl-2-pentenyl)nonylamino, (1-ethyl-2-pentenyl)decylamino, (1-cyclopropyl-2-pentenyl)heptylamino, (2-hexenyl)octylamino, (1-methyl-2-hexenyl)pentylamino, (1,1-dimethyl-2-hexenyl)decylamino, (3-hexenyl)butylamino, (1-methyl-3-hexenyl)octenylamino, (1,1-dimethyl-3-hexenyl)octenylamino, di(2-heptenyl)amino, (1-methyl-2-heptenyl)heptylamino, pentyl(2-octenyl)amino, (1-methyl-2-octenyl)hexylamino, heptyl(3-nonenyl)amino, (1-methyl-3-nonenyl)hexylamino, (1,1-dimethyl-3-nonenyl)hexylamino, (1-ethyl-3-nonenyl)pentylamino, butyl(1-propyl-3-nonenyl)amino, (8-nonenyl)pentylamino, (1-methyl-8-nonenyl)pentylamino, (1,1-dimethyl-8-nonenyl)butylamino, (1-ethyl-8-nonenyl)pentylamino, (9-decenyl)propylamino, (1-methyl-9-decenyl)pentylamino, (1,1-dimethyl-9-decenyl)butylamino, (1-ethyl-9-decenyl)propylamino, pentyl(6-undecenyl)amino, (1-methyl-6-undecenyl)butylamino, (1,1-dimethyl-6-undecenyl)propylamino, pentyl(6-tridecenyl)amino, (1-methyl-6-tridecenyl)pentylamino, (1,1-dimethyl-6-tridecenyl)ethylamino, butyl(8-tridecenyl)amino, butyl(1-methyl-8-tridecenyl)amino, (1,1-dimethyl-8-tridecenyl)ethylamino, ethyl(10-tridecenyl)amino, butyl(1-methyl-10-tridecenyl)amino, (1,1-dimethyl-10-tridecenyl)propylamino, butyl(10-pentadecenyl)amino, butyl(1-methyl-10-pentadecenyl)amino, (1,1-dimethyl-10-pentadecenyl)propylamino, (8-pentadecenyl)propylamino, (1-methyl-8-pentadecenyl)propylamino, ethyl(1,1-dimethyl-8-pentadecenyl)amino, butyl(12-heptadecenyl)amino, ethyl(1-methyl-12-heptadecenyl)amino, 1,1-dimethyl-12-heptadecenyl)propylamino, ethyl(10-heptadecenyl)amino, (1-methyl-10-heptadecenyl)propylamino, ethyl(1,1-dimethyl-10-heptadecenyl)amino, (8-heptadecenyl)methylamino, (1-methyl-8-heptadecenyl)amino, ethyl(1,1-dimethyl-8-heptadecenyl)amino, (1-ethyl-8-heptadecenyl)propylamino, (8,11-heptadecadienyl)methylamino, methyl(1-methyl-8,11-heptadecadienyl)amino, methyl(8,11,14-heptadecatrienyl)amino, (1-ethylcyclobutyl)pentylamino, heptyl(1-propylcyclobutyl)amino, (1-butylcyclobutyl)hexylamino, butyl(1-pentylcyclobutyl)amino, (1-hexylcyclobutyl)heptylamino, propyl(1-pentylcyclobutyl)amino, ethyl(1-octylcyclobutyl)amino, propyl(1-nonylcyclobutyl)amino, ethyl(1-decylcyclobutyl)amino, methyl(1-undecylcyclobutyl)amino, (1-dodecylcyclobutyl)methylamino, ethyl(1-pentadecylcyclobutyl)amino, methyl[1-(9-octadecenyl)cyclobutyl]amino, methyl(1-methylcyclopentyl)amino, (1-ethylcyclopentyl)propylamino, propyl(1-propylcyclopentyl)amino, (1-butylcyclopentyl)pentylamino, (1-hexylcyclopentyl)methylamino, methyl(1-octyl-cyclopentyl)amino, (1-decylcyclopentyl)methylamino, (1-dodecylcyclopentyl)methylamino, methyl(1-tridecylcyclopentyl)amino, methyl(1-tetradecylcyclopentyl)amino, methyl[1-(9-octadecenyl)cyclopentyl]amino, cyclohexyloctylamino, heptyl(1-cyclohexyl)amino, hexyl(1-propylcyclohexyl)amino, hexyl(1-pentylcyclohexyl)amino, (1-heptylcyclohexyl)pentylamino, butyl(1-monylcyclohexyl)amino, ethyl(1-undecylcyclohexyl)amino, ethyl(1-hexadecylcyclohexyl)amino, methyl[1-(9-octadecenyl)cyclohexyl]amino, benzylhexylamino, benzylheptylamino, benzyloctylamino, benzyldecylamino, benzylnonylamino, benzylundecylamino, nonyl(2-phenylethyl)amino, nonyl(4-phenylbutyl)amino, 4-neopentylbenzylnonylamino, 4-isopropylbenzylnonylamino, and heptyl(4-neopentylbenzylamino) groups.

$R_3$ in formula (I) above may preferably represent the following groups:

(1) a $C_5$–$C_{25}$-alkyl group which is linear or has a branched chain at the 1-position thereof, particularly pentyl, 1-isopropylpentyl, 1-t-butylpentyl, hexyl, 1-isopropylhexyl, 1-t-butylhexyl, heptyl, 1-isopropylheptyl, 1-butylheptyl, octyl, 1-t-butyloctyl, nonyl, 1-isobutylnonyl, decyl, 1-ethyldecyl, 1,1-diethyldecyl, 1-t-butyldecyl, undecyl, 1-isopropylundecyl, 1,1-diethylundecyl, dodecyl, 1-t-butyldodecyl, 1-isopropyldodecyl, 1,1-diethyldodecyl, tridecyl, 1,1-diethyltridecyl, 1-t-butyltridecyl, tetradecyl, 1-isobutyltetradecyl, pentadecyl, 1-methylpentadecyl, 1,1-dimethylpentadecyl, 1-ethylpentadecyl, 1,1-diethylpentadecyl, 1-isopropylpentadecyl, 1-t-butylpentadecyl, hexadecyl, 1,1-dimethylhexadecyl, 1-methylhexadecyl, 1-ethylhexadecyl, 1-isopropylhexadecyl, 1-t-butylhexadecyl, heptadecyl, 1-methylheptadecyl, 1,1-dimethylheptadecyl, 1-ethylheptadecyl, 1-isopropylheptadecyl, 1-t-butylheptadecyl, octadecyl, 1-methyloctadecyl, 1,1-dimethyloctadecyl, 1-ethyloctadecyl, or 1,1-diethyloctadecyl group.

(2) a $C_{12}$–$C_{18}$-alkenyl group which is linear or has a branched chain at the 1-position thereof, particularly 1,1-dimethyl-9-decenyl, 1-ethyl-9-decenyl, 1-methyl-6-undecenyl, 1,1-dimethyl-6-undecenyl, 6-tridecenyl, 1-methyl-6-tridecenyl, 1,1-dimethyl-6-tridecenyl, 8-tridecenyl, 1-methyl-8-tridecenyl, 1,1-dimethyl-8-tridecenyl, 10-tridecenyl, 1-methyl-10-tridecenyl, 1,1-dimethyl-10-tridecenyl, 10-pentadecenyl, 1-methyl-10-pentadecenyl, 1,1-dimethyl-10pentadecenyl, 8-pentadecenyl, 1-methyl-8-pentadecenyl, 1,1-dimethyl-8-pentadecenyl, 12-heptadecenyl, 1-methyl-12-heptadecenyl, 1,1-dimethyl-12-heptadecenyl, 10-heptadecenyl, 1-methyl-10-heptadecenyl, 1-methyl-10-heptadecenyl, 1,1-dimethyl-10-heptadecenyl, 8-heptadecenyl, 1-methyl-8-heptadecenyl, 1,1-dimethyl-8-heptadecenyl, 1-ethyl-8-heptadecenyl, 8,11-heptadecadienyl, 1-methyl-8,11-heptadecadienyl, or 8,11,14-heptadecadienyl group;

(3) a $C_8$–$C_{18}$-alkyl-$C_4$–$C_6$-cycloalkyl group, particularly 1-octyl-cyclobutyl, 1-nonylcyclobutyl, 1-decylcyclobutyl, 1-undecylcyclobutyl, 1-dodecylcyclobutyl, 1-pentadecylcyclobutyl, 1-(9-octadecenyl)cyclobutyl, 1-octylcyclopentyl, 1-decylcyclopentyl, 1-dodecylcyclopentyl, 1-tridecylcyclopentyl, 1-tetradecylcyclopentyl, 1-(9-octadecenyl)cyclopentyl, 1-nonylcyclohexyl, 1-undecylcyclohexyl, or 1-(9-octadecenyl)cyclohexyl group;

(4) a monosubstituted amino group substituted with a $C_8$–$C_{20}$-alkyl group or a $C_8$–$C_{20}$-alkenyl group, for example, 1-isopropylpentylamino, 1-t-butylpentylamino, 1-isopropylhexylamino, 1-t-butylhexylamino, 1-isopropylheptylamino, 1-t-butyloctylamino, 1-isobutylnonylamino, decylamino, 1-ethyldecylamino, 1,1-diethyldecylamino, 1-t-butyldecylamino, undecylamino, 1-isopropylundecylamino, 1,1-diethylundecylamino, dodecylamino, 1-t-butyldodecylamino, 1-isopropyldodecylamino, 1,1-diethyldodecylamino, tridecylamino, 1,1-diethyltridecylamino, 1-t-butyltridecylamino, tetradecylamino, 1-isobutyltetradecylamino, pentadecylamino, 1-methylpentadecylamino, 1,1-dimethylpentadecylamino, 1-ethylpentadecylamino, 1,1-diethylpentadecylamino, 1-isopropylpentadecylamino, 1-t-butylpentadecylamino, hexadecylamino, 1,1-dimethylhexadecylamino, 1-methylhexadecylamino, 1-ethylhexadecylamino, 1-isopropylhexadecylamino, 1-t-butylhexadecylamino, heptadecylamino, 1-methylheptadecylamino, 1,1-dimethylheptadecylamino, 1-ethylheptadecylamino, 1-isopropylheptadecylamino, 1-t-butylheptadecylamino, octadecylamino, 1-methyloctadecylamino, 1,1-dimethyloctadecylamino, 1-ethyloctadecylamino, 1,1-diethyloctadecylamino, 1,1-dimethyl-9-decenylamino, 1,1-methyl-6-undecenylamino, 1,1-dimethyl-6-undecenylamino, 1-methyl-6-tridecenylamino, 1,1-dimethyl-6-tridecenylamino, 8-tridecenylamino, 1-methyl-8-tridecenylamino, 1,1-dimethyltridecenylamino, 10-tridecenylamino, 1-methyl-10-tridecenylamino, 1,1-dimethyl-10-tridecenylamino, 10-pentadecenylamino, 1-methyl-10-pentadecenylamino, 1,1-dimethyl-10-pentadecenylamino, 8-pentadecenylamino, 1-methyl-8-pentadecenylamino, 1,1-dimethyl-8-pentadecenylamino, 12-heptadecenylamino, 1-methyl-12-heptadecenylamino, 1,1-dimethyl-12-heptadecenylamino, 10-heptadecenylamino, 1-methyl-10-heptadecenylamino, 1,1-dimethyl-10-heptadecenylamino, 8-heptadecenylamino, 1-methyl-8-heptadecenylamino, 1,1-dimethyl-8-heptadecenylamino, 1-ethyl-8-heptadecenylamino, 8,11-heptadecadienylamino, 1-methyl-8,11-heptadecadienylamino, 8,11-14-heptadecatrienylamino, 1-hexylcyclobutylamino, 1-heptylcyclobutylamino, 1-octylcyclobutylamino, 1-nonylcyclobutylamino, 1-decylcyclobutylamino, 1-undecylcyclobutylamino, 1-dodecylcyclobutylamino, 1-pentadecylcyclobutylamino, 1-(9-octadecenyl)cyclobutylamino, 1-pentylcyclopentylamino, 1-hexylcyclopentylamino, 1-heptylcyclopentylamino, 1-octylcyclopentylamino, 1-decylcyclopentylamino, 1-dodecylcyclopentylamino, 1-tridecylcyclopentylamino, 1-tetradecylcyclopentylamino, 1-(9-octadecenyl)cyclopentylamino, 1-nonylcyclohexylamino, 1 undecylcyclohexylamino, 1-hexadecylcyclohexylamino, or 1-(9-octadecenyl)cyclohexylamino; or (5) a disubstituted amino group disubstituted with an alkyl group or an alkenyl group and having total carbon atoms in a range of from 8 to 20, for example, decylhexylamino, octylpropylamino, hexyloctylamino, (1-butyloctyl)hexylamino, (1-ethyldecyl)butylamino, (1,1-diethyldecyl)pentylamino, butylundecylamino, butyldodecylamino, propyltetradecylamino, butylpentadecylamino, (1-methylpentadecyl)butylamino, (1,1-dimethylpentadecyl)propylamino, ethylhexadecylamino, ethyl(1-methylhexadecyl) amino, (1,1-dimethylhexadecyl)methylamino, heptadecylmethylamino, (1-methylheptadecyl)methylamino, (1,1-dimethylheptadecyl)methylamino, methyloctadecylamino, ethyl(1-methyloctadecyl)amino, ethyl(1,1-dimethyloctadecyl)amino, (1,1-dimethyl-9-decenyl)butylamino, (1-ethyl-9-decenyl)propylamino, pentyl(6-undecenyl)amino, (1-methyl-6-undecenyl)butylamino, (1,1-dimethyl-6-undecenyl)propylamino, pentyl(6-tridecenyl)amino, (1 -methyl-6-tridecenyl)pentylamino, (1,1-dimethyl-6-tridecenyl)ethylamino, butyl(8-tridecenyl)amino, butyl(1-methyl-8-tridecenyl)amino, (1,1-dimethyl-8-tridecenyl)ethylamino, ethyl(10-tridecenyl)amino, butyl(1-methyl10-tridecenyl)amino, (1,1-dimethyl-10-tridecenyl)propylamino, butyl(10-pentadecenyl)amino, butyl(1-methyl-10-pentadecenyl)amino, (1,1-dimethyl-10-pentadecenyl)propylamino, (8-pentadecenyl)propylamino, (1-methyl-8-pentadecenyl)propylamino, ethyl(1,1-methyl-8-pentadecenyl)propylamino, butyl(12-heptadecenyl)amino, ethyl(1-methyl-12-heptadecenyl)amino, (1,1-dimethyl-12-heptadecenyl)propylamino, ethyl(10-hepotadecenyl)amino, (1-methyl-10-heptadecenyl)propylamino, ethyl(1,1-dimethyl-10-heptadecenyl)amino, (8-heptadecenyl)methylamino, methyl(1-methyl-8-heptadecenyl)amino, ethyl(1,1-dimethyl-8-heptadecenyl)amino, (1-ethyl-8-heptadecenyl)propylamino, (8,11-heptadecadienyl)amino, or methyl(8,11,14-heptadecatrienyl)amino group. The specific examples exemplified in (1) to (5) above for the groups represented by $R^3$ may be substituted with an aromatic group, for example, a phenyl group, a napthyl group, a furyl group, a thienyl group. The aromatic groups may further be substituted with a halogen atom, a lower alkyl group, a cyano group or the like.

As for the "saturated or unsaturated, linear, branched or cyclic divalent aliphatic hydrocarbon group which may be substituted with an aromatic group", there can be cited, for example, the following groups: (1) alkylene groups or cycloalkylalkylene groups, for example, $C_2$-$C_{16}$-alkylene groups and $C_5$-$C_7$-cycloalkyl-$C_2$-$C_{10}$-alkylene groups such as ethylene, trimethylene, tetramethylene, pentamethylene, hexamethylene, heptamethylene, octamethylene, nonamethylene, decamethylene, propylene, ethylethylene, isopropylethylene, propylethylene, butylethylene, isobutylethylene, cyclopentylethylene, cyclohexylethylene, cycloheptylethylene, 1,1-dimethylethylene, 1-methyltrimethylene, 2-methyltrimethylene, 1-ethyltrimethylene, 1-isopropyltrimethylene, 1-isobutyltrimethylene, 1-cyclopentyltrimethylene, 1-cyclohexyltrimethylene, 2-isopropyltrimethylene, 2-isobutyltrimethylene, 2-cyclohexyltrimethylene, 1-methyltetramethylene, 1-isopropyltetramethylene, 1-isobutyltetramethylene, 1-cyclopetnyltetramethylene, 1-cyclohexyltetramethylene, 2-methyltetramethylene, 2-isopropyltetramethylene, 2-isobutyltetramethylene, 2-cyclopentyltetramethylene, 2-cyclohexyltetramethylene, 1-methylpentamethylene, 1-ethylpentamethylene, 1-isopropylpentamethylene, 1-isobutylpentamethylene, 1-cyclopentylpentamethylene, 1-cyclohexylpentamethylene, 2-methylpentamethylene, 2-ethylpentamethylene, 2-isopropylpentamethylene, 2-isobutylpentamethylene, 2-cyclopentylpentamethylene, 2-cyclohexylpentamethylene, methylpentamethylene, 3-ethylpentamethylene, 3-isopropylpentamethylene, 3-isobutylpentamethylene, 3-cyclopentylpentamethylene, 3-cyclohexylpentamethylene, 1-methylhexamethylene, 1-ethylhexamethylene, 1-isopropylhexamethylene, 1-isobutylhexamethylene, 1-cyclopentylhexamethylene, 1-cyclohexylhexamethylene, 2-methylhexamethylene, 2-ethylhexamethylene, 2-isopropylhexamethylene, 2-isobutylhexamethylene, 2-cyclopentylhexamethylene, 2-cyclohexylhexamethylene, 3-methylhexamethylene, 3-ethylhexamethylene, 3-isopropylhexamethylene, 3-isobutylhexamethylene, 3-cyclopentylhexamethylene, 3-cyclohexylhexamethylene, 1-methylheptamethylene, 1-ethylheptamethylene, 1-isopropylheptamethylene, 1-isobutylheptamethylene, 1-cyclopentylheptamethylene, 1-cyclohexylheptamethylene, 2-methylheptamethylene, 2-ethylheptamethylene, 2-isopropylheptamethylene, 2-isobutylheptamethylene, 2-cyclopentylheptamethylene, 2-cyclohexylheptamethylene, 3-methylheptamethylene, 3-ethylheptamethylene, 3-isopropylheptamethylene, 3-isobutylheptamethylene, 3-cyclopentylheptamethylene, 3-cyclohexylheptamethylene, 1-methyloctamethylene, 1-ethyloctamethylene, 1-isopropyloctamethylene, 1-isobutyloctamethylene, 1-cyclopentyloctamethylene, 1-cyclohexyloctamethylene, 2-methyloctamethylene, 2-ethyloctamethylene, 2-isopropyloctamethylene, 2-isobutyloctamethylene, 2-cyclopentyloctamethylene, 2-cyclohexyloctamethylene, 3-methyloctamethylene, 3-ethyloctamethylene, 3-isopropyloctamethylene, 3-isobutyloctamethylene, 3-cyclopentyloctamethylene, 3-cyclohexyloctamethylene, 1-methylnonamethylane, 1-ethylnonamethylene, 1-isopropylnonamethylene, 1-isobutylnonamethylene, 1-cyclopentylnonamethylene, 1-cyclohexylnonamethylene, 2-methylnonamethylene, 2-ethylnonamethylene, 2-isopropylnonamethylene, 2-isobutylnonamethylene, 2-cyclopentylnonamethylene, 2-cyclohexylnonamethylene, 3-methylnonamethylene, 3-ethylnonamethylene, 3-isopropylnonamthylene, 3-isobutylnonamethylene, 3-cyclopentylnonamethylene, 1-methyldecamethylene, 1-ethyldecamethylene, 1-isopropyldecamethylene, 1-isobutyldecamethylene, 1-cyclopentyldecamethylene, 1-cyclohexyldecamethylene, 2-methyldecamethylene, 2-ethyldecamethylene, 2-isopropyldecamethylene, 2-isobutyldecamethylene, 2-cyclopentyldecamethylene, 2-cyclohexyldecamethylene, 3-methyldecamethylene, 3-ethyldecamethylene, 3-isopropyldecamethylene, 3-isobutyldecamethylene, 3-cyclopentyldecamethylene, and 3-cyclohexyldecamethylene (2) cycloalkylene groups, for example, $C_5$-$C_8$-cycloalkylene groups such as 1,2-cyclopentylene, 1,3-cyclopentylene, 1,2-cyclohexylene, 1,3-cyclohexylene, 1,4-cyclohexylene, 1,2-cycloheptyl, 1,3-cycloheptyl, and 1,4-cycloheptyl groups;

(3) alkenylene groups and alkenylene groups, for example, $C_4$-C groups and $C_4$-$C_{10}$-groups such as 2-butenylene, 1-methyl-2-butenylene, 1-ethyl2-butenylene, 1-propylbutenylene, 1-butylbutenylene, 2-butenylene, 2-pentenylene, 2-pentynylene, 2-hexenylene, 3-hexenylene, 2-hexynylene, 3-hexynylene, 2-heptenylene, 3-heptenylene, 2-heptynylene, 3-heptynylene, 2-octenylene, and 4-octenylene groups; and (4) cycloalkylalkylene groups, for example, $C_4$-$C_8$-cycloalkylene-$C_1$-$C_7$-alkylene groups such as 1,1-pentamethyleneethylene, 1,1-tetramethyleneethylene, 1,1-hexamethyleneethylene, 1,1-tetramethylenetrimethylene, 1,1-pentamethylenetrimethylene, 1,2-trimethylenetrimethylene, 1,2-tetramethylenetrimethylene, 1,1-trimethylenepentamethylene, 1,1-tetramethylenepentamethylene, 1,1-pentamethylenepentamethylene, 1,2-trimethylenepentamethylene, 1,2-tetramethylenepentamethylene, 1,2-pentamethylenepentamethylene, 1,3-trimethylenepentamethylene, 1,1-trimethylenehexamethylene, 1,1-tetramethylenehexamethylene, 1,1-pentamethylenehexamethylene, 1,2-trimethylenehexamethylene, 1,2-tetramethylenehexamethylene, 1,2-pentamethylenehexamethylene, 1,3-trimethylhexamethylene, 1,1-trimethyleneheptamethylene, 1,1-tetramethylenehpetamethylene, 1,1-pentamethyleneheptamethylene, 1,2-trimethyleneheptamethylene, 1,2-trimethyleneheptamethylene, 1,2-tetramethyleneheptamethylene, 1,2-pentamethyleneheptamethylene, 1,3-trimethyleneheptamethylene, 1,1-trimethyleneoctamethylene, 1,1-tetramethyleneoctamethylene, 1,1-pentamethyleneoctamethylene, 1,2-trimethyleneoctamethylene, 1,2-tetramethyleneoctamethylene, 1,2-pentamethyleneoctamethylene, 1,2-trimethyleneoctamethylene, 1,1-trimethylenenonamethylene, 1,1-tetramethylenenonamethylene, 1,1-pentamethylenenonamethylene, 1,2-trimethylenenonamethylene, 1,2-tetramethylenenonamethylene, 1,2-pentamethylenenonamethylene, 1,3-trimethylenenonamethylene, 1,1-trimethylenedecamethylene, 1,1-tetramethylenedecamethylene, 1,1-pentamethylenedecamethylene, 1,2-trimethylenedecamethylene, 1,2-tetramethylenedecamethylene, 1,3 -pentamethylenedecamethylene, and 1,3-trimethylenedecamethylene groups.

The divalent aliphatic hydrocarbon groups described above may further be substituted with an aromatic group, for example, an aryl group such as phenyl or naphthyl group; or a heteroaryl group such as furyl, thienyl, pyridyl or indolyl group. Examples of such substituted divalent hydrocarbon group include phenylethylene, pyridylethylene, benzylethylene, naphthylmethylethylene, furylmethylethylene, thienylmethylethylene, pyridylmethylethylene, and indolylmethylethylene groups.

The "divalent aromatic hydrocarbon group" may be either monocyclic or polycyclic, and examples thereof include phenylene and naphthylene groups. Their aromatic rings may be substituted with 1 to 4 lower alkyl groups.

Further, the "divalent aromatic heterocyclic group" includes aromatic unsaturated heterocyclic groups which have at least one hetero atom selected from a nitrogen atom, an oxygen atom and a sulfur atom in the ring thereof. The heterocyclic group described above may form a condensed ring together with the above-described aromatic hydrocarbon ring. Examples of this type of divalent aromatic heterocyclic group includes pyridinediyl, pyrimidinediyl, pyrazinediyl, furanediyl, thiophenediyl, quinolinediyl, isoquinolinediyl, benzofuranediyl, benzothiophenediyl, benzoxazolediyl, benzothiazolediyl and indolediyl.

Therefore, in the case where Q in formula (I) above represents the above-described group (a), A may preferably represent:

(1) a linear or branched $C_2$-$C_{10}$-group, for example, ethylene, trimethylene, tetramethylene, pentamethylene, hexamethylene, heptamethylene, octamethylene, nonamethylene, decamethylene, propylene, ethylethylene, isopropylethylene, propylethylene, butylethylene, isobutylethylene, 1-methyltrimethylene, 1-ethyltrimethylene, 1-isopropyltrimethylene, 1-isobutyltrimethylene, 1-methyltetramethylene, 1-isopropyltetramethylene or 1-isobutyltetramethylene group;

(2) a $C_5$-$C_7$-cycloalkyl-$C_2$-$C_5$-alkylene group, for example, cyclopentylethyl, cyclohexylethyl, cyclobutylethyl, 1-cyclopentyltrimethylene, 1-cyclohexyltrimethylene, 1-cyclopentyltetramethylene or 1-cyclohexyltetramethylene group;

(3) a $C_5$-$C_7$-cycloalkylene group, for example, 1,2-cyclopentylene, 1,2-cyclopentylene, 1,2-cyclohexylene, 1,3-cyclohexylene, 1,4-cyclohexylene, 1,2-cycloheptylene or 1,3-cycloheptylene;

(4) a $C_4$-$C_8$-alkenylene group or a $C_4$-$C_8$-group, for example, 2-butenylene, 1-methyl 2-butenylene, 1-ethyl-2-butenylene, 1-propylbutenylene, 1-butylbutenylene, 2-butynylene, 2-pentenylene, 2-pentynylene, 2-hexenylene, 3-hexenylene, 2-hexynylene, 3-hexynylene, 2-heptenylene, 3-heptenylene, 2-heptynylene, 3-heptynylene, 2-octenylene or 4-octenylene;

(5) a $C_5$-$C_7$-cycloalkylene-$C_1$-$C_5$-alkylene group, for example, 1,1-pentamethyleneethylene, 1,1-tetramethyleneethylene, 1,1-hexamethyleneethylene, 1,1-dimethylethylene, 1,1-tetramethylenetrimethylene, 1,1-pentamethylenetrimethylene, 1,2-trimethylenetrimethylene or 1,2-tetramethylenetrimethylene;

(6) a $C_2$-$C_5$-alkylene group substituted with an aryl group or a heteroaryl group, for example, phenylethylene, naphthylethylene, furylethylene, thienylethylene, pyridylethylene, benzylethylene, naphthylmethylethylene, furylmethylethylene, thienylmethylethylene, pyridylmethylethylene or indolylmethylethylene; or (7) o-phenylene, m-phenylene or p-phenylene; and one of $X^1$ and $Y^1$ may preferably represent —NH— or $$-\overset{\overset{\displaystyle CH_3}{|}}{N}-,$$

and the other may preferably represent —O—, —S—, —NH—, $$-\overset{\overset{\displaystyle CH_3}{|}}{N}-.$$

Furthermore, in the case where Q in formula (I) above represents the group (b) described above, the 4- to 7-membered, preferably 5- or 6-membered divalent nitrogen-containing heterocyclic group represented by formula may include saturated nitrogen-containing heterocyclic groups, for example, and $X^2$ represents one of the nitrogen-containing heterocyclic groups, it may be bonded through its nitrogen atom to the left hand side carbonyl group in formula (I), and on the other hand when $Y^2$ represents the above-described nitrogen-containing heterocyclic group, it may be bonded through its nitrogen atom to the right hand side carbonyl group in formula (I) above. When $X^2$ represents one of the above-described nitrogen-containing heterocyclic groups, it is preferred that $Y^3$ represent $$-\overset{\overset{\displaystyle R^6}{|}}{N}-.$$

Particularly, it is preferred that one of $X^2$ and $Y^2$ represent and the other represent —O—, —S—, —NH— or $$-\overset{\overset{\displaystyle CH_3}{|}}{N}-.$$

Hence, representative examples of the compounds of formula (I) above provided by the present invention include the following compounds:

Group a

Compounds represented by the following formula (Ia)

$$\begin{array}{c} R^1O \quad OR^2 \\ | \quad \quad | \\ H_2C \quad CH-CONH-(CH_2)_n-CO-X^1-A-Y^1-CO-R^3 \\ \diagdown \diagup \\ C \\ \diagup \diagdown \\ H_3C \quad CH_3 \end{array}$$
(Ia)

wherein $R^1$, $R^2$, $R^3$, A, $X^1$, $Y^1$ and n are as defined above:

N-[4-(Oleoyloxy)phenyl]-3-[N-(2,2,5,5-tetramethyl-1,3-dioxane-4-carbonyl)amino]propanamide;
N-[4-(Oleoyloxy)phenyl]-3-[N-(2,4-dihydroxy-3,3-dimethyl-1-oxobutyl)amino]propanamide;
4-(Oleoylamino)phenyl-3-[N-(2,2,5,5-tetramethyl-1,3-dioxane-4-carbonyl)amino]propionate;
4-(Oleoylamino)phenyl-3-[N-(2,4-dihydroxy-3,3-dimethyl-1-oxobutyl)amino]propanoamide;
N-[4-(Oleoylthio)phenyl]-3-[N-(2,2,5,5-tetramethyl-1,3-dioxane-4-carbonyl)amino]propanamide;
N-[4-(Oleoylthio)phenyl]-3-[N-(2,4-dihydroxy-3,3-dimethyl-1-oxobutyl)amino]propanamide;
S-4-(Oleoylamino)phenyl]-3-[N-(2,2,5,5-tetramethyl-1,3-dioxane-4-carbonyl)amino]propanthioate;
S-4-(Oleoylamino)phenyl]-3-[N-(2,4-dihydro3,3-dimethyl-oxobutyl)amino]propanthioate;
N-[2-(Oleoylamino)phenyl]-3-[N-(2,2,5,5-tetramethyl-1,3-dioxane-4-carbonyl)amino]propanamide;
2-(Oleoylamino)phenyl]-3-[N-(2,2,5,5-tetramethyl-1,3-dioxane-4-carbonyl)amino]propionate;
N-[2-(Oleoyloxy)phenyl]-3-[N-(2,2,5,5-tetramethyl-1,3-dioxane-4-carbonyl)amino]propanamide;
N-[2-(Linoleoylamino)phenyl]-3-[N-(2,2,5,5-tetramethyl-1,3-dioxane-4-carbonyl)amino]propanamide;
N-[2-(Linolenoylamino)phenyl]-3-[N-(2,2,5,5-tetramethyl-1,3-dioxane-4-carbonyl)amino]propanamide;
N-[2-(Stearoylamino)phenyl]-3-[N-(2,2,5,5-tetramethyl-1,3-dioxane-4-carbonyl)amino]propanamide;
N-[2-(Lauroylamino)phenyl]-3-[N-(2,2,5,5-tetramethyl-1,3-dioxane-4-carbonyl)amino]propanamide;
N-[2-(Octanoylamino)phenyl]-3-[N-(2,2,5,5-tetramethyl-1,3-dioxane-4-carbonyl)amino]propanamide;
N-[3-(Linoleoylamino)phenyl]-3-[N-(2,2,5,5-tetramethyl-1,3-dioxane-4-carbonyl)amino]propanamide;

N-[4-(Lauroylamino)phenyl]-3-[N-(2,2,5,5-tetramethyl-1,3-dioxane-4-carbonyl)amino]propanamide;
b 4-(Linoleoylamino)phenyl]-3-[N-(2,2,5,5-tetramethyl-1,3-dioxane-4-carbonyl)amino]propionate;
N-[2-(Oleoylamino)phenyl]-3-[N-(2,4-diacetoxy-3,3-dimethyl-1-oxobutyl)amino]propanamide;
N-[2-(Oleoylamino)phenyl]-3-[N-(2,4-dihydroxy-3,3-dimethyl-1-oxobutyl)amino]propanamide;
N-[3-(Oleoylamino)phenyl]-3-[N-(2,4-diacetoxy-3,3-dimethyl-1-oxobutyl)amino]propanamide;
N-[3-(Oleoylamino)phenyl]-3-[N-(2,4-dihydroxy-3,3-dimethyl-1-oxobutyl)amino]propanamide;
N-[4-(Oleoylamino)phenyl]-3-[N-(2,4-diacetoxy-3,3-dimethyl-1-oxobutyl)amino]propanamide;
N-[4-(Oleoylamino)phenyl]-3-[N-(2,4-dihydroxy-3,3-dimethyl-1-oxobutyl)amino]propanamide;
4-(Oleoylamino)phenyl]-3-[N-(2,4-diacetoxy-3,3-dimethyl-1-oxobutyl)amino]propionate;
N-[4-(Oleoyloxy)phenyl]-3-[N-(2,4-diacetoxy-3,3-dimethyl-1-oxobutyl)amino]propanamide;
S-4-(Oleoylamino)phenyl]-3-[N-(2,4-diacetoxy-3,3-dimethyl-1-oxobutyl)amino]propionate;
N-[4-(Oleoylthio)phenyl]-3-[N-(2,4-diacetoxy-3,3-dimethyl-1-oxobutyl)amino]propanamide;
4-(Oleoylamino)phenyl[-3-[N-(2,4-dibenzyloxy-3,3-dimethyl-1-oxobutyl)amino]propionate;
N-(2-Oleoylaminoethyl)-3-[N-(2,4-diacetoxy-3,3-dimethyl-1-oxobutyl)amino]propanamide; N-(3-N-Oleoylaminopropyl)-3-[N-(2,2,5,5-tetramethyl-1,3-dioxane-4-carbonyl)amino]propanamide;
N-(2-N-Oleoylaminoethyl)-3-[N-(2,4-dihydroxy-3,3-dimethyl-1-oxobutyl)amino]propanamide;
2-(N-Oleoylamino)ethyl-3-[N-(2,2,5,5-tetramethyl-1,3-dioxane-4-carbonyl)amino]propionate;
2-(N-Oleoylamino)ethyl-3-[N-(2,4-dihydroxy-3,3-dimethyl-1-oxobutyl)amino]propionate;
3-(N-Oleoylamino)propyl-3-[N-(2,2,5,5-tetramethyl-1,3-dioxane-4-carbonyl)amino]propionate;
3-(N-Oleoylamino)propyl-3-[N-(2,4-dihydroxy-3,3-dimethyl-1-oxobutyl)amino]propionate;
3-(N-Oleoylamino)propyl-3-[N-(2,4-diacetoxy-3,3-dimethyl-1-oxobutyl)amino]propionate;
4-(N-Oleoylamino)butyl-3-[N-(2,2,5,5-tetramethyl-1,3-dioxane-4-carbonyl)amino]propionate;
4-(N-Oleoylamino)butyl-3-[N-(2,4-dihydroxy-3,3-dimethyl-1-oxobutyl)amino]propionate;
S-2-(N-Oleoylamino)ethyl-3-[N-(2,2,5,5-tetramethyl-1,3-dioxane-4-carbonyl)amino]propanthioate;
S-2-(N-Oleoylamino)ethyl-3-[N-(2,4-dihydroxy-3,3-dimethyl-1-oxobutyl)amino]propionate;
N-(3-Oleoylaminopropyl)-3-[N-(2,2,5,5-tetramethyl-1,3-dioxane-4-carbonyl)amino]propanamide;
N-(3-Oleoylaminopropyl)-3-[N-(2,4-dihydroxy-3,3-dimethyl-1-oxobutyl)amino]propanamide;
N-(3-Oleoylaminopropyl)-3-[N-(2,4-diacetoxy-3,3-dimethyl-1-oxobutyl)amino]propanamide;
N-(4-Oleoylaminobutyl)-3-[N-(2,2,5,5-tetramethyl-1,3-dioxane-4-carbonyl)amino]propanamide;
N-(4-Oleoylaminobutyl)-3-[N-(2,4-dihydroxy-3,3-dimethyl-1-oxobutyl)amino]propanamide;
N-(4-Oleoylaminobutyl)-3-[N-(2,4-diacetoxy-3,3-dimethyl-1-oxobutyl)amino]propanamide;
N-(6-Oleoylaminohexyl)-3-[N-(2,2,5,5-tetramethyl-1,3-dioxane-4-carbonyl)amino]propanamide;
N-(5-Oleoylaminopentyl)-3-[N-(2,2,5,5-tetramethyl-1,3-dioxane-4-carbonyl)amino]propanamide;
N-(8-Oleoylaminooctyl)-3-[N-(2,2,5,5-tetramethyl-1,3-dioxane-4-carbonyl)amino]propanamide;
N-(2-Oleoylaminoethyl)-3-[N-(2,2,5,5-tetramethyl-1,3-dioxane-4-carbonyl)amino]propanamide;
5-(N-Oleoylamino)pentyl-3-[N-(2,2,5,5-tetramethyl-1,3-dioxane-4-carbonyl)amino]propionate;
6-(N-Oleoylamino)hexyl-3-[N-(2,2,5,5-tetramethyl-1,3-dioxane-4-carbonyl)amino]propionate;
2-(N-Methyl-N-oleoylamino)ethyl-3-[N-2,2,5,5-tetramethyl-1,3-dioxane-4-carbonyl)amino]propionate;
3-(N-Oleoylamino)propyl-3-[N-(2,4-dibenzoyloxy-3,3-dimethyl-1-oxobutyl)amino]propionate;
3-(N-Oleoylamino)propyl-3-[N-(2-hydroxy-3,3-dimethyl-4-(trimethylacetyl)oxy-1-oxobutyl)amino]propionate;
3-(N-Oleoylamino)propyl-3-[N-(2-phenyl-5,5-dimethyl-1,3-dioxane-4-carbonyl)amino]propionate;
3-(N-Hexadecanoylamino)propyl-3-[N-(2,2,5,5-tetramethyl-1,3-dioxane-4-carbonyl)amino]propionate;
3-(N-Linoleoylamino)propyl-3-[N-(2,2,5,5-tetramethyl-1,3-dioxane-4-carbonyl)amino]propionate;
3-(N-Octadecanoylamino)propyl-3-[N-(2,2,5,5-tetramethyl-1,3-dioxane-4-carbonyl)amino]propionate;
3-(N-Tetradecanoylamino)propyl-3-[N-(2,2,5,5-tetramethyl-1,3-dioxane-4-carbonyl)amino]propionate;
3-(N-Dodecanoylamino)propyl-3-[N-(2,2,5,5-tetramethyl-1,3-dioxane-4-carbonyl)amino]propionate;
3-(N-Decanoylamino)propyl-3-[N-(2,2,5,5-tetramethyl-1,3-dioxane-4-carbonyl)amino]propionate;
3-(N-Octanoylamino)propyl-3-[N-(2,2,5,5-tetramethyl-1,3-dioxane-4-carbonyl)amino]propionate;
3-(N-Hexanoylamino)propyl-3-[N-(2,2,5,5-tetramethyl-1,3-dioxane-4-carbonyl)amino]propionate;
3-N-(2-Isopropylhexanoyl)amino]propyl-3-[N-(2,2,5,5-tetramethyl-1,3-dioxane-4-carbonyl)amino]propionate;
3-N-(2-t-Butylhexanoyl)amino]propyl-3-[N-(2,2,5,5-tetramethyl-1,3-dioxane-4-carbonyl)amino]propionate;
3-N-(2-t-Butylheptanoyl)amino]propyl-3-[N-(2,2,5,5-tetramethyl-1,3-dioxane-4-carbonyl)amino]propionate;
3-[N-(2-t-Butylnonanoyl)aminopropyl-3-[N-(2,2,5,5-tetramethyl-1,3-dioxane-4-carbonyl)amino]propionate;
3-[N-(2,2-Diethylundecanoyl)amino]propyl-3-[N-(2,2,5,5-tetramethyl-1,3-dioxane-4-carbonyl)amino]propionate;
3-[N-(2-Isopropyldodecanoyl)amino]propyl-3-[N-(2,2,5,5-tetramethyl-1,3-dioxane-4-carbonyl)amino]propionate;
3-[N-(2-t-Butyltetradecanoyl)amino]propyl-3-[N-(2,2,5,5-tetramethyl-1,3-dioxane-4-carbonyl)amino]propionate;
3-[N-(2-t-Butylhexadecanoyl)amino]propyl-3-]N-(2,2,5,5-tetramethyl-1,3-dioxane-4-carbonyl)amino]propionate;
3-[N-(2-Isopropylheptadecanoyl)amino]propyl-3-[N-(2,2,5,5-tetramethyl-1,3-dioxane-4-carbonyl)amino]propionate;
3-[N-(2-Ethyloctadecanoyl)amino]propyl-3-[N-(2,2,5,5-tetramethyl-1,3-dioxane-4-carbonyl)amino]propionate;
3-[N-(2,2-Dimethyl-10-undecenoyl)amino]propyl-3-[N-(2,2,5,5-tetramethyl-1,3-dioxane-4-carbonyl)amino]propionate;
3-[N-(2,2-Dimethyl-7-dodecenoyl)amino]propyl-3-[N-(2,2,5,5-tetramethyl-1,3-dioxane-4-carbonyl)amino]propionate;
3-[N-(2,2-Dimethyl-7-tetradecenoyl)amino]propyl-3-[N-(2,2,5,5-tetramethyl-1,3-dioxane-4-carbonyl)amino]propionate;

3-[N-(2,2-Dimethyl-9-tetradecenoyl)amino]propyl-3-[N-(2,2,5,5-tetramethyl-1,3-dioxane-4-carbonyl)amino]propionate;

3-[N-(2,2-Dimethyl-11-tetradecenoyl)amino]propyl-3-[N-(2,2,5,5-tetramethyl-1,3-dioxane-4-carbonyl)amino]propionate;

3-[N-(2,2-Dimethyl-11-pentadecenoyl)amino]propyl-3-[N-(2,2,5,5-tetramethyl-1,3-dioxane-4-carbonyl)amino]propionate;

3-[N-(2,2-Dimethyl-9-pentadecenoyl)amino]propyl-3-[N-(2,2,5,5-tetramethyl-1,3-dioxane-4-carbonyl)amino]propionate;

3-[N-(2,2-Dimethyl-9-hexadecenoyl)amino]propyl 3-[N-(2,2,5,5-tetramethyl-1,3-dioxane-4-carbonyl)amino]propionate;

3-[N-(2,2-Dimethyl-9-heptadecenoyl)amino]propyl-3-[N-(2,2,5,5-tetramethyl-1,3-dioxane-4-carbonyl)amino]propionate;

3-[N-(2,2-Dimethyl-9-octadecenoyl)amino]propyl-3-[N-(2,2,5,5-tetramethyl-1,3-dioxane-4-carbonyl)amino]propionate;

3-[N-(2-Methyl-9-octadecenoyl)amino]propyl-3-[N-(2,2,5,5-tetramethyl-1,3-dioxane-4-carbonyl)amino]propionate;

N-[2-(Oleoylamino)cyclohexane-1-yl]-3-[N-{(2R)-2,4-diacetoxy-3,3-dimethyl-1-oxobutyl}amino]propanamide;

N-[(1S,2S)-2-(Oleoylamino)cyclohexane-1-yl]-3-[N-{(2R)-2,4-diacetoxy-3,3-dimethyl-1-oxobutyl}amino]propanamide;

N-[(1R,2R)-2-(Oleoylamino)cyclohexane-1-yl]-3-[N-{(2R)-2,4-diacetoxy-3,3-dimethyl-1-oxobutyl}amino]propanamide;

N-[(1S,2S)-2-(Oleoylamino)cyclohexane-1-yl]-3-[N-{(2R)-2,4-dihydroxy-3,3-dimethyl-1-oxobutyl}amino]propanamide;

N-[2-(Oleoylamino)cyclohexane-1-yl]-3-[N-(2,4-diacetoxy-3,3-dimethyl-1-oxobutyl)amino]propanamide;

N-[(1S,2S)-2-(Oleoylamino)cyclohexane-1-yl]-3-[N-(2,2,5,5-tetramethyl-1,3-dioxane-4-carbonyl)amino]propanamide;

N-[(1R,2R)-2-(Oleoylamino)cyclohexane-1-yl]-3-[N-(2,2,5,5-tetramethyl-1,3-dioxane-4-carbonyl)amino]propionate;

N-[(1S,2S)-2-(Oleoylamino)cyclohexane-1-yl]-3-[N-(2,2,5,5-tetramethyl 1,3-dioxane-4-carbonyl)amino]propionate;

N-[(1R,2R)-2-(Stearoylamino)cyclohexane-1-yl]-3-[N-(2,2,5,5-tetramethyl-1,3-dioxane-4-carbonyl)amino]propionate;

N-[(1S,2S)-2-(Linoleoylamino)cyclohexane-1-yl]-3-[N-(2,2,5,5-tetramethyl-1,3-dioxane-4-carbonyl)amino]propionate;

2-(1-Octylcyclobutanoylamino)cyclohexane-1-yl-3-[N-(2,2,5,5-tetramethyl-1,3-dioxane-4-carbonyl)amino]propionate;

2-(1-Nonylcyclobutanoylamino)cyclohexane-1-yl-3-[N-(2,2,5,5-tetramethyl-1,3-dioxane-4-carbonyl)amino]propionate;

2-(Oleoylamino)cyclopentan-1-yl-3-[N-(2,2,5,5-tetramethyl-1,3-dioxane-4-carbonyl)amino]propionate;

2-(Oleoylamino)cycloheptan-1-yl-3-[N-(2,2,5,5-tetramethyl-1,3-dioxane-4-carbonyl)amino]propionate;

3-(Oleoylamino)cyclohexane-1-yl-3-[N-(2,2,5,5-tetramethyl-1,3-dioxane-4-carbonyl)amino]propionate;

4-(Oleoylamino)cyclohexane-1-yl-3-[N-(2,2,5,5-tetramethyl-1,3-dioxane-4-carbonyl)amino]propionate;

2-(1-Decylcyclobutanoylamino)cyclohexane-1-yl-3-[N-(2,2,5,5-tetramethyl-1,3-dioxane-4-carbonyl)amino]propionate;

2-(1-Undecylcyclobutanoylamino)cyclohexane-1-yl-3-[N-(2,2,5,5-tetramethyl-1,3-dioxane-4-carbonyl)amino]propionate;

2-(1-Pentadecylcyclobutanoylamino)cyclohexane-1-yl-3-[N-(2,2,5,5-tetramethyl-1,3-dioxane-4-carbonyl)amino]propionate;

2-[1-(9-Octadecenyl)cyclobutanoylamino)cyclohexane-1-yl-3-[N-(2,2,5,5-tetramethyl-1,3-dioxane-4-carbonyl)amino]propionate;

2-(1-Decylcyclobutanoylamino)cyclohexane-1-yl-3-[N-(2,2,5,5-tetramethyl-1,3-dioxane-4-carbonyl)amino]propionate;

2-(1-Decylcyclohexanoylamino)cyclohexane-1-yl-3-[N-(2,2,5,5-tetramethyl-1,3-dioxane-4-carbonyl)amino]propionate;

2-(1-Nonylcyclohexanoylamino)cyclohexane-1-yl-3-[N-(2,2,5,5-tetramethyl-1,3-dioxane-4-carbonyl)amino]propionate;

2-[1-(9-Octadecenyl)cyclohexanoylamino)cyclohexane-1-yl-3-[N-(2,2,5,5-tetramethyl-1,3-dioxane-4-carbonyl)amino]propionate;

2-(1-Isopropylpentylcarbamoylamino)cyclohexane-1-yl-3-[N-(2,2,5,5-tetramethyl-1,3-dioxane-4-carbonyl)amino]propionate;

2-(1-Isopropylhexylcarbamoylamino)cyclohexane-1-yl-3-[N-(2,2,5,5-tetramethyl-1,3-dioxane-4-carbonyl)amino]propionate;

2-(1-t-Butyldodecylcarbamoylamino)cyclohexane-1-yl-3-[N-(2,2,5,5-tetramethyl-1,3-dioxane-4-carbonyl)amino]propionate;

2-(1,1-Dimethylhexadecylcarbamoylamino)cyclohexane-1-yl-3-[N-2,2,5,5-tetramethyl-1,3-dioxane-4-carbonyl)amino]propionate;

2-(Octadecylcarbamoylamino)cyclohexane-1-yl-3-[N-(2,2,5,5-tetramethyl-1,3-dioxane-4-carbonyl)amino]propionate;

2-(1,1-Dimethyloctadecylcarbamoylamino)cyclohexane-1-yl-3-[N-2,2,5,5-tetramethyl-1,3-dioxane-4-carbonyl)amino]propionate;

2-(1,1-Dimethyl-9-decenylcarbamoylamino)cyclohexane-1-yl-3-[N-2,2,5,5-tetramethyl-1,3-dioxane-4-carbonyl)amino]propionate;

2-(1,1-Dimethyl-6-undecenylcarbamoylamino)cyclohexane-1-yl-3-[N-2,2,5,5-tetramethyl-1,3-dioxane-4-carbonyl)amino]propionate;

2-(1,1-Dimethyl-8-tridecenylcarbamoylamino)cyclohexane-1-yl-3-[N-2,2,5,5-tetramethyl-1,3-dioxane-4-carbonyl)amino]propionate;

2-(1,1-Methyl-10-pentadecenylcarbamoylamino)cyclohexane-1-yl-3-[N-2,2,5,5-tetramethyl-1,3-dioxane-4-carbonyl)amino]propionate;

2-(1,1-Dimethyl-10-heptadecenylcarbamoylamino)cyclohexane-1-yl-3-[N-2,2,5,5-tetramethyl-1,3-dioxane-4-carbonyl)amino]propionate;

2-(1,1-Methyl-8-heptadecenylcarbamoylamino)cyclohexane-1-yl-3-[N-2,2,5,5-tetramethyl-1,3-dioxane-4-carbonyl)amino]propionate;

2-(Octadecenylcarbamoylamino)cyclohexane-1-yl-3-[N-(2,2,5,5-tetramethyl-1,3-dioxane-4-carbonyl)amino]propionate;

2-(8,11-Octadecadienylcarbamoylamino)cyclohexane-1-yl-3-[N-(2,2,5,5-tetramethyl-1,3-dioxane-4-carbonyl)amino]propionate;

2-(1-Methyl-8,11,14-octadecatrienylcarbamoylamino)-cyclohexane-1-yl-3-[N-(2,2,5,5-tetramethyl-1,3-dioxane-4-carbonyl)amino]propionate;

2-(1-Hexylcyclobutylcarbamoylamino)cyclohexane-1-yl-3-[N-(2,2,5,5-tetramethyl-1,3-dioxane-4-carbonyl)amino]propionate;

2-(1-Octylcyclobutylcarbamoylamino)cyclohexane-1-yl-3-[N-(2,2,5,5-tetramethyl-1,3-dioxane-4-carbonyl)amino]propionate;

2-(1-Octylcyclopentylcarbamoylamino)cyclohexane-1-yl-3-[N-(2,2,5,5-tetramethyl-1,3-dioxane-4-carbonyl)amino]propionate;

2-(1-Octylcyclohexylcarbamoylamino)cyclohexane-1-yl-3-[N-(2,2,5,5-tetramethyl-1,3-dioxane-4-carbonyl)amino]propionate;

2-(1-Octylcyclopentylcarbamoylamino)cyclohexane-1-yl-3-[N-(2,2,5,5-tetramethyl-1,3-dioxane-4-carbonyl)amino]propionate;

2-(1-Decylcyclopentylcarbamoylamino)cyclohexane-1-yl-3-[N-(2,2,5,5-tetramethyl-1,3-dioxane-4-carbonyl)amino]propionate;

2-(Hexylcyclohexylcarbamoylamino)cyclohexane1-yl-3-[N-(2,2,5,5-tetramethyl-1,3-dioxane-4-carbonyl)amino]propionate;

2-[1-(6-Hexadecenyl)cyclohexylcarbamoylamino)cyclohexane-1-yl-3-[N-(2,2,5,5-tetramethyl-1,3-dioxane-4-carbonyl)amino]propionate;

2-[1-(6-Hexadecenyl)cyclobutylcarbamoylamino)cyclohexane-1-yl-3-[N-(2,2,5,5-tetramethyl-1,3-dioxane-4-carbonyl)amino]propionate;

2-[1-(6-Hexadecenyl)cyclopentylcarbamoylamino)cyclohexane-1-yl-3-[N-(2,2,5,5-tetramethyl-1,3-dioxane-4-carbonyl)amino]propionate;

2-[1-Decylhexylcarbamoylamino)cyclohexane-1-yl-3-[N-(2,2,5,5-tetramethyl-1,3-dioxane-4-carbonyl)amino]propionate;

2-(Hexyloctylcarbamoylamino)cyclohexane-1-yl-3-[N-(2,2,5,5-tetramethyl-1,3-dioxane-4-carbonyl)amino]propionate;

2-(Butyldodecylcarbamoylamino)cyclohexane-1-yl-3-[N-(2,2,5,5-tetramethyl-1,3-dioxane-4-carbonyl)amino]propionate;

2-(Methyloctadecylcarbamoylamino)cyclohexane-1-yl-3-[N-(2,2,5,5-tetramethyl-1,3-dioxane-4-carbonyl)amino]propionate;

2-[Butyl(1,1-dimethyl-6-undecenylcarbamoylamino)cyclohexane-1-yl-3-[N-(2,2,5,5-tetramethyl-1,3-dioxane-4-carbonyl)amino]propionate;

2-[Butyl(1,1-dimethyl-8-tridecenylcarbamoylamino)cyclohexane-1-yl-3-[N-(2,2,5,5-tetramethyl-1,3-dioxane-4-carbonyl)amino]propionate;

2-[Butyl(1-methyl-10-pentadecenylcarbamoylamino)-cyclohexane-1-yl-3-[N-(2,2,5,5-tetramethyl-1,3-dioxane-4-carbonyl)amino]propionate;

2-[(8-Pentadecenyl)propylcarbamoylamino)]cyclohexane-1-yl-3-[N-(2,2,5,5-tetramethyl-1,3-dioxane-4-carbonyl)amino]propionate;

2-[Butyl(1,1-dimethyl-8-heptadecenylcarbamoylamino)cyclohexane-1-yl-3-[N-(2,2,5,5-tetramethyl-1,3-dioxane-4-carbonyl)amino]propionate;

2-[Ethyl(1,1-dimethyl-8-heptadecenylcarbamoylamino)cyclohexane-1-yl-3-[N-(2,2,5,5-tetramethyl-1,3-dioxane-4-carbonyl)amino]propionate;

2-Methyl-2-(N-oeloylamino)ethyl-3-[N-(2,2,5,5-tetramethyl-1,3-dioxane-4-carbonyl)amino]propionate;

2-Ethyl-2-(N-oeloylamino)ethyl-3-[N-(2,2,5,5-tetramethyl-1,3-dioxane-4-carbonyl)amino]propionate;

2-Isopropyl-2-(N-oeloylamino)ethyl-3-[N-(2,2,5,5-tetramethyl-1,3-dioxane-4-carbonyl)amino]propionate;

2-Isobutyl-2-(N-oeloylamino)ethyl-3-[N-(2,2,5,5-tetramethyl-1,3-dioxane-4-carbonyl)amino]propionate;

2,2-Pentamethylene-2-(N-oeloylamino)ethyl-3-[N-(2,2,5,5-tetramethyl-1,3-dioxane-4-carbonyl)amino]propionate;

2-Penyl-2-(N-oeloylamino)ethyl-3-[N-(2,2,5,5-tetramethyl-1,3-dioxane-4-carbonyl)amino]propionate;

2-Benzyl-2-(N-oeloylamino)ethyl-3-[N-(2,2,5,5-tetramethyl-1,3-dioxane-4-carbonyl)amino]propionate;

2-Naphthyl-2-(N-oeloylamino)ethyl-3-[N-(2,2,5,5-tetramethyl-1,3-dioxane-4-carbonyl)amino]propionate;

2-(2-Furyl)-2-(N-oeloylamino)ethyl-3-[N-(2,2,5,5-tetramethyl-1,3-dioxane-4-carbonyl)amino]propionate;

2-Cyclopentyl-2-(N-oeloylamino)ethyl-3-[N-(2,2,5,5-tetramethyl-1,3-dioxane-4-carbonyl)amino]propionate;

2-(3-Indolyl)-2-(N-oeloylamino)ethyl-3-[N-(2,2,5,5-tetramethyl-1,3-dioxane-4-carbonyl)amino]propionate;

4-(N-Oleoylamino)-2-butenyl-3-[N-(2,2,5,5-tetramethyl-1,3-dioxane-4-carbonyl)amino]propionate;

4-(N-Oleoylamino)-2-butynyl-3-[N-(2,2,5,5-tetramethyl-1,3-dioxane-4-carbonyl)amino]propionate;

2-[N-(1-Undecylcyclobutanecarbonyl)amino]cyclopentan-1-yl-3-[N-(2,2,5,5-tetramethyl-1,3-dioxane-4-carbonyl)amino]propionate;

2-[N-(1-Pentadecylcyclobutanecarbonyl)amino]cyclopentan-1-yl-3-[N-(2,2,5,5-tetramethyl-1,3-dioxane-4-carbonyl)amino]propionate;

2-[N-[1-(9-Octadecenyl)cyclobutanecarbonyl)amino[cyclopentan-1-yl-3-[N-(2,2,5,5-tetramethyl-1,3-dioxane-4-carbonyl)amino]propionate;

2-[N-(1-Decylcyclopentanecarbonyl)amino]cyclopentan-1-yl-3-[N-(2,2,5,5-tetramethyl-1,3-dioxane-4-carbonyl)amino]propionate;

2-[N-(1-Tridecylcyclopentanecarbonyl)amino]cyclopentan-1-yl-3-[N-(2,2,5,5-tetramethyl-1,3-dioxane-4-carbonyl)amino]propionate;

2-[N-(1-Decylcyclohexanecarbonyl)amino]cyclopentan-1-yl-3-[N-(2,2,5,5-tetramethyl-1,3-dioxane-4-carbonyl)amino]propionate;

2-[N-(1-Nonylcyclohexanecarbonyl)amino]cyclopentan-1-yl-3-[N-(2,2,5,5-tetramethyl-1,3-dioxane-4-carbonyl)amino]propionate;

2-[N-[1-(9-Octadecenyl)cyclohexanecarbonyl)amino]-cyclopentan-1-yl-3-[N-(2,2,5,5-tetramethyl-1,3-dioxane-4-carbonyl)amino]propionate;

2-[N-[1-(Isopropylpentylcarbamoyl)amino)cycloheptan-1-yl-3-[N-(2,2,5,5-tetramethyl-1,3-dioxane-4-carbonyl)amino]propionate;

2-(1-Isopropylhexylcarbamoylamino)cycloheptan-1-yl-3-[N-(2,2,5,5-tetramethyl-1,3-dioxane-4-carbonyl)amino]propionate;

2-(1-t-Butyldodecylcarbamoylamino)cycloheptan-1-yl-3-[N-(2,2,5,5-tetramethyl-1,3-dioxane-4-carbonyl)amino]propionate;

2-(1,1-Dimethylhexanedecylcarbamoylamino)cycloheptan-1-yl-3-[N-(2,2,5,5-tetramethyl-1,3-dioxane-4-carbonyl)amino]propionate;

2-(Octadecylcarbamoylamino)cyclopentan-1-yl-3-[N-(2,2,5,5-tetramethyl-1,3-dioxane-4-carbonyl)amino]propionate;

2-(1,1-Dimethyloctadecylcarbamoylamino)cycloheptan-1-yl-3-[N-(2,2,5,5-tetramethyl-1,3-dioxane-4-carbonyl)amino]propionate;

2-(1,1-Dimethyl-9-decylcarbamoylamino)cycloheptan-1-yl-3-N-(2,2,5,5-tetramethyl-1,3-dioxane-4-carbonyl)amino]propionate;

2-(1,1-Dimethyl-6-undecylcarbamoylamino)cycloheptan-1-yl-3-[N-(2,2,5,5-tetramethyl-1,3-dioxane-4-carbonyl)amino]propionate;

2-(1,1-Dimethyl-8-tridecylcarbamoylamino)cycloheptan-1-yl-3-[N-(2,2,5,5-tetramethyl-1,3-dioxane-4-carbonyl)amino]propionate;

2-(1-Methyl-10-pentadecylcarbamoylamino)cycloheptan-1-yl-3-[N-(2,2,5,5-tetramethyl-1,3-dioxane-4-carbonyl)amino]propionate;

2-(1,1-Dimethyl-10-heptacarbamoylamino)cycloheptan-1-yl-3-[N-(2,2,5,5-tetramethyl-1,3-dioxane-4-carbonyl)amino]propionate;

2-(1-Methyl-8-heptadecylcarbamoylamino)cycloheptan-1-yl-3-[N-(2,2,5,5-tetramethyl-1,3-dioxane-4-carbonyl)amino]propionate;

2-(8-Octadecylcarbamoylamino)cycloheptan-1-yl-3-[N-(2,2,5,5-tetramethyl-1,3-dioxane-4-carbonyl)amino]propionate;

2-(8,11-Octadecadienylcarbamoylamino)cycloheptan-1-yl-3-[N-(2,2,5,5-tetramethyl-1,3-dioxane-4-carbonyl)amino]propionate;

2-(1-Methyl-8,11,14-octadecatrienylcarbamoylamino)cycloheptan-1-yl-3-[N-(2,2,5,5-tetramethyl-1,3-dioxane-4-carbonyl)amino]propionate;

2-(1-Hexylcyclobutylcarbamoylamino)cycloheptan-1-yl-3-[N-(2,2,5,5-tetramethyl-1,3-dioxane-4-carbonyl)amino]propionate;

2-(1-Octylcyclobutylcarbamoylamino)cycloheptan-1-yl-3-[N-(2,2,5,5-tetramethyl-1,3-dioxane-4-carbonyl)amino]propionate;

2-(1-Octylcyclopentylcarbamoylamino)cycloheptan-1-yl-3-[N-(2,2,5,5-tetramethyl-1,3-dioxane-4-carbonyl)amino]propionate;

2-(1-Octylcyclohexylcarbamoylamino)cycloheptan-1-yl-3-[N-(2,2,5,5-tetramethyl-1,3-dioxane-4-carbonyl)amino]propionate;

2-(1-Heptylcyclopentylcarbamoylamino)cyclopentan-1-yl-3-[N-(2,2,5,5-tetramethyl-1,3-dioxane-4-carbonyl)amino]propionate;

2-(1-Decylcyclopentylcarbamoylamino)cyclopentan-1-yl-3-[N-(2,2,5,5-tetramethyl-1,3-dioxane-4-carbonyl)amino]propionate;

2-(1-Hexylcyclohexylcarbamoylamino)cycloheptan-1-yl-3-[N-(2,2,5,5-tetramethyl-1,3-dioxane-4-carbonyl)amino]propionate;

2-[1-(6-Hexadecenyl)cyclohexylcarbamoylamino)cyclopentan-1-yl-3-[N-(2,2,5,5-tetramethyl-1,3-dioxane-4-carbonyl)amino]propionate;

2-1-(6-Hexadecenyl)cyclobutylcarbamoylamino)cycloheptan-1-yl-3-[N-(2,2,5,5-tetramethyl-1,3-dioxane-4-carbonyl)amino]propionate;

2-1-(6-Hexadecenyl)cyclopentylcarbamoylamino)cycloheptan-1-yl-3-[N-(2,2,5,5-tetramethyl-1,3-dioxane-4-carbonyl)amino]propionate;

2-(1-Decylhexylcarbamoylamino)cyclopentan-1-yl-3-[N-(2,2,5,5-tetramethyl-1,3-dioxane-4-carbonyl)amino]propionate;

2-(Hexyloctylcarbamoylamino)cycloheptan-1-yl-3-[N-(2,2,5,5-tetramethyl-1,3-dioxane-4-carbonyl)amino]propionate;

2-[Butyl(1,1-dimethyl8-heptadecenylcarbamoylamino)cyclopentan-1-yl-3-[N-(2,2,5,5-tetramethyl-1,3-dioxane-4-carbonyl)amino]propionate;

2-Methyl-2-(N-linoleoylamino)ethyl-3-[N-(2,2,5,5-tetramethyl-1,3-dioxane-4-carbonyl)amino]propionate;

2-Methyl-2-[N-(2-isopropylhexanoyl)amino]ethyl-3-[N-(2,2,5,5-tetramethyl-1,3-dioxane-4-carbonyl)amino]propionate;

2-Methyl-2-[N-(2-t-butylheptanoyl)amino]ethyl-3-[N-(2,2,5,5-tetramethyl-1,3-dioxane-4-carbonyl)amino]propionate;

2-Methyl-2-[N-(2,2-dimethylundecanoyl)amino]ethyl-3-[N-(2,2,5,5-tetramethyl-1,3-dioxane-4-carbonyl)amino]propionate;

2-Methyl-2-[N-(2,2-trimethylenedecanoyl)amino]ethyl-3-[N-(2,2,5,5-tetramethyl-1,3-dioxane-4-carbonyl)amino]propionate;

2-Methyl-2-(N-linolenoylamino)ethyl-3-[N-(2,2,5,5-tetramethyl-1,3-dioxane-4-carbonyl)amino]propionate;

2-Isopropyl-2-[N-(2-isopropylheptadecanoylamino)ethyl-3-[N-(2,2,5,5-tetramethyl-1,3-dioxane-4-carbonyl)amino]propionate;

2-Isobutyl-2-[N-(2-ethyloctadecanoylamino)ethyl-3-[N-(2,2,5,5-tetramethyl-1,3-dioxane-4-carbonyl)amino]propionate;

2,2-Pentamethylene-2-(N-linoleoylamino)ethyl-3-[N-(2,2,5,5-tetramethyl-1,3-dioxane-4-carbonyl)amino]propionate;

2-Phenyl-2-(N-linoleoylamino)ethyl-3-[N-(2,2,5,5-tetramethyl-1,3-dioxane-4-carbonylamino]propionate 2,2-Diphenyl-2-(N-linoleoylamino)ethyl-3-[N-(2,2,5,5-tetramethyl-1,3-dioxane-4-carbonyl)amino]propionate;

2-Benzyl-2-(N-linoleoylamino)ethyl 3-[N-(2,2,5,5-tetramethyl-1,3-dioxane-4-carbonyl)amino]propionate 2,2-Bisbenzyl-2-(N-linoleoylamino)ethyl-3-[N-(2,2,5,5-tetramethyl-1,3-dioxane-4-carbonyl)amino]propionate;

2,2-Naphthyl-2-[N-(2,2-dimethyl-9-tetradecenoyl)aminoethyl-3-[N-(2,2,5,5-tetramethyl-1,3-dioxane-4-carbonyl)amino]propionate;

2-(2-Furyl)-2-[N-(2,2-dimethyl-9-octadecenoyl)amino]ethyl-3-[N-(2,2,5,5-tetramethyl-1,3-dioxane-4-carbonyl)amino]propionate;

2-Cyclopentyl-2-[N-(2,2-dimethyl-9-octadecenoyl)amino]ethyl-3-[N-(2,2,5,5-tetramethyl-1,3-dioxane-4-carbonyl)amino]propionate;

2-(3-Indolyl)methyl-2-(N-linoleoylamino)ethyl-3-[N-(2,2,5,5-tetramethyl-1,3-dioxane-4-carbonyl)amino]propionate;

2-(8-Heptadecenylcarbamoylamino)cyclohexane-1-yl-2-[N-(2,2,5,5-tetramethyl-1,3-dioxane-4-carbonyl)amino]acetate;

2-(1-Methyl-8-heptadecenylcarbamoylamino)cyclohexane-1-yl-4-[N-(2,2,5,5-tetramethyl-1,3-dioxane-4-carbonyl)amino]butyrate; and 2-(1-Methyl-8-heptadecenylcarbamoylamino)cyclohexane-1-yl-5-[N-(2,2,5,5-tetramethyl-1,3-dioxane-4-carbonyl)amino]valerate.

Group b

Compounds represented by formula (Ib)

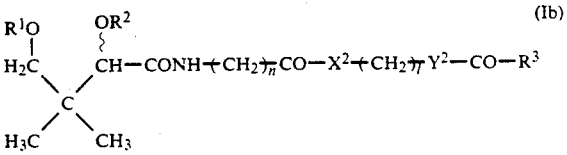

(Ib)

wherein $R^1$, $R^2$, $R^3$, $X^2$, $Y^2$, l and n are as defined above:

2-Dodecanoylaminomethyl-1-[3-[N-(2,2,5,5-tetramethyl-1,3-dioxane-4-carbonyl)amino]propanoyl]pyrrolidine;

2-Octanoylaminomethyl-1-[3-[N-(2,2,5,5-tetramethyl-1,3-dioxane-4-carbonyl)amino]propanoyl]pyrrolidine;

2-Decanoylaminomethyl-1-[3-[N-(2,2,5,5-tetramethyl-1,3-dioxane-4-carbonyl)amino]propanoyl]pyrrolidine;

2-Tetradecanoylaminomethyl-1-[3-[N-(2,2,5,5-tetramethyl-1,3-dioxane-4-carbonyl)amino]propanoyl]pyrrolidine;

2-Hexadecanoylaminomethyl-1-[3-[N-(2,2,5,5-tetramethyl-1,3-dioxane-4-carbonyl)amino]propanoyl]pyrrolidine;

2-Octadecanoylaminomethyl-1-[3-[N-(2,2,5,5-tetramethyl-1,3-dioxane-4-carbonyl)amino]propanoyl]pyrrolidine;

2-(7-Decanoyl)aminomethyl-1-[3-]N-(2,2,5,5-tetramethyl-1,3-dioxane-4-carbonyl)amino]propanoyl]pyrrolidine;

2-(9-Tridecanoyl)aminomethyl-1-[3-[N-(2,2,5,5-tetramethyl-1,3-dioxane-4-carbonyl)amino]propanoyl]pyrrolidine;

2-(9-Octadecanoyl)aminomethyl-1-[3-[N-(2,2,5,5-tetramethyl-1,3-dioxane-4-carbonyl)amino]propanoyl]pyrrolidine;

2-(9,12-Octadecanoyl)aminomethyl-1-[3-[N-(2,2,5,5-tetramethyl-1,3-dioxane-4-carbonyl)amino]propanoyl]pyrrolidine;

2-(9,12,15-Octadecanoyl)aminomethyl-1-[3-[N-(2,2,5,5-tetramethyl-1,3-dioxane-4-carbonyl)amino]propanoyl)pyrrolidine;

2-(2-Methyl-9-octadecanoyl)aminomethyl-1-[3-[N-(2,2,5,5-tetramethyl-1,3-dioxane-4-carbonyl)amino]propanoyl]pyrrolidine;

2-(2,2-Dimethyl-9-octadecanoyl)aminomethyl-1-[3-[N-(2,2,5,5-tetramethyl-1,3-dioxane-4-carbonyl)amino]propanoyl]pyrrolidine;

2-(2-Methyldecanoyl)aminomethyl-1-[3-[N-(2,2,5,5-tetramethyl-1,3-dioxane-4-carbonyl)amino]propanoyl]pyrrolidine;

2-(2-Methyloctanoyl)aminomethyl-1-[3-[N-(2,2,5,5-tetramethyl-1,3-dioxane-4-carbonyl)amino]propanoyl]pyrrolidine;

2-(2-Methylundecanoyl)aminomethyl-1-[3-[N-(2,2,5,5-tetramethyl-1,3-dioxane-4-carbonyl)amino]propanoyl]pyrrolidine;

2-(9-Octadecenoyl)aminomethyl-1-[3-[N-(2,2,5,5-tetramethyl-1,3-dioxane-4-carbonyl)amino]propanoyl]pyrrolidine;

3-(9-Octadecenoyl)amino-1-[3-[N-(2,2,5,5-tetramethyl-1,3-dioxane-4-carbonyl)amino]propanoyl]piperidine;

3-(9-Octadecenoyl)amino-1-[3-[N-(2,4-dihydroxy-3,3-dimethyl-1-oxobutyl)amino]propanoyl]piperidine;

1-(9-Octadecenoyl)amino-3-[3-[N-(2,4-dihydroxy-3,3-dimethyl-1-oxobutyl)amino]propanoyl]aminopiperidine;

1-(9-Octadecenoyl)amino-3-[3-[N-(2,2,5,5-tetramethyl-1,3-dioxane-4-carbonyl)amino]propanoyl]aminopiperidine;

1-(9-Octadecenoyl)amino-4-[3-[N-(2,2,5,5-tetramethyl-1,3-dioxane-4-carbonyl)amino]propanoyl]aminopiperidine;

1-(9-Octadecenoyl)-4-piperidinyl-3-[N-(2,2,5,5-tetramethyl-1,3-dioxane-4-carbonyl)amino]propionate;

1-(9-Octadecenoyl)-4-piperidinyl-3-[N-(2,4-dihydroxy-3,3-dimethyl-1-oxobutyl)amino]propionate;

1-(9-Octadecenoyl)-4-piperidinyl-3-[N-(2,4-diacetoxy-3,3-dimethyl-1-oxobutyl)amino]propionate;

1-(9-Octadecenoyl)-3-piperidinyl-3-[N-(2,4-dihydroxy-3,3-dimethyl-1-oxobutyl)amino]propionate;

1-(9-Octadecenoyl)-3-piperidinyl-3-[N-(2,4-diacetoxy-3,3-dimethyl-1-oxobutyl)amino]propionate;

1-(9-Octadecenoyl)-2-pyrrolidinylmethyl-3-[N-(2,2,5,5-tetramethyl-1,3-dioxane-4-carbonyl)amino]propionate;

1-Octadecenoyl-2-pyrrolidinylmethyl-3-[N-(2,2,5,5-tetramethyl-1,3-dioxane-4-carbonyl)amino]propionate;

1-(9,12-Octadecenoyl)-2-pyrrolidinylmethyl-3-[N-(2,2,5,5-tetramethyl-1,3-dioxane-4-carbonyl)amino]propionate;

1-(9-Octadecenoyl)-2-pyrrolidinylmethyl-3-(2,4-dihydroxy-3,3-dimethyl-1-oxobutyl)amino]propionate;

1-(9-Octadecenoyl)-2-pyrrolidinylmethyl-3-(2,4-diacetoxy-3,3-dimethyl-1-oxobutyl)amino]propionate;

1-(9-Octadecenoyl)-2-pyrrolidinylmethyl-2-[3(2,2,5,5-tetramethyl-1,3-dioxane-4-carbonyl)amino]-1-oxopropyl]aminomethylpyrrolidine;

2-[(8-Heptadecenylcarbamoyl)aminomethyl]-1-[3-N-(2,2,5,5-tetramethyl-1,3-dimethyl-4-carbonyl)amino]propanoyl]pyrrolidine;

3-[(8-Heptadecenylcarbamoyl)aminomethyl]-1-[3-N-(2,2,5,5-tetramethyl-1,3-dimethyl-4-carbonyl)amino]propanoyl]piperidine;

1-[(8-Heptadecenylcarbamoyl)aminomethyl]-3-[3-N-(2,2,5,5-tetramethyl-1,3-dimethyl-4-carbonyl)amino]propanoyl]piperidine;

1-[(8-Heptadecenylcarbamoyl)aminomethyl]-2-[3-N-(2,2,5,5-tetramethyl-1,3-dimethyl-4-carbonyl)amino]propanoyl]pyrrolidine;

4-(8-Heptadecenylcarbamoyl)amino-1-[3-[N-(2,2,5,5-tetramethyl-1,3-dimethyl-4-carbonyl)amino]propanoyl]piperidine;

1-(8-Heptadecenylcarbamoyl)-4-[3-[N-(2,2,5,5-tetramethyl-1,3-dimethyl-4-carbonyl)amino]propanoyl]aminopiperidine;

1-(8-Heptadecenylcarbamoyl)-4-piperidinyl-3-[N-(2,2,5,5-tetramethyl-1,3-dimethyl-4-carbonyl)amino]propionate;

1-(8-Heptadecenylcarbamoyl)-3-piperidinyl-3-[N-(2,2,5,5-tetramethyl-1,3-dimethyl-4-carbonyl)amino]propionate; and 1-(8-Heptadecenylcarbamoyl)-2-piperidinyl-3[N-(2,2,5,5-tetramethyl-1,3-dimethyl-4-carbonyl)amino]propionate.

Group c

Compounds represented by formula (Ic) below:

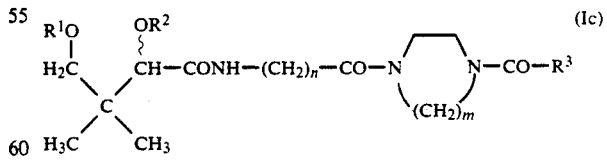

wherein $R^1$, $R^2$, $R^3$, m and n are as defined above:

1-Hexanoyl-4-[1-oxo-3-[N-(1-oxo-2,4-diacetoxy-3,3-dimethylbutyl)amino]propyl]piperazine;

1-Heptanoyl-4-[1-oxo-3-[N-(1-oxo-2,4-diacetoxy-3,3-dimethylbutyl)amino]propyl]piperazine;

1-Octanoyl-4-[1-oxo-3-]N-(1-oxo-2,4-diacetoxy-3,3-dimethylbutyl)amino]propyl]piperazine;

1-Decanoyl-4-[1-oxo-3-[N-(1-oxo-2,4-diacetoxy-3,3-dimethylbutyl)amino]propyl]piperazine;
1-undecanoyl-4-[1-oxo-3-[N-(1-oxo-2,4-diacetoxy-3,3-dimethylbutyl)amino]propyl]piperazine;
1-Tetradecanoyl-4-[1-oxo-3-[N-(1-oxo-2,4-diacetoxy-3,3-dimethylbutyl)amino]propyl]piperazine;
1-Hexadecanoyl-4-[1-oxo-3-[N-(1-oxo-2,4-diacetoxy-3,3-dimethylbutyl)amino]propyl]piperazine;
1-Octadecanoyl-4-[1-oxo-3-[N-(1-oxo-2,4-diacetoxy-3,3-dimethylbutyl)amino]propyl]piperazine;
1-(7-Tetradecanoyl)-4-[1-oxo-3-[N-(1-oxo-2,4-diacetoxy-3,3-dimethylbutyl)amino]propyl]piperazine;
1-(10-Hexadecanoyl)-4-[1-oxo-3-[N-(1-oxo-2,4-diacetoxy-3,3-dimethylbutyl)amino]propyl]piperazine;
1-(9-Octadecanoyl)-4-[1-oxo-3-[N-(1-oxo-2,4-diacetoxy-3,3-dimethylbutyl)amino]propyl]piperazine;
1-(13-Octadecanoyl)-4-[1-oxo-3-[N-(1-oxo-2,4-diacetoxy-3,3-dimethylbutyl)amino]propyl]piperazine;
1-(9,12-Octadecadienoyl)-4-[1-oxo-3-[N-(1-oxo-2,4-diacetoxy-3,3-dimethylbutyl)amino]propyl]piperazine;
1-(9,12,15-Octadecadienoyl)-4-[1-oxo-3-[N-(1-oxo-2,4-diacetoxy-3,3-dimethylbutyl)amino]propyl]piperazine;
1-(2-Methylheptadecanoyl)-4-[1-oxo-3-[N-(1-oxo-2,4-diacetoxy-3,3-dimethylbutyl)amino]propyl]piperazine;
1-(2,2-Dimethylheptadecanoyl)-4-[1-oxo-3-[N-(1-oxo-2,4-diacetoxy-3,3-dimethylbutyl)amino]propyl]piperazine;
1-(2-Methylheptadecanoyl)-4-[1-oxo-3-[N-(1-oxo-2,4-diacetoxy-3,3-dimethylbutyl)amino]propyl]piperazine;
1-(2,2-Dimethyloctadecanoyl)-4-[1-oxo-3-[N-(1-oxo-2,4-diacetoxy-3,3-dimethylbutyl)amino]propyl]piperazine;
1-(2-Methyl-9-octadecanoyl)-4-[1-oxo-3-[N-(1-oxo-2,4-diacetoxy-3,3-dimethylbutyl)amino]propyl]piperazine;
1(2-Ethyl-9-octadecanoyl)-4-[1-oxo-3-[N-(1-oxo-2,4-diacetoxy-3,3-dimethylbutyl)amino]propyl]piperazine;
1-(2,2-Dimethyl-9-octadecanoyl)-4-[1-oxo-3-[N-(1-oxo-2,4-diacetoxy-3,3-dimethylbutyl)amino]propyl]piperazine;
1-(9-Octadecanoyl)-4-[1-oxo-3-[N-(1-oxo-2,4-dihydroxy-3,3-dimethylbutyl)amino]propyl]piperazine;
1-(9-Octadecanoyl)-4-[1-oxo-3-[N-(1-oxo-2-hydroxy-4-benzoyloxy-3,3-dimethylbutyl)amino]propyl] piperazine;
1-(9-Octadecanoyl)-4-[1-oxo-3-[N-(1-oxo-2,4-dibenzoyloxy-3,3-dimethylbutyl)amino]propyl]piperazine;
1-(9-Octadecanoyl)-4-[1-oxo-3-[N-(1-oxo-2-hydroxy-4-pivaloyloxy-3,3-dimethylbutyl)amino]propyl]piperazine;
1-(9-Octadecenoyl)-4-[1-oxo-3-[N-(1oxo2,4-diacetoxy-3,3-dimethylbutyl)amino]propyl]tetrahydro-1,4-diazepine;
1-(9-Octadecenoyl)-4-[1-oxo-3-[N-(1-oxo2,4-dihydroxy-3,3-dimethylbutyl)amino]propyl]tetrahydro-1,4-diazepine;
1-(9-Octadecenoyl)-4-[3-[N-(2,2,5,5-tetramethyl-1,3-dioxane-4-carbonyl)amino]propanoyl]piperazine;
1-Octadecenoyl)-4-[3-[N-(2,2,5,5-tetramethyl-1,3-dioxane-4-carbonyl)amino]propanoyl]tetrahydro-1,4-diazepine;
1-(9-Octadecenoyl)-4-[3-[N-(2-phenyl-5,5-dimethyl-1,3-dioxane-4-carbonyl)amino]propanoyl]piperazine;
1-(8-Heptadecenyl)carbamoyl-4-[3-[N-(2,2,5,5-tetramethyl-1,3-dioxane-4-carbonylamino]propanoyl]piperazine;
1-(8,11-Heptadecadienyl)carbamoyl-4-[3-[N-(2,2,5,5-tetramethyl-1,3-dioxane-4-carbonylamino)-propanoyl]piperazine;
1-(8,11,14-Heptadecatrienyl)carbamoyl-4-[3-[N-(2,2,5,5-tetramethyl-1,3-dioxane-4-carbonylamino)-propanoyl]piperazine;
1-(8-Heptadecenyl)carbamoyl-4-[3-(2,2,5,5-tetramethyl-1,3-dioxane-4-carbonylamino]propanoyl]tetrahydro-1,4-diazepine;
2-(2-Benzylmethylcapryloyl)aminocyclohexane-1-yl-3-[N-(2,2,5,5-tetramethyl-1,3-dioxane-4-carbonylamino)propionate;
3-(2-Benzylmethylcapryloyl)aminocyclohexane-1-yl-3-[N-(2,2,5,5-tetramethyl-1,3-dioxane-4-carbonyl)amino]propionate;
2-(2-Benzylundecanoyl)aminocyclohexane-1-yl-3-[N-(2,2,5,5-tetramethyl-1,3-dioxane-4-carbonyl)amino]propionate;
3-(2-Benzylundecanoyl)aminocyclohexane-1-yl-3-[N-(2,2,5,5-tetramethyl-1,3-dioxane-4-carbonyl)amino]propionate;
4-(2-Benzylundecanoyl)aminocyclohexane-1-yl-3-[N-(2,2,5,5-tetramethyl-1,3-dioxane-4-carbonyl)amino]propionate;
2-(2-Benzyllauroyl)aminocyclohexane-1-yl-3-[N-(2,2,5,5-tetramethyl-1,3-dioxane-4-carbonyl)amino]propionate;
4-(2-Benzyllauroyl)aminocyclohexane-1-yl-3-[N-(2,2,5,5-tetramethyl-1,3-dioxane-4-carbonyl)amino]propionate;
3-(2-Phenyllauroyl)aminocyclohexane-1-yl-3-[N-(2,2,5,5-tetramethyl-1,3-dioxane-4-carbonyl)amino]propionate;
2-(2-Phenyllauroyl)aminocyclohexane-1-yl-3-[N-(2,2,5,5-tetramethyl-1,3-dioxane-4-carbonyl)amino]propionate;
3-(2-Benzylcapryloyl)aminocyclohexane-1-yl-3-[N-(2,2,5,5-tetramethyl-1,3-dioxane-4-carbonyl)amino]propionate;
2-(2,2-Diphenyllauroyl)aminocyclohexane-1-yl-3-[N-(2,2,5,5-tetramethyl-1,3-dihydroxy-3,3-dimethyl-1-oxobutyl)amino]propionate;
2-(2-Benzylcyclopentanecarbonyl)aminocyclohexane-1-yl-3-[N-(2,2,5,5-tetramethyl-1,3-dioxane-4-carbonyl)amino]propionate;
2-[1-(3-Phenylpropylcyclobupanecarbonyl)aminocyclohexane-1-yl-3-[N-(2,2,5,5-tetramethyl-1,3-dioxane-4-carbonyl)amino]propionate;
2-(1-Furfurylcyclobutanecarbonyl)aminocyclohexane-1-yl-3-[N-(2,2,5,5-tetramethyl-1,3-dioxane-4-carbonyl)amino]propionate;
2-(1-Cinnamylcyclobutanecarbonyl)aminocyclohexane-1-yl-3-[N-(2,2,5,5-tetramethyl-1,3-dioxane-4-carbonyl)amino]propionate;
2-(N-Benzyl-N-hexylcarbamoyl)aminocyclohexane-1-yl-3-[N-(2,2,5,5-tetramethyl-1,3-dioxane-4-carbonyl)amino]propionate;
2-(N-Benzyl-N-octylcarbamoyl)aminocyclohexane-1-yl-3-[N-(2,2,5,5-tetramethyl-1,3-dioxane-4-carbonyl)amino]propionate;

2-(N-Benzyl-N-decylcarbamoyl)aminocyclohexane-1-yl-3-[N-(2,2,5,5-tetramethyl-1,3-dioxane-4-carbonyl)amino]propionate;

(Z)-4-Oleoylamino-2-butenyl-3-[N-(2,2,5,5-tetramethyl-1,3-dioxane-4-carbonyl)amino]propionate;

2-Methylo-2-oleoylaminoethyl-3-[N-(2,2,5,5-tetramethyl-1,3-dioxane-4-carbonyl)amino]propionate;

2-(Oleoylamino)cyclopentane-1-yl-3-[N-(2,2,5,5-tetramethyl-1,3-dioxane-4-carbonyl)amino]propionate;

2-(Oleoylamino)cyclopentane-2-yl-3-[N-(2,2,5,5-tetramethyl-1,3-dioxane-4-carbonyl)amino]propionate;

1-Methyl-2-oleoylaminoethyl-3-[N-(2,2,5,5-tetramethyl-1,3-dioxane-4-carbonyl)amino]propionate;

2-(Oleoylamino)2-phenylethyl-3-[N-(2,2,5,5-tetramethyl-1,3-dioxane-4-carbonyl)amino]propionate;

4-(Oleoylamino)2-butynyl-3-[N-(2,2,5,5-tetramethyl-1,3-dioxane-4-carbonyl)amino]propionate;

(E)-4-(oleoylamino)-2-butenyl-3-[N-(2,2,5,5-tetramethyl-1,3-dioxane-4-carbonyl)amino]propionate;

2-Methyl-2-oleoylaminoethyl-3-[N-(2,2,5,5-tetramethyl-1,3-dioxane-4-carbonyl)amino]propionate;

1-Methyl-2-oleoylaminoethyl-3-[N-(2,2,5,5-tetramethyl-1,3-dioxane-4-carbonyl)amino]propionate;

2-Oleoylaminobutyl-3-[N-(2,2,5,5-tetramethyl-1,3-dioxane-4-carbonyl)amino]propionate;

3-Methyl-2-oleoylaminobutyl-3-[N-(2,2,5,5-tetramethyl-1,3-dioxane-4-carbonyl)amino]propionate;

2-(Oleoylamino)cycloheptanel-1-yl-3-[N-(2,2,5,5-tetramethyl-1,3-dioxane-4-carbonyl)amino]propionate;

2-(Oleoylamino)cycloheptanel-1-yl-3-[N-(2,2,5,5-tetramethyl-1,3-dioxane-4-carbonyl)amino]propionate;

2-(Oleoylamino)2-phenylethyl-3-[N-(2,2,5,5-tetramethyl-1,3-dioxane-4-carbonyl)amino]propionate;

2-Oleoylamino-2-cyclohexylethyl-3-[N-(2,2,5,5-tetramethyl-1,3-dioxane-4-carbonyl)amino]propionate;

4-Methyl-2-oleoylaminopentyl-3-[N-(2,2,5,5-tetramethyl-1,3-dioxane-4-carbonyl)amino]propionate;

2-Oleoylaminopentyl-3-phenylpropyl-3-[N-(2,2,5,5-tetramethyl-1,3-dioxane-4-carbonyl)amino]propionate;

2-Oleoylamino-1-pentylpropyl-3-phenylpropyl-3-[N-(2,2,5,5-tetramethyl-1,3-dioxane-4-carbonyl)amino]propionate;

2-(2-Methyloleoyl)aminocyclohexane-1-yl-3-[N-(2,2,5,5-tetramethyl-1,3-dioxane-4-carbonyl)amino]propionate;

2-(2,2-Dimethyloleoyl)aminocyclohexane-1-yl-3-[N-(2,2,5,5-tetramethyl-1,3-dioxane-4-carbonyl)amino]propionate;

2-(2,2-Dimethylstearoyl)aminocyclohexane-1-yl-3-[N-(2,2,5,5-tetramethyl-1,3-dioxane-4-carbonyl)amino]propionate;

2-Oleoylamino-2-phenylethyl)-5-[N-(2,2,5,5-tetramethyl-1,3-dioxane-4-carbonyl)amino]pentanoate;

2-Oleoylamino-2-phenylethyl)-4-[N-(2,2,5,5-tetramethyl-1,3-dioxane-4-carbonyl)amino]butanoate;

2-(2-Propylstearoyl)aminocyclohexane-1-yl-3-[N-(2,2,5,5-tetramethyl-1,3-dioxane-4-carbonyl)amino]propionate;

2-(2-Ethylmyristoyl)aminocyclohexane-1-yl-3-[N-(2,2,5,5-tetramethyl-1,3-dioxane-4-carbonyl)amino]propionate;

3-(2-Ethylmyristoyl)aminocyclohexane-1-yl-3-[N-(2,2,5,5-tetramethyl-1,3-dioxane-4-carbonyl)amino]propionate;

2-(2-Methylpalmitoyl)aminocyclohexane-1-yl-3-[N-(2,2,5,5-tetramethyl-1,3-dioxane-4-carbonyl)amino]propionate;

4-(2-Methylpalmitoyl)aminocyclohexane-1-yl-3-[N-(2,2,5,5-tetramethyl-1,3-dioxane-4-carbonyl)amino]propionate;

2-[(1-Methyl-8-heptadecenyl)carbamoyl]aminocyclohexane-1-yl-3-[N-(2,2,5,5-tetramethyl-1,3-dioxane-4-carbonyl)amino]propionate;

2-(1-Oleylcyclopentanecarbonyl)aminocyclohexane-1-yl-3-[N-(2,2,5,5-tetramethyl-1,3-dioxane-4-carbonyl)amino]propionate;

2-(1-Decylcyclobutanecarbonyl)aminocyclohexane-1-yl-3-[N-(2,2,5,5-tetramethyl-1,3-dioxane-4-carbonyl)amino]propionate;

2-(1-Laurylcyclopentanecarbonyl)aminocyclocarbonyl)amino]propionate;

3-(2-Propylstearoyl)aminocyclohexane-1-yl-3-[N-(2,2,5,5-tetramethyl-1,3-dioxane-4-carbonyl)amino]propionate;

2-(1-Hexylcyclobutanecarbonyl)aminocyclohexane-1-yl-3-[N-(2,2,5,5-tetramethyl-1,3-dioxane-4-carbonyl)amino]propionate;

4-(2-Isopropyllauroyl)aminocyclohexane-1-yl-3-[N-(2,2,5,5-tetramethyl-1,3-dioxane-4-carbonyl)amino]propionate;

2-(2-Isopropyllauroyl)aminocyclohexane-2-yl-3-[N-(2,2,5,5-tetramethyl-1,3-dioxane-4-carbonyl)amino]propionate;

2-(1-Octylcyclobutanecarbonyl)aminocyclohexane-1-yl-3-[N-(2,2,5,5-tetramethyl-1,3-dioxane-4-carbonyl)amino]propionate;

2-[(1-Methylpentadecenyl)carbamoyl]aminocyclohexane-1-yl-3-[N-(2,2,5,5-tetramethyl-1,3-dioxane-4-carbonyl)amino]propionate;

2-(2-Decyllauroyl)aminocyclohexane-1-yl-3-[N-(2,2,5,5-tetramethyl-1,3-dioxane-4-carbonyl)amino]propionate;

2-(2-Methyllauroyl)aminocyclohexane-1-yl-3-[N-(2,2,5,5-tetramethyl-1,3-dioxane-4-carbonyl)amino]propionate;

3-(1-Methyllauroyl)aminocyclohexane-1-yl-3-[N-(2,2,5,5-tetramethyl-1,3-dioxane-4-carbonyl)amino]propionate;

2-(1-Decylcyclobutanecarbonyl)aminocyclohexane-1-yl-3-[N-(2,4-dihydroxy-3,3-dimethyl-1-oxobutyl)amino]propionate;

2-(1-Butylcyclobutanecarbonyl)aminocyclohexane-1-yl-3-[N-(2,2,5,5-tetramethyl-1,3-dioxane-4-carbonyl)amino]propionate; and 2-[N-(2,2-Dimethylpropyl)-N-nonylcarbamoyl]aminocyclohexane-1-yl-3-[N-(2,2,5,5-tetramethyl-1,3-dioxane-4-carbonyl)amino]propionate.

The compounds of the present invention have at least one asymmetric carbon atom as indicated by an asterisk (*) in formula (I) and may include any of optically active isomers (R-form or S-form) and racemi form compounds.

The compound of the present invention represented by formula (I) above can be prepared by (a) reacting a compound of formula (II)

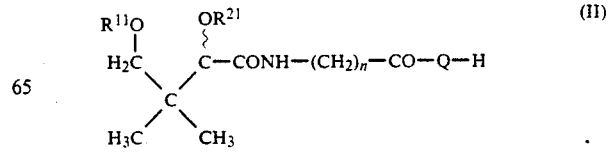

wherein $R^{11}$ and $R^{21}$, which are the same or different, each represent a protected hydroxyl group, Q and n have the same meanings as defined above;
with a compound of formula (III) or (IV) below

wherein $Z^1$ represents a hydrogen atom; a halogen atom such as chlorine or bromine; an alkoxy group such as methoxy or ethoxy; a substituted or unsubstituted phenyloxy group such as phenoxy, p-nitrophenoxy, 2,4-dinitrophenoxy; and $R^3$ and $R^4$ have the same meanings as defined above; or (b) reacting a compound of formula (V) below

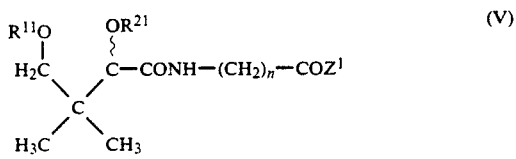

wherein $R^{11}$, $R^{21}$, n and $Z^1$ have the same meanings as defined above;
with a compound of formula (VI)

wherein $R^3$ and Q have the same meanings as defined above; or (c) eliminating the protective group for the hydroxyl group(s) in the resulting compound of formula (I-1) below

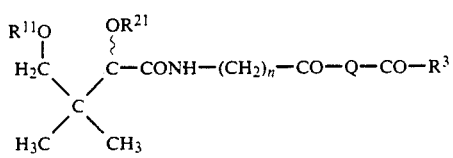

wherein $R^{11}$ and $R^{21}$, $R^3$ and n have the same meanings as defined above.

The reaction between the compound of formula (II) and the compound of formula (III) in the process (a) above and the reaction between the compound of formula (V) and the compound of formula (VI) in the process (b) above can be carried out in a suitable solvent, for example, aromatic hydrocarbons such as benzene, toluene and xylene; ethers such a ethyl ether, tetrahydrofuran and dioxane; esters such as methyl acetate and ethyl acetate; halogenated hydrocarbons such as methylene chloride, chloroform and carbon tetrachlorine; high boiling point polar solvents such as dimethylformamide and dimethyl sulfoxide; alcohols such as methanol and ethanol; water, and the like. The solvents may be used singly or two or more of the solvents may be used as mixtures. The reaction proceeds generally at a temperature in a range of from about −78° C. to the boiling temperature of the solvent used, preferably from about −10° C. to the boiling temperature of the solvent used.

In the processes (a) and (b) above, a catalyst or a reaction accelerator may be used. As for the catalyst or reaction accelerator which can be used in the present invention, there can be cited, for example, carbodiimides such as dicyclohexylcarbodiimide, diisopropylcarbodiimide and 1-ethyl-3-(3-dimethylaminopropyl)-carbodiimide hydrochloride; acid anhydrides such as acetic anhydride and benzoic anhydride; inorganic bases such as sodium hydroxide, potassium hydroxide, sodium carbonate and potassium carbonate; organic bases such as triethylamine, diethylamine, diisopropylamine and pyridine; and the like. The catalysts or reaction accelerators may be used in amounts in a range of from 0.01 to 10 equivalents, preferably from 0.1 to 1.1 equivalents per mol of the compound (II) or (III).

The proportion of the compound (III) or (IV) to the compound (II) is not limited strictly but can be usually in a range of from 0.8 to 1.2 moles, preferably from 1.0 to 1.1 moles, per mole of the compound (II). Similarly, the proportion of the compound (V) can be used in an amount in a range of from 0.8 to 1.2 moles, preferably from 1.0 to 1.1 moles, per mole of the compound (VI).

In the process (c), the reaction which eliminates the protective groups for the hydroxyl groups from the compound of formula (I-1) can be performed, for example, by hydrolysis in a solvent in the presence of a suitable catalyst. For example, the reaction can be carried out in a single solvent or a mixed solvent selected from aromatic hydrocarbons such as benzene, toluene and xylene; ethers such as ethyl ether, tetrahydrofuran and dioxane; esters such as methyl acetate and ethyl acetate; halogenated hydrocarbons such as methylene chloride, chloroform and carbon tetrachloride; high boiling point polar solvents such as dimethylformamide and dimethyl sulfoxide; alcohols such as methanol and ethanol; water; organic acids such as acetic acid and propionic acid; ketones such as acetone and methyl ethyl ketone; and the like at a temperature in a range of from about −78° C. to the boiling temperature of the solvent used, preferably from about −10° C. to the boiling temperature of the solvent used. As for the catalyst which can be used, there can be cited, for example, inorganic bases such as sodium hydroxide, potassium hydroxide, sodium carbonate and potassium carbonate; organic bases such as triethylamine, diethylamine, dimethylamine diisopropylamine and pyridine; minetal acids such as hydrochloric acid, nitric acid and sulfuric acid; hydrogen halides such as hydrogen fluorine, hydrogen bromide and hydrogen iodide; organic acids such as trifluoroacetic acid and trichloroacetic acid; and the like.

The protective groups can be eliminated from the compounds of formula (I-1) by a conventional catalyst hydrogenation reaction using a suitable metal catalyst. As for the metal catalyst, there can be used commonly used hydrogenation catalysts such as nickel, palladium, rhodium and platinum.

The products obtained by each of the above-described processes can be separated from the reaction mixtures or purified by proper combinations of known processes, for example, crystallization, chromatography, extraction and filtration.

In the above-described processes, the compounds of formulae (V), (II) and (VI) used as starting materials can be produced as follows.

Preparation of Compound of Formula (V)

Step-1:

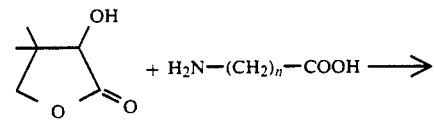

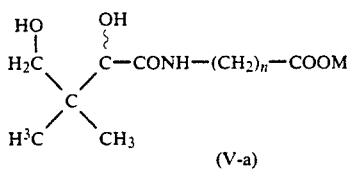

(V-a)

Step-2:

(V-a) + Ph—CH₂L ⟶

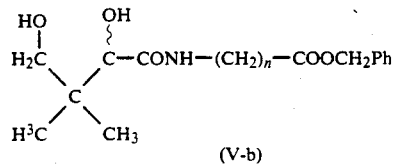

(V-b)

Step-3:

(V-b) ⟶

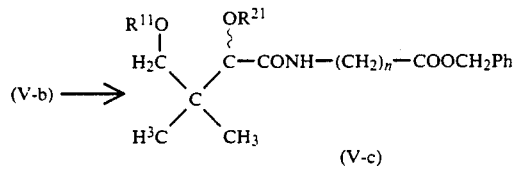

(V-c)

Step-4:

(V-c) ⟶

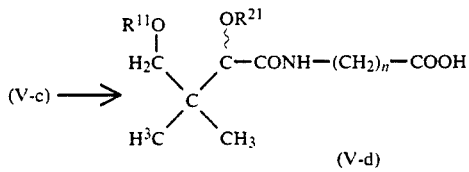

(V-d)

Step-5:

(V-d) ⟶

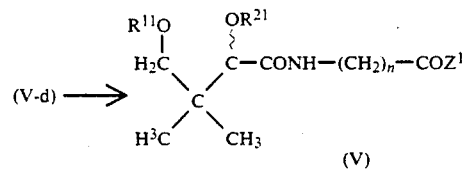

(V)

Step-6:

(V-a) ⟶ (V-d)

In the above formulae, M represents a hydrogen atom, an alkali metal atom such as sodium and potassium or an alkaline earth metal atom such as magnesium and calcium; L represents OH, Cl, Br, I or $N_2$; and $R^{11}$, $R^{21}$, n and $Z^1$ have the same meanings as defined above.

Hereafter, explanation will be made on each step more specifically.

Step-1

This step is to synthesize a compound of formula (V-a) by reacting pantolactone with an ω-aminocarboxylic acid. Pantolactone may be any one of (D)-, (L)- ane (DL)-forms. Examples of the ω-aminocarboxylic acid include aminoacetic acid (glycine), 3-aminopropionic acid (β-alanine), 4-aminobutyric acid (α-aminobutyric acid, abbreviated as "GABA") and 5-aminovaleric acid. It is preferred that the reaction be carried out in a solvent. As for the solvent, there can be used, for example, aromatic hdyrocarbons such as benzene, toluene and xylene; ethers such as ethyl ether, tetrahydrofuran and dioxane; high boiling point polar solvents such as dimethylformamide and dimethyl sulfoxide; alcohols such as methanol and ethanol; water, and the like. The solvents may be used singly or two or more of the solvents may be used as mixtures. The reaction proceeds generally at a temperature in a range of from about 0° C. to the boiling temperature of the solvent used, preferably from room temperature to the boiling temperature of the solvent used.

In this reaction, it is preferred to use a catalyst. As for the catalyst, there can be used, for example, inorganic bases such as sodium hydroxide, potassium hydroxide, sodium carbonate and potassium carbonate; organic bases such as triethylamine, diethylamine, dimethylamine, diisopropylamine and pyridine; and the like. The catalysts may be used in amounts in a range of from 0.01 to 10 equivalents, preferably from 0.1 to 1.1 equivalents per mole of pantolacone.

Step-2

This step is to benzylate the compound of formula (V-a) synthesized in Step-1 using a benzylation reagent to a compound of formula (V-b). As for the benzylation reagent, there can be used, for example, benzyl halides such as benzyl chloride, benzyl bromide and benzyl iodide; benzyl alcohol; phenyldiazomethane; and the like. The reaction can be carried out in a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as methylene chloride, chloroform and carbon tetrachlorine; high boiling point polar solvents such as dimethylformamide and dimethyl sulfoxide; alcohols such as methanol and ethanol; ketones such as acetone and methyl ethyl ketone; water, and the like. The solvents may be used singly or two or more of the solvents may be used as mixtures. The reaction proceeds usually at a temperature in a range of from about −78° C. to the boiling temperature of the solvent used, preferably from about −10° C. to the boiling temperature of the solvent used. In the reaction, a catalyst or a reaction accelerator may be used. As for the catalyst or reaction accelerator, there can be cited, for example, carbodiimides such as dicyclohexylcarbodiimide, diisopropylcarbodiimide and 1-ethyl-3-(3-dimethylaminopropyl)carbodiimide hydrochloride; acid anhydrides such as acetic anhydride and benzoic anhydride; inorganic bases such as sodium hydroxide, potassium hydroxide, sodium carbonate and potassium carbonate; organic bases such as triethylamine, diethylamine, dimethylamine, diisopropylamine and pyridine; and the like. The catalysts or reaction accelerators may be used in amounts in a range of from 0.01 to 10 equivalents, preferably from 0.1 to 1.1 equivalents pler mole of the compound of formula (V-a).

Step-3

This step is to protect the hydroxyl groups of the compound of formula (V-b) in Step-2 above using a reagent for introducing protective groups to synthesize a compound of formula (V-c). As for the reagent for introducing protective groups ($R^{11}$, $R^{21}$), there can be used acid anhydrides such as acetic anhydride and benzoic anhydride; acid chlorides such as acetyl chloride and benzoyl chloride; organic acids such as acetic acid, benzoic acid and p-toluenesulfonic acid; ortho esters such as ethyl orthoformate and methyl orthoformate; ketones such as acetone and cyclohexanone; aldehydes such as benzaldehyde and acetaldehyde; ilylation agent such as trimethylsilyl chloride and dimethylphenylsilyl chloride; alkylation agents such as diazomethane and dimethyl sulfate; alkyl halides such as methyl iodide and benzyl chloride; and the like. The reaction can be carried out in a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as dmethylene chloride, chloroform and carbon tetrachloride; high boiling point polar solvents such as dimethylformamide and dimethyl sulfoxide; alcohols such as methanol and ethanol; ketones such as acetone and methyl ethyl ketone; water, and the like. The solvents may be used singly or two or more of the solvents may be used as mixtures. The reaciton proceeds usually at a temperature in a range of from about $-78°$ C. to the boiling temperature of the solvent used, preferably from about $-10°$ C. to the boiling temperature of the solvent used. In the reaction, a catalyst or a reaciton accelerator may be used. As for the catalyst or reaction accelerator, there can be cited, for example, carbodiimides such as dicyclohexylcarbodiimide, diisopropylcarbodiimide and 1-ethyl-3-(3-dimethylminopropyl)carbodiimide hydrochloride; acid anhydrides such as acetic anhydride and benzoic anhydride; inorganic bases such as sodium hydroxide, potassium hydroxide, sodium carbonate and potassium carbonate; organic bases such as triethylamine, diethylamine, dimethylamine, diisopropylamine and pyridine; organic acids such as acetic acid, p-toluenesulfonic acid and camphorsulfonic acid; and the like. The catalysts or reaction accelerators may be used in amounts in a range of from 0.01 to 10 equivalents, preferably from 0.1 to 1.1 equivalents per mole of the compound of formula (V-b).

Step-4

This step is to hydrolyze or catalytically hydrogenate the compound of formula (V-c) to convert it to a compound of formula (V-d). The reaction can be carried out in a solvent in the presence of a suitable catalyst. The hydrolysis can be performed in a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as methylene chloride, chloroform and carbon tetrachloride; high boiling point polar solvents such as dimethylformamide and dimethyl sulfoxide; alcohols such as methanol and ethanol; ketones such as acetone and methyl ethyl ketone; water, and the like. The solvents may be used singly or two or more of the solvents may be used as mixtures. The reaction proceeds usually at a temperature in a range of from about $-78°$ C. to the boiling temperature of the solvent used, preferably from about $-10°$ C. to the boiling temperature of the solvent used. In the reaction, a catalyst may be used. As for the catalyst, there can be cited, for example, inorganic bases such as sodium hydroxide, potassium hydroxide, sodium carbonate and potassium carbonate; organic bases such as triethylamine, diethylamine, dimethylamine, diisopropylamine and pyridine; mineral acids such as hydrochloric acid, nitric acid and sulfuric acid; hydrogen halides such as hydrogen fluoride, hydrogen bromide and hydrogen iodide; organic acids such as trifluoroacetic acid and trichloroacetic acid; and the like. On the other hand, the catalytic hydrogenation can be carried out by a conventional process known per se using a metal catalyst. As the metal catalyst, there can be used, for example, nickel palladium, rhodium and platinum a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as methylene chloride, chloroform and carbon tetrachloride; high boiling point polar solvents such as dimethylformaide and dimethylsulfoxide; alcohols such as methanol and ethanol; ketones such as acetone and methyl ethyl ketone; water, and the like. The solvents may be used singly or two or more of the solvents may be used as mixtures. The reaction proceeds usually at a temperature in a range of from about $-78°$ C. to the boiling temperature of the solvent used, preferably from about $-10°$ C. to the boiling temperature of the solvent used. In the reaction, a catalyst or a reaction accelerator may be used. As for the catalyst or reaction accelerator, there can be cited, for example, carbodiimides such as dicyclohexylcarbodiimide, diisopropylcarbodiimide and 1-ethyl-3-(3-dimethylaminopropyl)carbodiimide hydrochloride; acid anhydrides such as acetic anhydride and benzoic anhydride; inorganic bases such as sodium hydroxide, potassium hydroxide, sodium carbonate and potassium carbonate; organic bases such as triethylamine, diethylamine, dimethylamine, diisopropylamine and pyridine; organic acids such as acetic acid, p-toluenesulfonic acid and camphorsulfonic acid; and the like. The catalysts or reaction accelerators may be used in amounts in a range of from 0.01 to 10 equivalents, preferably from 0.1 to 1.1 equivalents per mole of the compound of formula (V-b).

Step-5

This step is to convert the compound of formula (V-d) to the compound of formula (V). The reagent used in the reaction includes, for example, halogenating agents such as thionyl chloride, phosphorus oxychloride and phosphorus pentachloride; or esterifying agents, e.g., alcohols such as methanol and ethanol; and phenols such as p-nitrophenol and 2,4-dinitrophenol. The reaction in this step can be carried out in a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as methylene chloride, chloroform and carbon tetrachloride; high boiling point polar solvents such as dimethylformamide and dimethyl sulfoxide; alcohols such as methanol and ethanol; water, and the like. The solvents may be used singly or two or more of the solvents may be used as mixtures. The reaction proceeds usually at a temperature in a range of from about $-78°$ C. to the boiling temperature of the solvent used, preferably from about $-10°$ C. to the boiling temperature of the solvent used. In the reaction, a catalyst or a reaction accelerator may be used. As for the catalyst or reaction accelerator, there can be cited, for example, carbodiimides such as dicyclohexylcarbodiimide, diisopropylcarbodiimide and 1-ethyl-3-(3-dimethylaminopropyl)-carbodiimide hydrochloride; acid anhydrides such as acetic anhydride and benzoic anhydride; inorganic bases such as sodium hydroxide, potassium hydroxide, sodium carbonate and potassium carbonate; organic bases such as triethylamine, diethylamine, dimethylamine, diisopropylamine and pyridine; and the like. The catalysts or reaction accelerators may be used in amounts in a range of from 0.01 to 10 equivalents, preferably from 0.1 to 1.1 equivalents per mole of the compound of formula (V-d).

Step-6

This step is to synthesize the compound of v formula (V-d) from the compound of formula (V-a). The reagent which can be reacted with the compound of formula (V-a) includes acid anhydrides such as acetic anhydride and benzoic anhydride; acid chlorides such as acetyl chloride and benzoyl chloride; organic acids such as acetic acid, benzoic acid and p-toluenesulfonic acid; ortho esters such as ethyl orthoformate and methyl orthoformate; ketones such as acetone and cyclohexanone; aldehydes such as benzaldehyde and acetaldehyde; silylation agent such as trimethylsilyl chloride and dimethylphenylsilyl chloride; alkylation agents such as diazomethane and dimethyl sulfate; alkylhalides such as methyl iodide and benzyl chloride; and the like. The reaction can be carried out in a suitable solvent, for example, aromatic hydrocarbons such as benzene, toluene and xylene; ethers such as ethyl ether, tetrahydrofuran and dioxane; esters such as methyl acetate and ethyl acetate; halogenated hydroarbons such as methylene chlorine, chloroform and carbon tetrachlorine; high boiling point polar solvents such as dimethylformamide and dimethyl sulfoxide; alcohols such as methanol and ethanol; ketones such as acetone and methyl ethyl ketone; water, and the like. The solvents may be used singly or two or more of the solvents may be used as mixtures. The reaction proceeds usually at a temperature in a range of from about $-78°$ C. to the boiling temperature of the solvent used, preferably from about $-10°$ C. to the boiling temperature of the solvent used. In the reaction, a catalyst or a reaction accelerator may be used. As for the catalyst or reaction accelerator, there can be cited, for example, carbodiimides such as dicyclohexylcarbodiimide, diisopropylcarbodiimide and 1-ethyl-3-(3-dimethylaminopropyl)carbodiimide hydrochloride; acid anhydrides such as acetic anhydride and benzoic anhydride; inorganic bases such as sodium hydroxide, potassium hydroxide, sodium carbonate and potassium carbonate; organic bases such as triethylamine, diethylamine, dimethylamine, diisopropylamine and pyridine; organic acids such as acetic acid, p-toluenesulfonic acid and camphorsulfonic acid; and the like. The catalysts or reaction accelerators may be used in amounts in a range of from 0.01 to 10 equivalents, preferably from 0.1 to 1.1 equivalents per mole of the compound of formula (V-a).

Preparation of Compound of Formula (II)

The compound of formula (II) can be obtained by reacting the compound of formula (V)

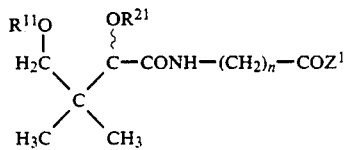

(V)

wherein $R^{11}$, $R^{21}$, n and $Z^1$ have the same meanings as defined above;

with a compound of formula (VII)

H—Q—H  (VII)

wherein Q has the same meaning as defined above.

This reaction can be carried out in a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as methylene chlorine, chloroform and carbon tetrachloride; high boiling point polar solvents such as dimethylformamide and dimethyl sulfoxide; alcohols such as methanol and ethanol; water, and the like. The solvents may be used singly or two or more of the solvents may be used as mixtures. The reaction proceeds usually at a temperature in a range of from about $-78°$ C. to the boiling temperature of the solvent used, preferably from about $-10°$ C. to the boiling temperature of the solvent used.

In the reaction, a catalyst or a reaction accelerator may be used. As for the catalyst or reaction accelerator, there can be cited, for example, carbodiimides such as dicyclohexylcarbodiimide, diisopropylcarbodiimide and 1-ethyl-3-(3-dimethylaminopropyl)carbodiimide hydrochloride; halogenating agents such as thionyl chloride, phosphorus oxychloride and phosphorus pentachloride; acid anhydrides such as acetic anhydride and benzoic anhydride; inorganic based such as sodium hydroxide, potassium hydroxide, sodium carbonate and potassium carbonate; organic bases such as triethylamine, diethylamine, dimethylamine, diisopropylamine and pyriidine; organic acids such as acetic acid, p-toluenesulfonic acid and camphorsulfonic acid; and the like. The catalyst or reaction accelerators may be used in amounts in a range of from 0.01 to 10 equivalents, preferably from 0.1 to 1.1 equivalents per mole of the compound of formula (V).

Preparation of Compound of Formula (VI)

The compound of formula (VI) can be obtained by reacting the compound of formula (VII)

H—Q—H  (VII)

wherein Q has the same meaning as defined above.
with a compound of formula (VIII)

$R^3$—CO—$Z^1$  (VIII)

wherein $R^3$ and $Z^1$ have the same meanings as defined above.

H—Q—H  (VII)

wherein Q has the same meanning as defined above.

This reaction can be carried out in a suitable solvent, for example, aromatic hydrocarbons such as benzene, toluene and xylene; ethers such as ethyl ether, tetrahydrofuran and dioxane; esters such as methyl acetate and ethyl acetate; halogenated hydrocarbons such as methylene chloride, chloroform and carbon tetrachloride; high boiling point polar solvents such as dimethylformamide and dimethyl sulfoxide; alcohols such as methanol and ethanol; water, and the like. The solvents may be used singly or two or more of the solvents may be used as mixtures. The reaction proceeds usually at a temperature in a range of from about $-78°$ C. to the boiling temperature of the solvent used, preferably from about −10° C. to the boiling temperature of the solvent used.

In the reaction, a catalyst or a reaction accelerator may be used. As for the catalyst or reaction accelerator, there can be cited, for example, carbodiimides such as dicyclohexylcarbodiimide, diisopropylcarbodiimide and 1-ethyl-3-(3-dimethylaminopropyl)carbodiimide hydrochloride; halogenating agents such as thionyl chloride, phosphorus oxychloride and phosphorus pentachloride; acid anhydrides such as acetic anhydride and benzoic anhydride; inorganic bases such as sodium hydroxide, potassium hydroxide, sodium carbonate and potassium carbonate; organic bases such as triethylamine, diethylamine, dimethylamine, diisopropylamine and pyridine; organic acids such as acetic acid, p-toluene-sulfonic acid and camphorsulfonic acid; and the like. The catalysts or reaction accelerators may be used in amounts in a range of from 0.01 to 10 equivalents, preferably from 0.1 to 1.1 equivalents per mole of the compound of formula (VII).

The compounds of the general formula (I) provided by the present invention have an excellent ACAT inhibiting activity and are expected to be useful as drugs for the therapy, treatment or prevention of hyperlipemia, arteriosclerosis, angina pectoris, myocardial infraction, thrombosis and the like.

The ACAT inhibiting activity of the compounds of the present invention can be confirmed by the test method described below.

ACAT inhibition tests were carried out by measuring cholesteryl oleate produced from [1-$^{14}$C]oleoylCoA and endocellular cholesterol similarly to the method of Helgerud et al. [cf. *Journal of Lipid Research*, 22, 497 (1987)] and the method of Folch et al. [cf. *Journal of Biological Chemistry*, 226, 497 (1957)].

More specifically, 10 μl of a solution of a microsome fraction prepared from a rat liver (0.3 mg protein) in 0.514M potassium phosphate buffer (pH 7.4) and 5 μl of a solution of $10^7$M of a test drug in dimethyl sulfoxide were added to 0.5 ml of a solution of 2 μM [1-$^{14}$C]oleoylCoA in 0.514M potassium phosphate buffer, and the mixture was allowed to react at 37° C. for 4 minutes.

Thereafter, 4.2 ml of methanol and 8.3 ml of chloroform were added to the reaction mixture to stop the reaction. Then, 2.5 ml of water was added and after shaking the mixture sufficiently a chloroform layer was separated. After concentrating it, the chloroform layer was subjected to thin layer chromatography. The cholesteryl oleate formed was separated and its radioactivity was measured by a liquid scientilaltion counter.

On the other hand, the same tests as above were repeated without using test compounds. The radioactivity of the control thus obtained was used as a standard for calculating the ACAT inhibiting activity of each test compound.

The results obtained are shown in Tables 1a, 1b and 1c.

TABLE 1a

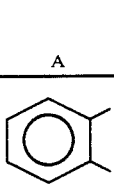

| EXAMPLE | R$^1$ | R$^2$ | n | X$^1$ | Y$^1$ | A | R$^3$ | ACAT Inhibition (%) $10^{-6}$M [IC$_{50}$ × $10^{-7}$M] |
|---|---|---|---|---|---|---|---|---|
| 1 | \/ | \/ | 2 | NH | NH | phenyl | −(CH$_2$)$_7$−CH=CH−(CH$_2$)$_7$−CH$_3$ | 83.6 [2.95 (1.95–4.47)] |
| 2 | Ac | Ac | 2 | NH | NH | phenyl | −(CH$_2$)$_7$−CH=CH−(CH$_2$)$_7$−CH$_3$ | 64.8 [2.74 (1.87–4.02)] |
| 4 | \/ | \/ | 2 | NH | NH | phenyl | −(CH$_2$)$_7$−CH=CH−CH$_2$−CH=CH−(CH$_2$)$_4$−CH$_3$ | 79.8 |
| 5 | \/ | \/ | 2 | NH | NH | phenyl | −(CH$_2$)$_7$−(CH=CHCH$_2$)$_3$−CH$_3$ | 56.0 |
| 15 | \/ | \/ | 2 | O | NH | phenyl | −(CH$_2$)$_7$−CH=CH−(CH$_2$)$_7$−CH$_3$ | 79.6 |

TABLE 1a-continued

Structure: R¹O-CH₂-C(CH₃)₂-CH(OR²)-C(=O)-NH-(CH₂)ₙ-C(=O)-X¹-A-Y¹-C(=O)-R³

| EXAMPLE | R¹ | R² | n | X¹ | Y¹ | A | R³ | ACAT Inhibition (%) 10⁻⁶M [IC₅₀ × 10⁻⁷M] |
|---|---|---|---|---|---|---|---|---|
| 9 | ✕ | | 2 | NH | NH | 1,3-phenylene | —(CH₂)₇—CH=CH—CH₂—CH=CH—(CH₂)₄—CH₃ | 51.8 |
| 33 | ✕ | | 2 | NH | NH | —(CH₂)₂— | —(CH₂)₇—CH=CH—(CH₂)₇—CH₃ | 73.1 [2.99 (1.55–5.69)] |
| 34 | ✕ | | 2 | NH | NH | —(CH₂)₃— | —(CH₂)₇—CH=CH—(CH₂)₇—CH₃ | 65.1 [3.85 (2.07–7.16)] |
| 37 | ✕ | | 2 | NH | NH | —(CH₂)₄— | —(CH₂)₇—CH=CH—(CH₂)₇—CH₃ | 72.6 [2.86 (1.44–5.68)] |
| 40 | ✕ | | 2 | NH | NH | —(CH₂)₅— | —(CH₂)₇—CH=CH—(CH₂)₇—CH₃ | 75.6 |
| 41 | ✕ | | 2 | NH | NH | —(CH₂)₆— | —(CH₂)₇—CH=CH—(CH₂)₇—CH₃ | 66.2 |
| 42 | ✕ | | 2 | NH | NH | —(CH₂)₇— | —(CH₂)₇—CH=CH—(CH₂)₇—CH₃ | 62.0 |
| 44 | ✕ | | 2 | O | NH | —(CH₂)₂— | —(CH₂)₇—CH=CH—(CH₂)₇—CH₃ | 69.3 [6.86 (4.37–10.8)] |
| 45 | H | H | 2 | O | NH | —(CH₂)₂— | —(CH₂)₇—CH=CH—(CH₂)₇—CH₃ | 51.1 |
| 46 | ✕ | | 2 | O | N—CH₃ | —(CH₂)₂— | —(CH₂)₇—CH=CH—(CH₂)₇—CH₃ | 56.6 |
| 47 | ✕ | | 2 | O | NH | —(CH₂)₃— | —(CH₂)₇—CH=CH—(CH₂)₇—CH₃ | 81.3 [2.50 (1.45–4.37)] |
| 48 | H | H | 2 | O | NH | —(CH₂)₃— | —(CH₂)₇—CH=CH—(CH₂)₇—CH₃ | 58.7 |
| 51 | PhCO | H | 2 | O | NH | —(CH₂)₃— | —(CH₂)₇—CH=CH—(CH₂)₇—CH₃ | 64.9 |
| 52 | iPr(Ph) | | 2 | O | NH | —(CH₂)₃— | —(CH₂)₇—CH=CH—(CH₂)₇—CH₃ | 65.5 |

TABLE 1a-continued

Structure:
$R^1O-CH_2-C(CH_3)_2-CH(OR^2)-C(=O)-NH-(CH_2)_n-C(=O)-X^1-A-Y^1-C(=O)-R^3$

| EX-AMPLE | R¹ | R² | n | X¹ | Y¹ | A | R³ | ACAT Inhibition (%) $10^{-6}$M [IC$_{50}$ × $10^{-7}$M] |
|---|---|---|---|---|---|---|---|---|
| 53 | cyclohexyl (R¹,R² joined) | | 2 | O | NH | —(CH$_2$)$_3$— | —(CH$_2$)$_7$—CH=CH—(CH$_2$)$_7$—CH$_3$ | 64.6 |
| 54 | tBuCO | H | 2 | O | NH | —(CH$_2$)$_3$— | —(CH$_2$)$_7$—CH=CH—(CH$_2$)$_7$—CH$_3$ | 83.2 |
| 58 | cyclohexyl (R¹,R² joined) | | 2 | O | NH | —(CH$_2$)$_3$— | —(CH$_2$)$_{10}$—CH$_3$ | 53.2 |
| 59 | cyclohexyl (R¹,R² joined) | | 2 | O | NH | —(CH$_2$)$_3$— | —(CH$_2$)$_{12}$—CH$_3$ | 54.3 |
| 60 | cyclohexyl (R¹,R² joined) | | 2 | O | NH | —(CH$_2$)$_3$— | —(CH$_2$)$_{14}$—CH$_3$ | 64.5 |
| 61 | cyclohexyl (R¹,R² joined) | | 2 | O | NH | —(CH$_2$)$_3$— | —(CH$_2$)$_{16}$—CH$_3$ | 61.6 |
| 62 | cyclohexyl (R¹,R² joined) | | 2 | O | NH | —(CH$_2$)$_3$— | —(CH$_2$)$_7$—CH=CH—CH$_2$—CH=CH—(CH$_2$)$_4$—CH$_3$ | 79.0 |
| 63 | cyclohexyl (R¹,R² joined) | | 2 | O | NH | —(CH$_2$)$_3$— | —(CH$_2$)$_7$—(CH=CHCH$_2$)$_3$—CH$_3$ | 77.5 |
| 64 | cyclohexyl (R¹,R² joined) | | 2 | O | N–CH$_3$ | —(CH$_2$)$_4$— | —(CH$_2$)$_7$—CH=CH—(CH$_2$)$_7$—CH$_3$ | 81.1 [1.95 (0.91–4.17)] |
| 65 | H | H | 2 | O | NH | —(CH$_2$)$_4$— | —(CH$_2$)$_7$—CH=CH—(CH$_2$)$_7$—CH$_3$ | 60.7 |
| 66 | cyclohexyl (R¹,R² joined) | | 2 | O | NH | —(CH$_2$)$_5$— | —(CH$_2$)$_7$—CH=CH—(CH$_2$)$_7$—CH$_3$ | 83.6 [3.55 (1.82–7.08)] |
| 67 | cyclohexyl (R¹,R² joined) | | 2 | O | NH | —(CH$_2$)$_6$— | —(CH$_2$)$_7$—CH=CH—(CH$_2$)$_7$—CH$_3$ | 84.4 [3.89 (2.29–6.61)] |
| 68 | cyclohexyl (R¹,R² joined) | | 2 | S | NH | —(CH$_2$)$_2$— | —(CH$_2$)$_7$—CH=CH—(CH$_2$)$_7$—CH$_3$ | 63.8 |
| 69 | H | H | 2 | S | NH | —(CH$_2$)$_2$— | —(CH$_2$)$_7$—CH=CH—(CH$_2$)$_7$—CH$_3$ | 61.8 |

TABLE 1a-continued

[Structure: R¹O-CH₂-C(CH₃)₂-CH(OR²)-C(=O)-NH-(CH₂)ₙ-C(=O)-X¹-A-Y¹-C(=O)-R³]

| EX-AMPLE | R¹ | R² | n | X¹ | Y¹ | A | R³ | ACAT Inhibition (%) 10⁻⁶M [IC₅₀ × 10⁻⁷M] |
|---|---|---|---|---|---|---|---|---|
| 70 | ⤫ | | 2 | NH | NH | cyclohexyl (S,S) | $-(CH_2)_7-CH=CH-(CH_2)_7-CH_3$ | 85.8 [1.62 (0.80–3.29)] |
| 71 | Ac | Ac | 2 | NH | NH | cyclohexyl (S,S) | $-(CH_2)_7-CH=CH-(CH_2)_7-CH_3$ | 81.7 [1.98 (1.95–4.47)] |
| 74 | H | H | 2 | NH | NH | cyclohexyl (S,S) | $-(CH_2)_7-CH=CH-(CH_2)_7-CH_3$ | 87.3 [1.55 (1.12–2.14)] |
| 76 | Ac | Ac | 2 | NH | NH | cyclohexyl (S,S) | $-(CH_2)_7-CH=CH-(CH_2)_7-CH_3$ | 86.0 [3.60 (1.88–6.92)] |
| 77 | ⤫ (S) | | 2 | O | NH | cyclohexyl R,R | $-(CH_2)_7-CH=CH-(CH_2)_7-CH_3$ | 86.9 [2.1 (1.86–2.34)] |
| 78 | ⤫ | | 2 | O | NH | cyclohexyl S,S | $-(CH_2)_7-CH=CH-(CH_2)_7-CH_3$ | 96.9 [0.401 (0.29–0.553)] |
| 79 | ⤫ | | 2 | O | NH | cyclohexyl R,R | $-(CH_2)_{16}-CH_3$ | 51.3 |
| 80 | ⤫ | | 2 | O | NH | cyclohexyl S,S | $-(CH_2)_7-CH=CH-CH_2-CH=CH-(CH_2)_4-CH_3$ | 93.5 [1.08] |

5,120,738

TABLE 1a-continued $$\underset{R^1-O}{\overset{R^2-O}{\diagdown}}\underset{O}{\overset{}{\diagup}}\underset{}{\overset{H}{N}}(CH_2)_n\underset{O}{\overset{}{\diagup}}X^1-A-Y^1\underset{O}{\overset{}{\diagup}}R^3$$

| EXAMPLE | R¹ | R² | n | X¹ | Y¹ | A | R³ | ACAT Inhibition (%) $10^{-6}$M [IC$_{50}$ × $10^{-7}$M] |
|---|---|---|---|---|---|---|---|---|
| 81 | × | | 2 | O | NH | —CH—CH₂— with CH₃ (R) | —(CH₂)₆CH=CH(CH₂)₇CH₃ | 77.1 |
| 82 | × | | 2 | O | NH | —CH—CH₂— with CH₃ (S) | —(CH₂)₆CH=CH(CH₂)₇CH₃ | 82.4 |
| 83 | × | | 2 | O | NH | cyclopentane (S,S) | —(CH₂)₇CH=CH(CH₂)₇CH₃ | 95.4 |
| 84 | × | | 2 | O | NH | cyclopentane (R,R) | —(CH₂)₇CH=CH(CH₂)₇CH₃ | 88.2 |
| 85 | × | | 2 | O | NH | cis-CH₂CH=CHCH₂ | —(CH₂)₇CH=CH(CH₂)₇CH₃ | 77.9 |
| 86 | × | | 2 | O | NH | —CH₂—CH— with CH₃ (R) | —(CH₂)₇CH=CH(CH₂)₇CH₃ | 51.5 |
| 87 | × | | 2 | O | NH | —CH₂—CH— with CH₃ (S) | —(CH₂)₇CH=CH(CH₂)₇CH₃ | 81.3 |
| 88 | × | | 2 | O | NH | trans-CH₂CH=CHCH₂ | —(CH₂)₇CH=CH(CH₂)₇CH₃ | 81.7 |
| 89 | × | | 2 | O | NH | —CH₂C≡CCH₂— | —(CH₂)₇CH=CH(CH₂)₇CH₃ | 68.9 |
| 90 | × | | 2 | O | NH | phenyl with sec-butyl | —(CH₂)₇CH=CH(CH₂)₇CH₃ | 69.4 |
| 91 | × | | 2 | O | NH | phenyl with sec-butyl | —(CH₂)₇CH=CH(CH₂)₇CH₃ | 90.6 |
| 92 | × | | 2 | O | NH | dimethyl cyclopentane | —(CH₂)₇CH=CH(CH₂)₇CH₃ | 86.4 |

TABLE 1a-continued

[Structure shown at top of table: R¹O-CH₂-C(CH₃)₂-CH(OR²)-C(=O)-NH-(CH₂)ₙ-C(=O)-X¹-A-Y¹-C(=O)-R³]

| EXAMPLE | R¹ | R² | n | X¹ | Y¹ | A | R³ | ACAT Inhibition (%) 10⁻⁶M [IC₅₀ × 10⁻⁷M] |
|---|---|---|---|---|---|---|---|---|
| 93 | X | | 2 | O | NH | bicyclic (bridged) | —(CH₂)₇CH═CH(CH₂)₇CH₃ | 95.3 |
| 94 | X | | 2 | O | NH | isopropyl-branched alkyl | —(CH₂)₇CH═CH(CH₂)₇CH₃ | 94.3 |
| 95 | X | | 2 | O | NH | sec-butyl | —(CH₂)₇CH═CH(CH₂)₇CH₃ | 90.0 |
| 96 | X | | 2 | O | NH | sec-butylphenyl | —(CH₂)₇CH═CH(CH₂)₇CH₃ | 88.4 |
| 97 | X | | 2 | O | NH | sec-butylphenyl | —(CH₂)₇CH═CH(CH₂)₇CH₃ | 84.2 |
| 98 | X | | 2 | O | NH | 2-methyl-4-ethylpentyl | —(CH₂)₇CH═CH(CH₂)₇CH₃ | 89.1 |
| 99 | X | | 2 | O | NH | diethylmethyl cyclohexyl | —(CH₂)₇CH═CH(CH₂)₇CH₃ | 65.8 |
| 100 | X | | 1 | O | NH | (S)-sec-butylphenyl | —(CH₂)₇CH═CH(CH₂)₇CH₃ | 90.0 |
| 101 | X | | 3 | O | NH | (S)-sec-butylphenyl | —(CH₂)₇CH═CH(CH₂)₇CH₃ | 84.6 |
| 102 | X | | 4 | O | NH | (S)-sec-butylphenyl | —(CH₂)₇CH═CH(CH₂)₇CH₃ | 84.3 |

TABLE 1a-continued

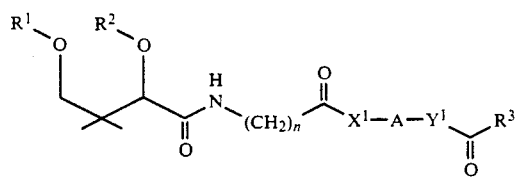

| EX-AMPLE | R¹ | R² | n | X¹ | Y¹ | A | R³ | ACAT Inhibition (%) $10^{-6}$M [IC$_{50}$ × $10^{-7}$M] |
|---|---|---|---|---|---|---|---|---|
| 103 | ╳ | | 2 | O | NH | cyclohexyl | $-\underset{\underset{CH_3}{\mid}}{\overset{\overset{CH_3}{\mid}}{C}}-(CH_2)_{15}CH_3$ | 63.9 |
| 104 | ╳ | | 2 | O | NH | cyclohexyl | $-\underset{\underset{CH_3}{\mid}}{\overset{\overset{CH_3}{\mid}}{C}}-(CH_2)_6CH=CH(CH_2)_7CH_3$ | 94.2 |
| 105 | ╳ | | 2 | O | NH | cyclohexyl | $-\underset{}{\overset{\overset{CH_3}{\mid}}{CH}}(CH_2)_6CH=CH(CH_2)_7CH_3$ | 95.6 |
| 106 | ╳ | | 2 | O | NH | cyclohexyl | $-\underset{*}{\overset{\overset{CH_3}{\mid}}{CH}}-(CH_2)_{13}-CH_3$ | 91.5 |
| 107 | ╳ | | 2 | O | NH | cyclohexyl | $-\underset{*}{\overset{\overset{CH_3}{\mid}}{CH}}-(CH_2)_{13}-CH_3$ | 92.9 |
| 108 | ╳ | | 2 | O | NH | cyclohexyl | $-\underset{*}{\overset{\overset{CH_2CH_3}{\mid}}{CH}}-(CH_2)_{11}-CH_3$ | 93.6 |
| 109 | ╳ | | 2 | O | NH | cyclohexyl | $-\underset{*}{\overset{\overset{CH_2CH_3}{\mid}}{CH}}-(CH_2)_{11}-CH_3$ | 93.3 |
| 110 | ╳ | | 2 | O | NH | cyclohexyl | $-\underset{*}{\overset{\overset{(CH_2)_2-CH_3}{\mid}}{CH}}-(CH_2)_{15}-CH_3$ | 68.3 |
| 111 | ╳ | | 2 | O | NH | cyclohexyl | $-\underset{*}{\overset{\overset{(CH_2)_2-CH_3}{\mid}}{CH}}-(CH_2)_{15}-CH_3$ | 56.3 |

TABLE 1a-continued $$\underset{R^1-O}{\overset{R^2-O}{\diagdown}}\!\!\!\!\!\!\!\!\!\!\!\!\!\!\!\!\!\!\!\!\!\!\!\!\!\!\!\!\!\!\!\!\!\!\!\diagup\!\!\!\!\!\!\!\!\!\!\!\!\!\!\!\!\!\!\!\!\!\!\!\!\!\!\!\!\!\!\!\!\!\!\!\!\!\!\!\!\!\!\overset{H}{N}\!\!-\!\!(CH_2)_n\!\!-\!\!\overset{O}{\overset{\|}{C}}\!\!-\!\!X^1\!\!-\!\!A\!\!-\!\!Y^1\!\!-\!\!\overset{O}{\overset{\|}{C}}\!\!-\!\!R^3$$

| EXAMPLE | R¹ R² | n | X¹ | Y¹ | A | R³ | ACAT Inhibition (%) $10^{-6}$M [IC$_{50}$ × $10^{-7}$M] |
|---|---|---|---|---|---|---|---|
| 112 | ✕ | 2 | O | NH | cyclohexyl | $-C(CH_2CH_2)(CH_2CH_2)(CH_3)(CH_2)_{11}-CH_3$ | 95.4 |
| 113 | ✕ | 2 | O | NH | cyclohexyl | $-C(CH_2)(CH_2)(CH_2)(CH_2)(CH_3)(CH_2)_9CH_3$ | 96.1 |
| 114 | ✕ | 2 | O | NH | cyclohexyl | $-C(CH_2-CH_2)(CH_2)(CH_2)(CH_3)(CH_2)_8CH=CH(CH_2)_7CH_3$ | 64.2 |
| 115 | ✕ | 2 | O | NH | cyclohexyl | $-NH-CH(CH_3)-(CH_2)_6CH=CH(CH_2)_7CH_3$ | 95.1 |
| 116 | ✕ | 2 | O | NH | cyclohexyl | $-NH-CH(CH_3)-(CH_2)_{13}-CH_3$ | 92.7 |
| 117 | ✕ | 2 | O | NH | cyclohexyl | $-C(CH_2)(CH_2)(CH_2)(CH_3)(CH_2)_7CH_3$ | 79.0 |
| 118 | ✕ | 2 | O | NH | cyclohexyl | $-\overset{*}{CH}(CH(CH_3)_2)-(CH_2)_9-CH_3$ | 88.2 |
| 119 | ✕ | 2 | O | NH | cyclohexyl | $-\overset{*}{CH}(CH(CH_3)_2)-(CH_2)_9-CH_3$ | 76.0 |
| 120 | ✕ | 2 | O | NH | cyclohexyl | $-C(CH_2)(CH_2)(CH_2)(CH_2)(CH_2)_5CH_3$ | 41.0 |

TABLE 1a-continued

Structure:
R¹O—CH₂—C(CH₃)₂—CH(OR²)—C(=O)—NH—(CH₂)ₙ—C(=O)—X¹—A—Y¹—C(=O)—R³

| EX-AMPLE | R¹ | R² | n | X¹ | Y¹ | A | R³ | ACAT Inhibition (%) 10⁻⁶M [IC₅₀ × 10⁻⁷M] |
|---|---|---|---|---|---|---|---|---|
| 123 | × | | 2 | O | NH | trans-cyclohexyl | —CH(CH₃)—(CH₂)₉—CH₃ * | 94.1 |
| 124 | × | | 2 | O | NH | cis-cyclohexyl | —CH(CH₃)—(CH₂)₉—CH₃ * | 87.7 |
| 126 | × | | 2 | O | NH | trans-cyclohexyl | —N(CH(CH₃)₂)—(CH₂)₉—CH₃ | 88.2 |
| 127 | × | | 2 | O | NH | trans-cyclohexyl | —N(CH₂C(CH₃)₃)—(CH₂)₈—CH₃ | 88.2 |
| 122 | H | H | 2 | O | NH | trans-cyclohexyl | cyclic —C((CH₂)₃)((CH₂)₉—CH₃)— | 71.9 |
| 128 | × | | 2 | O | NH | 1,2-cyclohexyl | —CH(CH₂—C₆H₅)—(CH₂)₅CH₃ * | 81.8 |
| 129 | × | | 2 | O | NH | 1,2-cyclohexyl | —CH(CH₂—C₆H₅)—(CH₂)₅CH₃ * | 87.5 |
| 130 | × | | 2 | O | NH | trans-cyclohexyl | —CH(C₆H₅)—(CH₂)₉CH₃ * | 91.9 |
| 131 | × | | 2 | O | NH | trans-cyclohexyl | —CH(C₆H₅)—(CH₂)₉CH₃ | 87.6 |

TABLE 1a-continued $$\underset{\underset{O}{\parallel}}{R^1O-CH_2-C(CH_3)_2-CH(OR^2)-C}-NH-(CH_2)_n-\underset{\underset{O}{\parallel}}{C}-X^1-A-Y^1-\underset{\underset{O}{\parallel}}{C}-R^3$$

| EXAMPLE | R¹ | R² | n | X¹ | Y¹ | A | R³ | ACAT Inhibition (%) $10^{-6}$ M [IC$_{50}$ × $10^{-7}$M] |
|---|---|---|---|---|---|---|---|---|
| 132 | ╳ | | 2 | O | NH | cyclohexyl | $-C(CH_2)_3(CH_2-C_6H_5)(CH_3)$ (spiro) | 8.6 |
| 133 | ╳ | | 2 | O | NH | cyclohexyl | $-C(CH_2)_3(CH_3)-CH_2-$furan | 27.5 |
| 134 | ╳ | | 2 | O | NH | cyclohexyl | $-CH^*(CH_2-C_6H_5)-(CH_2)_9-CH_3$ | 95.1 |
| 135 | ╳ | | 2 | O | NH | cyclohexyl | $-CH^*(CH_2-C_6H_5)-(CH_2)_9-CH_3$ | 93.9 |
| 136 | ╳ | | 2 | O | NH | cyclohexyl | $-C(CH_2)_3(CH_3)-CH_2-CH=CH-C_6H_5$ | 59.7 |
| 137 | ╳ | | 2 | O | NH | cyclohexyl | $-C(CH_2)_3(CH_3)-(CH_2)_3-C_6H_5$ | 63.5 |
| 138 | ╳ | | 2 | O | NH | cyclohexyl | $-C(C_6H_5)_2-(CH_2)_9-CH_3$ | 88.3 |
| 139 | H | H | 2 | O | NH | cyclohexyl | $-CH(CH_2-C_6H_5)-(CH_2)_5-CH_3$ | 63.9 |
| 140 | ╳ | | 2 | O | NH | cyclohexyl | $-N(CH_2-C_6H_5)-(CH_2)_5-CH_3$ | 84.4 |

TABLE 1a-continued $$\begin{array}{c} R^1O \quad R^2O \quad O \\ \phantom{xx} \diagdown \phantom{x} | \phantom{x} \diagup \phantom{x} \| \\ \phantom{xxxxxx} \text{—C—C—N—}(CH_2)_n\text{—C—}X^1\text{—A—}Y^1\text{—C—}R^3 \end{array}$$

| EXAMPLE | R¹ | R² | n | X¹ | Y¹ | A | R³ | ACAT Inhibition (%) $10^{-6}$M [IC$_{50}$ × $10^{-7}$M] |
|---|---|---|---|---|---|---|---|---|
| 141 | × | | 2 | O | NH | cyclohexyl (trans) | $-\underset{\|}{N}\underset{CH_2-C_6H_5}{}-(CH_2)_7-CH_3$ | 89.9 |
| 142 | × | | 2 | O | NH | cyclohexyl (trans) | $-\underset{\|}{N}\underset{CH_2-C_6H_5}{}-(CH_2)_9-CH_3$ | 87.9 |
| 143 | × | | 2 | O | NH | cyclohexyl (trans) | $-\underset{*}{CH}\underset{\|}{}-(CH_2)_8-CH_3$ with CH—C$_6$H$_5$ | 82.2 |
| 144 | × | | 2 | O | NH | cyclohexyl (trans) | $-\underset{*}{CH}\underset{\|}{}-(CH_2)_8-CH_3$ with CH$_2$—C$_6$H$_5$ | 80.0 |
| 145 | × | | 2 | O | NH | cyclohexyl (trans) | $-CH=C\big(\substack{(CH_2)_5CH_3 \\ (CH_2)_5CH_3}\big)$ | 89.0 |
| 146 | × | | 2 | O | NH | cyclohexyl (trans) | $-CH=C\big(\substack{CH_2-C_6H_5 \\ CH_2-C_6H_5}\big)$ | 77.6 |
| 147 | × | | 2 | O | NH | cyclohexyl (trans) | $-CH=C\big(\substack{(CH_2)_2CH_3 \\ (CH_2)_5CH_3}\big)$ | 88.1 |
| 148 | × | | 2 | O | NH | cyclohexyl (trans) | $-CH=C\big(\substack{CH_3 \\ (CH_2)_9CH_3}\big)$ | 30.7 |
| 149 | × | | 2 | O | NH | cyclohexyl (trans) | $\substack{H_3C \\ \phantom{x}}\!\!>\!\!C=C\!\!<\!\!\substack{CH_3 \\ (CH_2)_9CH_3}$ | 15.0 |

TABLE 1a-continued

Structure: R¹O-CH₂-C(CH₃)₂-CH(OR²)-C(=O)-NH-(CH₂)ₙ-C(=O)-X¹-A-Y¹-C(=O)-R³

| EX-AMPLE | R¹ R² | n | X¹ | Y¹ | A | R³ | ACAT Inhibition (%) $10^{-6}$M [IC$_{50}$ × $10^{-7}$M] |
|---|---|---|---|---|---|---|---|
| 150 | ✕ | 2 | O | NH | cyclohexyl (trans) | $-CH_2-\underset{(CH_2)_5CH_3}{\overset{(CH_2)_5CH_3}{CH}}$ | 97.3 |
| 151 | ✕ | 2 | O | NH | cyclohexyl (trans) | $-C=\underset{C_6H_5}{\overset{(CH_2)_8CH_3}{C}}$ | 97.7 |
| 152 | ✕ | 2 | O | NH | cyclohexyl (trans) | $-C=\underset{(CH_2)_8CH_3}{\overset{C_6H_5}{C}}$ | 97.3 |
| 153 | ✕ | 2 | O | NH | cyclohexyl (trans) | $-C=\underset{(CH_2)_5CH_3}{\overset{C_6H_5}{C}}$ | 97.5 |
| 154 | ✕ | 2 | O | NH | cyclohexyl (trans) | $-C=\underset{C_6H_5}{\overset{(CH_2)_5CH_3}{C}}$ | 91.6 |
| 155 | ✕ | 2 | O | NH | cyclohexyl (trans) | $-\underset{(CH_2)_5CH_3}{\overset{(CH_2)_4CH_3}{C}}=CH$ | 92.5 |
| 156 | ✕ | 2 | O | NH | cyclohexyl (trans) | $-\underset{(CH_2)_5CH_3}{\overset{(CH_2)_4CH_3}{C}}=CH$ | 96.3 |
| 157 | ✕ | 2 | O | NH | cyclohexyl (trans) | $-N\underset{(CH_2)_8CH_3}{\overset{CH_2-C_6H_5}{}}$ | 97.3 |
| 158 | ✕ | 2 | O | NH | cyclohexyl (trans) | $-\underset{(CH_2)_8CH_3}{\overset{CH_2-C_6H_5}{CH}}$ | 97.8 |

TABLE 1a-continued

[Structure: R¹O-CH₂-C(R²O)(...)-C(=O)-NH-(CH₂)ₙ-C(=O)-X¹-A-Y¹-C(=O)-R³]

| EX-AMPLE | R¹ R² | n | X¹ | Y¹ | A | R³ | ACAT Inhibition (%) 10⁻⁶M [IC₅₀ × 10⁻⁷M] |
|---|---|---|---|---|---|---|---|
| 159 | ✕ | 2 | O | NH | cyclohexyl | $-\text{CH}\begin{smallmatrix}(CH_2)_6CH_3\\(CH_2)_6CH_3\end{smallmatrix}$ | 96.2 |
| 160 | ✕ | 2 | O | NH | cyclohexyl | $-\text{NH}-\text{CH}\begin{smallmatrix}(CH_2)_6CH_3\\(CH_2)_6CH_3\end{smallmatrix}$ | 98.9 |
| 161 | ✕ | 2 | O | NH | cyclohexyl | $-\text{CH}\begin{smallmatrix}CH_2-C_6H_5\\CH_2-C_6H_5\end{smallmatrix}$ | 64.3 |
| 162 | ✕ | 2 | O | NH | cyclohexyl | $-\text{CH}\begin{smallmatrix}(CH_2)_3-C_6H_5\\(CH_2)_3-C_6H_5\end{smallmatrix}$ | 97.1 |
| 163 | ✕ | 2 | O | NH | cyclohexyl | $-\text{CH}\begin{smallmatrix}(CH_2)_4-C_6H_5\\(CH_2)_4-C_6H_5\end{smallmatrix}$ | 98.1 |
| 164 | ✕ | 2 | O | NH | cyclohexyl | $-\text{CH}\begin{smallmatrix}CH_2-C_6H_4-C(CH_3)_3\\CH_2-C_6H_4-C(CH_3)_3\end{smallmatrix}$ | 94.6 |

NOTE:

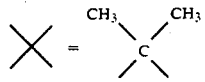

$\times = \begin{smallmatrix}CH_3\\ \\CH_3\end{smallmatrix}C\begin{smallmatrix}CH_3\\ \\CH_3\end{smallmatrix}$ Ac = CH₃CO, Ph = phenyl, tBu = tert-butyl (Same as Tables 1b and 1c)

TABLE 1b

Structure: R¹O-CH₂-C(O-R²)(...)C(=O)-NH-(CH₂)ₙ-C(=O)-X²-(CH₂)ₗ-Y²-C(=O)-R³

| EXAMPLE | R¹ | R² | n | X² | l | Y² | R³ | ACAT Inhibition (%) $10^{-6}$M |
|---|---|---|---|---|---|---|---|---|
| 165 | ✕ | | 2 | (S)-pyrrolidin-2-yl-N– | 1 | NH | $-(CH_2)_7CH=CH(CH_2)_7CH_3$ | 82.8 |
| 166 | H | H | 2 | (S)-pyrrolidin-2-yl-N– | 1 | NH | $-(CH_2)_7CH=CH(CH_2)_7CH_3$ | 65.7 |
| 167 | ✕ | | 2 | pyrrolidin-2-yl-N– | 1 | NH | $-(CH_2)_7CH=CH(CH_2)_7CH_3$ | 64.0 |
| 168 | ✕ | | 2 | 3-methylpiperidin-1-yl-N– | 0 | NH | $-(CH_2)_7CH=CH(CH_2)_7CH_3$ | 75.7 |
| 169 | H | H | 2 | 3-methylpiperidin-1-yl-N– | 0 | NH | $-(CH_2)_7CH=CH(CH_2)_7CH_3$ | 58.3 |
| 171 | ✕ | | 2 | NH | 0 | piperidin-3-yl-N– | $-(CH_2)_7CH=CH(CH_2)_7CH_3$ | 61.1 |
| 172 | ✕ | | 2 | NH | 0 | piperidin-4-yl-N– | $-(CH_2)_7CH=CH(CH_2)_7CH_3$ | 65.3 |
| 173 | ✕ | | 2 | O | 0 | piperidin-4-yl-N– | $-(CH_2)_7CH=CH(CH_2)_7CH_3$ | 66.9 |
| 174 | H | H | 2 | O | 0 | piperidin-4-yl-N– | $-(CH_2)_7CH=CH(CH_2)_7CH_3$ | 21.5 |
| 175 | Ac | Ac | 2 | O | 0 | piperidin-4-yl-N– | $-(CH_2)_7CH=CH(CH_2)_7CH_3$ | 29.3 |

TABLE 1b-continued $$R^1-O \quad O-R^2$$
Structure: R¹O-CH₂-C(CH₃)₂-CH(OR²)-C(=O)-NH-(CH₂)ₙ-X²-(CH₂)ₗ-Y²-C(=O)-R³

| EXAMPLE | R¹ | R² | n | X² | l | Y² | R³ | ACAT Inhibition (%) $10^{-6}$M |
|---------|----|----|---|----|----|----|----|----|
| 177 | ╳ | | 2 | O | 0 | piperidine-N— | $-(CH_2)_7CH=CH(CH_2)_7CH_3$ | 57.5 |
| 178 | ╳ | | 2 | O | 0 | piperidine-N— | $-(CH_2)_7CH=CH(CH_2)_7CH_3$ | 66.2 |
| 179 | ╳ | | 2 | O | 1 | pyrrolidine-N— (S) | $-(CH_2)_7CH=CH(CH_2)_7CH_3$ | 80.4 |
| 180 | ╳ | | 2 | O | 1 | pyrrolidine-N— | $-(CH_2)_7CH=CH(CH_2)_7CH_3$ | 59.6 |
| 181 | ╳ | | 2 | O | 1 | pyrrolidine-N— | $-(CH_2)_{16}CH_3$ | 35.4 |
| 182 | ╳ | | 2 | O | 1 | pyrrolidine-N— (S) | $-(CH_2)_7-CH=CH-CH_2-CH=CH-(CH_2)_4CH_3$ | 55.2 |
| 183 | H | H | 2 | O | 1 | pyrrolidine-N— | $-(CH_2)_7CH=CH(CH_2)_7CH_3$ | 44.0 |
| 184 | Ac | Ac | 2 | O | 1 | pyrrolidine-N— | $-(CH_2)_7CH=CH(CH_2)_7CH_3$ | 59.9 |
| 185 | ╳ | | 2 | NH | 1 | pyrrolidine-N— | $-(CH_2)_7CH=CH(CH_2)_7CH_3$ | 51.1 |
| 186 | ╳ | | 2 | NH | 1 | pyrrolidine-N— (S) | $-(CH_2)_7CH=CH(CH_2)_7CH_3$ | 62.4 |

TABLE 1b-continued

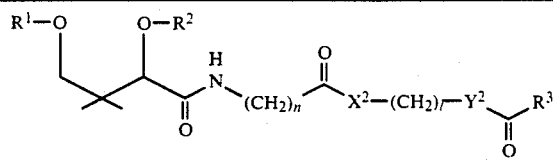

| EXAMPLE | R¹ R² | n | X² | l | Y² | R³ | ACAT Inhibition (%) $10^{-6}$M |
|---|---|---|---|---|---|---|---|
| 187 | X | 2 | O | 0 | 4-piperidinyl (N-) | $-\underset{\underset{CH_3}{\|}}{CH}-(CH_2)_9-CH_3$ | 90.3 |
| 188 | X | 2 | O | 0 | 4-piperidinyl (N-) | $C$ with $(CH_2)_9-CH_3$ and $(CH_2)_3$ ring | 96.9 |
| 191 | X | 2 | O | 0 | 4-piperidinyl (N-) | CH(NH)-benzyl with long alkyl chain | 83.1 |
| 190 | X | 2 | O | 0 | 4-piperidinyl (N-) | branched alkyl with benzyl | 69.0 |

TABLE 1c

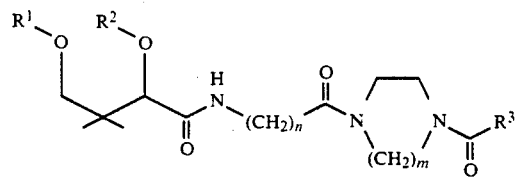

| EXAMPLE | R¹ | R² | n | m | R³ | ACAT Inhibition (%) $10^{-6}$M |
|---|---|---|---|---|---|---|
| 192 | Ac | Ac | 2 | 2 | $-(CH_2)_7-CH=CH-(CH_2)_7CH_3$ | 44.8 |
| 193 | H | H | 2 | 2 |  | 18.9 |
| 194 | Ac | Ac | 2 | 3 | $-(CH_2)_7CH=CH$ / $CH_3-(CH_2)_7$ | 62.6 |
| 195 | H | H | 2 | 3 |  | 48.7 |
| 198 | X |  | 2 | 2 | $-N(H)-(CH_2)_7-CH=CH-(CH_2)_7-CH_3$ | 84.3 |
| 199 | X |  | 2 | 2 | $-\underset{\underset{CH_3}{\|}}{CH}-(CH_2)_9-CH_3$ | 53.7 |
| 200 | X |  | 2 | 2 | $C$ with $(CH_2)_9-CH_3$ and $(CH_2)_3$ ring | 45.7 |

TABLE 1c-continued

Structure:
R¹-O-CH₂-C(CH₃)₂-CH(O-R²)-C(=O)-NH-(CH₂)ₙ-C(=O)-N(piperazine with (CH₂)ₘ)-N-C(=O)-R³

| EXAMPLE | R¹ | R² | n | m | R³ | ACAT Inhibition (%) $10^{-6}$M |
|---------|----|----|---|---|----|-------------------------------|
| 201 | ╳ | | 2 | 2 | H<br>—C—(CH₂)₈—CH₃<br>\|<br>CH₂—C₆H₅ | 64.8 |
| 202 | ╳ | | 2 | 2 | CH₂—C₆H₅<br>\|<br>—NH—C—(CH₂)₈—CH₃<br>H | 56.8 |

In the case where the compounds of the present invention are used as a drug for the therapy, treatment or prevention of various diseases such as hyperlipemia, arteriosclerosis, angina pectoris, myocardial infraction and thrombosis, the compounds can be formulated together with pharmaceutically accepted carriers, diluents, excipients, binders, disintegrants, lubricants, antiseptics, stabilizers, dissolving aids, corrigents or the like into formulations suitable for administration such as those unit administration formulas, for example, tablets, capsules, powders, granules, microcapsules, syrups, elixirs, injectable liquids and suppositories.

While the contents of the active ingredients in the formulations will vary depending on the kinds of the compounds of as the present invention used, types of the formulations, purposes for which the formulations are used, generally the active ingredients are contained in a range of from 0.5 to 90% by weight, and preferably from 5 to 60% by weight.

In the case of solid preparations such as tablets, capsules, powders and granules, the compounds of the present invention can be formulated in a conventional manner together with carriers or diluents such as lactose, mannitol, glucose, hydroxypropylcellulose, crystallite cellulose, carboxymethylcellulose, starch, polyvinylpyrrolidone, aluminum metasilicate and talc; lubricants such as magnesium stearate; disintegrants such as cellulose calcium gluconate; dissolving aids such as glutamic acid and aspartic acid; stabilizers such as lactose; and the like. The tablets may if desired be coated with a substance which is soluble in the stomach or intestine such as white sugar, gelatin, hydroxypropylmethylcellulose. The capsules may be either hard capsules or soft capsules.

In the case of liquid formulations such as syrups, elixirs, solutions, emulsions and suspensions, the compounds of the present invention can be formulated by dissolving or dispersing them in a pharmaceutically acceptable liquid medium such as deionized water, physiological saline, buffers and ethanol, and optionally adding thereto one or more substances selected from surfactants, edulcorants, corrigents, flavors and antiseptics.

On the other hand, injections, which are administered parenterally, include sterile, aqueous or non-aqueous solutions, suspensions and emulsions. Such types of injections can be prepared by mixing the compounds of the present invention with aqueous diluents such as distilled water for injection and physiological saline or non-aqueous diluents such as polyethylene glycol, propylene glycol, olive oil, ethanol and polysolvate 80 (trademark). The injections may contain one or more auxiliaries such as antiseptics, wetting agents, surfactants, dispersants, stabilizers and dissolving aids, if desired. The injections can be sterilized usually by filtering them through bacteria trapping filters or by blending or spraying sterilizers. Furthermore, it is also possible to use solid formulations prepared by lyophilization or the like after the above-described treatments and in addition thereto adding sterilized water or diluent for injection immediately before use.

The compounds of the present invention can be administered by oral administration or rectal administration, or alternatively by parenteral administration such as intravenous administration, intramuscular administration and subcutaneous administration. While their dosage will vary depending on the kinds of the compounds to be used, administration methods, severity of symptoms of patients to be treated, age and body weight of patients and judgements by the doctors, it is suitable that the compounds of the present invention are administered generally in a dosage of from about 2 to about 500 mg/kg/day once a day or dividedly 2 to 4 times a day. However, the dosage is not limited to the above-described conditions but dosage either higher or lower than the above-described one may of course be used depending on the judgements by the doctors and severity of the symptoms.

Hereafter, the present invention will be explained in greater detail with reference to nonlimitative examples.

REFERENCE EXAMPLE 1

Preparation of Benzyl 3-[N-(2,4-Dihydroxy-3,3-dimethyl-1-oxo)amino]propionate

A solution of 75 g of calcium pantothenate and 53.8 g of benzyl bromide in 1 liter of diemthylformamide was stirred at 100° C. for one night. After completion of the reaction, the solvent was distilled off under reduced pressure. The residue was dissolved in water extracted with ethyl acetate. The organic layer was washed with water and then with saturated saline, and dried over anhydrous sodium sulfate. Removal of the solvent by evaporation afforded 90.3 g of the objective compound (yield: 93%).
Property: Oily.
IR(cm$^{-1}$, neat): $\nu_{CO}$1738, 1662.
Mass Spectrometric Analysis: Molecular formula: $C_{16}H_{23}NO_5$, Calculated: 309.1576, Found: 309.1577.
NMR($\delta$, CDCl$_3$): 0.88 (3H,s), 1.00 (3H,s), 2.62 (2H,t,J=7Hz), 3.45 (1H,d,J=11Hz), 3.48 (1H,d,J=11Hz), 3.52-3.64 (2H,m), 3.99 (1H,s), 5.14 (2H,s), 7.10-7.20 (1H,m), 7.33-7.42 (5H,m).

REFERENCE EXAMPLE 2

Preparation of Benzyl 3-[N-(2,2,5,5-Tetramethyl-1,3-dioxane-4-carbonyl-)amino]propionate p-Toluenesulfonic acid hydrate (5.6 g) was added to solution of 90 g of benzyl 3-[N-(2,4-dihydroxy-3,3,-dimethyl-1-oxo)amino]-propionate in 700 ml of acetone, and the mixture was stirred at room temperature for one night. After completion of the reaction, the solvent was disstilled off under reduced pressure. The residue was dissolved in ethyl acetate, washed with saturated aqueous sodium bicarbonate solution, with water and then with extracted with ethyl acetate. The organic layer was washed with saturated saline, and dried over anhydrous sodium sulfate. The residue was subjected to silica gel column chromatography and purified to obtain 85 g of the objective compound (yield: 84%).
Property: Oily.
IR(cm$^{-1}$, neat): $\nu_{NH}$3456, $\nu_{CO}$1740,1676.
Mass Spectrometric Analysis: Molecular formula: $C_{19}H_{27}NO_5$, Calculated: 349.1889, Found: 349.1882.
NMR($\delta$, CDCl$_3$): 0.94 (3H,s), 1.03 (3H,s), 1.41 (3H,s), 1.44 (3H,s), 2.62 (2H,t,J=7Hz), 3.28 (1H,d,J=12Hz), 3.67 (1H,d,J=12Hz), 3.42-3.65 (2H,m), 4.07 (1H,s), 5.14 (2H,s), 6.90-7.10 (1H,m), 7.30-7.40 (5H,m).

REFERENCE EXAMPLE 3

Preparation of 3-[N-(2,2,5,5-Tetramethyl-1,3-dioxane-4-carbonyl-)amino)propionic Acid An aqueous 1N sodium hydroxide solution (100 ml) was added to a solution 35 g of benzyl 3-[N-(2,2,5,5-Tetramethyl-1,3-dioxane-4-carbonyl)amino]propionate in 350 ml of methanol, and the mixture was stirred under ice cooling for 1 hour. After completion of the reaction, methanol was distilled off under reduced pressure. The aqueous layer was extracted with ethyl acetate. After adding 1N hydrochloric acid to the aqueous layer to render it acidic, the aqueous layer was extracted with ethyl acetate. The organic layer washed with water and then with saturated saline, and dried over anhydrous sodium sulfate. Removal of the solvent by evapoation afforded 20.4 g of the objective compound (yield: 78%).
Property: Melting point, 87.2° to 89.2° C.
IR(cm$^{-1}$, neat): $\nu_{MH}$3420, $\nu_{CO}$1734,1636,
Mass Spectrometric Analysis: Molecular formula: $C_{12}H_{21}NO_5$, Calculated: 259.1419, Found: 259.1425.
NMR($\delta$, CDCl$_3$): 0.98 (3H,s), 1.04 (3H,s), 1.43 (3H,s), 1.46 (3H,s), 2.62 (2H,t,J=7Hz), 3.29 (1H,d,J=12Hz), 3.68 (1H,d,J=12Hz), 3.43-3.66 (2H,m), 4.11 (1H,s), 6.90-7.10 (1H,m).

REFERENCE EXAMPLE 4

Preparation of Benzyl 3-[N-(5,5-Dimethyl-2-phenyl-1,3-dioxane-4-carbonyl-)amino]propionate A solution of 3.09 g of benzyl 3-[N-(2,4-dihydroxy-3,3,-dimethyl-1-oxo)amino]propionate, 6.90 g of benzaldehyde dimethylacetal, and 0.19 g of p-toluene-sulfonic acid in 100 ml of benzene was refluxed for 2 hours with removing water produced by azeotropy. After completion of the reaction, the reaction mixture was washed with saturated aqueous sodium bicarbonate solution, with water and then with saturated saline, and dried over anhydrous sodium sulfate. After removing the solvent by evapoation, the residue obtained was purified by silica gel column chromatography to obtain 3.18 g of the objective compound (yield: 80%).
Property: Oily
IR(cm$^{-1}$, neat): $\nu_{NH}$3456, $\nu_{CO}$1740, 1676,
Mass Spectrometric Analysis: Molecular formula: $C_{19}H_{27}NO_5$, Calculated: 397.1889, Found: 397.1882.
NMR($\delta$, CDCl$_3$): 1.08 (3H,s), 1.10 (3H,s), 2.62 (2H,t,J=6Hz), 3.68 (1H,d,J=11Hz), 3.45-3.64 (2H,m), 3.72 (1H,d,J=1Hz), 4.09 (1H,s), 5.10(2H,s), 5.51 (1H,s), 6.92-7.04 (1H,m), 7.38-7.52 (10H,m).

REFERENCE EXAMPLE 5

Preparation of Benzyl 3-[N-(3,3-Dimethyl-1,5-dioxaspiro[5,5]-dodecane-2-carbonyl)amino]propionate Benzyl 3-[N-(2,4-dihydroxy-3,3,-dimethyl-1-oxo)amino]-propionate (3.09 g and 1.47 g of cyclohexanone were reacted in the same manner as in Reference Example 4 to obtain 3.07 g of the objected compound (yield: 79%).
Property: Oily
IR(cm$^{-1}$, neat): $\nu_{CO}$1738, 1680
Mass Spectrometric Analysis: Molecular formula: $C_{22}H_{31}NO_5$, Calculated: 389.2202, Found: 389.2214.
NMR($\delta$, CDCl$_3$): 0.95 (3H,s), 1.03 (3H,s), 1.32-1.50 (4H,m), 1.54-1.70 (4H,m), 1.78-1.90 (2H,m), 2.62 (2H,t,J=7Hz), 3.25 (1H,d,J=12Hz), 3.46-3.66 (2H,m), 3.69 (1H,d,J=12Hz), 4.08 (1H,s), 5.14 (2H,s), 7.00-7.10 (1H,m), 7.30-7.42 (5H,m).

REFERENCE EXAMPLE 6

Preparation of 3-[N-(5,5-Dimethyl-2-phenyl-1,3-dioxane-4-carbonyl)amino]propionic Acid
Benzyl 3-[N-(5,5-Dimethyl-2-phenyl-1,3-dioxane-4-carbonyl)amino]propionate (1.0 g) was reacted in the same manner as in Reference Example 3 to obtain 0.77 g of the objctived compound (yield: quantitiative).
Property: Oily
IR(cm$^{-1}$, neat): $\nu_{NH}$3420, $\nu_{CO}$1732, 1636.
Mass Spectrometric Analysis: Molecular formula: $C_{16}H_{21}NO_5$, Calculated: 307.1419, Found: 307.1423.
NMR($\delta$, CDCl$_3$): 1.11 (3H,s), 2.62 (2H,t,J=7Hz), 3.28 (1H,d,J=12Hz), 3.44-3.64 (2H,m), 3.68 (1H,d,J=1Hz), 3.73 (1H,d,J=11Hz), 4.12 (1H,s), 5.51 (1H,s), 7.00-7.10 (1H,m), 7.38-7.45 (3H,m), 7.45-7.52 (2H,m).

REFERENCE EXAMPLE 7

Preparation of 3-[N-(3,3-Dimethyl-1,5-dioxaspiro[5,5]dodecane-2-carbonyl)amino]propionic Acid In a solution of 0.95 g of benzyl 3-[N-(3,3-dimethyl-1,5-dioxaspiro[5,5]-dodecane-2-carbonyl)amino]propionate in 20 ml of methanol was suspended 20 mg of 10% palladium-on-carbon, and the suspension was stirred at room temperature for one night under hydrogen gas atmosphere. After completion of the reaction, insoluble matter was filtered. Removal of the solvent by evaporation afforded 1.50 g of the objective compound.

Property: Oily.
IR(cm$^{-1}$, neat): $\nu_{CO}$1728, 1670.
Mass Spectrometric Analysis: Molecular formula: $C_{15}H_{25}NO_5$, Calculated: 299.1732, Found: 299.1718.
NMR($\delta$, CDCl$_3$): 0.99 (3H,s), 1.04 (3H,s), 1.32–1.51 (4H,m), 1.54–1.94 (7H,m), 2.64 (2H,t,J=6Hz), 3.26 (1H,d,J=12Hz), 3.71 (1H,d,J=12Hz), 3.46–3.64 (2H,m), 4.12 (1H,s), 7.08–7.14 (1H,m).

REFERENCE EXAMPLE 8

Preparation of 3-[N-(3,3-Dimethyl-1,5-dioxaspiro[5,5]dodecane-2-carbonyl)amino]propionic Acid Acetic anhydride (10.2 g) was added to a suspension 4.47 g of calcium pantothenate in 20 ml of pyridine, and the mixture was stirred for one night. After completion of the reaction, the reaction mixture was poured in ice water. After stirring for 2 hours, 1N Hydrochloric acid was added to the reaction mixture to adjust pH to a value of about 2, followed by extraction with ethyl acetate. The organic layer was washed with saturated saline, and dried over anhydrous sodium sulfate. After removal of the solvent, 4.19 g of the objective compound was obtained as a residue (yield: 69%).

Property: Oily.

REFERENCE EXAMPLE 9

Preparation of 4-Nitropheny 3-[N-(2,4-diacetoxy 3,3-dimethyl-1-oxobutyl)amino]propionate Dicyclohexylcarbodiimide (15.5 g) was added to a solution of 22.6 g of 3-[N-(2,4-diacetoxy-3,3-dimethyl-1-oxobutyl)amino]propionic acid and 10.4 g of p-nitrophenol in 500 ml of tetrahydrofuran, and the mixture was stired for one night. After completion of the reaction, insoluble matter was removed and the solvent was distilled off under reduced pressure. The residue was dissolved in ethyl acetate. The resulting solution was washed with saturated aqueous sodium bicarbonate solution, with water and then with saturated saline, and dried over anhydrous sodium sulfate. After removing the solvent by evaporation, 10.2 g of the objectived compound was obtained as a residue (yield: 32%).

Porperty: Oily
IR(cm$^{-1}$, neat): $\nu_{NH}$3456, $\nu_{CO}$1740, 1676.
Mass Spectrometric Analysis: Molecular formula: $C_{19}H_{24}N_2O_9$, Calculated: 424.1481, Found: 424.1467.
NMR($\delta$, CDCl$_3$): 1.04 (3H,s), 1.08 (3H,s), 2.06 (3H,s), 2.10 (3H,s), 2.84–2.91 (2H,m), 3.50–3.76 (2H,m), 3.86 (1H,d,J=11Hz), 6.06 (1H,d,J=11Hz), 4.93 (1H,s), 6.50–6.66 (1H,m), 7.29 (2H,d,J,7Hz), 8.28 (2H,d,7Hz).

REFERENCE EXAMPLE 10

Preparation of Benzyl 2-[N-(2,4-Dihydroxy-3,3-dimethylbutanoyl)-amino]acetate

A solution of 13.0 g of pantolactone, 8.3 g of glycine and potassium hydroxide (final concentration: 85%) in 100 ml of methanol was heated under reflux for 3 hours. The solvent was distilled off under reduced pressure. After drying, the residue was dissolved in 150 ml of dimethylformamide, and 18.8 g of benzyl bromide was added to the resulting solution, followed by stirring at room temperature for 20 hours. The reaction mixture was distilled under pressure, and the residue obtained was dissolved in water and extracted with ethyl acetate. The organic layer was washed with water and then with saturate saline, and dried over anhydrous sodium sulfate. The residue obtained was purified by silica gel column chromatography to obtain 12.8 g of the objective compound (yield: 43%).

NMR($\delta$, CDCl$_3$): 0.95 (3H,s), 1.60 (3H,s), 2.73 (2H,brs), 3.51 (1H,d,J=11Hz), 3.56 (1H,d,J=11Hz), 4.03–4.21 (2H,m), 4.09 (1H,s), 5.19 (2H,s), 7.23–7.28 (1H,m), 7.33–7.42 (5H,m).

REFERENCE EXAMPLE 11

Preparation of o-Oleoylaminoaniline

N,N'-Dicyclohexylcarbodiimide (2.27 g) was added to a solution of 2.82 g of oleic acid and 1.62 g of o-phenylenediamine in 50 ml of methylene chloride with stirring under ice cooling. The mixture was stirred at room temperature for one night. After completion of the reaction insoluble matter was filtered, followed by removal of the solvent by evaporation. The residue obtained was purified by silica gel column chromatography to obtain 2.84 g of the objective compound (yield: 76%).

Property: Oily
IR(cm$^{-1}$, neat): $\nu_{NH}$3284, $\nu_{CO}$1646
Mass Spectrometric Analysis: Molecular formula: $C_{24}H_{40}N_2O$, Calculated: 372.3140, Found: 372.3129, 0.88 (3H,t,J=7Hz), 1.18–1.45 (20H,m), 1.65–1.81 (2H,m), 1,90–2.09 (4H,m), 5.28–5.43 (2H,m), 6.76–6.83 (2H,m), 7.02–7.13 (2H,m), 7.17 (1H,d,J=8Hz).

REFERENCE EXAMPLE 12

Preparation of m-Oleoylaminoaniline

Oleic acid (2.82 g) and m-phenylenediamine (1.62 g) were reacted in the same manner as Reference Example 11 to obtain 2.60 g of the objective compound (yield: 70%).

Property: Oily.
IR(cm$^{-1}$, neat): $\nu_{NH}$3324, $\nu_{CO}$1658.
Mass Spectrometric Analysis: Molecular formula: $C_{24}H_{40}N_2O$, Calculated: 372.3140, Found: 372.3143.
NMR($\delta$, CDCl$_3$): 0.88 (3H,t,J=7Hz), 1.20–1.42 (20H,m), 1.64–1.78 (2H,m), 1.90–2.09 (4H,m), 2.32 (2H,t,J=7Hz), 3.70 (2H,brs), 5.29–5.40 (2H,m), 6.42 (1H,d,J=8Hz), 6.62 (1H,d,J=8Hz), 7.00 (1H,brs), 7.21 (1H,s).

REFERENCE EXAMPLE 13

Preparation of p-Oleoylaminoaniline

Oleic acid (2.82 g) and p-phenylenediamine (1.62 g) were reacted in the same manner as in Reference Example 11 to obtain 2.85 g of the objective compound (yield: 77%).
Property: Oily.
IR(cm$^{-1}$, neat): $\nu_{NH}$3294, $\nu_{CO}$1656.
Mass Spectrometric Analysis: Molecular formula: $C_{24}H_{40}N_2O$, Calculated: 372.3140, Found: 372.3138,
NMR($\delta$, CDCl$_3$): 0.88 (3H,t,J=7Hz), 1.18-1.42 (20H,m), 1.64-1.77 (2H,m), 1.92-2.09 (4H,m), 2.31 (2H,t,J=7Hz), 3.60 (2H,brs), 5.29-5.40 (2H,m), 6.65 (2H,d,J=9Hz), 6.92 (1H,brs), 7.26 (2H,d,J=9Hz).

REFERENCE EXAMPLE 14

Preparation of p-Oleoylaminoaniline

Oleic acid (2.82 g) and p-aminophnol (1.64 g) were reacted in the same manner as in Reference Example 11 to obtain 1.57 g of the objective compound (yield: 42%).
Property: Oily.
IR(cm$^{-1}$, neat): $\nu_{NH}$, $\nu_{CO}$1646,
Mass Spectrometric Analysis: Molecular formula: $C_{24}H_{39}NO_2$, Calculated: 373.2980, Found: 373.2988,
NMR($\delta$, CDCl$_3$): 0.88 (3H,t,J=7Hz), 1.20-1.42 (20H,m), 1.65-1.79 (2H,m), 1.89-2.09 (4H,m), 2.31 (2H,t,J=7Hz), 5.28-5.41 (2H,m), 6.77 (2H,d,9Hz), 7.04 (1H,brs), 7.32 (2H,d,J=9Hz).

REFERENCE EXAMPLE 15

Preparation of 2,4-Diacetoxy-N-[3-[(4-hydroxyphenyl)amino]-3-oxopropyl]-3,3-dimethylbutanamide 1-Ethyl-3-(3-dimethylaminopropyl)carbodiimide (2.30 g) was added to a solution of 3.03 g of 3-[N-(2,4-diacetoxy-3,3-dimethyl-1-oxobutyl)amino]propionic acid and 2.18 g of p-aminophenol in 50 ml of methylene chloride, and the mixture was stirred for one night. After completion of the reaction, the reaction mixture was washed with water, and dried over anhydrous sodium sulfate. After removing the solvent by evaporation, the residue obtained was purified by silica gel column chromatography to obtain 1.92 g of the objective compound was obtained as a residue (yield: 50%).
Property: Oily,
IR(cm$^{-1}$, neat): $\nu_{CO}$1750, 1660,
Mass Spectrometric Analysis: Molecular formula: $C_{19}H_{26}N_2O_7$, Calculated: 394.1740, Found: 394.1746,
NMR($\delta$, CDCl$_3$): 1.02 (3H,s), 1.06 (3H,s), 2.05 (3H,s), 2.07 (3H,s), 2.55 (2H,t,J=6Hz), 3.50-3.71 (2H,m), 3.84 (1H,d,J=12Hz), 4.03 (1H,d,J=12Hz), 4.90 (1H,s), 6.74-6.83 (1H,m), 6.79 (2H,d,J=8Hz), 7.35 (2H,d,J=8Hz), 7.47 (1H,brs).

REFERENCE EXAMPLE 16

Preparation of S-4-Aminophenyl 3-[N-(2,4,-Diacetoxy-3,3-dimethyl-1-oxobutyl)amino]propanethioate 3-[N-(2,4-Diacetoxy-3,3-dimethyl-1-oxobutyl)amino]propionic acid (1.52 g) and 1.00 g of p-aminothiophenol were reacted in the same manner as in Reference Example 11 to obtain 0.335 mg of the objective compound (yield: 16%)
Property: Oily.
Mass Spectrometric Analysis: Molecular formula: $C_{19}H_{26}N_2O_6S$, Calculated: 410.1511, Found: 410.1520.
NMR($\delta$, CDCl$_3$): 1.01 (3H,s), 1.06 (3H,s), 2.06 (3H,s), 2.11 (3H,s), 2.87 (2H,t,J=6Hz), 3.44-3.69 (2H,m), 3.81 (1H,d,J=11Hz), 4.03 (1H,d,J=11Hz), 4.97 (1H,s), 6.50 (1H,t,J=6Hz), 6.92 (2H,d,J=8Hz), 7.24 (2H,d,J=8Hz).

REFERENCE EXAMPLE 17

Preparation of S-4-Aminophenyl 9-Octadecenethioate

Oleic acid (2.82 g) and 1.88 g of p-aminothiophenol were reacted in the same manner as in Reference Example 11 to obtain 2.86 g of the objective compound (yield: 74%).
Property: Oily.
IR(cm$^{-1}$, neat): $\nu_{NH}$3500, $\nu_{CO}$1698,
Mass Spectrometric Analysis: Molecular formula: $C_{24}H_{39}NOS$, Calculated: 389.2752, Found: 389.2754.
NMR($\delta$, CDCl$_3$): 0.88 (3H,t,J=7Hz), 1.19-1.41 (20H,m), 1.62-1.75 (2H,m), 1.91-2.09 (4H,m), 2.60 (2H,t,J=7Hz), 3.83 (2H,brs), 5.29-5.41 (2H,m), 6.68 (2H,d,8Hz), 7.16 (2H,d,J=8Hz).

REFERENCE EXAMPLE 18

Preparation of N-(4-Hydroxyphenyl)-3-[N-(2,2,5,5-tetramethyl-1,3-dioxane-4-carbonyl)amino]propanamide 3-[N-(2,2,5,5-Tetramethyl-1,3-dioxane-4-carbonyl)amino]propionic acid (1.04 g) and 0.665 g of p-aminophenol were reacted in the same manner as in Reference Example 15 to obtain 1.37 g of the objective compound (yield: 98%).
Property: Oily.
IR(cm$^{-1}$, neat): $\nu_{CO}$1660.
Mass Spectrometric Analysis: Molecular formula: $C_{18}H_{26}N_2O_5$, Calculated: 350.1841, Found: 350.1846.
NMR($\delta$, CDCl$_3$): 0.97 (3H,s), 1.04 (3H,s), 1.41 (3H,s), 1.45 (3H,s), 2.26 (2H,t,J=6Hz), 3.50-3.72 (2H,m), 3.28 (1H,d,J=12Hz), 3.68 (1H,d,J=12Hz), 4.10 (1H,s), 6.78 (2H,d,J=8Hz), 7.13 (1H,d,J=6Hz), 7.32 (2H,d,J=8Hz), 8.02 (1H,s).

REFERENCE EXAMPLE 19

Preparation of N-(4-Hydroxyphenyl)-3-[N-(2,2,5,5-tetramethyl-1,3-dioxane-4-carbonyl)amino]propanamide 3-[N-(2,2,5,5-Tetramethyl-1,3-dioxane-4-carbonyl)amino]propionic acid (1.30 g) and 1.00 g of p-aminothiophenol were reacted in the same manner as in Reference Example 15 to obtain 0.28 g of the objective compound (yield: 15%).
IR(cm$^{-1}$, neat): $\nu_{CO}$1692,
Mass Spectrometric Analysis: Molecular formula: $C_{18}H_{26}N_2O_4S$, Calculated: 366.16, Found: 366.1608.
NMR($\delta$, CDCl$_3$): 1.00 (3H,s), 1.04 (3H,s), 1.42 (3H,s), 1.45 (3H,s), 2.78-2.97 (2H,m), 3.29 (1H,d,J=11Hz), 3.45-3.71 (2H,m), 3.69 (1H,d,J=11Hz), 4.08 (1H,s), 6.69 (2H,d,J=8Hz), 6.84-6.92 (1H,m), 7.15 (2H,d,J=8Hz).

REFERENCE EXAMPLE 20

Preparation of p-Oleoylaminophenol

Sodium carbonate (1.27 g) was added to a solution of 1.09 g of 2-aminophenol in a mixed solvent composed of 20 ml of ethyl acetate and 20 ml of water. To the resulting mixture was added a solution of 3.01 g of oleoyl chloride in 10 ml of ethyl acetate portion-wise with stirring under ice cooling. The stirring was continued for additional 2 hours. After completion of the reaction, the organic layer was separated, washed with water and then with saturated saline, and dried over anhydrous sodium sulfate. After removal of the solvent by evaporation, the residue obtained was purified by silica gel column chromatography to obtain 3.40 g of the objective compound (yield: 91%).
Property: Oily.
IR(cm$^{-1}$, neat): $\nu_{CO}$1646.
Mass Spectrometric Analysis: Molecular formula: $C_{24}H_{39}NO_2$, Calculated: 373.2980, Found: 373.2988.
NMR($\delta$, CDCl$_3$): 0.88 (3H,t,J=7Hz), 1.18-1.45 (20H,m), 1.66-1.80 (2H,m), 1.92-2.10 (4H,m), 2.45 (2H,d,J=7Hz), 5.28-5.40 (2H,m), 6.85 (2H,d,8Hz), 6.97 (1H,d,J=8Hz), 7.02 (1H,d,J=8Hz), 7.13 (1H,d,J=8Hz), 7.45 (1H,brs).

REFERENCE EXAMPLE 21

Preparation of N-(2-Hydroxyphenyl)-3-[N-(2,2,5,5-tetramethyl-1,3-dioxane-4-carbonyl)amino]propanamide 3-[N-(2,2,5,5-Tetramethyl-1,3-dioxane-4-carbonyl)amino]propionic acid (0.26 g) and 0.13 g of o-aminophenol were reacted in the same manner as in Reference Example 15 to obtain 0.34 g of the objective compound (yield: 98%).
Property: Oily
IR(cm$^{-1}$, neat): $\nu_{CO}$1660
Mass Spectrometric Analysis: Molecular formula: $C_{18}H_{26}N_2O_5$, Calculated: 350.1841, Found: 350.1843.
NMR($\delta$, CDCl$_3$): 0.97 (3H,s), 1.03 (3H,s), 1.42 (3H,s), 1.46 (3H,s), 2.77 (2H,t,J=6Hz), 3.28 (1H,d,J=12Hz), 3.59-3.77 (2H,m), 4.11 (1H,s), 6.86 (1H,t,J=8Hz), 7.01 (1H,d,J=8Hz), 7.08-7.22 (3H,m) 8.80 (1H,s).

REFERENCE EXAMPLE 22

Preparation of N-(2-aminophenyl)-3-[N-(2,2,5,5-tetramethyl-1,3-dioxane-4-carbonyl)amino]propanamide 3-[N-(2,2,5,5-Tetramethyl-1,3-dioxane-4-carbonyl)amino]propionic acid (3.89 g) and 2.16 g of o-phenylenediamine were reacted in the same manner as in Reference Example 15 to obtain 2.48 g of the objective compound (yield: 47%).
Property: Oily.
IR(cm$^{-1}$, neat): $\nu_{CO}$1660.
Mass Spectrometric Analysis: Molecular formula: $C_{18}H_{27}N_3O_4$, Calculated: 349.2001, Found: 349.1993.
NMR($\delta$, CDCl$_3$): 0.99 (3H,s), 1.03 (3H,s), 1.42 (3H,s), 1.45 (3H,s), 2.67 (2H,t,J=6Hz), 3.59-3.70 2H,m), 3.28 (1H,d,J=12Hz), 3.68 (1H,d,J=12Hz), 4.10 (1H,s), 6.72.-6.82 (2H,m), 7.03-7.16 2H,m), 7.20 (1H,d,J=8Hz), 7.87 (1H,s).

REFERENCE EXAMPLE 23

Preparation of m-Linoleoylaminoaniline

Linolic acid (0.841 g) and 0.541 g of o-phenylenediamine were reacted in the same manner as in Reference Example 11 to obtain 0.79 g of the objective compound (yield: 62%).
Property: Oily.
IR(cm$^{-1}$, neat): $\nu_{CO}$1646
Mass Spectrometric Analysis: Molecular formula: $C_{24}H_{38}N_2O$, Calculated: 370.2984, Found: 370.2981.
NMR($\delta$, CDCl$_3$): 0.89 (3H,t,J=7Hz), 1.22-1.43 (14H,m), 1.63-1.88 (2H,m), 1.98-2.11 (4H,m), 2.32 (2H,t,J=7Hz), 2.77 (2H,t,J=6Hz), 5.28.-5.46 (4H,m), 6.47 (1H,d,J=8Hz), 6.69 (1H,d,8Hz), 7.07 (1H,t,J=8Hz), 7.14 (1H,s), 7.24 (1H,s).

REFERENCE EXAMPLE 24

Preparation of o-Lauroylaminoaniline p-Phenylenediamine (342 mg) and 219 mg of 1-lauroyl chloride were reacted in the same manner as in Reference Example 20 to obtain 250 mg of the objective compound (yield: 86%).
Property: Oily.
IR(cm$^{-1}$, neat): $\nu_{CO}$1651.
Mass Spectrometric Analysis: Molecular formula: $C_{18}H_{30}N_2O$, Calculated: 290.2358, Found: 290.2362.
NMR($\delta$, CDCl$_3$): 0.88 (3H,t,J=7Hz), 1.17-1.42 (16H,m), 1.63-1.78 (2H,m), 2.31 (2H,t,J=7Hz), 3.581 (2H,bris), 6.64 (2H,d,z), 6.98 (1H,brs), 7.26 (2H,d,J=9Hz).

REFERENCE EXAMPLE 25

Preparation of p-Linolenoylaminoaniline

Linolenic acid (835 mg) and 546 mg of p-aminophenol were reacted in the same manner as in Reference Example 11 to obtain 1.03 g of the objective compound (yield: 55%)
Porperty: Oily.
IR(cm$^{-1}$, neat): $\nu_{CO}$1646.
Mass Spectrometric Analysis: Molecular formula: $C_{24}H_{35}NO_2$, Calculated: 369.2667, Found: 369.2672.
NMR($\delta$, CDCl$_3$): 0.97 (3H,t,J=7Hz), 1.19-1.44 (8H,m), 1.56-1.77 (2H,m), 1.98-2.12 (4H,m), 2.33 (2H,t,J=7Hz), 2.71-2.88 (4H,m), 5.26-5.45 (6H,m), 6.77 (2H,d,9Hz), 7.05 (1H,s), 7.31 (2H,d,J=9Hz).

REFERENCE EXAMPLE 26

Preparation of trans-2-(Oleoylamino)cyclohexylamine

Sodium methoxide (0.60 g) was added to a solution of 1.14 g of trans-1,2-diaminocyclohexane and 2.96 g of methyl oleate in 15 ml of benzene, and the mixture was heated under reflux for 20 hours. After completion of the reaction, the solvent was distilled off under reduced pressure and the residue was dissolved in ethyl acetate-water. The organic layer was washed with saturated saline, and dried over anhydrous sodium sulfate. After drying it over anhydrous sodium sulfate, the residue obtained was purified by silica gel column chromatography to obtain 2.54 g of the objective compound (yield: 68%).
Property: Oily.
Mass Spectrometric Analysis: Molecular formula: $C_{24}H_{46}N_2O$, Calculated: 378.3610, Found: 378.3611.
NMR($\delta$, CDCl$_3$): 0.88 (3H,t,J=7Hz), 1.12-1.48 (24H,m), 1.53-1.79 (4H,m), 1.91 (6H,m), 2.18-2.35 (2H,m), 2.52-2.95 (3H,m), 3.62-3.78 (1H,m), 5.28-5.40 (2H,m), 6.08-6.20 (1H,m).

REFERENCE EXAMPLE 27

Preparation of (S,S)-2-(Oleoylamino)cyclohexylamine (S,S)-1,2-Diaminocyclohexane (1.14 g) and 2.96 g of methyl oleate were reacted in the same manner as in Reference Example 26 to obtain 2.41 g of the objective compound (yield: 65%)
Property: Oily.
Mass Spectrometric Analysis: Molecular formula: $C_{24}H_{46}N_2O$, Calculated: 378.3610, Found: 378.3612.
NMR($\delta$, CDCl$_3$): 0.88 (3H,t,J=7Hz), 1.12-1.48 (24H,m), 1.53-1.79 (4H,m), 1.91 (6H,m), 2.18-2.35 (2H,m), 2.52-2.95 (3H,m), 3.62-3.78 (1H,m), 5.28-5.40 (2H,m), 6.08-6.20 (1H,m).

REFERENCE EXAMPLE 28

Preparation of (1R,2R)-2-(Oleoylamino)cyclohexanol (1R,2R)-2-Aminocyclohexanol (1.15 g) and 3.0 g of oleyl chloride were reacted in the same manner as in Reference Example 20 to obtain 3.74 g of the objective comound (yield: 99%).

Property: Oily.

Mass Spectrometric Analysis: Molecular formula: $C_{24}H_{45}NO_2$, Calculated: 379.3450, Found: 379.3453.

NMR($\delta$, $CDCl_3$): 0.88 (3H,t,J=7Hz), 1.10-1.42 (24H,m), 1.57-1.78 (4H,m), 1.89-2.10 (6H,m), 2.22 (2H,t,J=7Hz), 3.32 (1H,ddd,J=11Hz,11Hz,5Hz), 3.58-3.70 (1H,m), 5.28-5.50 (3H,m).

REFERENCE EXAMPLE 29

Preparation of (1S,2S)-2-(Oleoylamino)cyclohexanol (1S,2S)-2-Aminocyclohexanol (1.15 g) and 3.0 g of oleyl chloride were reacted in the same manner as in Reference Example 20 to obtain 3.76 g of the objective compound (yield: 99%).

Property: Oily.

Mass Spectrometric Analysis: Molecular formula: $C_{24}H_{45}NO_2$, Calculated: 379.3450, Found: 379.3453.

NMR($\delta$, $CDCl_3$): 0.88 (3H,t,J=7Hz), 1.10-1.42 (24H,m), 1.57-1.78 (4H,m), 1.89-2.10 (6H,m), 2.22 (2H,t,J=7Hz), 3.32 (1H,ddd,J=11Hz,11Hz, 5Hz), 3.58-3.70 (1H,m), 5.28-5.50 (3H,m).

REFERENCE EXAMPLE 30

Preparation of (1R,2R)-2-(Stearoylamino)cyclohexanol (1R,2R)-2-Aminocyclohexanol (1.15 g) and 3.02 g of stearyl chloride were reacted in the same manner as in Reference Example 20 to obtain 3.0 g of the objective compound (yield: 100%).

Property: Oily.

Mass Spectrometric Analysis: Molecular formula: $C_{24}H_{47}NO_2$, Calculated: 381.3606, Found: 381.3611.

NMR($\delta$, $CDCl_3$): 0.88 (3H,t,J=7Hz), 1.11-1.41 (32H,m), 1.57-1.78 (4H,m), 1.89-2.11 (2H,m), 2.22 (2H,t,J=7Hz), 3.31 (1H,ddd,J=11Hz,11Hz, 5Hz), 3.58-3.70 (1H,m), 5.42-5.51 (1H,m).

REFERENCE EXAMPLE 31

Preparation of (1S,2S)-2-(Linoleoylamino)cyclohexanol (1S,2S)-2-Aminocyclohexanol (1.15 g) and 2.98 g of linolyl chloride were reacted in the same manner as in Reference Example 20 to obtain 3.76 g of the objective compound (yield: 99%).

Property: Oily.

Mass Spectrometric Analysis: Molecular formula: $C_{24}H_{43}NO_2$, Calculated: 377.3293, Found: 377.3299.

NMR($\delta$, $CDCl_3$): 0.89 (3H,t,J=7Hz), 1.12-1.41 (18H,m), 1.58-1.77 (4H,m), 1.89-2.18 (6H,m), 2.22 (2H,t,J=8Hz), 2.77 (2H,t,J=6Hz), 3.31 (2H,ddd,J=11Hz,11Hz, 5Hz), 3.59-3.70 (1H,m), 5.29-5.47 (5H,m).

REFERENCE EXAMPLE 32

Preparation of (1S,2S)-2-(N-Benzyl-N-hexylcarbamoyl)aminocyclohexanol

A solution of 470 mg of phenyl chlorocarbonate in 5 ml of ethyl acetate was added portion-wise to a solution of 345 mg of (1S,2S)-2-aminocyclohexanol and 424 mg of sodium carbonate in a mixed solvent composed of 10 ml of ethyl acetate and 10 ml of water with stirring under ice cooling. After completion of the addition, the resulting mixture was stirred for additional 2 hours. After completion of the reaction, the aqueous layer was separated and extracted with ethyl acetate. The extract was combined with the organic layer, which was then washed with saturated saline. After drying it over anhydrous sodium sulfate, the combined organic layer was distilled to remove the solvent. Then, N-benzylhexylamine (1.15 g) was added to the residue obtained, and the mixture was stirred at 100° C. for 1 hour. After completion of the reaction, the residue obtained was purified by silica gel column chromatography to obtain 866 mg of the objective compound (yield: 87%).

NMR($\delta$, $CDCl_3$): 0.87 (3H,t,J=7Hz), 0.96-2.08 (16H,m), 3.15-3.54 (4H,m), 4.25 (1H,d,J=6Hz), 4.47 (2H,s), 4.67 (1H,d,J=3Hz), 7.20-7.41 (5H,m).

REFERENCE EXAMPLE 33

Preparation of (S)-1-(t-Butoxycarbonel)-2-(oleoylaminomethyl)-pyrrolidine (S)-2-Aminomethyl-1-(t-butoxycarbonyl)pyrrolidine (607 mg) and 903 mg of oleyl chloride were reacted in the same manner as in Reference Example 20 to obtain 1.16 g of the objective compound (yield: 83%).

Property: Oily.

Mass Spectrometric Analysis: Molecular formula: $C_{28}H_{52}N_2O_3$, Calculated: 464.3977, Found: 464.3969.

NMR($\delta$, $CDCl_3$): 0.88 (3H,t,J=7Hz), 1.16-1.37 (20H,m), 1.16-1.37 (20H,m), 1.48 (9H,s), 1.53-2.09 (10H,m), 2.17 (2H,t,J=7Hz), 3.13-3.45 (4H,m), 3.97-4.10 (1H,m), 5.28-5.41 (2H,m), 7.42 (1H,brs).

REFERENCE EXAMPLE 34

Preparation of (R)-1-(t-Butoxycarbonel)-2-(oleoylaminomethyl)-pyrrolidine (R)-2-Aminomethyl-1-(t-butoxycarbonyl)pyrrolidine (401 mg) and 600 mg of oleyl chloride were reacted in the same manner as in Reference Example 20 to obtain 816 mg of the objective compound (yield: 88%).

Property: Oily.

Mass Spectrometric Analysis: Molecular formula: $C_{28}H_{52}N_2O_3$, Calculated: 464,3977, Found: 464.3969.

NMR($\delta$, $CDCl_3$): 0.88 (3H,t,J=7Hz), 1.16-1.37 (20H,m), 1.48 (9H,s), 1.53-2.09 (10H,m), 2.17 (2H,t,J=7Hz), 3.13-3.45 (4H,m), 3.97-4.10 (1H,m), 5.28-5.41 (2H,m), 7.42 (1H,brs).

REFERENCE EXAMPLE 35

(A) Preparation of (R)-1-(t-Butoxycarbonel)-2-(oleoylaminomethyl)pyrrolidine

3-Amino-1-(t-butoxycarbonyl)piperidine (400 mg) and 600 mg of oleyl chloride were reacted in the same manner as in Reference Example 20 to obtain 742 mg of the ojective compound (yield: 85%).

Property: Oily.

Mass Spectrometric Analysis: Molecular formula: $C_{28}H_{52}N_2O_3$, Calculated: 464.3977, Found: 464.3984.

NMR($\delta$, $CDCl_3$): 0.88 (3H,t,J=7Hz), 1.17-1.41 (20H,m), 1.49-1.84 (6H,m), 1.91-2.09 (4H,m), 2.15 (2H,t,J=7Hz), 2.15 (2H,t,J=7Hz), 3.22-3.53 (4H,m), 3.92-4.03 (1H,m), 5.28-5.41 (2H,m), 5.47-5.62 (1H,m).

(B) Preparation of 3-Oleoylaminopiperidine

A solution 464 mg of 1-(t-butoxycarbonyl)-3-(oleoylamino)piperidine in 6 ml of 50% trifluoroacetic acid-methylene chloride was stirred at room temperature for 1 hour. After completion of the reaction, the solvent was distilled off. The residue obtained was dissolved in 20 ml of ethyl acetate. After adding saturated aqueous sodium carbonate solution to the solution to neutralize it, the organic layer was separated. The organic layer was washed with saturated saline, and dried over anhydrous sodium sulfate, followed by removal of the solvent therefrom by evaporation. The residue obtained was purified by silica gel column chromatography to obtain 332 g of the objective compound (yield: 91%).

Mass Spectrometric Analysis: Molecular formula: $C_{23}H_{44}N_2O$, Calculated: 364.3453, Found: 364.3451.

NMR($\delta$, CDCl$_3$): 0.88 (3H,t,J=7Hz), 1.17-1.39 (20H,m), 1.54-1.86 (6H,m), 1.90-2.08 (4H,m), 2.20 (2H,t,J=7Hz), 2.70-3.07 (4H,m), 4.00-4.07 (1H,m), 5.28-5.44 (2H,m), 6.49-6.63 (1H,m).

REFERENCE EXAMPLE 36

(A) Preparation of 1-(t-Butoxycarbonel)-3-[3-[N-(2,2,5,5-Tetramethyl-1,3-dioxane-4-carbonyl)amino]propanoyl]aminopiperidine 3-Amino-1-(t-butoxycarbonyl)piperidine (681 mg) and 0.88 g of 3-[N-(2,2,5,5-Tetramethyl-1,3-dioxane-4-carbonyl)amino]propionic acid were reacted in the same manner as in Reference Example 25 to obtain 1.38 g of the objective compound (yield: 97%).

Property: Oily.

Mass Spectrometric Analysis: Molecular formula: $C_{22}H_{39}N_3O_6$, Calculated: 441.2838, Found: 441.2861.

NMR($\delta$, CDCl$_3$): 0.97-0.98 (3H,m), 1.05 (3H,s), 1.42-1.43 (3H,m), 1.46 (10H,s), 2.43 (2H,t,J=7Hz), 3.05-3.27 (2H,m), 3.28 (1H,d,J=12Hz), 3.36-3.67 (5H,m), 3.69 (1H,d,J=12Hz), 3.87-4.00 (1H,m), 4.07-4.08 (1H,m), 5.93-6.02 (1H,m), 6.99-7.08 (1H,m).

REFERENCE EXAMPLE 37

Preparation of 1-Oleoyl-4-hydroxypiperidine

4-Hydroxypiperidine (2.02 g) and oleyl chloride (6 g) were reacted in the same manner as in Reference Example 20 to obtain 5.8 g of the objective compound (yield: 79%).

Property: Oily.

IR(cm$^{-1}$, neat): $\nu_{NH}$3428, $\nu_{CO}$1628.

Mass Spectrometric Analysis: Molecular formula: $C_{23}H_{43}NO_2$, Calculated: 365.3293, Found: 365.3309.

NMR($\delta$, CDCl$_3$): 1.88 (3H,t,J=7Hz), 1.22-1.40 (2H,s), 1.42-1.68 (4H,s), 1.82-2.06 (6H,m), 2.33 (2H,t,J=7Hz), 3.10-3.28 (2H,m), 3.68-3.82 (1H,m), 3.88-3.98 (1H,m), 4.02-4.18 (1H,m), 5.30-5.42 (2H,m).

REFERENCE EXAMPLE 38

Preparation of 1-Oleoyl-3-hydroxypiperidine

3-Hydroxypiperidine (1.38 g) and oleyl chloride (3.01 g) were reacted in the same manner as in Reference Example 20 to obtain 3.33 g of the objective compound (yield: 91%).

Property: Oily.

IR(cm$^{-1}$, neat): $\nu_{OH}$3428, $\nu_{CO}$1628.

Mass Spectrometric Analysis: Molecular formula: $C_{23}H_{43}NO_2$, Calculated: 365.3293, Found: 365.3286.

NMR($\delta$, CDCl$_3$): 0.88 (3H,t,J=7Hz), 1.20-1.39 (20H,m), 1.40-2.09 (10H,m), 2.32 (2H,t,J=7Hz), 3.18-3.35 (2H,m), 3.67-3.84 (5H,m), 5.28-5.40 (2H,m).

REFERENCE EXAMPLE 39

Preparation of (R)-1-Oleoyl-2-pyrrolidinemethanol

D-2-pyrrolidinemethanol (405 mg) and oleyl chloride (1.20 g) were reacted in the same manner as in Reference Example 20 to obtain 1.46 g of the ojective compound (yield: 100%).

Property: Oily.

IR(cm$^{-1}$, neat): $\nu_{OH}$3430, $\nu_{CO}$1625.

Mass Spectrometric Analysis: Molecular formula: $C_{23}H_{43}NO_2$, Calculated: 365.3293, Found: 365.3290.

NMR($\delta$CDCl$_3$): 0.83 (3H,t,J=7Hz), 1.18-1.48 (20H,m), 1.50-1.71 (3H,m), 1.79-2.10 (7H,m), 2.30 (2H,t,J=7Hz), 3.41-3.69 (4H,m), 4.18-4.27 (1H,m), 5.29-5.42 (2H,m).

REFERENCE EXAMPLE 40

Preparation of (S)-1-Oleoyl-2-pyrrolidinemethanol

L-2-pyrrolidinemethanol (506 mg) and oleyl chloride (1.50 g) were reacted in the same manner as in Reference Example 20 to obtain 1.73 g of the ojective compound (yield: 100%).

Property: Oily.

IR(cm$^{-1}$, neat): $\nu_{OH}$3430, $\nu_{CO}$1625.

Mass Spectrometric Analysis: Molecular formula: $C_{23}H_{43}NO_2$, Calculated: 365.3293, Found: 365.3288.

NMR($\delta$, CDCl$_3$): 0.88 (3H,t,J=7Hz), 1.88-1.48 (20H,m), 1.50-1.71 (3H,m), 1.79-2.10 (2H,t,J=7Hz), 2.30 (2H,t,J=7Hz), 3.41-3.69 (4H,m), 4.18-4.27 (1H,m), 5.29-5.42 (2H,m).

REFERENCE EXAMPLE 41

Preparation of (S)-1-Stearoyl-2-pyrrolidinemethanol

L-2-pyrrolidinemethanol (101 mg) and stearyl chloride (303 mg) were reacted in the same manner as in Reference Example 20 to obtain 366 mg of the ojective compound (yield: 100%).

Property: Oily.

Mass Spectrometric Analysis: Molecular formula: $C_{23}H_{45}NO_2$, Calculated: 367.3450, Found: 367.3471.

NMR($\delta$, CDCl$_3$): 0.88 (3H,t,J=7Hz), 1.17-1.47 (28H,m), 1.52-1.69 (3H,m), 1.79-2.11 (3H,m), 2.30 (2H,t,J=7Hz), 3.41-3.70 (4H,m), 4.17-4.28 (1H,m).

REFERENCE EXAMPLE 42

Preparation of (S)-1-Linoloyl-2-pyrrolidinemethanol

L-2-pyrrolidinemethanol (101 mg) and linolyl chloride (315 mg) were reacted in the same manner as in Reference Example 20 to obtain 360 mg of the ojective compound (yield: 100%).

Property: Oily.

Mass Spectrometric Analysis: Molecular formula: $C_{23}H_{41}NO_2$, Calculated: 363.3137, Found: 363.3152.

NMR($\delta$, CDCl$_3$): 0.89 (3H,t,J=7Hz), 1.21-1.44 (14H,m), 1.52-1.76 (3H,m), 1.77-2.11 (7H,m), 2.30 (2H,t,J=7Hz), 2.77 (2H,t,J=6Hz), 3.42-3.70 (4H,m), 4.18-4.28 (1H,m), 5.28-5.44 (4H,m).

REFERENCE EXAMPLE 43

(A) Preparation of
(S)-1-Benzyloxycarbonyl-2-[1-oxo-3-[N-(2,2,5,5-tetramethyl-1,3-dioxane-4-carbonyl)amino]propyl-aminomethylpyrrolidine (S)-2-Aminomethyl-1-benzyloxycarbonylpyrrolidine (234 mg) and 3-[N-(2,2,5,5-tetramethyl-1,3-dioxane-4-carbonyl)amino]-propionic acid (259 mg) were reacted in the same manner as in Reference Example 25 to obtain 424 mg of the ojective compound (yield: 89%).
Property: Oily.
Mass Spectrometric Analysis: Molecular formula: $C_{25}H_{37}N_3O_6$, Calculated: 475.2682, Found: 475.2701.
NMR($\delta$, CDCl$_3$): 0.98 (3H,s), 1.04 (3H,s), 1.42 (3H,s), 1.46 (3H,s), 1.62-2.13 (4H,m),2.30-2.44 (2H,m), 3.16-3.62 (4H,m), 3.27 (1H,d,J=12Hz), 3.68 (1H,d,J=12Hz), 3.92-4.09 (1H,m), 4.07 (1H,s), 5.07-5.24 (2H,m), 7.05-7.16 (1H,m), 7.17-7.25 (1H,m), 7.28-7.48 (5H,m).

(B) Preparation of
(S)-2-[1-Oxo-3-(2,2,5,5,-tetramethyl-1,3-dioxane-4-carbonyl)amino]propyl]aminomethylpyrrolidine (S)-1-Benzyloxycarbonyl-2-[1-Oxo-3-(2,2,5,5,-tetramethyl-1,3-dioxane-4-carbonylaminopropyl-)aminomethylpyrrolidine (424 mg) was reacted in the same manner as in Reference Example 7 to obtain 298 mg of the ojective compound (yield: 98%).
Property: Oily.
Mass Spectrometric Analysis: Molecular formula: $C_{17}H_{31}N_3O_4$, Calculated: 341.2314, Found: 341.2327.
NMR($\delta$, CDCl$_3$): 1.00 (3H,s), 1.01 (3H,s), 1.45 (3H,s), 1.47 (3H,s), 1.58-1.78 (1H,m), 1.82-2.15 (3H,m), 2.36-2.56 (2H,m), 3.07-3.85 (9H,m), 4.12 (1H,s) 7.09 (1H,t,J=6Hz), 7.48 (1H,t,J=6Hz).

REFERENCE EXAMPLE 44

Preparation of
(R)-1-Benzyloxycarbonyl-2-[1-oxo-3-(2,2,5,5-tetramethyl-1,3-dioxane-4-carbonylamino)propyl]aminomethylpyrrolidine (R)-2-Aminomethyl-1-benzyloxycarbonylpyrrolidine (750 mg) and 3-[N-(2,2,5,5-tetramethyl-1,3-dioxane-4-carbonyl)amino]propionic acid (829 mg) were Example reacted in the same manner as in Reference Example 25 to obtain 1.10 g of the ojective compound (yield: 72%).
Property: Oily.
Mass Spectrometric Analysis: Molecular formula: $C_{25}H_{37}N_3O_6$, Calculated: 475.2682, Found: 475.2701.
NMR($\delta$, CDCl$_3$): 0.96 (3H,s), 1.03 (3H,s), 1.41 (3H,s), 1.46 (3H,s), 1.65-2.17 (4H,m), 2.33 (2H,t,J=6Hz), 3.14-3.32 (1H,m), 3.27 (1H,d,J=12Hz), 3.35-3.63 (5H,m), 3.68 (1H,d,J=12Hz), 3.93-4.09 (1H,s) 4.07 (1H,s), 5.07-5.28 (2H,m), 7.01-7.16 (1H,m), 7.20-7.44 (6H,m).

REFERENCE EXAMPLE 45

Preparation of 1-Oleoylpiperazine

A solution of 3.0 g of oleyl chloride in 10 mg of methylene chloride was added portion-wise to a solution of 4.3 g of piperazine in 30 ml of methylene chloride with stirring under ice cooling. After stirring the mixture in situ for additional 2 hours, 10 ml of water was added to the reaction mixture to separate the organic layer. The organic layer was further washed with water and dried over anhydrous sodium sulfate, followed by removal of the solvent by evaporation. The residue obtained was purified by silica gel column chromatography to obtain 2.68 g of the objective compound (yield: 76%).
Property: Oily.
Mass Spectrometric Analysis: Molecular formula: $C_{22}H_{42}N_2O$, Calculated: 350.3297, Found: 350.3308.
NMR($\delta$, CDCl$_3$): 0.88 (3H,t,J=7Hz), 1.18-1.39 (20H,m), 1.62-1.78 (2H,m), 1.91-2.07 (4H,m), 2.31 (2H,t,J=7Hz), 2.90-3.00 (4H,m), 3.62-3.73 (4H,m), 3.62-3.73 (4H,m), 5.28-5.41 (2H,s).

REFERENCE EXAMPLE 46

Preparation of 1-Oleoyltetrahydro-1,4-diazepine

Tetrahydro-1,4-diazepine (5.0 g) and 3.0 g of oleyl chloride were Example reacted in the same manner as in Reference Example 44 to obtain 2.76 g of the objective compound (yield: 75%).
Property: Oily.
Mass Spectrometric Analysis: Molecular formula: $C_{23}H_{44}N_2O$, Calculated: 364.3453, Found: 364.3451.
NMR($\delta$, CDCl$_3$): 0.88 (3H,t,J=7Hz), 1.21-1.39 (20H,m), 1.59-2.08 8H,m), 2.27-2.38 (2H,m), 2.85-3.01 (4H,m), 3.50-3.68 (4H,m), 5.29-5.40 (2H,m).

REFERENCE EXAMPLE 47

(A) Preparation of
1-Benzyloxycarbonyl-4-[1-oxo-3-[N-(2,2,5,5,-tetramethyl-1,3-dioxane-4-carbonyl)amino]propyl)amino]piperazine 3-[N-(2,2,5,5-tetramethyl-1,3-dioxane-4-carbonyl)amino]propionic acid (5.18 g) and 6.60 g of 1-benzyloxycarbonyl-piperazine were reacted in the same manner as in Reference Example 25 to obtain 8.60 g of the ojective compound (yield: 94%).
Property: Oily.
IR(cm$^{-1}$, neat): $\nu_{CO}$1706, 1648.
Mass Spectrometric Analysis: Molecular formula: $C_{24}H_{35}N_3O_6$, Calculated: 461.2525, Found: 461.2537.
NMR($\delta$, CDCl$_3$): 0.95 (3H,s), 1.03 (3H,s), 1.41 (3H,s), 1.46 (3H,s), 2.49-2.64 (2H,m), 3.27 (1H,d,J=12Hz), 3.35-3.62 (10H,m), 3.67 (1H,d,J=12Hz), 4.06 (1H,m), 5.15 (2H,s), 7.09 (1H,t,J=6Hz), 7.28-7 43 (5H,m).

(B) Preparation of 1-[1-Oxo-3-[N (2,2,5,5-tetramethyl-1,3-dioxane-4-carbonyl)amino]-propyl]piperazine 1-Benzyloxycarbonyl-4-[1-oxo-3-[N-(2,2,5,5-tetramethyl-1,3-dioxane-4-carbonyl)amino]propyl]piperazine (1.4 g) was reacted in the same manner as in Reference Example 7 to obtain 0.993 g of the ojective compound (yield: 100%).
Property: Oily.
Mass Spectrometric Analysis: Molecular formula: $C_{16}H_{29}N_3O_4$, Calculated: 327.2158, Found: 327.2166.
NMR($\delta$, CDCl$_3$): 0.97 (3H,s), 1.04 (3H,s), 1.42 (3H,s), 1.47 (3H,s), 2.47-2.63 (2H,m), 2.79-2.97 (4H,m), 3.40-3.76 (7H,m), 3.28 (1H,d,J=12Hz), 4.07 (1H,s), 7.12 (1H,t,J=6Hz).

EXAMPLE 1

Preparation of
N-[2-(Oleoylamino)phenyl]-3-[N-(2,2,5,5-tetramethyl-1,3-dioxane-4-carbonyl)amino]propanamide 1-Ethyl-3-(3-dimethylaminopropyl)carbodiimide hydrochloride (211 mg) was added to a solution of 372 mg of 2-oleoylaminoaniline and 259 mg of 3-[N-(2,2,5,5-tetramethyl-1,3-dioxane-4-carbonyl)amino]propionic acid in 30 ml of methylene chloride under ice cooling. The mixture was stirred in situ for one night. The reaction mixture was washed with water and dried over anhydrous sodium sulfate, filtered and the filtate evaporation under vacuum to obtain the crude title products. Then, the residue obtained was subjected to silica gel column chromatography to obtain 500 mg of the title compound (yield: 82%).

Property: Oily.

Specific Rotary Power $[\alpha]_D$: +29.0°(C=1.0, CHCl$_3$).

IR(cm$^{-1}$, neat): $\nu_{C=O}$1664.

Mass Spectrometric Analysis: Molecular formula: C$_{36}$H$_{59}$N$_3$O$_5$, Calculated: 613.4454, Found: 613.4425.

NMR($\delta$, CDCl$_3$): 0.88 (3H,t,J=7Hz), 0.98 (3H,s), 1.04 (3H,s), 1.22–1.40 (20H,m), 1.42 (3H,s), 1.45 (3H,s), 1.62–1.77 (2H,m), 1.94–2.09 (4H,m), 2.36 (2H,t,J=7Hz), 2.60 (2H,t,J=6Hz), 3.28 (1H,d,J=12Hz), 3.55–3.66 (2H,m), 3.69 (1H,d,J=12Hz), 4.10 (1H,s), 5.29–5.42 (2H,m), 7.14–7.48 (2H,m), 7.39–7 48 (2H,m), 8.18 (1H,s), 8.60 (1H,brs).

EXAMPLE 2

Preparation of N-[2-(Oleoylamino)phenyl]-3-[N-(2,4-diacetoxy-3,3-dimethyl-1-oxobutyl)amino]propanamide 2-Oleoylaminoaniline (744 mg) and 606 mg of 3-[N-(2,4-diacetoxy-3,3-dimethyl-1-oxobutyl)amino]propionic acid were reacted in the same manner as in Example 1 to obtain 810 mg of the title compound (yield: 65%).

Property: Oily.

Specific Rotary Power $[\alpha]_D$: +6.30° (C=1.0, CHCl$_3$).

IR(cm$^{-1}$, neat): $\nu_{C=O}$1750, 1660.

Mass Spectrometric Analysis Molecular formula: C$_{37}$H$_{59}$N$_3$O$_7$, Calculated: 657.4352, Found: 657.4369.

NMR($\delta$, CDCl$_3$):

0.88 (3H,t,J=7Hz), 1.02 (3H,s), 1.06 (3H,s), 1.23–1.45 (20H,m), 1.67–1.79 (2H,m), 1.95–2.09 (4H,m), 2.03 (2H,s), 2.04 (3H,s), 2.42 (2H,t,J =7Hz), 2.58 (2H,t,J=6Hz), 3.49–3.72 (2H,m), 3.83 (1H,d,J=11Hz), 4.02 (1H,d,J=11Hz), 4.89 (1H,s), 5.30–5.44 (2H,m), 6.72–6.81 (1H,m), 7.19–7.32 (2H,m), 7.37 (1H,d,J=8Hz), 7.59 (1H,d,J=8Hz), 7.88 (1H,brs), 8.19 (1H,brs).

EXAMPLE 3

Preparation of N-2-(Oleoylamino)phenyl]-3-[N-(2,4-dihydroxy-3,3-dimethyl-1-oxobutyl)amino]propanamide An aqueous 1N sodium hydroxide solution (1,5 ml) was added to a solution of 470 mg of N-[2-(oleoylamino)phenyl]-3-[N-(2,4-diacetoxy-3,3-dimethyl-1-oxobutyl)amino]propanamide in 4 ml of methanol with stirring at room tempeature, and the mixture was stirred for additional 30 minutes. After completion of the reaction, 10 ml of water was added to the reaction mixture, which was then extracted with 20 ml of methylene chloride. The methylene chloride layer was washed with water and then with brine, and dried over anhydrous sodium sulfate. After removing the solvent by evaporation, the residue obtained was subjected to silica gel column chromatography to obtain 377 mg of the title compound (yield: 94%).

Property: Oily,

Specific Rotary Power $[\alpha]_D$: +21.9° (C=1.0, CHCl$_3$).

IR(cm$^{-1}$, neat): $\nu_{NH}$, $\nu_{ON}$, $\nu_{C=O}$1660.

Mass Spectrometric Analysis: Molecular formula: C$_{33}$H$_{55}$N$_3$O$_5$, Calculated: 573.4141, Found: 573.4146.

NMR($\delta$, CDCl$_3$): 0.88 (3H,t,J=7Hz), 0.90 (3H,s), 0.97 (3H,s), 1.20–1.42 (20H,m), 1.62–1.76 (2H,m), 1.94–2.01 (4H,m), 2.38 (2H,t,J=7Hz), 2.52 (2H,t,J=6Hz), 3.44 (2H,s), 3.49–3.72 (2H,m), 3.94 (1H,s), 5.28–5.42 (2H,m), 7.13–7.21 (2H,m), 7.29–7.49 (3H,m), 8.31 (1H,s), 8.69 (1H,s).

EXAMPLE 4

Preparation of N-2-(Linoleoylamino)phenyl]-3-[[N-(2,2,5,5-tetramethyl-1,3-dioxane-4-carbonyl)amino]propanamide A solution of 349 mg of N-(2-aminophenyl-3-[N-(2,2,5,5-tetramethyl-1,3-dioxane-4-carbonyl)amino]propanamide, 280 mg of linolic acid and 227 mg of dicyclohexylcarbodiimide in 15 ml of toluene was heated under reflux for 2 hours. After cooling the reaction mixture, the crystals formed were filtered. The filtrate was concentrated and the residue obtained was subjected to silica gel column chromatogrpphy to obtain 266 mg of the title compound (yield: 44%).

Property: Oily,

Specific Rotary Power $[\alpha]_D$: +27.3° (C=1.0, CHCl$_3$).

IR(cm$^{-1}$, neat): $\nu_{C=O}$1662,

Mass Spectrometric Analysis: Molecular formula: C$_{36}$H$_{57}$N$_3$O$_5$, Calculated: 611.4298, Found: 611.4264, NMR($\delta$, CDCl$_3$): 0.89 (3H,t,J=7Hz), 0.98 (3H,s), 1.04 (3H,s), 1.23–1.44 (14H,m), 1.42 (3H,s), 1.45 (3H,s), 1.65–1.77 (2H,m), 1.91–2.10 (4H,m), 2.37 (2H,t,J=7Hz), 2.62 (2H,t,J=6Hz), 2.77 (2H,t,J=6Hz), 3.28 (1H,d,J=12Hz), 3.56–3.67 (2H,m), 3.69 (1H,d,J=12Hz), 4.10 (1H,m), 5.29–5.44 (4H,m), 7.09 (1H,t,J=6Hz), 7.15–7.22 (2H,m), 7.42–7.49 (2H,m), 8.11 (1H,s), 8.55 (1H,s).

EXAMPLE 5

Preparation of [N-(2-(Linoleoylamino)phenyl]-3-[N-(2,2,5,5-tetramethyl-1,3-dioxane-4-carbonyl)amino]propanamide N-(2-Aminophenyl)-3-[N-(2,2,5,5-tetramethyl-1,3-dioxane-4-carbonyl)amino]propanamide (349 mg) and 278 mg of linoleic acid were reacted in the same manner as in Example 4 to obtain 271 mg of the title compound (yield: 45%).

Property: Oily.

Specific Rotary Power $[\alpha]_D$: +26.2° (C=1.0, CHCl$_3$).

IR(cm$^{-1}$, neat): $\nu_{C=O}$1666.

Mass Spectrometric Analysis: Molecular formula: C$_{36}$H$_{55}$N$_3$O$_5$, Calculated: 609.4141, Found: 609.4144.

NMR($\delta$, CDCl$_3$): 0.97 (3H,t,J=7Hz), 0.98 (3H,s), 1.04 (3H,s), 1.23–1.43 (8H,m), 1.42 (3H,s), 1.46 (3H,s), 1.65–1.77 (2H,m), 2.03–2.12 (4H,m), 2.38 (2H,t,J=7Hz), 2.63 (2H,t,J=6Hz), 2.75–2.83 (4H,m), 3.28 (1H,d,J=12Hz), 3.58–3.70 (2H,m), 3.69 (1H,d,J=12Hz), 4.11 (1H,s), 5.29–5.43 (6H,m), 7.09 (1H,t,J=6Hz), 7.17–7.22 (2H,m), 7.42–7.51 (2H,m), 8.06 (1H,brs), 8.51 (1H,brs).

EXAMPLE 6

Preparation of N-2-(Stearoylamino)phenyl)-3-[N-(2,2,5,5-tetramethyl-1,3-dioxane-4-carbonyl)amino]propanamide To a solution of 349 mg of N-(2-aminophenyl)-3-[N-(2,2,5,5-tetramethyl-1,3-dioxane-4-carbonyl)amino]- propanamide in 20 ml of methylene chloride were added portion-wise 1 ml of pyridine and then a solution of 303 mg of stearoyl chloride in 3 ml of methylene chloride with stirring under ice cooling. The mixture obtained was stirred for additional 1 hour. The reaction mixture was then washed with water and dried over anhydrous sodium sulfate, followed by removal of the solvent by evaporation. The residue obtained was subjected to silica gel column chromatography to obtain 507 mg of the title compound (yield: 82%).
Property: Oily.
Specific Rotary Power $[\alpha]_D$: +27.3° (C=1.0, CHCl$_3$).
IR(cm$^{-1}$, neat): $\nu_{C=O}$1664.
Mass Spectrometric Analysis: Molecular formula: $C_{36}H_{61}N_3O_5$, Calculated : 615.4611, Found : 615.4582.
NMR($\delta$, CDCl$_3$):
0.88 (3H,t,J=7Hz), 0.98 (3H,s), 1.04 (3H,s), 1.20-1.43 (28H,m), 1.42 (3H,s), 1.46 (3H,s), 1.68-1.78 (2H,m), 2.40 (2H,t,J=7Hz), 2.65 (2H,t,J=6Hz), 3.28 (1H,d,J=12Hz), 3.58-3.72 (2H,m), 3.69 (1H,d,J=12Hz), 4.11 (1H,s), 7.08 (1H,t,J=6Hz), 7.17-7.23 (2H,m), 7.42-7.53 (2H,m), 8.00 (1H,s), 8.49 (1H,s).

EXAMPLE 7

Preparation of N-!2-(Lauroylamino)phenyl]-3-[N-(2,2,5,5-tetramethyl-1,3-dioxane-4-carbonyl)amino]-propanamide
N-(2-Aminophenyl)-3-[N-(2,2,5,5-tetramethyl-1,3-dioxane-4-carbonyl)aminopropanamide (349 m9) and 219 mg of lauroyl chloride were reacted in the same manner as in Example 6 to obtain 454 m9 of the title compound (yield: 86%).
Property: Oily.
Specific Rotary Power $[\alpha]_D$: +31.7° (C=1.0, CHCl$_3$).
IR(cm$^{-1}$, neat): $\nu_{C=O}$1664.
Mass Spectrometric Analysis: Molecular formula: $C_{30}H_{49}N_3O_5$, Calculated : 531.3672, Found : 531.3692.
NMR($\delta$, CDCl$_3$): 0.88 (3H,t,J=7Hz), 0.98 (3H,s), 1.04 (3H,s), 1.21-1.43 (16H,m), 1.42 (3H,s), 1.45 (3H,s), 1.65-1.77 (2H,m), 2.38 (2H,t,J=7Hz), 2.61 (2H,t,J=6Hz), 3.28 (1H,d,J=12Hz), 3.55-3.68 (2H,m), 3.69 (1H,d,J=12Hz), 4.10 (1H,s), 7.09 (1H,t,J=12Hz), 7.14-7.22 (2H,m), 7.40-7.49 (2H,m), 8.13 (1H,s), 8.57 (1H,s).

EXAMPLE 8

Preparation of [N-2-(Octanoylamino)phenyl]-3-[N-(2,2,5,5-tetramethyl-1,3-dioxane-4-carbonyl)amino]-propanamide
N-(2-Aminophenyl)-3-[N-(2,2,5,5-tetramethyl-1,3-dioxane-4-carbonyl)amino]propanamide (349 mg) and 163 mg of octanoyl chloride were reacted in the same manner as in Example 6 to obtain 413 mg of the title compound (yield: 87%).
Property: Oily.
Specific Rotary Power $[\alpha]_D$: +35.1° (C=1.0, CHCl$_3$).
IR(cm$^{-1}$, neat): $\nu_{C=O}$1664.
Mass Spectrometric Analysis: Molecular formula: $C_{26}H_{41}N_3O_5$, Calculated : 475.3046, Found : 475.3039.
NMR($\delta$, CDCl$_3$): 0.89 (3H,t,J=7Hz), 0.98 (3H,s), 1.04 (3H,s), 1.23-1.38 (8H,m), 1.42 (3H,s), 1.45 (3H,s), 1.62-1.77 (2H,m), 2.37 (2H,t,J=7Hz), 2.60 (2H,t,J=6Hz), 3.28 (1H,d,J=12Hz), 3.57-3.71 (2H,m), 3.69 (1H,d,J=12Hz), 4.10 (1H,s), 7.09 (1H,t,J=6Hz), 7.14-7.21 (2H,m), 7.40-7.49 (2H,m), 8.16 (1H,s), 8.59 (1H,s).

EXAMPLE 9

Preparation of [N-3-(Linoleylamino)phenyl]-3-[N-(2,2,5,5-tetramethyl-1,3-dioxane-4-carbonyl)amino]-propanamide
3-Linoleoylaminoaniline (555 mg) and 389 mg of 3-[N-(2-Aminophenyl)-3-[N-(2,2,5,5-tetramethyl-1,3-dioxane-4-carbonyl)amino]propionic acid were reacted in the same manner as in Example 1 to obtain 786 mg of the title compound (yield: 86%).
Property: Oily.
Specific Rotary Power $[\alpha]_D$:+30.8° (C=1.0, CHCl$_3$)
IR(cm$^{-1}$, neat): $\nu_{C=O}$1664.
Mass Spectrometric Analysis: Molecular formula: $C_{36}H_{57}N_3O_5$, Calculated : 611.4298, Found : 611.4389.
NMR($\delta$, CDCl$_3$): 0.89 (3H,t,J=7Hz), 0.96 (3H,s), 1.03 (3H,s), 1.23-1.42 (14H,m), 1.41 (3H,s), 1.45 (3H,s), 1.62-1.78 (2H,m), 1.99-2.08 (4H,m), 2.33 (2H,t,J=7Hz), 2.64 (2H,t,J=6Hz), 2.77 (2H,t,J=6Hz), 3.26 (1H,d,J=12Hz), 3.52-3.73 (2H,m), 3.68 (1H,d,J=12Hz), 4.11 (1H,s), 5.29-5.43 (2H,m), 7.09 (1H,t,J=6Hz), 7.22-7.29 (2H,m), 7.34-7.42 (2H,m), 7.79 (1H,s), 8.36 (1H,brs).

EXAMPLE 10

Preparation of [N-3-(Oleoylamino)phenyl]-3-[N-(2,4-diacetoxy-3,3-dimethyl-1-oxobutyl)amino]propanamide
3-Oleoylaminoaniline (744 mg) and 606 mg of 3-[N-(2,4-diacetoxy-3,3-dimethyl-1-oxobutyl)amino]propionic acid were reacted in the same manner as in Example 1 to obtain 860 mg of the title compound (yield: 65%).
Property: Oily.
Specific Rotary Power $[\alpha]_D$: +12.8° (C=1.0, CHCl$_3$).
IR(cm$^{-1}$, neat) $\nu_{C=O}$1750, 1668,
Mass Spectrometric Analysis: Molecular formula: $C_{37}H_{59}N_3O_7$, Calculated : 657.4352, Found : 657.4342.
NMR($\delta$, CDCl$_3$): 0.89 (3H,t,J=7Hz), 1.03 (3H,s), 1.05 (3H,s), 1.21-1.42 (20H,m), 1.61-1.77 (2H,m), 1.97-2.13 (4H,m), 2.05 (3H,s), 2.10 (3H,s), 2.33 (2H,t,J=7Hz), 2.56 (2H,t,J=6Hz), 3.55-3.68 (2H,m), 3.87 (1H,d,J=11Hz), 4.02 (1H,d,J=10Hz), 4.91 (1H,s), 5.29-5.42 (2H,m), 6.84 (1H,d,J=6Hz), 7.25 (1H,d,J=8Hz), 7.33 (1H,d,J=8Hz), 7.41 (1H,d,J=8Hz), 7.54 (1H,brs), 7.63 (1H,brs), 8.01 (1H,brs).

EXAMPLE 11

Preparation of [N-3-(Oleoylamino)phenyl]-3-[N-(2,4-dihydroxy-3,3-dimethyl-1 oxobutyl)amino]propanamide
N-[3-(Oleoylamino)phenyl]-3-[N-(2,4-diacetoxy-3,3-dimethyl-1-oxobutyl)amino1propanamide (470 m9) was reacted in the same manner as in Example 3 to obtain 378 mg of the title compound (yield: 94%).
Property: Oily.
Specific Rotary Power $[\alpha]_D$:+23.1° (C=1.0, CHCl$_3$).
IR(cm$^{-1}$, neat): $\nu_{C=O}$1660.
Mass Spectrometric Analysis: Molecular formula: $C_{33}H_{55}N_3O_5$, Calculated : 573.4141, Found : 573.4146.
NMR($\delta$, CDCl$_3$): 0.88 (3H,t,J=7Hz), 0.91 (3H,s), 0.98 (3H,s), 1.21-1.42 (20H,m), 1.62-1.73 (2H,m); 1.93-2.10 (4H,m), 2.32 (2H,t,J=7Hz), 2.52 (2H,brs), 3.50–3.70 (2H,m), 4.01 (1H,s), 5.29–5.43 (2H,m), 7.17–7.31 (3H,m), 7.53–7.62 (1H,m), 7.71 (1H,brs), 7.92–8.00 (1H,m), 8.46–8.55 (1H,m).

EXAMPLE 12

Preparation of N-[4-(Oleoylamino)phenyl]-3-[N-(2,4-diacetoxy-3,3-dimethyl-1-oxobutyl)amino]propanamide 4-Oleoylaminoaniline (744 mg) and 606 mg of 3-[N-(2,4-diacetoxy-3,3-dimethyl-1-oxobutyl)amino]propionic acid were reacted in the same manner as in Example 1 to obtain 900 mg of the title compound (yield: 69%).

Property: Oily.

Specific Rotary Power $[\alpha]_D$: +17.3° (C=1.0, CHCl$_3$).

IR(cm$^{-1}$, neat): $\nu_{C=}$)1754, 1660,

Mass Spectrometric Analysis: Molecular formula: $C_{37}H_{59}N_3O_7$, Calculated : 657.4352, Found : 657.4357.

NMR($\delta$, CDCl$_3$): 0.88 (3H,t,J=7Hz), 1.02 (3H,s), 1.05 (3H,s), 1.19–1.43 (20H,m), 1.66–1.77 (2H,m), 1.92–2.09 (4H,m), 2.05 (3H,s), 2.08 (3H,s), 2.34 (1H,t,J=7Hz), 2.56 (2H,t,J=6Hz), 3.50–3.71 (2H,m), 3.84 (1H,d,J=11Hz), 4.02 (1H,d,J=11Hz), 4.89 (1H,s), 5.29–5.42 (2H,m), 6.76 (1H,t,J=6Hz), 7.13 (1H,brs), 7.44–7.52 (4H,m), 7.64 (1H,brs).

EXAMPLE 13

Preparation of [N-4-(Oleoylamino)phenyl]-3-[N-(2,4-dihydroxy-3,3-dimethyl-1-oxobutyl)amino]propanamide N-[4-(Oleoylamino)phenyl]-3-[N-(2,4-diacetoxy-3,3-dimethyl-1-oxobutyl)amino]propanamide (657 mg) was reacted in the same manner as in Example 3 to obtain 495 mg of the title compound (yield 86%).

Property: Melting Point 146.2°–148.1° C.

Specific Rotary Power $[\alpha]_D$: +10.2° (C=1.0, CHCl$_3$).

IR(cm$^{-1}$, neat): $\nu_{C=O}$1664.

Mass Spectrometric Analysis Molecular formula: $C_{37}H_{59}N_3O_7$, Calculated : 573.4141, Found : 573.4144.

NMR($\delta$, CDCl$_3$): 0.88 (3H,t,J=7Hz), 0.89 (3H,s), 0.95 (3H,s), 1.15–1.43 (20H,m), 1.62–1.77 (2H,m), 1.92–2.08 (4H,m), 2.34 (2H,t,J=7Hz), 2.56 (2H,brs), 3.45 (2H,s), 3.58 (2H,brs), 3.96 (1H,s), 5.27–5.42 (2H,m), 7.25–7.39 (4H,m), 7.48 (1H,brs), 7.71 (1H,brs), 8.54 (1H,brs).

EXAMPLE 14

Preparation of N-[4-(Lauroylamino)phenyl]-3-[N-(2,2,5,5-tetramethyl-1,3-dioxane-4-carbonyl)amino]propanamide 4-Lauroylaminoaniline (250 mg) and 223 mg of 3-[N-(2,2,5,5-tetramethyl-1,3-dioxane-4-carbonyl)amino]propionic acid were reacted in the same manner as in Example 1 to obtain 381 mg of the title compound (yield: 72%).

Property Melting Point 144.3°–144.9° C.

Specific Rotary Power $[\alpha]_D$: +34.6° (C=1.0, CHCl$_3$).

IR(cm$^{-1}$, neat): $\nu_{C=O}$1664.

Mass Spectrometric Analysis: Molecular formula: $C_{30}H_{49}N_3O_5$, Calculated : 531.3672, Found : 531.3675.

NMR($\delta$, CDCl$_3$): 0.88 (3H,t,J=7Hz), 0.95 (3H,s), 1.04 (3H,s), 1.22–1.40 (16H,m), 1.41 (3H,s), 1.45 (3H,s), 1.68–1.80 (2H,m), 2.34 (2H,t,J=7Hz), 2.65 (2H,t,J=6Hz), 2.34 (2H,t,J=7Hz), 2.65 (2H,t,J=7Hz), 3.27 (1H,d,J=12Hz), 3.50–3.75 (2H,m), 3.68 (1H,d,J=12Hz), 4.10 (1H,s), 7.08 (1H,d,J=6Hz), 7.16 (1H,s), 7.46 (2H,d,J=8Hz), 7.49 (2H,d,J=8Hz), 8.09 (1H,s).

EXAMPLE 15

Preparation of 2-(Oleoylamino)phenyl 3-[N-(2,2,5,5-tetramethyl-1,3-dioxane-4-carbonyl)amino]propionate A solution of 303 mg of 2-oleoylaminophenol, mg of 3-[N-(2,2,5,5-tetramethyl-1,3-dioxane-4-carbonyl)amino]propionic acid, 227 mg of dicyclohexylcarbodiimide and 122 mg of 4-dimethylamino pyridine in 15 ml of toluene was heated under reflux for 2 hours. After cooling the reaction mixture, the crystals formed were filtered. The filtrate was concentrated and the residue obtained was subjected to silica gel column chromatography to obtain 445 mg of the title compound (yield: 72%).

Property: Oily.

Specific Rotary Power $[\alpha]_D$: +26.9° (C=1.0, CHCl$_3$).

IR(cm$^{-1}$, neat): $\nu_{C=O}$1772, 1658.

Mass Spectrometric Analysis: Molecular formula: $C_{36}H_{58}N_2O_6$, Calculated : 614.4294, Found : 614.4271.

NMR($\delta$, CDCl$_3$): 0.88 (3H,t,J=7Hz), 0.99 (3H,s), 1.00 (3H,s), 1.22–1.43 (20H,m), 1.43 (3H,s), 1.47 (3H,s), 1.65–1.78 (2H,m), 1.93–2.08 (4H,m), 2.44 (2H,t,J=7Hz), 2.80 (2H,t,J=6Hz), 3.28 (1H,d,J=12Hz), 3.69–3.82 (2H,m), 3.68 (1H,d,J=12Hz), 4.09 (1H,s), 5.29–5.39 (2H,m), 7.00 (1H,t,J=6Hz), 7.06–7.12 (2H,m), 7.19–7.27 (1H,m), 8.22 (1H,d,J=8Hz), 8.39 (1H,s).

EXAMPLE 16

Preparation of 4-(Oleoylamino)phenyl 3-[N-(2,2,5,5-tetramethyl-1,3-dioxane-4-carbonyl)amino]propionate 4-Hydroxyoleoylanilide (565 mg) and 393 mg of 3-[N-(2,2,5,5-tetramethyl-1,3-dioxane-4-carbonyl)amino]propionic acid were reacted in the same manner as in Example 15 to obtain 930 mg of the title compound (yield: 99%).

Property: Oily.

Specific Rotary Power $[\alpha]_D$: +18.8° (C=1.0, CHCl$_3$).

IR(cm, neat): $\nu_{C=O}$1760, 1662.

Mass Spectrometric Analysis: Molecular formula: $C_{36}H_{58}N_2O_6$, Calculated : 614.4294, Found : 614.4312.

NMR($\delta$, CDCl$_3$): 0.88 (3H,t,J=7Hz), 1.00 (3H,s), 1.06 (3H,s), 1.23–1.43 (20H,m), 1.43 (3H,s), 1.45 (3H,s), 1.65–1.78 (2H,m), 1.93–2.09 (4H,m), 2.35 (2H,t,J=7Hz), 2.82 (2H,t,J=6Hz), 3.29 (1H,d,J=12Hz), 3.52–3.77 (2H,m), 3.70 (1H,d,J=12Hz), 4.11 (1H,s), 5.29–5.41 (2H,m), 6.98–7.07 (1H,m), 7.03 (2H,d,J=8Hz), 7.54 (2H,d,J=8Hz) 7.18 (1H,s).

EXAMPLE 17

Preparation of 4-(Oleoylamino)phenyl 3-[N-(2,4-diacetoxy-3,3-dimethyl-1-oxobutyl)amino]propionate 4-Oleoylaminophenol (372 mg) and 259 mg of 3-[N-(2,4-diacetoxy-3,3-dimethyl-1-oxobutyl)amino]propionic acid were reacted in the same manner as in Example 1 to obtain 255 mg of the title compound (yield: 39%).

Property: Oily.

Specific Rotary Power $[\alpha]_D$: +19.4° (C=1.0, CHCl$_3$).

IR(cm$^{-1}$, neat): $\nu_{C=O}$1750, 1666.

Mass Spectrometric Analysis: Molecular formula $C_{37}H_{58}N_2O_8$ Calculated : 658.4193, Found : 658.4191.

NMR($\delta$, CDCl$_3$): 0.88 (3H,t,J=7Hz), 1.03 (3H,s), 1.08 (3H,s), 1.22–1.42 (20H,m), 1.66–1.78 (2H,m), 1.96–2.07 (4H,m), 2.01 (3H,s), 2.04 (3H,s), 2.35 (2H,t,J=7Hz), 2.77–2.82 (2H,m), 3.84 (1H,d,J=12Hz), 4.05 (1H,d,J=12Hz), 4.97 (1H,s), 5.27–5.42 (2H,m), 6.61 (1H,t,J=6Hz), 7.04 (2H,d,J=8Hz), 7.15 (1H,brs), 7.54 (2H,d,J=8Hz).

EXAMPLE 18

Preparation of 4-(Oleoylamino)phenyl 3-[N-(2,4-dibenzyloxy-3,3-dimethyl-1-oxobutyl)amino]propionate 3-[N-(2,4-Dibenzyloxy-3,3-dimethyl-1-oxobutylamino]propionic acid (200 mg) and 186 mg of 4-(Oleoylamino)phenol were reacted in the same manner as in Example 15 to obtain 312 mg of the title compound (yield: 97%).
Property: Oily.
Specific Rotary Power $[\alpha]_D: +19.3°$ (C=1.0, CHCl$_3$).
IR(cm$^{-1}$, neat): $\nu_{C=O}$1760, 1652.
Mass Spectrometric Analysis: Molecular formula: C$_{47}$H$_{66}$N$_2$O$_6$, Calculated : 754.4920, Found : 754.4890.
NMR($\delta$, CDCl$_3$): 0.88 (3H,t,J=7Hz), 0.94 (3H,s), 1.05 (3H,s), 1.20–1.41 (20H,m), 1.64–1.75 (2H,m), 1.95–2.09 (4H,m), 2.34 (3H,s), 2.75 (3H,t,J=7Hz), 3.23 (1H,t,J=9Hz), 3.61 (2H,dd,J=6Hz,6Hz), 3.41 (1H,d,J=9Hz), 3.90 (1H,s), 4.34–4.55 (4H,m), 5.29–5.42 (2H,m), 6.95 (2H,d,J=8Hz), 7.03 (1H,d,J=8Hz), 7.23–7.39 (10H,m), 7.50 (2H,d,J=8Hz),

EXAMPLE 19

Preparation of 4-(Oleoylamino)phenyl 3-[N-(2,4-dihydroxy-3,3-dimethyl-1-oxobutyl)amino]propionate A solution of 500 mg of 4-(Oleoylamino)phenyl 3-[N-(2,2,5,5-tetramethyl-1,3-dioxane-4-carbonyl)amino]propionate in a mixed solvent composed of 20 ml of acetic acid and 10 ml of water was stirred at room temperature for 15 hours. 20 ml of water was then added to the reaction mixture, which was then extracted with methylene chloride. The methylene chloride layer was washed with water, and dried over anhydrous sodium sulfate. After removal of the solvent under vacuum evaporation, the residue obtained was subjected to silica gel column chromatography to obtain 395 mg of the title compound (yield: 85%).
Property Oily.
Specific Rotary Power $[\alpha]_D: +14.3°$ (C=1.0, CHCl$_3$) TM
IR(cm$^{-1}$, neat): $\nu_{C=O}$1758, 1662.
Mass Spectrometric Analysis: Molecular formula: C$_{33}$H$_{54}$N$_2$O$_6$, Calculated : 574.3981, Found : 574.3952.
NMR($\delta$, CDCl$_3$): 0.88 (3H,t,J=7Hz), 0.93 (3H,s), 1.03 (3H,s), 1.21–1.43 (20H,m), 1.65–1.71 (2H,m), 1.71–2.18 (6H,m), 2.35 (2H,t,J=7Hz), 3.82 (2H,t,J=6Hz), 3.50 (1H,d,J=10Hz,), 3.60–3.74 (2H,m), 3.54 (1H,d,J=10Hz), 4.04 (1H,s), 5.28–5.43 (2H,m), 7.15–7.26 (2H,m), 7.04 (2H,d,J=8Hz), 7.52 (2H,d,J=8Hz).

EXAMPLE 20

Preparation of 4-(Linolenoylamino)phenyl 3-[N-(2,2,5,5-tetramethyl-1,3-dioxane-4-carbonyl)amino]propionate 4-Linolenoylaminoanilide (369 mg) and 259 mg of 3-[N-(2,2,5,5-tetramethyl-1,3-dioxane-4-carbonyl)amino]propionic acid were reacted in the same manner as in Example 15 to obtain 431 mg of the title compound (yield: 71%).
Property: Oily.

Specific Rotary Power $[\alpha]_D: +20.6°$ (C=1.0, CHCl$_3$).
IR(cm$^{-1}$, neat): $\nu_{C=O}$1760, 1662.
Mass Spectrometric Analysis: Molecular formula: C$_{36}$H$_{52}$N$_2$O$_6$, Calculated : 608.3825, Found : 608.3836.
NMR($\delta$, CDCl$_3$): 0.98 (3H,t,J=7Hz), 1.00 (3H,s), 1.06 (3H,s), 1.24–1.42 (8H,m), 1.43 (3H,s), 1.45 (3H,s), 1.64–1.78 (2H,m), 2.01–2.12 (4H,m), 2.35 (2H,t,J=7Hz), 2.72–2.86 (6H,m), 3.29 (1H,d,J=12Hz), 3.52–3.77 (2H,m), 3.70 (1H,d,J=12Hz), 4.11 (1H,s), 5.28–5.44 (6H,m), 7.00 (1H,t,J=6Hz), 7.03 (2H,d,J=8Hz), 7.15 (1H,s), 7.54 (2H,d,J=8Hz).

EXAMPLE 21

Preparation of N-[4-(Oleoylthio)phenyl-3-[N-(2,2,5,5-tetramethyl-1,3-dioxane-4-carbonyl)amino]propanamide S-4-Aminophenyl thiooleate (778 mg) and 518 mg of 3-[N-(2,2,5,5-tetramethyl-1,3-dioxane-4-carbonyl)amino]propionic acid were reacted in the same manner as in Example 1 to obtain 1.05 g of the title compound (yield: 83%).
Property: Oily.
Specific Rotary Power $[\alpha]_D: +29.8°$ (C=1.0, CHCl$_3$).
IR(cm$^{-1}$, neat): $\nu_{C=O}$1696, 1666.
Mass Spectrometric Analysis: Molecular formula: C$_{36}$H$_{58}$N$_2$O$_5$S, Calculated : 630.4066, Found : 630.4069.
NMR($\delta$, CDCl$_3$): 0.88 (3H,t,J=7Hz), 0.90 (3H,s), 1.04 (3H,s), 1.21–1.39 (20H,m), 1.42 (3H,s), 1.46 (3H,s), 1.60–1.74 (2H,m), 1.92–2.09 (4H,m), 2.63 (2H,t,J=7Hz), 2.68 (2H,t,J=6Hz), 3.28 (1H,d,J=12Hz), 3.54–3.75 (2H,m), 3.68 (1H,d,J=12Hz), 4.10(1H,s), 5.30–5.42 (2H,m), 7.08 (1H,t,J=6Hz), 7.35 (2H,d,J=8Hz), 7.63 (2H,d,J=8Hz), 8.29 (1H,s).

EXAMPLE 22

Preparation of N-[4-(Oleoylthio)phenyl-3-[N-(2,4-dihydro-3,3-dimethyl-1-oxobutyl)amino]propanamide N-[4-(Oleoylthio)phenyl]-3-[N-(2,2,5,5-tetramethyl-1,3-dioxane-4-carbonyl)amino]propanamide (500 mg) was reacted in the same manner as in Example 19 to obtain 406 mg of the title compound (yield: 87%).
Property: Oily.
Specific Rotary Power $[\alpha]_D: +16.0°$ (C=1.0, CHCl$_3$).
IR(cm$^{-1}$, neat) $\nu C=O$1670.
Mass Spectrometric Analysis: Molecular formula: C$_{33}$H$_{54}$N$_2$O$_5$S, Calculated : 590.3753, Found : 590.3731.
NMR($\delta$, CDCl$_3$): 0.88 (3H,t,J=7Hz), 0.91 (3H,s), 0.98 (3H,s), 1.20–1.42 (20H,m), 1.65–1.77 (2H,m), 1.93–2.09 (4H,m), 2.57 (2H,t,J=6Hz), 2.66 (2H,t,J=6Hz), 3.25 (2H,brs), 3.48 (2H,brs), 3.50–3.69 (2H,m), 4.01 (1H,s), 5.30–5.42 (2H,m), 7.28 (2H,t,J=9Hz), 7.50 (2H,d,J=9Hz), 7.54 (2H,d,J=6Hz), 8.62 (1H,s).

EXAMPLE 23

Preparation of S-4-(Oleoylamino)phenyl 3-[N-(2,2,5,5-tetramethyl-1,3-dioxane-4-carbonyl)amino]propanethioate S-4-Aminophenyl 3-[N-(2,2,5,5-tetramethyl-1,3-dioxane-4-carbonyl)amino]propanethioate (281 mg) and mg oleoyl chloroide were reacted in the same manner as in Example 6 to obtain 185 mg of the title compound (yield: 38%).
Property: Oily.

Sepcific Rotary Power $[\alpha]_D$: +7.90° (C=1.0, CHCl₃),

IR(cm⁻¹, neat): $\nu_{C=O}$1704, 1652.

Mass Spectrometric Analysis: Molecular formula: $C_{36}H_{58}N_2O_5S$, Calculated : 630.4066, Found : 630.4044.

NMR(δ, CDCl₃): 0.88 (3H,t,J=7Hz), 1.00 (3H,s), 1.05 (3H,s), 1.15-1.42 (20H,m), 1.42 (3H,s), 1.45 (3H,s), 1.65-1.79 (2H,m), 1.92-2.08 (4H,m), 2.37 (2H,t,J=7Hz), 2.82-3.01 (2H,m), 3.29 (1H,d,J=6Hz), 3.47-3.69 (2H,m), 3.69 (1H,d,J=12Hz), 4.09 (1H,s), 5.29-5.42 (2H,m), 6.85-6.92 (1H,m), 7.16 (1H,s), 7.34 (2H,d,J=8Hz), 7.60 (2H,d,J=8Hz).

EXAMPLE 24

Preparation of S-4-(Oleoylamino)phenyl 3-[N-(2,4-dihydroxy-3,3-dimethyl-1-oxobutyl)amino]propanethioate S-4-(Oleoylamino)phenyl 3-[N-(2,2,5,5-tetramethyl-1,3-dioxane-4-carbonyl)amino]propanethioate (483 mg) was reacted in the same manner as in Example 19 to obtain 404 mg of the title compound (yield: 89%).

Property: Oily.

Specific Rotary Power $[\alpha]_D$: +8.80° (C=1.0, CHCl₃).

IR(cm⁻¹, neat): $\nu_{C=O}$1698, 1670.

Mass Spectrometric Analysis: Molecular formula: $C_{33}H_{54}N_2O_5S$, Calculated : 590.3753, Found : 590.3762.

NMR(δ, CDCl₃): 0.88 (3H,t,J=7Hz), 0.91 (3H,s), 1.02 (3H,s), 1.19-1.43 (20H,m), 1.67-1.79 (2H,m), 1.87-2.17 (6H,m), 2.36 (2H,t,J=7Hz), 2.92 (2H,t,J=6Hz), 3.48 (1H,d,J=12Hz), 3.53 (1H,d,J=12Hz), 3.56-3.65 (2H,m), 4.01 (1H,s), 5.28-5.42 (2H,m), 7.12 (1H,t,J=6Hz), 7.26 (1H,brs), 7.34 (2H,d,J =8Hz), 7.59 (2H,d,J=8Hz).

EXAMPLE 25

Preparation of S-4-(Oleoylamino)phenyl 3-[N-(2,4-diacetoxy-3,3-dimethyl-1-oxobutyl)amino]propanethioate S-4-aminophenyl 3-[N-(2,4-dacetoxy-3,3-dimethyl-1-oxobutyl)amino]propanethioate (276 mg) and 196 mg of oleoyl chloride were reacted in the same manner as in Example 6 to obtain 304 mg of the title compound (yield: 69%).

Property: Oily.

Specific Rotary Power $[\alpha]_D$: +21.3° (C=1.0, CHCl₃).

IR(cm⁻¹, neat): $\nu_{C=O}$1750, 1670.

Mass Spectrometric Analysis: Molecular formula: $C_{37}H_{58}N_2O_7S$, Calculated : 674.3964, Found : 674.3976.

NMR(δ, CDCl₃): 0.88 (3H,t,J=7Hz), 1.00 (3H,s), 1.06 (3H,s), 1.21-1.33 (20H,m), 1.62-1.77 (2H,m), 1.94-2.08 (4H,m), 2.06 (3H,s), 2.10 (3H,s), 2.37 (2H,t,J=7Hz), 2.89 (2H,t,J=6Hz), 3.44-3.68 (2H,m), 3.82 (1H,d,J=11Hz), 4.03 (1H,d,J=11Hz), 4.97 (1H,s), 5.29-5.41 (2H,m), 6.47 (1H,t,J=6Hz), 7.19-7.32 (2H,m), 7.17 (1H,s), 7.35 (2H,d,J=8Hz), 7.61 (2H,d,J=8Hz).

EXAMPLE 26

Preparation of N-[2-(Oleoyloxy)phenyl]-3-[N-(2,2,5,5-tetramethyl-1,3-dioxane-4-carbonyl)amino]-propanamide N-(2-Hydroxyphenyl)-3-[N-(2,2,5,5-tetramethyl-1,3-dioxane-4-carbonyl)amino]propanamide (350 mg) and 282 mg of oleic acid were reacted in the same manner as in Example 15 to obtain 411 mg of the title compound (yield: 67%).

property: Oily.

Secific Rotary Power $[\alpha]_D$: +32.3° (C=1.0, CHCl₃).

IR(cm⁻¹, neat): $\nu_{C=O}$1768, 1668.

Mass Spectrometric Analysis: Molecular Formula: $C_{36}H_{58}N_2O_6$, Calculated : 614.4294, Found : 614.4294.

NMR(δ, CDCl₃): 0.88 (3H,t,J=7Hz), 0.96 (3H,s), 1.03 (3H,s), 1.23-1.45 (20H,m), 1.40 (3H,s), 1.45 (3H,s), 1.71-1.83 (2H,m), 1.92-2.08 (4H,m), 2.58-2.67 (4H,m), 3.27 (1H,d,J=12Hz), 3.56-3.64 (2H,m), 3.67 (1H,d,J=12Hz), 4.07 (1H,s), 5.30-5.42 (2H,m), 7.03-7.17 (3H,m), 7.19-7.29 (1H,m), 7.49 (1H,brs), 8.18 (1H,s,J=8Hz).

EXAMPLE 27

Preparation of N-[4-(Oleoyloxy)phenyl]-3-[N-(2,4-diacetoxy-3,3-dimethyl-1-oxobutyl)amino]propanamide N-(4-hydroxyphenyl)-3-[N-(2,4-diacetoxy-3,3-dimethyl-1-oxobutyl)amino]propanamide (394 mg) and 301 mg of oleoyl chloride were reacted in the same manner as in Example 6 to obtain 530 mg of the title compound (yield 81%)

property: Oily.

Secific Rotary Power·$[\alpha]_D$: +14.9° (C=1.0, CHCl₃).

IR(cm⁻¹, neat): $\nu_{C=O}$1746, 1666.

Mass Spectrometric Analysis: Molecular Formula: $C_{37}H_{58}N_2O_8$, Calculated : 658.4193, Found : 658.4184.

NMR(δ, CDCl₃): 0.88 (3H,t,J=7Hz), 1.02 (3H,s), 1.05 (3H,s), 1.22-1.42 (20H,m), 1.68-1.79 (2H,m), 1.94-2.09 (4H,m), 2.07 (3H,s), 2.51-2.59 (4H,m), 3.54-3.71 (2H,m), 3.84 (1H,d,J=12Hz), 4.02 (1H,d,J=12Hz), 4.88 (1H,s), 5.28-5.42 (2H,m), 6.72 (1H,d,J=6Hz), 7.34 (2H,d,J=8Hz), 7.54 (2H,d,J=8Hz), 7.71 (1H,brs).

EXAMPLE 28

Preparation of N-4-(Oleoyloxy)phenyl]-3-[N-(2,4-dihydroxy-3,3-dimethyl-1-oxobutyl)amino]propanamide N-[4-(Oleoyloxyphenyl]-3-N-(2,2,5,5-tetramethyl-1,3-dioxane-4-carbonyl)amino]propanamide (1.0 g) was reacted in the same manner as in Example 19 to obtain 830 mg of the title compound (yield 89%).

property: Oily.

Secific Rotary Power $[\alpha]_D$: +21.0° (C=1.0, CHCl₃).

IR(cm⁻¹, neat): $\nu_{C=O}$1760, 1660.

Mass Spectrometric Analysis: Molecular Formula: $C_{33}H_{54}N_2O_6$, Calculated : 574.3981, Found : 574.3977.

NMR(δ, CDCl₃): 0.88 (3H,t,J=7Hz), 0.90 (3H,s), 0.98 (3H,s), 1.19-1.46 (20H,m), 1.41 (3H,s), 1.68-1.79 (2H,m), 1.93-2.09 (4H,m), 2.55 (2H,t,J=7Hz), 2.59 (2H,t,J=6Hz), 2.72 (2H,brs), 3.55-3.68 (2H,m), 3.48 (2H,s), 3.98 (1H,s), 5.29-5.42 (2H,m) 7.45-7.53 (1H,m), 7.00 (2H,d,J=8Hz), 7.52(2H,d,J=8Hz), 8.35 (1H,s).

EXAMPLE 29

Preparation of N-[4-(Oleoyloxy)phenyl]-3-[N-(2,2,5,5-tetramethyl-1,3-dioxane-4-carbonyl)amino]-propanamide N-(4-(Hydroxyphenyl)-3-[N-(2,2,5,5-tetramethyl-1,3-dioxane-4-carbonyl)amino]propanamide (1.44 g) and 1.20 g of oleoyl chloride were reacted in the same manner as in Example 6 to obtain 1.93 g of the title compound (yield: 79%).

property: Oily.

Specific Rotary Power $[\alpha]_D$: +32.6° (C=1.0, CHCl₃).

IR(cm⁻¹, neat): $\nu_{C=O}$1764, 1668.

Mass Spectrometric Analysis: Molecular Formula: $C_{36}H_{58}N_2O_6$, Calculated : 614.4294, Found : 614.4319.

NMR(δ, CDCl₃): 0.88 (3H,t,J=7Hz), 0.96 (3H,s), 1.04 (3H,s), 1.23-1 45 (20H,m), 1.41 (3H,s), 1.46 (3H,s), 1.66-1.70 (2H,m), 1.93-2.09 (4H,m), 2.54 (2H,t,J=7Hz), 2.66 (2H,t,J=6Hz), 3.27 (1H,d,J =12Hz), 3.52-3.77 (2H,m), 3.68 (1H,d,J=12Hz), 4.10 (1H,s), 5.29-5.42 (2H,m), 7.01-7.10 (1H,m), 7.01 (2H,d,J=8Hz), 7.57 (2H,d,J=8Hz), 8.11 (1H,s).

EXAMPLE 30

Preparation of N-[4-(Oleoythio)phenyl]-3-[N-(2,4-diacetoxy-3,3-dimethyl-1-oxobutyl)amino]propanamide S-p-aminophenyl thiooleate (799 mg) and 606 mg of 3-[N-(2,4-diacetoxy-3,3-dimethyl-1-oxobutyl)amino]-propionic acid were reacted in the same manner as in Example 1 to obtain 780 mg of the title compound (yield: 58%).

property: Oily.

Specific Rotary Power [α]$_D$: +14.5° (C=1.0, CHCl₃).

IR(cm⁻¹, neat): $\nu_{C=O}$1748, 1672.

Mass Spectrometric Analysis: Molecular Formula: $C_{37}H_{58}N_2O_7S$, Calculated : 674.3964, Found : 674.3991.

NMR(δ, CDCl₃): 0.88 (3H,t,J=7Hz), 1.03 (3H,s), 1.06 (3H,s), 1.22-1.41 (20H,m), 1.64-1.75 (2H,m), 1.96-2.08 (4H,m), 2.05 (3H,s), 2.08 (3H,s), 2.58 (2H,t,J =6Hz), 2.64 (2H,t,J=7Hz), 3.55-3.70 (2H,m), 3.85 (1H,d,J=11Hz), 4.02 (1H,d,J=11Hz), 4.87 (1H,s), 5.28-5.43 (2H,m), 6.69 (1H,t,J=6Hz), 7.34 (2H,d,J=8Hz), 7.60 (2H,d,J=8Hz), 7.81 (1H,brs).

EXAMPLE 31

Preparation of N-[2-(Oleoylaminoethyl)-3[N-(2,4-diacetoxy-3,3-dimethyl-1-oxobutyl)amino]propanamide A solution of 1.07 g of N-(2-aminoethyl)oleamide and 1.40 g of 4-nitrophenyl 3-[N-(2,4-diacetoxy-3,3-dimethyl-1-oxobutyl)amino]propionate in 40 ml of tetrahydrofuran was stirred at room temperature for 15 hours. The solvent was then distilled off under reduced pressure. The residue was dissolved in ethyl acetate, and the solution was washed with aqueous potassium carbonate solution and then with water. The organic layer was dried over anhydrous sodium sulfate, and the solvent was distilled off. The residue was subjected to silica gel column chromatography to obtain 4.45 g of the refined title compound (yield: 75%).

property: Oily.

IR(cm⁻¹, neat): 2980, 1740, 1650.

Mass Spectrometric Analysis: Molecular Formula $C_{33}H_{59}N_3O_7$, Calculated : 609.4352, Found : 609.4342.

NMR(δ, CDCl₃): 0.88 (3H,t,J=7Hz), 1.05 (3H,s), 1.09 (3H,s), 1.10-1.40 (18H,m), 1.54-2.42 (12H,m), 2.07 (3H,s), 2.16 (3H,s), 3.20-3.60 (6H,m), 3.86 (1H,t,J=11Hz), 4.05 (1H,d,J=11Hz), 4.86 (1H,s), 5.30-5.40 (2H,m), 6.14-6.22 (1H,brs), 6.52-6.60 (1H,brs), 7.04-7.12 (1H,brs).

EXAMPLE 32

Preparation of N-[2-(Oleoylaminoethyl)-3-[N-(2,4-dihyroxy-3,3-dimethyl-1-oxobutyl)amino]propanamide N-(2-Oleoylaminoethyl)-3-[N-(2,4-diacetoxy-3,3-dimethyl-1-oxobutyl)amino]propanamide (200 mg) was reacted in the same manner as in Example 3 to obtain 150 mg of the title compound (yield: 86%).

property: Oily.

IR(cm⁻¹, neat): $\nu_{OH}$3324, $\nu_{C=O}$1650.

Mass Spectrometric Analysis: Molecular Formula: $C_{29}H_{53}N_3O_4$, Calculated : 507.4011, Found : 507.4044.

NMR(δ, CDCl₃): 0.88 (3H,t,J=7Hz), 0.94 (3H,s), 1.00 (3H,s), 1.16-1.40 (17H,m), 1.50-1.64 (2H,m), 1.92-2.08 (4H,m), 2.19 (2H,t,J=7Hz), 2.30-2.80 (6H,s), 3.20-3.54 (6H,m), 3.62-3.74 (1H,m), 4.02 (1H,s), 5.39-5.44 (2H,m), 6.40-6.50 (1H,m), 6.96-7.04 (1H,m), 7.45-7.53 (1H,m).

EXAMPLE 33

Preparation of N-[3-N-(Oleoylaminopropyl)-3-[N-(2,2,5,5-tetramethyl-1,3-dioxane-4-carbonyl)amino]-propanamide N-(3-Aminopropyl)olelamide (3.38 g) and 2.59 g of 3-[N-(2,2,5,5-tetramethyl-1,3-dioxane-4-carbonyl)amino]propionic acid were reacted in the same manner as in Example 1 to obtain 4.58 g of the title compound (yield: 81%).

property: Oily.

IR(cm⁻¹, neat): $\nu_{C=O}$1650.

Mass Spectrometric Analysis: Molecular Formula: $C_{32}H_{59}N_3O_5$, Calculated : 565.4455, Found : 565.4454.

NMR(δ, CDCl₃): 0.88 (3H,t,J=7Hz), 0.97 (3H,s), 1.04 (3H,s), 1.23-1.40 (14H,m), 1.43 (3H,s), 1.47 (H,s), 1.52-1.86 (6H,m), 1.92-2.10 (4H,m), 2.18 (2H,t,J=7Hz), 2.46 (2H,t,J=6Hz), 3.29 (1H,d,J =12Hz), 3.38 (3H,brs), 3.44-3.62 (4H,m), 3.67 (1H,d,J=12Hz), 4.08 (1H,s), 5.30-5.42 (2H,m), 6.20-6.30 (1H,brs), 6.65-6.73 (1H,brs), 6.99-7.08 (1H,brs).

EXAMPLE 34

Preparation of N-(3-(Oleoylaminopropyl)-3-[N-(2,2,5,5-tetramethyl-1,3-dioxane-4-carbonyl)amino]-propanamide N-(3-Aminopropyl)oleamide (3.39 g) and 2.59 g of 3-[N-(2,2,5,5-tetramethyl-1,3-dioxane-4-carbonyl)amino]propionic acid were reacted in the same manner as in Example 1 to obtain 2.7 g of the title compound (yield: 47%).

property: Oily.

IR(cm⁻¹, neat): $\nu_{C=O}$1660.

Mass Spectrometric Analysis: Molecular Formula: $C_{33}H_{61}N_3O_5$, Calculated : 579.4611, Found : 579.4630.

NMR(δ, CDCl₃): 0.88 (3H,t,J=7Hz), 0.97 (3H,s), 1.04 (3H,s), 1.10-1.40 (20H,m), 1.42 (3H,s), 1.46 (3H,s), 1.54-1.90 (5H,m), 1.90-2.10 (3H,m), 2.20 (2H,t,J=7Hz), 2.47 (2H,t,J=6Hz), 3.20-3.36 (5H,m), 3.48-3.66 (2H,m), 3.69 (1H,d,J=12Hz), 4.08 (1H,s), 5.30-5.40 (2H,m), 6.15-6.25 (1H,m), 6.58-6.66 (1H,m), 7.02-7.10 (1H,m).

EXAMPLE 35

Preparation of N-(3-(Oleoylaminopropyl)-3-[N-(2,4-dihydroxy-3,3-dimethyl-1-oxobutyl)amino]propanamide N-(3-Oleoylaminopropyl)- 3-[N-(2,2,5,5-tetramethyl-1,3-dioxane-4-carbonyl)amino]propanamide (0.58 g) was reacted in the same manner as in Example 19 to obtain 0.48 g of the title compound (yield: 89%).

property: Oily.

IR(cm⁻¹, neat): $\nu_{C=O}$1650.

Mass Spectrometric Analysis: Molecular Formula: $C_{33}H_{61}N_3O_5$, Calculated : 539.4297, Found : 539.4291.

NMR(δ, CDCl₃): 0.88 (3H,t,J=7Hz), 0.90 (3H,s), 1.01 (3H,s), 1.20-1.40 (20H,m), 1.55-1.68 (4H,m), 1.92-2.08 (4H,m), 2.19 (2H,t,J=6Hz), 2.36-2.54 (2H,m), 3.16-3.40 (6H,m), 3.48 (2H,s), 3.42-3.56 (1H,m), 3.62-3.76 (1H,m), 4.00 (1H,s), 5.28-5.42 (2H,m), 6.18-6.24 (1H,m), 6.85-6.94 (1H,m), 7.42-7.52 (1H,m).

EXAMPLE 36

Preparation of N-(3-(Oleoylaminopropyl)-3-[N-(2,4-dihydroxy-3,3-dimethyl-1-oxobutyl)amino]propanamide Acetic anhydride (10 ml) was added to a solution N-(3-Oleoylaminopropyl)-3-[N-(2,4-dihydroxy-3,3-dimethyl-1-oxobutyl)amino]propanamide (0.54 g) in 5 ml of pyridine was stirred for 15 hours. The solvent was then distilled off under reduced pressure. The residue was subjected to silica gel column chromatography to obtain 0.62 g of the refined title compound (yield: 99%).

Property: Oily.
IR(cm$^{-1}$, neat): $\nu_{C=O}$1738, 1658.
Mass Spectrometric Analysis: Molecular Formula: $C_{34}H_{61}N_3O_7$, Calculated : 623.4508, Found : 623.4499.
NMR($\delta$, CDCl$_3$): 0.88 (3H,t,J=7Hz), 1.04 (3H,s), 1.08 (3H,s), 1.16-1.50 (23H,m), 1.56-1.72 (2H,m), 1.90-2.06 (2H,m), 2.07 (3H,s), 2.15 (3H,s), 2.19 (2H,t,J=7Hz), 2.46 (2H,t,J=6Hz), 2.32-2.48 (2H,m), 3.16-3.40 (5H,m), 3.48-3.62 (2H,m), 3.86 (1H,d,J=11Hz), 4.03 (1H,s), 4.90 (1H,s), 5.28-5.40 (2H,m), 5.59-6.06 (1H,m), 6.60-6.70 (1H,m), 7.18-7.28 (1H,m).

EXAMPLE 37

Preparation of N-(4-Oleoylaminobutyl)-3-[N-(2,2,5,5-tetramethyl-1,3-dioxane-4-carbonyl)amino]propanamide N-(4-Aminobutyl)oleamide (3.77 g) and 2.59 g of 3-[N-(2,2,5,5-tetramethyl-1,3-dioxane-4-carbonyl)amino]propionic acid were reacted in the same manner as in Example 1 to obtain 2.66 g of the title compound (yield: 45%).

Property: Oily.
IR(cm$^{-1}$, neat): $\nu_{C=O}$1648.
Mass Spectrometric Analysis: Molecular Formula: $C_{34}H_{63}N_3O_5$, Calculated : 593.4768, Found : 539.4797.
NMR($\delta$, CDCl$_3$): 0.88 (3H,t,J=7Hz), 0.97 (3H,s), 1.04 (3H,s), 1.20-1.40 (18H,m), 1.43 (3H,s), 1.46 (3H,s), 1.50-1.70 (6H,m), 1.86-2.10 (6H,m), 2.16 (2H,t,J=8Hz), 2.45 (2H,t,J=6Hz), 3.20-3.32 (5H,m), 3.20-3.32 (5H,m), 3.42-3.66 (2H,m), 3.69 (1H,d,J=12Hz), 4.08 (1H,s), 5.26-5.42 (2H,m), 5.78-5.86 (1H,m), 6.35-6.45 (1H,m), 7.20-7.12 (1H,m).

EXAMPLE 38

Preparation of N-(4-Oleoylaminobutyl)-3-[N-(2,4-dihydroxy-3,3-dimethyl-1-oxobutyl)amino]propanamide N-(4-Oleoylaminobutyl)-3-[N-(2,2,5,5-tetramethyl-1,3-dioxane-4-carbonyl)amino]propanamide (1.19 g) was reacted in the same manner as in Example 19 to obtain 0.43 g of the title compound (yield: 39%).

property: Oily.
IR(cm$^{-1}$, neat): $\nu_{C=O}$1650.
Mass Spectrometric Analysis: Molecular Formula: $C_{31}H_{59}N_3O_5$, Calculated : 553.4455, Found : 553.4474.
NMR($\delta$, CDCl$_3$): 0.88 (3H,t,J=7Hz), 0.95 (3H,s), 0.99 (3H,s), 1.18-1.40 (17H,m), 1.40-1.66 (6H,m), 1.92-2.10 (4H,m), 2.18 (2H,t,J=6Hz), 2.40-2.50 (2H,m), 2.70-3.32 (6H,m), 3.32-3.72 (6H,m), 4.00 (1H,s), 5.30-5.42 (2H,m), 6.04-6.10 (1H,m), 6.60-6.70 (1H,m), 7.42-7.52 (1H,m).

EXAMPLE 39

Preparation of N-(4-Oleoylaminobutyl)-3-[N-(2,4-diacetoxy-3,3-dimethyl-1-oxobutyl)amino]propanamide N-(4-Oleoylaminobutyl)-3-[N-(2,4-dihydroxy-3,3-dimethyl-1-oxobutyl)amino]propanamide (0.55 g) and 10 ml of acetic anhydride were reacted in the same manner as in Example 36 to obtain 0.52 g of the title compound (yield: 82%).

property: Oily.
IR(cm$^{-1}$, neat): $\nu_{C=O}$1650.
Mass Spectrometric Analysis: Molecular Formula: $C_{35}H_{63}N_3O_7$, Calculated : 637.4566, Found : 637.4584.
NMR($\delta$, CDCl$_3$): 0.88 (3H,t,J=7Hz), 1.03 (3H,s), 1.07 (3H,s), 1.20-1.40 (18H,m), 1.50-1.70 (6H,m), 1.70-2.10 (6H,m), 2.07 (3H,s), 2.16 (3H,s), 2.16 (2H,t,J=7Hz), 2.38 (2H,t,J=6Hz), 3.20-3.30 (4H,m), 3.42 -3.62 (2H,m), 3.85 (1H,d,J=11Hz), 4.20 (1H,d,J=11Hz), 4.93 (1H,s), 5.30-5.42 (2H,m), 5.76-5.86 (1H,m), 6.22-6.30 (1H,m), 7.00-7.08 (1H,m).

EXAMPLE 40

Preparation of N-(5-Oleoylaminopentyl)-3-[N-(2,2,5,5-tetramethyl-1,3-dioxane-4-carbonyl)amino]propanamide N-(5-Aminopentyl)oleamide (3.66 g) and 2.59 g of 3-[N-(2,2,5,5-tetramethyl-1,3-dioxane-4-carbonyl)amino]propionic acid were reacted in the same manner as in Example 1 to obtain 3.64 g of the title compound (yield: 60%).

property: Oily.
IR(cm$^{-1}$, neat): $\nu_{C=O}$1660.
Mass Spectrometric Analysis: Molecular Formula: $C_{35}H_{65}N_3O_5$, Calculated : 607.4923, Found : 607.4906.
NMR($\delta$, CDCl$_3$): 0.88 (3H,t,J=7Hz), 0.97 (3H,s), 1.04 (3H,s), 1.20-1.74 (30H,m), 1.46 (3H,s), 1.48 (3H,s), 1.90-2.10 (4H,m), 2.16 (2H,t,J=7Hz), 2.44 (2H,t,J=7Hz), 3.24 (2H,dt,J=6Hz,7Hz), 3.29 (1H,d,J=12Hz), 3.44-3.665 (2H,m), 3.68 (1H,d,J=12Hz), 4.07 (1H,s), 5.32-5.44 (2H,m), 5.44-5.62 (1H,m), 6.05-6.12 (1H,m) 6.96-7.08 (1H,m).

EXAMPLE 41

Preparation of N-(6-Oleoylaminohexyl)-3-[N-(2,2,5,5-tetramethyl-1,3-dioxane-4-carbonyl)amino]propanamide N-(6-Aminohexyl)oleamide (3.81 g) and 2.59 g of 3-[N-(2,2,5,5-tetramethyl-1,3-dioxane-4-carbonyl)amino]propionic acid were reacted in the same manner as in Example 1 to obtain 2.92 g of the title compound (yield: 47%).

property: Oily.
IR(cm$^{-1}$, neat): $\nu_{C=O}$1664, 1644.
Mass Spectrometric Analysis: Molecular Formula: $C_{36}H_{67}N_3O_5$, Calculated : 621.5080, Found : 621.5057.
NMR($\delta$, CDCl$_3$): 0.88 (3H,t,J=7Hz), 0.97 (3H,s), 1.04 (3H,s), 1.18-1.76 (32H,m), 1.42 (3H,s), 1.46 (3H,s), 1.92-2.10 (4H,m), 2.15 (2H,t,J=7Hz), 2.44 (2H,t,J=7Hz), 3.23 (2H,dt,J=6Hz,7Hz), 3.29 (1H,d,J=12Hz), 2.44-3.66 (4H,m), 3.68 (1H,d,J=12Hz), 4.07 (1H,s), 5.30-5.42 (2H,m), 5.48-5.58 (1H,m), 5.96-6.06 (1H,m), 7.00-7.06 (1H,m).

EXAMPLE 42

Preparation of N-(8-Oleoylaminooctyl)-3-[N-(2,2,5,5-tetramethyl-1,3-dioxane-4-carbonyl)amino]propanamide N-(8-Aminooctyl)oleamide (4.08 9) and 2.59 g of 3-[N-(2,2,5,5-tetramethyl-1,3-dioxane-4-carbonyl)amino]propionic acid were reacted in the same manner as in Example 1 to obtain 1.36 g of the title compound (yield: 21%).

property: Oily.

IR(cm$^{-1}$, neat): $\nu_{C=O}$1664, 1644.

Mass Spectrometric Analysis: Molecular Formula: $C_{38}H_{71}N_3O_5$, Calculated : 649.5392, Found : 649.53886.

NMR($\delta$, CDCl$_3$): 0.88 (3H,t,J=7Hz), 0.97 (3H,s), 1.04 (3H,s), 1.20–1.40 (27H,m), 1.42 (3H,s), 1.46 (3H,s), 1.56–1.72 (4H,m), 1.92–2.10 (4H,m), 2.15 (2H,t,J=7Hz), 2.43 (2H,t,J=7Hz), 3.18–3.26 (5H,m), 3.28 (1H,d,J=12Hz), 3.44–3.66 (4H,m), 3.68 (1H,d,J=12Hz), 4.07 (1H,s), 5.30–5.40 (2H,m), 5.40–5.48 (1H,m), 5.86–5.94 (1H,m), 6.98–7.06 (1H,m).

EXAMPLE 43

Preparation of N-(2-Oleoyloxyethyl)-3-[N-(2,2,5,5-tetramethyl-1,3-dioxane-4-carbonyl)amino]propanamide 2-Aminoethyl oleate (3.26 g) and 2.59 g of 3-[N-(2,2,5,5-tetramethyl-1,3-dioxane-4-carbonyl)amino]propionic acid were reacted in the same manner as in Example 1 to obtain 1.75 g of the title compound (yield: 31%).

property: Oily,

IR(cm$^{-1}$, neat): $\nu_{C=O}$1742, 1660.

Mass Spectrometric Analysis: Molecular Formula: $C_{32}H_{58}N_2O_6$, Calculated : 566.4294, Found : 566.4304.

NMR($\delta$, CDCl$_3$): 0.88 (3H,t,J=7Hz), 0.97 (3H,s), 1.04 (3H,s), 1.16–1.40 (H,m), 1.42 (3H,s), 1.46 (3H,s), 1.52–1.70 (4H,m), 1.70–1.90 (2H,m), 1.96–2.08 (2H,m), 2.32 (2H,t,J=7Hz), 2.46 (2H,t,J=7Hz), 3.29 (1H,d,J=12Hz), 3.42–3.66 (4H,m), 3.68 (1H,d,J=12Hz), 4.07 (1H,s), 4.15 (2H,t,J =12Hz), 5.32–5.40 (2H,m), 6.08–6.18 (1H,m), 6.98–7.08 (1H,m).

EXAMPLE 44

Preparation of 2-(N-Oleoylamino)ethyl 3-[N-(2,2,5,5-tetramethyl-1,3-dioxane-4-carbonyl)amino]propionate N-(2-Hydroxyethyl)oleamide (0.97 g) and 0.78 g of 3-[N-(2,2,5,5-tetramethyl-1,3-dioxane-4-carbonyl)amino]propionic acid were reacted in the same manner as in Example 15 to obtain 1.50 g of the title compound (yield: 90%).

property: Oily,

IR(cm$^{-1}$, neat): $\nu_{C=O}$1742, 1658.

Mass Spectrometric Analysis: Molecular Formula: $C_{32}H_{58}N_2O_6$, Calculated : 566.4254, Found : 566.4274.

NMR($\delta$, CDCl$_3$): 0.88 (3H,t,J=7Hz), 0.98 (3H,s), 1.03 (3H,s), 1.22–1.38 (18H,m), 1.43 (3H,s), 1.47 (3H,s), 1.50–1.72 (5H,m), 1.92–2.08 (4H,m), 2.21 (2H,t,J=7Hz), 2.56 (2H,t,J=6Hz). 3.29 (1H,d,J=12Hz), 3.42–3.70 (4H,m), 3.66 (1H,d,J=12Hz), 4.08 (1H,s), 4.18 (1H,s), 5.28–5.40 (2H,m), 6.27–6.38 (1H,brs), 6.88–6.96 (1H,brs),

EXAMPLE 45

Preparation of 2-(N-Oleoylamino)ethyl 3-[N-(2,4-dihydroxy-3,3-dimethyl-1-oxobutyl)amino]propionate 2-(N-oleoyl)amino)ethyl 3-[N-(2,2,5,5-tetramethyl-1,3-dioxane-4-carbonyl)amino]propionic acid (880 mg) was reacted in the same manner as in Example 19 to obtain 740 mg of the title compound (yield: 91%).

property Oily.

IR(cm$^{-1}$, neat): $\nu_{NH}$3324, $\nu_{C=O}$1740, 1650.

Mass Spectrometric Analysis: Molecular Formula: $C_{29}H_{54}N_2O_6$, Calculated : 526.3952, Found : 526.3961.

NMR($\delta$, CDCl$_3$): 0.88 (3H,t,J=7Hz), 0.94 (3H,s), 1.04 (3H,s), 1.20–1.40 (20H,m), 1.52–1.68 (2H,m), 1.90–2.10 (3H,m), 2.20 (2H,t,J=7Hz), 2.49–2.58 (2H,m), 2.80–3.20 (3H,m), 3.38–3.76 (6H,m), 4.02 (1H,s), 4.05–5.42 (2H,m), 6.20–6.30 (1H,brs), 7.30–7.40 (1H,brs).

EXAMPLE 46

Preparation of 2-(N-Methyl-N-oleoylamino)ethyl 3-[N-(2,2,5,5-tetramethyl-1,3-dioxane 4-carbonyl)amino]propionate N-Methyl-(2-hydroxyethyl)oleamide (3.40 g) and 2.59 g of 3-N-(2,2,5,5-tetramethyl-1,3-dioxane-4-carbonyl)amino]propionic acid were reacted in the same manner as in Example 15 to obtain 3.42 g of the title compound (yield: 59%).

property: Oily.

IR(cm$^{-1}$, neat): $\nu_{C=O}$1740, 1658.

Mass Spectrometric Analysis: Molecular Formula: $C_{33}H_{60}N_2O_6$, Calculated : 580.4452, Found : 580.4478.

NMR($\delta$, CDCl$_3$): 0.88 (3H,t,J=7Hz), 0.97 (3H,s), 1.04 (3H,s), 1.22–1.42 (19H,m), 1.43 (3H,s), 1.47 (3H,s), 1.55–1.70 (3H,m), 1.90–2.10 (4H,m), 2.30 (2H,tt,J=7Hz,7Hz), 2.52–2.60 (2H,m), 3.05 (3H,s), 3.29 (1H,d,J=12Hz), 3.42–3.60 (4H,m), 3.68 (1H,d,J=12Hz), 4.08 (1H,s), 4.24 (2H,t,J=7Hz), 5.30–5.42 (2H,m), 6.98–7.08 (1H,m).

EXAMPLE 47

Preparation of 3-(N-oleoylamino]propyl 3-[N-(2,2,5,5-tetramethyl-1,3-dioxane-4-carbonyl)amino]propionate N-(3-hydroxyethyl)oleamide (3.40 g) and 2.59 g of 3-[N-(2,2,5,5-tetramethyl-1,3-dioxane-4-carbonyl)amino]propionic acid were reacted in the same manner as in Example 15 to obtain 4.52 g of the title compound (yield: 59%).

property: Oily.

IR(cm$^{-1}$, neat): $\nu_{C=O}$1740, 1654.

Mass Spectrometric Analysis: Molecular Formula: $C_{33}H_{60}N_2O_6$, Calculated : 580.4450, Found : 580.4449.

NMR($\delta$, CDCl$_3$): 0.88 (3H,t,J=7Hz), 0.98 (3H,s), 1.04 (3H,s), 1.10–1.50 (21H,m), 1.43 (3H,s), 1.46 (3H,s), 1.52–1.86 (2H,m), 1.84 (2H,tt,J=6Hz,7Hz), 1.90–2.10 (3H,m), 2.17 (2H,t,J=7Hz), 2.56 (1H,t,J=6Hz), 3.28 (1H,d,J=12Hz), 3.33 (2H,dd,J=6Hz,7Hz), 3.35–3.60 (2H,m), 3.68 (1H,d,J=12Hz), 4.08 (1H,s), 4.15 (2H,t,J=7Hz), 5.28–5.42 (2H,m), 5.92–6.02 (1H,brs), 6.90–7.00 (1H,brs).

EXAMPLE 48

Preparation of 3-(N-oleoylamino]propyl 3-[N-(2,4-dihydroxy-3,3-dimethyl-4-oxobutyl)aminopropionate 3-(N-Oleoylamino]propyl 3-[N-(2,2,5,5-tetramethyl-1,3-dioxane-4-carbonyl)amino]propionate (0.58 g) was reacted in the same manner as in Example 19 to obtain 0.49 g of the title compound (yield: 90%).

property: Oily.

IR(cm$^{-1}$, neat): $\nu_{C=O}$1740, 1652.

Mass Spectrometric Analysis: Molecular Formula: $C_{30}H_{56}N_2O_6$, Calculated : 540.4145, Found : 540.4138.

NMR($\delta$, CDCl$_3$): 0.88 (3H,t,J=7Hz), 0.93 (3H,s), 1.04 (3H,s), 1.18–1.40 (19H,m), 1.52–1.66 (2H,m), 1.83 (2H,tt,J=6Hz,7Hz), 1.92–2.06 (4H,m), 2.19 (2H,t,J=6Hz), 2.46–2.72 (2H,m), 3.00–3.56 (8H,m), 3.64–3.76 (1H,m), 3.98–4.10 (1H,m), 20 4.03 (1H,s), 4.19–4.30 (1H,m), 5.28–5.42 (2H,m), 5.86–5.98 (1H,m), 7.44–7.52 (1H,m) .

EXAMPLE 49

Preparation of 3-(N-Oleoylamino]propyl 3-[N-(2,4-diacetoxy-3,3-dimethyl-4-oxobutyl)amino]propionate 3-(N-Oleoylamino)propyl 3-[N-(2,4-dihydroxy-3-dimethyl-1-oxobutyl)amino]propionate (540 mg) and 10 ml of acetic anhydride were reacted in the same manner as in Example 36 to obtain 500 mg of the title compound (yield: 80%).

property: Oily.

IR(cm$^{-1}$, neat): $\nu_{C=O}$1740, 1650.

Mass Spectrometric Analysis: Molecular Formula: $C_{34}H_{60}N_2O_8$, Calculated : 624.4348, Found : 624.4323.

NMR($\delta$, CDCl$_3$): 0.88 (3H,t,J=7Hz), 1.04 (3H,s), 1.07 (3H,s), 1.15–1.40 (21H,m), 1.55–1.72 (2H,m), 1.84 (2H,tt,J=6Hz,6Hz), 1.92–2.10 (3H,m), 2.07 (3H,s), 2.15 (3H,s), 2.16 (2H,t,J=7Hz), 2.54 (2H,t,J=6Hz), 3.20–3.68 (4H,m), 3.83 (1H,d,J=11Hz), 4.09 (1H,d,J=11Hz), 4.12 (2H,d,J=6Hz), 4.93 (1H,s), 5.30–5.38 (2H,m), 5.92–6.02 (1H,m), 6.70–6.80 (1H,m).

EXAMPLE 50

Preparation of 3-(N-Oleoylamino)propyl 3-[N-(2,4-dibenzyloxy-3,3-dimethyl-4-oxobutyl)amino]propionate 3-(N-Oleoylamino)propyl 3-[N-(2,4-dihydroxy-3,3-dimethyl-1-oxobutyl)amino]propionate (270 mg) and 281 mg of benzoyl chloride were reacted in the same manner as in Example 36 to obtain 260 mg of the title compound (yield: 69%).

property Oily.

IR(cm$^{-1}$, neat): $\nu_{C=O}$1722, 1650.

Mass Spectrometric Analysis: Molecular Formula: $C_{44}H_{64}N_2O_8$, Calculated : 748.4662, Found : 748.4673.

NMR($\delta$, CDCl$_3$): 0.88 (3H,t,J=7Hz), 1.20–1.40 (25H,m), 1.52–1.64 (2H,m), 1.76 (2H,tt,J=6Hz,6Hz), 1.94–2.06 (4H,m), 2.11 (2H,t,J=7Hz), 2.51 (2H,t,J=6Hz), 3.18–3.40 (2H,m), 3.40–3.66 (2H,m), 4.02 (2H,t,J=6Hz), 4.28 (1H,d,J=10Hz), 4.33 (1H,d,J=10Hz), 5.30–5.40 (2H,m), 5.82–5.92 (1H,m), 6.78–6.86 (1H,m), 7.40–7.50 (4H,m), 7.52–7.64 (2H,m), 8.00–8.10 (4H,m).

EXAMPLE 51

Preparation of 3-(N-Oleoylamino)propyl 3-[N-(4-benzyloxy-2-hydroxy-3,3-dimethyl-1-oxobutyl)amino]propionate 3-(N-Oleoylamino]propyl 3-[N-(2,4-dihydroxy-3,3-dimethyl-1-oxobutyl)amino]propionate (540 mg) and 140 mg of benzoyl chloride were reacted in the same manner as in Example 36 to obtain 318 mg of the title compound (yield: 51%).

property: Oily.

IR(cm$^{-1}$, neat): $\nu_{C=O}$1740, 1720, 1660.

Mass Spectrometric Analysis: Molecular Formula: $C_{37}H_{60}N_2O_6$, Calculated : 628.4449, Found : 628.4423.

NMR($\delta$, CDCl$_3$): 0.88 (3H,t,J=7Hz), 1.06 (3H,s), 1.18 (3H,s), 1.16–1.40 (17H,m), 1.48–1.62 (2H,m), 1.62–1.70 (3H,m), 1.81 (2H,tt,J=7Hz,7Hz), 1.92–2.08 (3H,m), 2.11 (3H,t,J=7Hz), 2.42–2.70 (2H,m), 3.18–3.30 (1H,m), 3.34–3.48 (2H,m), 3.64–3.76 (1H,m), 4.00–4.05 (2H,m), 4.12 (1H,d,J=12Hz), 4.14–4.24 (1H,m), 4.38 (1H,t,J=12Hz), 4.64–4.68 (1H,brs), 5.28–5.40 (2H,m), 5.72–5,82 (1H,brs), 7.30–7.38 (1H,m), 7.44 (2H,dd,J=7Hz,7Hz), 7.56 (1H,dd,J=7Hz,7Hz), 8.05 (2H,d,J=7Hz).

EXAMPLE 52

Preparation of 3-(N-Oleoylamino)propyl 3-[N-(2-phenyl-5,5-dimethyl-1,3-dioxane-4-carbonyl)amino]propionate N-(3-hydroxypropyl)oleamide (3.40 g) and 3.07 g of 3-[N-(2-phenyl-5,5-dimethyl-1,3-dioxane-4-carbonyl)amino]propionic acd were reacted in the same manner as in Example 15 to obtain 5.34 g of the title compound (yield property: Oily.

IR(cm$^{-1}$, neat): $\nu_{C=O}$1738, 1662.

Mass Spectrometric Analysis: Molecular Formula: $C_{37}H_{60}N_2O_6$, Calculated : 628.4452, Found : 628.4465.

NMR($\delta$, CDCl$_3$): 0.88 (3H,t,J=7Hz), 1.11 (3H,s), 1.20 (3H,s), 1.22–1.43 (13H,m), 1.52–1.72 (6H,m), 1.77 (2H,tt,J=7Hz,7Hz), 1.90–2.06 (4H,m), 2.14 (2H,tt,J=7Hz,7Hz), 2.38 (2H,t,J=7Hz), 2.52 (2H,t,J=7Hz), 3.26 (1H,dt,J=6Hz,7Hz), 3.46–3.62 (4H,m), 3.69 (1H,d,J=12Hz), 4.10 (1H,t,J=7Hz), 4.11 (1H,s), 5.30–5.42 (2H,m), 5.52 (1H,s), 5.82–5.92 (1H,m), 6.90–7.04 (1H,m), 7.38–7.44 (3H,m), 7.48–7.53 (2H,m).

EXAMPLE 53

Preparation of 3-(N-Oleoylamino)propyl 3-[N-(3,3-dimethyl-1,5-dioxaspiro[5,5]-3-carbonyl)amino]propionate N-(3-hydroxypropyl)oleamide (3.40 g) and 2.99 g of 3-[N-(3,3-dimethyl-1,5-dioxaspiro5,5)-3-carbonyl)amino]propionic acid were reacted in the same manner as in Example 15 to obtain 5.46 g of the title compound (yield: 88%).

property: Oil.

IR(cm$^{-1}$, neat): $\nu_{C=O}$1740, 1652.

Mass Spectrometric Analysis: Molecular formula: $C_{36}H_{64}N_2O_6$, Calculated : 620.4763, Found : 620.4761.

NMR($\delta$, CDCl$_3$): 0.88 (3H,t,J=7Hz), 0.98 (3H,s), 1.03 (3H,s), 1.22–2.10 (36H,m), 2.17 (2H,t,J=7Hz), 2.56 (2H,t,J=7Hz), 3.26 (1H,d,J=12Hz), 3.32 (2H,dt,J=6Hz,7Hz), 3.50–3.68 (4H,m), 3.71 (1H,d,J=12Hz), 4.10 (1H,s), 4.15 (2H,t,J=7Hz), 5.28–5.40 (2H,m), 5.90–5.98 (1H,m), 6.98–7.10 (1H,m).

EXAMPLE 54

Preparation of 3-(N-Oleoylamino)propyl 3-[N-(2-hydroxy-3,3-dimethyl-4-(trimethyloxy-1-oxobutyl)amino]propionate 3-(N-Oleoylamino]propyl 3-[N-(2,4-dihydroxy-3,3-dimethyl-1-oxobutyl)amino]propionate (540 mg) and mg of pivaloyl chloride were reacted in the same manner as in Example 36 to obtain 139 mg of the title compound (yield: 22%).

property: Oil.

IR(cm$^{-1}$, neat): $\nu_{C=O}$1740, 1660.

NMR($\delta$, CDCl$_3$): 0.88 (3H,t,J=7Hz), 1.20–1.38 (25H,m), 1.57 (9H,s), 1.52–1.70 (2H,m), 1.85 (2H,tt,J=7Hz, 7Hz), 1.94–2.06 (6H,m), 2.17 (2H,t,J=7Hz), 2.56 (1H,t,J=7Hz), 3.28–3.40 (2H,m), 3.54–3.62 (2H,m), 4.07 (1H,d,J=12Hz), 4.10–4.20 (2H,m), 4.68 (1H,d,J=12Hz), 5.11 (1H,s), 5.28–5.40 (2H,m), 5.70–5.80 (1H,m), 6.94–7.02 (1H,m).

EXAMPLE 55

Preparation of 3-(N-Hexanoylamino)propyl 3-[N-(2,2,5,5-tetramethyl-1,3-dioxane-4-carbonyl)amino]propionate N-(3-Hydroxypropyl)hexamide (1.75 g) and 2.59 g of 3-[N-(2,2,5,5-tetramethyl-1,3-dioxane-4-carbonyl)amino]propionic acid were reacted in the same manner as in Example 15 to obtain 1.90 g of the title compound (yield: 46%)

Property: Oily.

IR(cm$^{-1}$, neat): $\nu_{C=O}$1740, 1658.

Mass Spectrometric Analysis Molecular Formula : C$_{21}$H$_{38}$N$_2$O$_6$, Calculated : 414.2730, Found : 414.2741.

NMR(δ, CDCl$_3$): 0.90 (3H,t,J=7Hz), 0.98 (3H,s), 1.04 (3H,s), 1.22–1.36 (3H,m), 1.43 (3H,s), 1.46 (3H,s), 1.58–1.74 (1H,m), 1.85 (2H,tt,J=7Hz,7Hz), 2.18 (2H,t,J=7Hz), 2.56 (2H,t,J=7Hz), 3.29 (1H,d,J=12Hz), 3.33 (2H,dt,J=6Hz,7Hz), 3.46–3.66 (4H,m), 3.68 (1H,d,J=12Hz), 4.08 (1H,s), 4.16 (2H,t,J=12Hz), 5.94–6.02 (1H,m), 6.92–7.04 (1H,m).

EXAMPLE 56

Prepartion of 3-(N-Octanoylamino)propyl 3-[N-(2,2,5,5-tetramethyl-1,3-dioxane-4-carbonyl)amino]propionate N-(3-Hydroxypropyl)octamide (2.-3 g) and 2.56 g of 3-[N-(2,2,5,5-tetramethyl)-1,3-dioxane-4-carbonyl)amino]propionic acid were reacted in the same manner as in Example 15 to obtain 2.91 g of the title compound (yield: 66%)

Property: Oily.

IR(cm$^{-1}$, neat): ν$_{C=O}$1738, 1658.

Mass Spectrometric Analysis Molecular Formula : C$_{23}$H$_{42}$N$_2$O$_6$, Calculated : 442.3043, Found : 442.3054.

NMR(δ, CDCl$_3$): 0.88 (3H,t,J=7Hz), 0.98 (3H,s), 1.04 (3H,s), 1.20–1.36 (5H,m), 1.42 (3H,s), 1.46 (3H,s), 1.56–1.74 (3H,m), 1.84 (2H,tt,J=7Hz,7Hz), 2.17 (2H,t,J=7Hz), 2.56 (2H,t,J=7Hz), 3.29 (1H,d,J=12Hz), 3.33 (2H,dt,J=6Hz,7Hz), 3.46–3.66 (4H,m), 3.68 (1H,d,J=12Hz), 4.08 (1H,s), 4.15 (2H,t,J=7Hz), 5.94–6.02 (1H,m), 6.92–7.04 (1H,m).

EXAMPLE 57

Preparation of 3-(N-Decanoylamino)propyl 3-[N-(2,2,5,5-tetramethyl-1,3-dioxane-4-carbonyl)amino]propionate N-(3-Hydroxypropyl)decanamide (2.29 g) and 2.59 g of 3-[N-(2,2,5,5-tetramethyl-1,3-dioxane-4-carbonyl)amino]propionic acid were reacted in the same manner as in Example 15 to obtain 4.61 g of the title compound (yield: 98%)

Property: Oily.

IR(cm$^{-1}$, neat): ν$_{C=O}$1740, 1662.

Mass Spectrometric Analysis Molecular Formula : C$_{25}$H$_{46}$N$_2$O$_6$. Calculated : 470.3356, Found : 470.3377.

NMR(δ, CDCl$_3$): 0.88 (3H,t,J=7Hz), 0.98 (3H,s), 1.04 (3H,s), 1.20–1.34 (6H,m), 1.42 (3H,s), 1.46 (3H,s), 1.56–1.78 (4H,m), 1.82–1.94 (3H,m), 2.17 (2H,t,J=7Hz), 2.36–2.44 (1H,m), 2.56 (2H,t,J=7Hz), 3.29 (1H,d,J=12Hz), 3.33 (2H,dt,J=6Hz,7Hz), 3.46–3.66 (4H,m), 3.68 (1H,d,J=12Hz), 4.08 (1H,s), 4.15 (2H,t,J=12Hz), 5.92–6.02 (1H,m), 6.08–6.18 (1H,m), 6.92–7.07 (1H,m).

EXAMPLE 58

Preparation of 3-(N-Dodecanoylamino)propyl 3-[N-(2,2,5,5-tetramethyl-1,3-dioxane-4-carbonyl)amino]propionate N-(3-Hydroxypropyl)dodecanamide (2.57 g) and 2.59 g of 3-[N-(2,2,5,5-tetramethyl-1,3-dioxane-4-carbonyl)amino]propionic acid were reacted in the same manner as in Example 15 to obtain 3.19 g of the title compound (yield: 64%)

Property: Oily.

IR(cm$^{-1}$, neat): ν$_{C=O}$1738, 1660.

Mass Spectrometric Analysis Molecular Formula : C$_{27}$H$_{50}$N$_2$O$_6$, Calculated : 498.3668, Found : 498.3676.

NMR(δ, CDCl$_3$): 0.87 (3H,t,J=7Hz), 0.97 (3H,s), 1.03 (3H,s), 1.18–1.36 (7H,m), 1.41 (3H,s), 1.45 (3H,s), 1.56–1.76 (6H,m), 1.78–1.94 (4H,m), 2.16 (2H,t,J=7Hz), 2.36–2.42 (2H,m), 2.55 (2H,t,J=7Hz), 3.28 (1H,d,J=7Hz), 3.31 (2H,dt,J=6Hz,7Hz), 3.44–3.65 (4H,m), 3.67 (1H,d,J=12Hz), 4.06 (1H,s), 4.14 (2H,t,J=7Hz), 5.96–6.02 (1H,m), 6.90–7.04 (1H,m).

EXAMPLE 59

Preparation of 3-(N-Tetradecanoylamino)propyl 3-[N-(2,2,5,5-tetramethyl-1,3-dioxane-4-carbonyl)amino]propionate N-(3-Hydroxypropyl)tetradecanamide (2.87 g) and 2.59 g of 3-[N-(2,2,5,5-tetramethyl-1,3-dioxane-4-carbonyl)amino]propionic acid were reacted in the same manner as in Example 15 to obtain 4.63 g of the title compound (yield: 88%)

Property: Oily.

IR(cm$^{-1}$, neat): ν$_{C=O}$1740, 1656.

Mass Spectrometric Analysis Molecular Formula : C$_{29}$H$_{54}$N$_2$O$_6$, Calculated : 526.3981, Found : 526.3983.

NMR(δ, CDCl$_3$): 0.88 (3H,t,J=7Hz), 0.98 (3H,s), 1.04 (3H,s), 1.20–1.34 (15H,m), 1.42 (3H,s), 1.46 (3H,s), 1.52–1.64 (4H,m), 1.84 (2H,tt,J=7Hz,7Hz), 2.17 (2H,t,J=7Hz), 2.36–2.44 (1H,m), 2.56 (2H,t,J=7Hz), 3.29 (1H,d,J=12Hz), 3.33 (2H,dt,J=6Hz,7Hz), 3.48–3.66 (4H,m), 3.68 (1H,d,J=12Hz), 4.08 (1H,s), 4.16 (2H,t,J=7Hz), 5.92–5.96 (1H,m), 6.90–7.02 (1H,m).

EXAMPLE 60

Preparation of 3-(N-Hexadecanoylamino)propyl 3-[N-(2,2,5,5-tetramethyl-1,3-dioxane-4-carbonyl)amino]propionate N-(3-Hydroxypropyl)hexadecanamide (3.13 g) and 2.59 g of 3-[N-(2,2,5,5-tetramethyl-1,3-dioxane-4-carbonyl)amino]propionic acid were reacted in the same manner as in Example 15 to obtain 5.48 g of the title compound (yield: 99%)

Property: Oily.

IR(cm$^{-1}$, neat): ν$_{C=O}$1740, 1658.

Mass Spectrometric Analysis Molecular Formula : C$_{31}$H$_{58}$N$_2$O$_6$, Calculated : 554.4294, Found : 554.4301.

NMR(δ, CDCl$_3$): 0.88 (3H,t,J=7Hz), 0.98 (3H,s), 1.04 (3H,s), 1.21–1.36 (22H,m), 1.43 (3H,s), 1.46 (3H,s), 1.56–1.98 (6H,m), 1.84 (2H,tt,J=7Hz,7Hz), 2.17 (2H,t,J=7Hz), 2.56 (2H,t,J=7Hz), 3.29 (1H,d,J=12Hz), 3.32 (2H,dt,J=6Hz,7Hz), 3.67 (2H,d,J=12Hz), 4.08 (1H,s), 4.16 (2H,t,J=12Hz), 5.92–5.98 (1H,m), 6.92–7.04 (1H,m).

EXAMPLE 61

Preparation of 3-(N-Octadecanoylamino)propyl 3-[N-(2,2,5,5-tetramethyl-1,3-dioxane-4-carbonyl)amino]propionate N-(3-Hydroxypropyl)otadecanamide (3.42 g) and 2.59 g of 3-[N-(2,2,5,5-tetramethyl-1,3-dioxane-4-carbonyl)amino]propionic acid were reacted in the same manner as in Example 15 to obtain 3.90 g of the title compound (yield: 67%)

Property: Oily.

IR(cm$^-$, neat): ν$_{C=O}$1738, 1652.

Mass Spectrometric Analysis Molecular Formula C$_{33}$H$_{62}$N$_2$O$_6$, Calculated : 582,4608, Found : 582,4619.

NMR(67 , CDCl$_3$): 0.88 (3H,t,J=7Hz), 0.98 (3H,s), 1.04 (3H,s), 1.20–1.36 (17H,m), 1.42 (3H,s), 1.46 (3H,s), 1.54–1.96 (10H,m), 2.17 (3H,t,J=7Hz), 2.56 (2H,t,J=7Hz), 3.28 (1H,t,J=12Hz), 3.33 (2H,dt,J=6Hz,7Hz), 3.44–3.62 (4H,m), 3.67 (1H,d,J=12Hz), 4.08 (1H,s), 4.16 (2H,t,J=7Hz), 5.96–6.02 (1H,m), 6.92–7.04 (1H,m).

EXAMPLE 62

Preparation of 3-(N-Linoleoylamino)propyl 3-[N-(2,2,5,5-tetramethyl-1,3-dioxane-4-carbonyl)amino]propionate N-(3-Hydroxypropyl)linoleamide (3.38 g) and 2.59 g of 3-[N-(2,2,5,5-tetramethyl-1,3-dioxane-4-carbonyl)amino]propionic acid were reacted in the same manner as in Example 15 to obtain of the title compound (yield: 67%)

Property: Oily.

IR(cm$^{-1}$, neat): $\nu_{C=O}$1740, 1654.

Mass Spectrometric Analysis Molecular Formula : $C_{33}H_{58}N_2O_6$, Calculated : 578.4294, Found : 578.4291.

NMR($\delta$, CDCl$_3$): 0.89 (3H,t,J=7Hz), 0.98 (3H,s), 1.04 (3H,s), 1.20–1.44 (17H,m), 1.43 (3H,s), 1.46 (3H,s), 1.52–1.76 (4H,m), 1.84 (2H,tt,J=7Hz,7Hz), 2.00–2.10 (6H,m), 2.17 (2H,t,J=7Hz), 2.36–2.44 (1H,m), 2.56 (2H,t,J=7Hz), 2.77 (2H,t,J=7Hz), 3.29 (1H,d,J=12Hz), 3.32 (2H,dd,J=6Hz,7Hz), 3.46–3.64 (4H,m), 3.67 (1H,d,J=12Hz), 4.08 (1H,s), 4.16 (2H,t,J=12Hz), 5.28–5.42 (4H,m), 5.92–6.00 (1H,m), 6.94–7.02 (1H,m).

EXAMPLE 63

Preparation of 3-(N-Linolenoylamino)propyl 3-[N-(2,2,5,5-tetramethyl-1,3-dioxane-4-carbonyl)amino]propionate N-(3-Hydroxypropyl)linolenamide (3.35 g) and 2.59 g of 3-[N-(2,2,5,5-tetramethyl-1,3-dioxane-4-carbonyl)amino]propionic acid were reacted in the same manner as in Example 15 to obtain 4.09 g of the title compound (yield: 67%)

Property: Oily.

IR(cm$^{-1}$, neat): $\nu_{C=O}$1738, 1652.

Mass Spectrometric Analysis Molecular Formula : $C_{33}H_{56}N_2O_6$, Calculated : 576.4138, Found : 576.4126.

NMR($\delta$, CDCl$_3$): 0.97 (3H,t,J=7Hz), 0.98 (3H,s), 1.05 (3H,s), 1.26–1.44 (12H,m), 1.43 (3H,s), 1.46 (3H,s), 1.58–1.74 (6H,m), 1.80–1.92 (4H,m), 2.02–2.10 (2H,m), 2.17 (2H,t,J=7Hz), 2.34–2.42 (2H,m), 2.56 (2H,t,J=7Hz), 3.29 (1H,d,J=12Hz), 2.74–2.86 (2H,m), 3.28 (1H,d,J=12Hz), 3.32 (2H,dd,J=6Hz,7Hz), 3.42–3.66 (4H,m), 3.68 (1H,d,J=12Hz), 4.07 (1H,s), 4.15 (2H,t,J=12Hz), 5.26–5.44 (6H,m), 5.90–6.00 (1H,m), 6.92–7.06 (1H,m).

EXAMPLE 64

Preparation of 3-(N-Oleoylamino)propyl 3-[N-(2,2,5,5-tetramethyl-1,3-dioxane-4-carbonyl)amino]propionate N-(3-Hydroxypropyl)oleamide (3.54 g) and 2.59 g of 3-[N-(2,2,5,5-tetramethyl-1,3-dioxane-4-carbonyl)amino]propionic acid were reacted in the same manner as in Example 15 to obtain 5.05 g of the title compound (yield: 85%)

Property: Oily.

IR(cm$^{-1}$, neat): $\nu_{C=O}$1740, 1662.

Mass Spectrometric Analysis Molecular Formula : $C_{34}H_{62}N_2O_6$, Calculated : 594.4608, Found : 594.4618.

NMR($\delta$, CDCl$_3$): 0.88 (3H,t,J=7Hz), 0.97 (3H,s), 1.04 (3H,s), 1.20–1.40 (23H,m), 1.43 (3H,s), 1.47 (3H,s), 1.50–1.80 (6H,m), 1.86–2.10 (3H,m), 2.17 (2H,dt,J=6Hz,7Hz), 2.56 (2H,t,J=6Hz), 3.28 (1H,d,J=12Hz), 3.40–3.66 (2H,m), 3.69 (1H,d,J=12Hz), 4.08 (1H,s), 4.12 (2H,t,J=6Hz), 5.30–5.40 (2H,m), 5.48–5.56 (1H,m), 6.90–7.00 (1H,m).

EXAMPLE 65

Preparation of 4-(N-Oleoylamino)propyl 3-[N-(2,4-dihydroxy-3,3-dimethyl-1-oxobutyl)amino]propionate 4-(N-Oeloylamino)butyl 3-[N-(2,2,5,5-tetramethyl-1,3-dioxane-4-carbonyl)amino]propionate (0.59 g) was reacted in the same manner as in Example 19 to obtain 0.50 g of the title compound (yield: 91%)

Property: Oily.

IR(cm$^{-1}$, neat): $\nu_{C=O}$1740, 1658.

Mass Spectrometric Analysis Molecular Formula : $C_{31}H_{58}N_2O_6$, Calculated : 554.4293, Found : 554.4291.

NMR($\delta$, CDCl$_3$): 0.88 (3H,t,J=7Hz), 0.94 (3H,s), 1.01 (3H,s), 1.18–1.42 (21H,m), 1.50–1.80 (6H,m), 1.90–2.12 (3H,m), 2.18 (1H,d,J=7Hz), 2.45–2.57 (2H,m), 3.10–3.80 (8H,m), 4.02 (1H,m), 4.05 4.13 (1H,m), 4.18–4.26 (1H,m), 5.30–5.41 (2H,m), 5.88–5.96 (1H,m), 7.34–7.44 (1H,m).

EXAMPLE 66

Preparation of 5-(N-Oleoylamino)propyl 3-[N(2,2,5,5-tetramethyl-1,3-dioxane-4-carbonyl)amino]propionate N-(5-Hydroxypentyl)oleamide (3.68 g) and 2.59 of 3-[N-(2,2,5,5-tetramethyl-1,3-dioxane-4-carbonyl)amino]propionic acid were reacted in the same manner as in Example 15 to obtain 4.99 g of the title compound (yield: 82%)

Property: Oily.

IR(cm$^{-1}$, neat): $\nu_{C=O}$1738, 1658.

Mass Spectrometric Analysis Molecular Formula : $C_{35}H_{64}N_2O_6$, Calculated : 608.4764, Found : 608.4764.

NMR(67 , CDCl$_3$): 0.88 (3H,t,J=7Hz), 0.97 (3H,s), 1.04 (3H,s), 1.20–1.80 (26H,m), 1.42 (3H,s), 1.46 (3H,s), 1.84–2.10 (4H,m), 2.15 (2H,t,J=6Hz), 2.56 (2H,t,J=6Hz), 3.25 (1H,dt,J=6Hz,6Hz), 3.29 (1H,d,J=12Hz), 3.40–3.68 (4H,m), 3.68 (1H,d,J=Hz), 4.08 (1H,s), 4.10 (2H,t,J=12Hz), 5.30–5.40 (2H,m), 5.48–5.54 (1H,m), 6.90–7.02 (1H,m).

EXAMPLE 67

Preparation of 6(N-Oleoylamino)propyl 3-[N(2,2,5,5-tetramethyl-1,3-dioxane-4-carbonyl)amino]propionate N-(6-Hydroxypentyl)oleamide (3.82 g) and 2.59 of 3-[N-(2,2,5,5-tetramethyl-1,3-dioxane-4-carbonyl)amino]propionic acid were reacted in the same manner as in Example 15 to obtain 2.80 g of the title compound (yield: 45%)

Property: Oily.

IR(cm$^{-1}$, neat): $\nu_{C=O}$1740, 1656.

Mass Spectrometric Analysis Molecular Formula : $C_{36}H_{66}N_2O_6$, Calculated : 622.4920, Found :, 622.4923.

NMR($\delta$, CDCl$_3$): 0.88 (3H,t,J=7Hz), 0.97 (3H,s), 1.04 (3H,s), 1.20–1.54 (24H,m), 1.43 (3H,s), 1.47 (3H,s), 1.56–1.70 (6H,m), 1.90–2.10 (4H,m), 2.15 (2H,t,J=6Hz), 2.55 (2H,t,J=6Hz), 3.24 (2H,dt,J =6Hz,6Hz), 3.29 (1H,d,J=12Hz), 3.40–3.66 (2H,m), 3.68 (1H,d,J=12Hz), 4.08 (1H,s), 4.09 (2H,t,J=6Hz), 5.30–5.40 (2H,m), 5.40–5.50 (1H,m), 6.92–7.02 (1H,m).

EXAMPLE 68

Preparation of S-2-(N-Oleoylamino)propyl 3-[N-(2,2,5,5-tetramethyl-1,3-dioxane-4-carbonyl)amino]propanethionate N-(2-Mercaptoethyl)oleamide (3.42 g) and 2.59 of 3-[N-(2,2,5,5-tetramethyl-1,3-dioxane-4carbonyl)amino]propionic acid were reacted in the same manner as in Example 15 to obtain 4.77 g of the title compound (yield: 82%)
Property: Oily.
IR(cm$^{-1}$, neat): $\nu_{C=O}$1730, 1656.
Mass Spectrometric Analysis Molecular Formula: $C_{32}H_{58}N_2O_5S$, Calculated: 582.4123, Found: 582.4095.
NMR($\delta$, CDCl$_3$): 0.88 (3H,t,J=7Hz), 0.98 (3H,s), 1.04 (3H,s), 1.20–1.40 (19H,m), 1.43 (3H,s), 1.47 (3H,s), 1.58–1.70 (2H,m), 1.84–2.10 (4H,m), 2.17 (2H,t,J=7Hz), 2.78–2.86 (2H,m), 3.05 (2H,t,J=6Hz), 3.29 (1H,dt,J=12Hz), 3.35–3.62 (5H,m), 3.67 (1H,d,J=12Hz), 4.07 (1H,s), 5.34–5.41 (2H,m), 5.93–6.02 (1H,m), 6.83–6.92 (1H,m).

EXAMPLE 69

Preparation of S-2-(N-Oleoylamino)ethyl 3-[N-(2,4-dihydroxy3,3-dimethyl-1-oxobutyl)aminopropanethionate S-2-(N-Oleoylamino)ethyl 3-[N-(2,2,5,5-tetramethyl-1,3-dioxane-4-carbonyl)amino]propanethionate (0.58 g) was reacted in the same manner as in Example 19 to obtain 0.16 g of the title compound (yield: 29%)
Property: Oily.
IR(cm$^{-1}$, neat): $\nu_{C=O}$1650.
Mass Spectrometric Analysis Molecular Formula: $C_{29}H_{54}N_2O_5S$, Calculated: 542.3753, Found: 542.3765.
NRM($\delta$, CDCl$_3$): 0.88 (3H,t,J=7Hz), 0.93 (3H,s), 1.04 (3H,s), 1.15–1.40 (16H,m), 1.50–1.70 (2H,m), 1.90–2.06 (4H,m), 2.17 (2H,t,J=8Hz), 2.25–2.60 (6H,m), 2.70–2.80 (1H,m), 2.82–2.98 (2H,m), 3.05–3.15 (1H,m), 3.30–3752 (6H,m), 4.01 (1H,s), 5.30–5.42 (2H,m), 5.90–6.00 (1H,brs), 7.22–7.32 (1H,brs).

EXAMPLE 70

Preparation of N-[(1S,2S)-2-(Oleoylamino)cyclohexane]-3-[N-(2,2,5,5-tetramethyl-1,3-dioxane-4-carbonyl)amino]propanamide 3-N-(2,2,5,5-Tetramethyl-1,3-dioxane-4-carbonyl)amino]propionic acid (745 mg) and 800 mg of N-(2-aminocyclohexyl)-oleamide were reacted in the same manner as in Example 1 to obtain 504 mg of the title compound (yield: 34%)
Property: Oily.
Specific Rotary Power [$\alpha$]$_D$: $-15.1°$ (C=1.0, CHCl$_3$).
IR(cm$^{-1}$, neat): $\nu_{C=O}$1662, 1642.
Mass Spectrometric Analysis Molecular Formula: $C_{36}H_{65}N_3O_5$, Calculated: 619.4924, Found: 619.4913.
NMR($\delta$, CDCl$_3$): 0.88 (3H,t,J=7Hz), 0.97 (3H,s), 1.04 (3H,s), 1.15–1.37 (24H,m), 1.43 (3H,s), 1.46 (3H,s), 1.50–1.62 (2H,m), 1.68–1.82 (2H,m), 1.90–2.08 (6H,m), 2.11 (2H,t,J=7Hz), 2.28–2.44 (2H,m), 3.28 (1H,d,J=12Hz), 3.36–3.48 (1H,m), 3.55–3.68 (3H,m), 3.69 (1H,d,J=12Hz), 4.08 (1H,d,J=11Hz), 5.29–5.40 (2H,m), 5.84 (1H,brs), 6.38 (1H,brs), 7.00 (1H,t,J=6Hz).

EXAMPLE 71

Preparation of N-[(1S,2S)-2-(Oleoylamino)cyclohexane]-3-[(2R)-2,4-diacetoxy-3,3-dimethyl-1-oxobutyl]amino]propanamide 3-N-[(2R)-2,4-Diacetoxy-3,3-dimethyl-1-oxo-butyl]amino]propionic acid (187 mg) and 172 mg of (1S,2S)-N-(2-aminocyclohexyl)oleamide were reacted in the same manner as in Example 1 to obtain 194 mg of the title compound (yield: 56%)
Property: Oily.
Specific Rotary Power [$\alpha$]$_D$: $-3.10°$ (C=1.0, CHCl$_3$).
IR(cm$^{-1}$, neat): $\nu_{C=O}$1750, 1660.
Mass Spectrometric Analysis Calculated: 663.4822, Found 663.4833.
NMR($\delta$, CDCl$_3$): 0.88 (3H,t,J=7Hz), 1.03 (3H,s), 1.08 (3H,s), 1.18–1.39 (24H,m), 1.07–1.83 (2H,m), 1.92–2.09 (6H,m), 2.08 (3H,s), 2.14 (2H,t,J=7Hz), 2.20 (3H,s), 2.32 (2H,t,J=7Hz), 3.28–3.40 (1H,m), 3.49–3.59 (2H,m), 3.61–3.74 (1H,m), 3.82 (1H,d,J=12Hz), 4.04 (1H,d,J=12Hz), 4.09 (1H,s), 5.29–5.40 (2H,m), 5.79 (1H,d,J=8Hz), 6.19 (1H,d,J=8Hz), 7.03 (1H,t,J=6Hz).

EXAMPLE 72

Preparation of N-[2-(Oleoylamino)cyclohexane]-3-[(2R)-2,4-diacetoxy-3,3-dimethyl-1-oxobutyl]amino]propanamide 3-N-[(2,4-Diacetoxy-3,3-dimethyl-1-oxobutyl-]amino]propionic acid (1.01 g) and 1.26 g of N-(2-aminocyclohexyl)oleamide were reacted in the same manner as in Example 1. The crude products was purified by silica gel column chromatography to obtain two diastereomers of the title compound, i.e., diastereomer A: N-[(1R,2R)-2-(oleoylamino)cyclohexane-1- yl]-3-[N-[(2R)-2,4-diacetoxy-3,3-dimethyl-1-oxobutyl]amino]propanamide in an amount of 603 mg (yield: 28%) and diastereomer B: N-[(1S,2S)-2-(oleoylamino)cyclo-hexane-1-yl]-3-[N-[(2R)-2,4-diacetoxy-3,3-dimethyl-1-oxobutyl]amino]propanamide in an amount of 714 mg (yield: 33%)

A
Property: Oily.
Specific Rotary Power [$\alpha$]$_D$: $-32.0°$ (C=1.0, CHCl$_3$).
IR(cm$^-$, neat): $\nu_{C=O}$1750, 1660.
Mass Spectrometric Analysis Molecular Formula: $C_{37}H_{65}N_3O_7$, Calculated: 663.4822, Found: 663.4834.
NMR(67, CDCl$_3$): 0.88 (3H,t,J=7Hz), 1.08 (3H,s), 1.10 (3H,s), 1.21–1.38 (24H,m), 1.46–1.65 (2H,m), 1.69–1.79 (2H,m), 1.88–2.08 (6H,m), 2.08 (3H,s), 2.13 (2H,t,J=7Hz), 2.14–2.26 (1H,m), 2.16 (3H,s), 2.23–2.42 (1H,m), 3.06–3.16 (1H,m), 3.56–3.79 (3H,m), 3.90 (1H,d,J=11Hz), 4.07 (1H,d,J=11Hz), 4.80 (1H,s), 5.29–5.42 (1H,m), 5.69 (1H,d,J=8Hz), 6.56 (1H,d,J=8Hz), 7.41 (1H,t,J=6Hz).

B
Property: Oily.
Specific Rotary Power [$\alpha$]$_D$: $-3.10°$ (C=1.0, CHCl$_3$).
IR(cm$^{-1}$, neat): $\nu_{C=O}$1750, 1660.
Mass Spectrometric Analysis Molecular Formula: $C_{37}H_{65}N_3O_7$, Calculated: 663.4822, Found: 663.4833.
NMR($\delta$, CDCl$_3$): 0.88 (3H,t,J=7Hz), 1.03 (3H,s), 1.08 (3H,s), 1.18–1.39 (24H,m), 1.07–1.83 (2H,m), 1.92–2.09 (6H,m), 2.08 (3H,s), 2.14 (2H,t,J=7Hz), 2.20 (3H,s), 2.32 (2H,t,J=7Hz), 3.28–3.40 (1H,m), 3.49–3.59 (2H,m), 3.61–3.74 (1H,m), 3.82 (1H,d,J=12Hz), 4.04 (1H,d,J=12Hz), 4.09 (1H,s), 5.29–5.40 (2H,m), 5.79 (1H,d,J=8Hz), 6.19 (1H,d,J=8Hz), 7.03 (1H,t,J=6Hz).

EXAMPLE 73

Preparation of N-[(1R,2R)-2-(Oleoylamino)cyclohexane-1-yl]-3-[N-[(2R)-2,4-dihydroxy-3,3-dimethyl-1-oxobutyl]amino]propanamide N-[(1R,2R)-2-(Oleoylamino)cyclohexane-1-yl]-3-N-[(2R)-2,4-diaceotxy-3,3-dimethyl-1 oxobutyl]amino]propanamide (380 mg) was reacted in the same manner as in Example 3 to obtain 293 mg of the title compound (yield: 89%)
Property: Oily.

Specific Rotary Power $[\alpha]_D$: +34.1° (C=1.0, CHCl$_3$).

IR(cm$^{-1}$, neat): $\nu_{C=O}$1642.

Mass Spectrometric Analysis Molecular Formula : C$_{33}$H$_{61}$N$_3$O$_5$, Calculated : 579.4611, Found : 579.4596.

NMR($\delta$, CDCl$_3$): 0.88 (3H,t,J=7Hz), 0.95 (3H,s), 1.04 (3H,s), 1.17-1.38 (24H,m), 1.49-1.62 (2H,m), 1.73-1.82 (2H,m), 1.93-2.08 (6H,m), 2.14 (2H,t,J=7Hz), 3.31-2.45 (2H,m), 2.52-2.86 (2H,m), 3.44-3.73 (6H,m), 3.98 (1H,s), 5.28-5.40 (2H,m), 6.08 (1H,brs), 6.63 (1H,brs), 7.34 (1H,t,J=6Hz).

EXAMPLE 74

Preparation of N-[(1S,2S)-2-(Oleoylamino)cyclohexane-1-yl]-3-[N-[(2R)-2,4-dihydroxy-3,3-dimethyl-1-oxobutyl]amino]propanamide N-[(1S,2S)-2-(Oleoylamino)cyclohexane-1-yl]-3-[N-[(2R)-2,4-diaceotxy-3,3-dimethyl-1-oxobutyl]amino]propanamide (485 mg) was reacted in the same manner as in Example 3 to obtain 410 mg of the title compound (yield: 97%)

Property: Oily.

Specific Rotary Power $[\alpha]_D$: −0.60° (C=1.0, CHCl$_3$).

IR(cm$^-$, neat): $\nu_{C=O}$1644.

Mass Spectrometric Analysis Molecular Formula : C$_{33}$H$_{61}$N$_3$O$_5$, Calculated : 579.4611, Found : 579.4603.

NMR($\delta$, CDCl$_3$): 0.88 (3H,t,J=7Hz), 0.94 (3H,s), 1.05 (3H,s), 1.16-1.38 (24H,m), 1.46-1.62 (2H,m), 1.71-1.82 (2H,m), 1.87-2.07 (6H,m), 2.12 (2H,t,J=7Hz), 2.32-2.44 (1H,m), 2.48-2.58 (1H,m), 2.63-3.05 (2H,m), 3.18-3.29 (1H,m), 3.46 (2H,d,J=11Hz), 3.51 (2H,d,J=11Hz), 3.86-3.99 (1H,m), 4.12 (1H,s), 5.29-5.41 (2H,m), 5.99 (1H,d,J=8Hz), 7.02 (1H,d,J=8Hz), 7.11-7.19 (1H,m).

EXAMPLE 75

Preparation of N-[2-(Oleoylamino)cyclohexane-1-yl]-3-[N-[(2R)-2,4-diacetoxy-3,3-dimethyl-1-oxobutyl]amino]propanamide dl-3-[N-2,4-Diaceotxy-3,3-dimethyl-1-oxobutyl]amino]propionic (1.51 g) and 1.90 g of (1R,2R)-N-(2-aminocyclohexyl)oleamide were reacted in the same manner as in Example 1. The crude products was purified by silica gel column chromatography to obtain two diastereomers of the title compound, diastereomer A: N-(1R,2R)-2-(oleoylamino)cyclohexane-1-yl]-3-[N-[(2R)-2,4-diacetoxy-3,3-dimethyl-1-oxobutyl]amino]propanamide in an amount of 0.848 g (yield: 28%) and diastereomer B: N-[(1R,2R)-2-(oleoylamino)cyclo-hexane-1-yl]-3-[N-[(2R)-2,4-diacetoxy-3,3-dimethyl-1-oxobutyl]amino]propanamide in an amount of 1.00 g (yield: 33%)

A

Property: Oily.

Specific Rotary Power $[\alpha]_D$: −32.0° (C=1.0, CHCl$_3$).

IR(cm$^{-1}$, neat): $\nu_{C=O}$1750, 1660.

Mass Spectrometric Analysis Molecular Formula : C$_{37}$H$_{65}$N$_3$O$_7$, Calculated : 663.4822, Found 663.4834.

NMR($\delta$, CDCl$_3$): 0.88 (3H,t,J=7Hz), 1.08 (3H,s), 1.10 (3H,s), 1.21-1.38 (24H,m), 1.46-1.65 (2H,m), 1.69-1.79 (2H,m), 1.88-2.08 (6H,m), 2.08 (3H,s), 2.13 (2H,t,J=7Hz), 2.14-2.26 (1H,m), 2.16 (3H,s), 2.23-2.42 (1H,m), 3.06-3.16 (1H,m), 3.56-3.79 (3H,m), 3.90 (1H,d,J=11Hz), 4.07 (1H,d,J=11Hz), 4.80 (1H,s), 5.29-5.42 (1H,m), 5.69 (1H,d,J=8Hz), 6.56 (1H,d,J=8Hz), 7.41 (1H,t,J=6Hz).

Property: Oily.

Specific Rotary Power $[\alpha]_d$: +2.04° (C=1.0, CHCl$_3$).

IR(cm$^{-1}$, neat): $\nu_{C=O}$1750, 1660.

Mass Spectrometric Analysis Molecular Formula : C$_{37}$H$_{65}$N$_3$O$_7$, Calculated : 663.4822, Found : 663.4833.

NMR($\delta$, CDCl$_3$): 0.88 (3H,t,J=7Hz), 1.03 (3H,s), 1.08 (3H,s), 1.18-1.39 (24H,m), 1.07-1.83 (2H,m), 1.92-2.09 (6H,m), 2.08 (3H,s), 2.14 (2H,t,J=7Hz), 2.20 (3H,s), 2.32 (2H,t,J=7Hz), 3.28-3.40 (1H,m), 3.49-3.59 (2H,m), 3.61-3.74 (1H,m), 3.82 (1H,d,J=12Hz), 4.04 (1H,d,J=12Hz), 4.09 (1H,s), (1H,d,J=8Hz), 7.03 (1H,t,J=6Hz).

EXAMPLE 76

Preparation of N-[2-(Oleoylamino)cyclohexane-1-yl]-3-[N-2,4-diacetoxy-3,3-dimethyl-1-oxobutyl]amino]propanamide dl-3-[N-2,4-Diaceotxy-3,3-dimethyl-1-oxobutyl]amino]propionic (1.44 g) and 1.80 g of (1S,2S)-N-(2-aminocyclohexyl)oleamide were reacted in the same manner as in Example 1. The crude products was purified by silica gel column chromatography to obtain two diastereomers of the title compound, diastereomer A: N-[(1S,2S)-2-(oleoylamino)cyclohexane-1-yl]-3-[N-[(2R)-2,4-diacetoxy-3,3-dimethyl-1-oxobutyl]amino]propanamide in an amount of 0.859 g (yield: 29%) and diastereomer B: N-[(1S,2S)-2-(oleoylamino)cyclo-hexane-1-yl]-3-[N-[(2S)-2,4-diacetoxy-3,3-dimethyl-1-oxobutyl]amino]propanamide in an amount of 0.80 g (yield: 27%)

B

Property: Oily.

Specific Rotary Power $[\alpha]_D$: −32.0° (C=1.0, CHCl$_3$).

IR(cm$^{-1}$, neat): $\nu_{C=O}$1750, 1660.

Mass Spectrometric Analysis Molecular Formula : C$_{37}$H$_{65}$H$_3$O$_6$, Calculated : 663.4822, Found : 663.4834.

NMR($\delta$, CDCl$_3$): 0.88 (3H,t,J=7Hz), 1.08 (3H,s), 1.10 (3H,s), 1.21-1.38 (24H,m), 1.46-1.65 (2H,m), 1.69 (2H,m), 1.88-2.08 (6H,m), 2.08 (3H,s), 2.13 (2H,t,J=7Hz), 2.14-2.26 (1H,m), 2.16 (3H,s), 2.23-2.42 (1H,m), 3.06-3.16 (1H,m), 3.56-3.79 (3H,m), 3.90 (1H,d,J=11Hz), 4.07 (1H,d,J=11Hz), 4.80 (1H,s), 5.29-5.42 (1H,m), 5.69 (1H,d,J=8Hz), 6.56 (1H,d,J=8Hz), 7.41 (1H,t,J=6Hz).

EXAMPLE 77

Preparation of (1R,2R)-2-(Oleoylamino)cyclohexane-1-yl 3-[N-(2,2,5,5-tetramethyl-1,3-dioxane-4-carbonyl)amino]propionate (1S,2S)-2-(N-Oleoylamino)cyclohexanol (3.79 g) and 2.59 g of 3-[N-(2,2,5,5-tetramethyl-1,3-dioxane-4-carbonyl)amino]propionic acid were reacted in the same manner as in Example 15 to obtain 3.52 g of the title compound (yield: 57%)

Property: Oily.

Specific Rotary Power $[\alpha]_D$: +26.2° (C=1.0, CHCl$_3$).

IR(cm$^{-1}$, neat): $\nu_{C=O}$1736, 1654.

Mass Spectrometric Analysis Molecular Formula : C$_{36}$H$_{64}$N$_2$O$_6$, Calculated : 620.4764, Found : 620.4759.

NMR($\delta$, CDCl$_3$): 0.88 (3H,t,J=7Hz), 0.99 (3H,s), 1.04 (3H,s), 1.07-1.39 (24H,m), 1.43 (3H,s), 1.48 (3H,s), 1.50-1.83 (4H,m), 1.92-2.17 (6H,m), 2.10 (2H,t,J=7Hz), 2.51 (2H,t,J=6Hz), 3.32-3.43 (1H,m) 3.57-3.68 (1H,m), 3.69 (1H,d,J=12Hz), 3.83-3.95 (1H,m), 4.08 (1H,s), 4.64

(1H,td,J=11Hz,5Hz), 5.28-5.40 (1H,m), 5.74 (1H,d,J=8Hz), 6.95 (1H,d,J=6Hz).

EXAMPLE 78

Preparation of (1S,2S)-2-(Oleoylamino)cyclohexane-1-yl 3-[N-(2,2,5,5-tetramethyl-1,3-dioxane-4-carbonyl)amino]propionate (1S,2S)-2-(N-Oleoylamino)cyclohexanol (3.79 g) and 2.59 g of 3-[N-(2,2,5,5-tetramethyl-1,3-dioxane-4-carbonyl)amino]propionic acid were reacted in the same manner as in Example 15 to obtain 3.52 g of the title compound (yield: 57%)

Property: Oily.

Specific Rotary Power $[\alpha]_D$: +14.3° (C=1.0, CHCl$_3$).

IR(cm$^{-1}$, neat): $\nu_{C=O}$1734, 1654.

Mass Spectrometric Analysis Molecular Formula: C$_{36}$H$_{64}$N$_2$O$_6$, Calculation: 620.4764, Found: 620.4777.

NMR(δ, CDCl$_3$): 0.88 (3H,t,J=7Hz), 0.96 (3H,s), 1.04 (3H,s), 1.06-1.38 (24H,m), 1.43 (3H,s), 1.47 (3H,s), 1.48-1.80 (4H,m), 1.92-2.17 (6H,m), 2.10 (2H,t,J=7Hz), 2.51 (2H,t,J=6Hz), 3.28 (1H,t,J=12Hz), 3.45-3.57 (2H,m), 3.69 (1H,d,J=12Hz), 3.82-3.93 (1H,m), 4.08 (1H,s), 4.64 (1H,td,J=11Hz,5Hz), 5.79 (1H,d,J=8Hz), 6.91 (1H,d,J=6Hz).

EXAMPLE 79

Preparation of (1R,2R)-2-(Stearoylamino)cyclohexane-1-yl 3-[N-(2,2,5,5-tetramethyl-1,3-dioxane-4-carbonyl)amino]propionate (1R,2R)-2-(N-Stearoylamino)cyclohexanol (3.81 g) and 2.59 g of 3-[N-(2,2,5,5-tetramethyl-1,3-dioxane-4-carbonyl)amino]propionic acid were reacted in the same manner as in Example 15 to obtain 2.82 g of the title compound (yield: 45%)

Property: Oily.

Melting Point: 69.1-70.2.

Specific Rotary Power $[\alpha]_D$+25.8° (C=1.0, CHCl$_3$).

IR(cm$^{-1}$, neat): $\nu_{C=O}$1734, 1660, 1646.

Mass Spectrometric Analysis Molecular Formula: C$_{36}$H$_{66}$N$_2$O$_6$, Calculated: 622.4920, Found: 622.4930.

NMR(δ, CDCl$_3$): 0.88 (3H,t,J=7Hz), 0.99 (3H,s), 1.04 (3H,s), 1.11-1.34 (32H,m), 1.43 (3H,s), 1.48 (3H,s), 1.50-1.82 (4H,m), 1.95-2.18 (2H,m), 2.10 (2H,t,J=7Hz), 2.51 (1H,t,J=6Hz), 3.29 (1H,d,J=12Hz), 3.31-3.34 (1H,m), 3.57-3.68 (1H,m), 3.69 (1H,d,J=12Hz), 3.83-3.95 (1H,m), 4.08 (1H,s), 4.64 (1H,td,J=11Hz,5Hz), 5.74 (1H,d,J=8Hz), 6.95 (1H,d,J=6Hz).

EXAMPLE 80

Preparation of (1S,2S)-2-(Linoleoylamino)cyclohexane-1-yl 3-[N-(2,2,5,5-tetramethyl-1,3-dioxane-4-carbonyl)amino]propionate (1S,2S)-2-(N-Linoleoylamino)cyclohexanol (3.77 g) and 2.59 g of 3-[N-(2,2,5,5-tetramethyl-1,3-dioxane-4-carbonyl)amino]propionic acid were reacted in the same manner as in Example 15 to obtain 2.72 g of the title compound (yield: 44%)

Property: Oily.

Specific Rotary Power $[\alpha]_D$+13.5° (C=1.0, CHCl$_3$).

IR(cm$^{-1}$, neat): $\nu_{C=O}$1736, 1654.

Mass Spectrometric Analysis Molecular Formula: C$_{36}$H$_{62}$N$_2$O$_6$, Calculated: 618.4607, Formula: 618.4612.

NMR(δ, CDCl$_3$): 0.88 (3H,t,J=7Hz), 0.96 (3H,s), 1.04 (3H,s), 1.11-1.39 (18H,m), 1.43 (3H,s), 1.47 (3H,s), 1.51-1.81 (4H,m), 1.95-2.18 (6H,m), 2.10 (2H,t,J=7Hz), 2.50 (2H,t,J=6Hz), 2.77 (2H,d,J=Hz), 3.28 (1H,d,J=12Hz), 3.46-3.57 (2H,m), 3.69 (1H,d,J=12Hz), 3.32-3.43 (1H,m), 4.09 (1H,s), 4.64 (1H,td,J=11Hz,5Hz), 5.28-5.43 (4H,m), 5.80 (1H,d,J=8Hz), 6.91 (1H,d,J=6Hz).

In a similar manner as described above, the following compounds were synthesized.

EXAMPLE 81

(R)-1-Methyl-2-eleoylaminoethyl 3-[N-(2,2,5,5-tetramethyl-1,3-dioxane-4-carbonyl)amino]propionate Molecular Formula: C$_{33}$H$_{60}$N$_2$O$_6$.

Molecular Weight: 580.85,

Mass Spectrometric Analysis: Calculated: 580.4451, Found: 580.4448.

Melting Point (° C.): Oil.

Specific Rotary Power: $[\alpha]^{22}_D$+31.1° (C=1.0, CHCl$_3$).

IR($\nu$neat, cm$^{-1}$): 3332, 2932, 2860, 1740, 1660.

NMR(δ, CDCl$_3$): 0.88 (3H,t,J=7Hz), 0.99 (3H,s), 1.02 (3H,s), 1.21-1.38 (23H,m), 1.43 (3H,s), 1.47 (3H,s), 1.55-1.69 (2H,m), 1.91-2.08 (4H,m), 2.28 (2H,t,J=7Hz), 2.44-2.62 (2H,m), 3.29 (1H,t,J=12Hz), 3.30-3.53 (3H,m), 3.65-3.78 (1H,m), 3.68 (1H,d,J=12Hz), 4.07 (3H,s), 4.92-5.03 (1H,m), 5.29-5.40 (2H,m), 6.30-6.38 (1H,m), 6.91 (1H,t,J=6Hz).

EXAMPLE 82

(S)-1-Methyl-2-oleoylaminoethyl-3-[N-(2,2,5,5-tetramethyl-1,3-dioxane-4-carbonyl)amino]propionate Molecular Formula: C$_{33}$H$_{60}$N$_2$O$_6$.

Molecular Weight: 580.85,

Mass Spectrometric Analysis: Calculated: 580.4451, Found: 580.4458.

Melting Point (° C.): Oil.

Specific Rotary Power: $[\alpha]^{22}_D$+21.6° (C=1.0, CHCl$_3$).

IR($\nu$neat, cm$^{-1}$): 3332, 2932, 2860, 1738, 1662.

NMR(δ, CDCl$_3$): 0.88 (3H,t,J=7Hz), 0.97 (3H,s), 1.04 (3H,s), 1.20-1.37 (23H,m), 1.43 (3H,s), 1.47 (3H,s), 1.56-1.68 (2H,m), 1.91-2.08 (4H,m), 2.20 (2H,t,J=7Hz), 2.44-2.62 (2H,m), 3.26-3.35 (1H,m), 3.28 (1H,d,J=12Hz), 3.42-3.58 (2H,m), 3.64-3.75 (1H,m), 3.70 (1H,d,J=12Hz), 4.07 (1H,s), 4.93-5.03 (1H,m), 5.28-5.41 (2H,m), 6.27-6.34 (1H,m), 6.88-6.96 (1H,m).

EXAMPLE 83

(1S,2S)-2-(Oleoylamino)cyclopentane-1-yl-3-[N-2,2,5,5-tetramethyl-1,3-dioxane-4-carbonyl)amino]propionate Molecular Formula: C$_{35}$H$_{62}$N$_2$O$_6$.

Molecular Weight: 606.89.

Mass Spectrometric Analysis: Calculated: 606.4607, Found: 606.4617.

Melting Point (° C.): Oil.

Specific Rotary Power: $[\alpha]^{23}_D$+24.5° (C=1.0, CHCl$_3$).

IR($\nu$neat, cm$^{-1}$) 3324, 2932, 2860, 1736, 1654.

NMR(δ, CDCl$_3$): 0.88 (3H,t,J=7Hz), 0.96 (3H,s), 1.04 (3H,s), 1.20-1.48 (22H,m), 1.43 (3H,s), 1.46 (3H,s), 1.52-2.09 (9H,m), 2.13 (2H,t,J=7Hz), 2.18-2.22 (1H,m), 2.54 (2H,t,J=6Hz), 3.28 (1H,d,J=12Hz), 3.48-3.59 (2H,m), 3.69 (1H,d,J=12Hz), 4.08 (1H,s), 4.08-4.19 (1H,m), 4.92-5.01 (1H,m), 5.29-5.40 (2H,m), 5.72 (1H,d,J=7Hz), 6.98 (1H,t,J=6Hz).

EXAMPLE 84

(1R,2R)-2-(Oleoylamino)cyclopentane-1-yl-3-N-2,2,5,5-tetramethyl-1,3-dioxane-4-carbonyl)amino)propionate
Molecular Formula : $C_{35}H_{62}N_2O_6$.
Molecular Weight : 606.89,
Mass Spectrometric Analysis: Calculated : 606.4607, Found : 606.4614.
Melting Point (° C.): Oil.
Specific Rotary Power: $[\alpha]^{24}_D +14.9°$ (C=1.0, $CHCl_3$).
IR($\nu$neat, cm$^{-1}$) 3328, 2932, 2860, 1740, 1656.
NMR($\delta$, $CDCl_3$): 0.88 (3H,t,J=7Hz), 0.99 (3H,s), 1.04 (3H,s), 1.21–1.47 (22H,m), 1.43 (3H,s), 1.46 (3H,s), 1.53–2.12 (9H,m), 2.13 (2H,t,J=7Hz), 2.18–2.31 (1H,m), 2.54 (2H,t,J=6Hz), 3.28 (1H,d,J=12Hz), 3.36–3.49 (1H,m), 3.58–3.69 (1H,m), 3.69 (1H,d,J=12Hz), 4.08 (1H,s), 4.09–4.20 (1H,m), 4.95–5.02 (1H,m), 5.29–5.40 (2H,m), 5.72 (1H,d,J=7Hz), 7.02 (1H,t,J=6Hz).

EXAMPLE 85

(Z)-4-Oleoylamino-2-butenyl-3-[N-(2,2,5,5-tetramethyl-1,3-dioxane-4-carbonyl)amino]propionate
Molecular Formula : $C_{34}H_{60}N_2O_6$.
Molecular Weight : 592.80.
Mass Spectrometric Analysis: Calculated : 592.4451, Found : 592.4424.
Melting Point (° C.): Oil.
Specific Rotary Power: $[\alpha]^{24}_D+22.2°$ (C=1.0, $CHCl_3$).
IR($\nu$neat, cm$^{-1}$): 3336, 2932, 2860, 1740, 1660.
NMR($\delta$, $CDCl_3$): 0.88 (3H,t,J=7Hz), 0.90 (3H,s), 1.04 (3H,s), 1.20–1.38 (20H,m), 1.43 (3H,s), 1.46 (3H,s), 1.54–1.69 (2H,m), 1.91–2.08 (4H,m), 2.17 (2H,t,J=7Hz), 2.57 (2H,t,J=6Hz), 3.28 (1H,d,J=12Hz), 3.42–3.67 (2H,m), 3.69 (1H,d,J=12Hz), 3.97 (2H,dd,J=6Hz,6Hz), 4.08 (1H,s), 4.70 (2H,d,J=6Hz), 5.29–5.40 (2H,m), 5.59–5.80 (3H,m), 6.88–6.96 (1H,m).

EXAMPLE 86

(R)-2-Methyl-2-oleoylaminoethyl 3-[N-(2,5,5,5-tetramethyl-1,3-dioxane-4-carbonyl)amino]propionate
Molecular Formula : $C_{33}H_{60}N_2O_6$,
Molecular Weight : 580.85,
Mass Spectrometric Analysis: Calculated : 580.4451, Found : 580.4458.
Melting Point (° C.): Oil.
Specific Rotary Power: $[\alpha]^{25}_D+31.0°$ (C=1 0, $CHCl_3$).
IR($\nu$neat, cm$^{-1}$) 3324, 2932, 2860, 1740, 1660.
NMR($\delta$, $CDCl_3$): 0.88 (3H,t,J=7Hz), 0.98 (3H,s), 1.04 (3H,s), 1.18 (3H,d,J=6Hz), 1.23–1.39 (20H,m), 1.43 (3H,s), 1.47 (3H,s), 1.57–1.68 (2H,m), 1.92–2.08 (4H,m), 2.16 (2H,t,J=7Hz), 2.58 (2H,t,J=6Hz), 3.28 (1H,d,J=12Hz), 3.57 (2H,dt,J=6Hz,6Hz), 3.69 (1H,d,J=12Hz), 4.03–4.14 (2H,m), 4.07 (1H,s), 4.26–4.37 (1H,m), 5.29–5.40 (2H,m), 5.84 (1H,d,J=8Hz), 6.98 (1H,t,J=6Hz).

EXAMPLE 87

(S)-2-Methyl-2-oleoylaminoethyl 3-[N-(2,2,5,5-tetramethyl-1,3-dioxane-4-carbonyl)amino]propionate
Molecular Formula : $C_{33}H_{60}N_2O_6$,
Molecular Weight : 580.85.
Mass Spectrometric Analysis: Calculated : 580.4451, Found : 580.4442.
Melting Point (° C.): Oil.
Specific Rotary Power: $[\alpha]^{25}_D+13.1°$ (C=1.0, $CHCl_3$).
IR($\nu$neat, cm$^{-1}$) 3320, 2932, 2860, 1744, 1654.
NMR($\delta$, $CDCl_3$): 0.88 (3H,t,J=7Hz), 0.97 (3H,s), 1.03 (3H,s), 1.16 (3H,d,J=6Hz), 1.21–1.39 (20H,m), 1.42 (3H,s), 1.47 (3H,s), 1.54–1.68 (2H,m), 1.92–2.08 (4H,m), 2.17 (2H,t,J=7Hz), 2.58 (2H,t,J=6Hz), 3.28 (1H,d,J=12Hz), 3.49–3.67 (2H,m), 3.69 (1H,d,J=12Hz), 4.05 (1H,dd,J=11Hz, 4Hz), 4.07 (1H,s), 4.13 (1H,dd,J=11Hz,5Hz), 4.22–4.36 (1H,m), 5.29–5.42 (2H,m), 5.92 (1H,d,J=8Hz), 6.92 (1H,t,J=5Hz).

EXAMPLE 88

(E)-4-Oleoylaminobutenyl 3-[N-(2,2,5,5-tetramethyl-1,3-dioxane-4-carbonyl)amino]propionate
Molecular Formula : $C_{34}H_{60}N_2O_6$.
Molecular Weight : 592.86.
Mass Spectrometric Analysis: Calculated : 592.4451, Found : 592.4459.
Melting Point (° C.): Oil.
Specific Rotary Power: $[\alpha]^{25}_D+22.1°$ (C=1.0, $CHCl_3$).
IR($\nu$neat, cm$^{-1}$) 3328, 2932, 2860, 1740, 1660.
NMR($\delta$, $CDCl_3$): 0.88 (3H,t,J=7Hz), 0.96 (3H,s), 1.04 (3H,s), 1.21–1.38 (20H,m), 1.43 (3H,s), 1.46 (3H,s), 1.56–1.69 (2H,m), 1.91–2.08 (4H,m), 2.18 (2H,t,J=7Hz), 2.58 (2H,t,J=6Hz), 3.28 (1H,d,J=12Hz), 3.41–3.68 (2H,m), 3.69 (1H,d,J=12Hz), 3.90 (2H,dd,J=6Hz,6Hz), 4.08 (1H,s), 4.57 (2H,d,J=6Hz), 5.28–5.41 (2H,m), 5.52–5.62 (1H,m), 5.65–5.83 (2H,m), 6.95 (1H,t,J=6Hz).

EXAMPLE 89

4-Oleoylaminobutenyl 3-N-(2,2,5,5-tetramethyl-1,3-dioxane-4-carbonyl)amino]propionate
Molecular Formula : $C_{34}H_{58}N_2O_6$.
Molecular Weight : 590.85.
Mass Spectrometric Analysis: Calculated : 590.4294, Found : 590.4279.
Specific Rotary Power: $[\alpha]^{25}_D+21.2°$ (C=1.0, $CHCl_3$).
IR($\nu$neat, cm$^{-1}$) 3320, 2932, 2860, 1748, 1662.
NMR($\delta$, $CDCl_3$): 0.88 (3H,t,J=7Hz), 0.97 (3H,s), 1.04 (3H,s), 1.21–1.39 (20H,m), 1.43 (3H,s), 1.47 (3H,s), 1.58–1.72 (2H,m), 1.92–2.08 (4H,m), 2.18 (2H,t,J=7Hz), 2.61 (2H,t,J=6Hz), 3.28 (1H,d,J=12Hz), 3.42–3.68 (2H,m), 3.70 (1H,d,J=12Hz), 4.08 (1H,s), 4.08–4.11 (2H,m), 4.69–4.72 (2H,m), 5.29–5.42 (2H,m), 5.68–5.78 (1H,m), 6.96 (1H,t,J=5Hz).

EXAMPLE 90

(R)-2-Oleoylamino-2-phenylethyl 3-[N-(2,2,5,5-tetramethyl-1,3-dioxane-4-carbonyl)amino]propionate
Molecular Formula : $C_{38}H_{62}N_2O_6$.
Molecular Weight : 642.92.
Mass Spectrometric Analysis: Calculated : 642.4607, Found : 642.4613.
Melting Point (° C.): Oil.
Specific Rotary Power : $[\alpha]^{24}_D-0.4°$ (C=1 0, $CHCl_3$).
IR($\nu$neat, cm ): 3320, 2932, 2864, 1744, 1654.
NMR(($\delta$, $CDCl_3$): 0.88 (3H,t,J=7Hz), 0.90 (3H,s), 1.04 (3H,s), 1.21–1.38 (20H,m), 1.44 (3H,s), 1.47 (3H,s), 1.57–1.70 (2H,m), 1.92–2.08 (4H,m), 2.25 (2H,t,J=7Hz), 2.52 (2H,t,J=6Hz), 3.28 (1H,d,J=12Hz), 3.46–3.65 (2H,m), 3.69 (1H,d,J=12Hz), 4.08 (1H,s), 4.29–4.39

(2H,m), 5.29–5.42 (3H,m), 6.60 (1H,d,J=8Hz), 6.93 (1H,t,J=5Hz), 7.26–7.38 (5H,m).

EXAMPLE 91

(S)-2-Oleoylamino-2-phenylethyl 3-N-(2,2,5,5-tetramethyl-1,3-dioxane-4-carbonyl)amino)propionate Molecular Formula : $C_{38}H_{62}N_2O_6$.

Molecular Weight : 642.92.

Mass Spectrometric Analysis: Calculated : 642.4607, Found : 642.4613.

Melting Point (° C.): Oil.

Specific Rotary Power: $[\alpha]^{26}_D +40.2°$ (C=1.0, $CHCl_3$).

IR($\nu$neat, cm$^{-1}$): 3320, 2932, 2860, 1742, 1660.

NMR($\delta CDCl_3$): 0.88 (3H,t,J=7Hz), 0.90 (3H,s), 1.03 (3H,s), 1.21–1.39 (20H,m), 1.42 (3H,s), 1.46 (3H,s), 1.57–1.74 (2H,m), 1.91–2.08 (4H,m), 2.25 (2H,t,J=7Hz), 2.51 (2H,t,J=6Hz), 3.28 (1H,d,J=12Hz), 3.42–3.67 (2H,m), 3.68 (1H,d,J=12Hz), 4.05 (1H,s), 4.31 (1H,dd,J=12Hz,5Hz), 4.39 (1H,dd,J=12Hz,6Hz), 5.28–5.41 (3H,m), 6.59 (1H,d,J=8Hz) 6.91 (1H,t,J=5Hz), 7.25–7.38 (5H,m).

EXAMPLE 92

(Trans)-2-(oleoylamino)cyclopentane-1-yl 3-[N-(2,2,5,5-tetramethyl-1,3-dioxane-4-carbonyl)amino)propionate Molecular Formula : $C_{37}H_{66}N_2O_6$.

Molecular Weight : 634.94.

Mass Spectrometric Analysis: Calculated : 634.4920, Found : 634.4911.

Melting Point (° C.): Oil.

Specific Rotary Power: $[\alpha]^{26}_D +22.0°$ (C=1.0, $CHCl_3$).

IR($\nu$neat, cm$^{-1}$): 3328, 2932, 2864, 1734, 1660.

NMR($\delta$, $CDCl_3$): 0.88 (3H,t,J=7Hz), 1.00 (3H,s), 1.04 (3H,s), 1.21–1.38 (20H,m), 1.41–2.08 (16H,m), 1.43 (3H,s), 1.47 (3H,s), 2.09 (2H,t,J=7Hz), 2.50 (2H,t,J=6Hz), 3.28 (1H,d,J=12Hz), 3.32–3.44 (1H,m), 3.57–3.68 (1H,m), 3.69 (1H,d,J=12Hz), 3.99–4.09 (1H,m), 4.08 (1H,s), 4.77–4.84 (1H,m), 5.29–5.40 (2H,m), 5.82 (1H,d,J=8Hz), 6.97 (1H,t,J=6Hz).

EXAMPLE 93

(Trans)-2-(oleoylamino)cyclopentane-1-yl 3-[N-(2,2,5,5-tetramethyl-1,3-dioxane-4-carbonyl)amino]propionate Molecular Formula : $C_{37}H_{66}N_2O_6$.

Molecular Weight : 634.94.

Mass Spectrometric Analysis: Calculated : 634.4920, Found : 634.4904.

Melting Point (° C.): Oil.

Specific Rotary Power: $[\alpha]^{26}_D +13.1°$ (C=1.0, $CHCl_3$).

IR($\nu$neat, cm$^{-1}$) 3324, 2932, 2864, 1734, 1650.

NMR($\delta$, $CDCl_3$): 0.88 (3H,t,J=7Hz), 0.96 (3H,s), 1.04 (3H,s), 1.21–1.38 (20H,m), 1.40–2.08 (16H,m), 1.43 (3H,s), 1.47 (3H,s), 2.10 (2H,t,J=7Hz), 2.50 (2H,t,J=6Hz), 3.28 (1H,d,J=12Hz), 3.51 (2H,tt,J=6Hz,6Hz), 3.69 (1H,d,J=12Hz), 3.97–4.08 (1H,m), 4.09 (1H,s), 4.77–4.84 (1H,m), 5.29–5.42 (2H,m), 5.89 (1H,d,J=8Hz), 6.92 (1H,t,J=6Hz).

EXAMPLE 94

(S)-3-Methyl-2-oleoylaminobutyl 3-[N-(2,2,5,5-tetramethyl-1,3-dioxane-4-carbonyl)amino)propionate Molecular Formula : $C_{35}H_{64}N_2O_6$.

Molecular Weight : 608.91.

Mass Spectrometric Analysis: Calculated : 608.4764, Found : 608.4741.

Melting Point (° C.): Oil.

Specific Rotary Power: $[\alpha]^{24}_D +4.9°$ (C=1.0, $CHCl_3$).

IR($\nu$neat, cm$^{-1}$) 3324, 2932, 2860, 1734, 1652.

NMR($\delta$, $CDCl_3$): 0.88 (3H,t,J=7Hz), 0.93 (3H,d,J=6Hz), 0.95 (3H,d,J=6Hz), 0.97 (3H,s), 1.03 (3H,s), 1.21–1.39 (20H,m), 1.43 (3H,s), 1.47 (3H,s), 1.56–1.86 (3H,s), 1.90–2.08 (4H,m), 2.20 (2H,t,J=7Hz), 2.56 (2H,t,J=6Hz), 3.28 (1H,d,J=12Hz), 3.56 (2H,dt,J=6Hz,6Hz), 3.68 (1H,d,J=12Hz), 3.95–4.29 (3H,m), 4.07 (1H,s), 5.29–5.41 (2H,m), 5.79 (1H,d,J=8Hz), 6.93 (1H,t,J=6Hz).

EXAMPLE 95

(S)-2-Oleoylaminobutyl 3-[N-(2,2,5,5-tetramethyl-1,3-dioxane-4-carbonyl)amino]propionate Molecular Formula : $C_{34}H_{62}N_2O_6$.

Molecular Weight : 594.88.

Mass Spectrometric Analysis: Calculated : 594.4607, Found : 594.4597.

Melting Point (° C.): Oil.

Specific Rotary Power: $[\alpha]^{25}_D +6.2°$ (C=1.0, $CHCl_3$).

IR($\nu$neat, cm$^{-1}$) 3320, 2932, 2864, 1742, 1652.

NMR($\delta$, $CDCl_3$): 0.88 (3H,t,J=7Hz), 0.91 (3H,d,J=7Hz), 0.97 (3H,s), 1.03 (3H,s), 1.21–1.38 (20H,m), 1.42 (3H,s), 1.44–1.68 (4H,m), 1.47 (3H,s), 1.91–2.08 (4H,m), 2.17 (2H,t,J=7Hz), 2.58 (2H,t,J=6Hz), 3.29 (1H,d,J=12Hz), 3.57 (2H,dt,J=6Hz,6Hz), 3.68 (1H,d,J=12Hz), 4.03–4.24 (3H,m), 4.07 (1H,s), 5.29–5.42 (2H,m), 5.84 (1H,d,J=8Hz), 6.92 (1H,t,J=6Hz).

EXAMPLE 96

2-Oleoylamino-1-phenylethyl 3-[N-(2,2,5,5-tetramethyl-1,3-dioxane-4-carbonyl)amino]propionate Molecular Formula : $C_{38}H_{62}N_2O_6$.

Molecular Weight : 642.92.

Mass Spectrometric Analysis: Calculated : 642.4607, Found : 642.4606.

Melting Point (° C.): Oil.

Specific Rotary Power: $[\alpha]^{24}_D +24.3°$ (C=1.0, $CHCl_3$).

IR($\nu$neat, cm$^{-1}$) 3324, 2932, 2864, 1744, 1660.

NMR($\delta$, $CDCl_3$): 0.88 (3H,t,J=7Hz), 0.91 (3/2H,s), 0.99 (3/2H,s), 1.03 (3/2H,s), 1.04 (3/2H,s), 1.19–1.38 (20H,m), 1.41 (3/2H,s), 1.42 (3/2H,s), 1.43 (3H,s), 1.52–1.66 (2H,m), 1.92–2.08 (4H,m), 2.12–2.22 (2H,m), 2.48–2.67 (2H,m), 3.26 (1/2H,d,J=12Hz), 3.29 (1/2H,d,J=12Hz), 3.42–3.85 (4H,m), 3.68 (1H,d,J=12Hz), 4.06 (1/2H,s), 4.07 (1/2H,s), 5.29–5.41 (2H,m), 5.84 (1/2H,d,J=8Hz), 5.86 (1/2H,d,J=8Hz), 6.16–6.27 (1H,m), 6.88–6.97 (1H,m), 7.27–7.38 (5H,m).

EXAMPLE 97

(S)-2-Oleoylamino-3-phenylpropyl 3-N-(2,2,5,5-tetramethyl-1,3-dioxane-4-carbonyl)amino]propionate Molecular Formula : $C_{39}H_{64}N_2O_6$.

Molecular Weight : 656.95.

Mass Spectrometric Analysis: Calculated : 656.4764, Found : 656.4740.

Melting Point (° C.): Oil.

Specific Rotary Power: $[\alpha]^{25}_D +18.3°$ (C=1.0, $CHCl_3$).

IR($\nu$neat, cm$^{-1}$) 3316, 2932, 2860, 1742, 1660.

NMR(δ, CDCl$_3$): 0.88 (3H,t,J=7Hz), 0.97 (3H,s), 1.03 (3H,s), 1.17-1.38 (20H,m), 1.41 (3H,s), 1.46 (3H,s), 1.50-1.68 (2H,m), 1.92-2.08 (4H,m), 2.16 (2H,t,J=7Hz), 2.59 (2H,t,J=6Hz), 2.78 (1H,dd,J=13Hz,7Hz), 2.89 (1H,dd,J=13Hz,6Hz), 3.28 (1H,d,J=12Hz), 3.39-3.69 (2H,m), 3.69 (1H,d,J=12Hz), 4.04-4.09 (2H,m), 4.08 (1H,s), 4.37-4.44 (1H,m), 5.28-5.41 (2H,m), 6.07 (1H,d,J=8Hz), 6.93 (1H,t,J=5Hz), 7.16-7.32 (5H,m).

EXAMPLE 98

(S)-4-Methyl-2-oleoylaminopentyl 3-[N-(2,2,5,5-tetramethyl-1,3-dioxane-4-carbonyl)amino)propionate
Molecular Formula : $C_{36}H_{66}N_2O_6$.
Molecular Weight : 622.93.
Mass Spectrometric Analysis: Calculated : 622.4920 Found : 622.4895.
Melting Point (° C.): Oil.
Specific Rotary Power: $[\alpha]^{25}_D$+7.6° (C=1.0, CHCl$_3$).
IR($\nu$neat, cm$^{-1}$) 3320, 2932, 2864, 1742, 1652.
NMR(δ, CDCl$_3$): 0.88 (3H,t,J=7Hz), 0.91 (3H,t,J=6Hz), 0.93 (3H,t,J=6Hz), 0.97 (3H,s), 1.03 (3H,s), 15 1.19-1.41 (20H,m), 1.42 (3H,s), 1.47 (3H,s), 1.53-1.77 (5H,m), 1.90-2.08 (4H,m), 2.17 (2H,t,J=7Hz), 2.57 (2H,t,J=6Hz), 3.28 (1H,d,J=12Hz), 3.56 (2H,dt,J=6Hz,6Hz), 3.68 (1H,d,J=12Hz), 4.07 (1H,s), 4.07 (1H,dd,J=11Hz,4Hz), 4.13 (1H,dd,J=11Hz,4Hz), 4.21-4.35 (1H,m), 5.28-5.41 (2H,m), 5.72 (1H,d,J=8Hz), 6.94 (1H,t,J=6Hz).

EXAMPLE 99

2-(1-Oleoylaminocyclohexyl)ethyl 3-[N-(2,2,5,5-tetramethyl-1,3-dioxane-4-carbonyl)amino)propionate
Molecular Formula : $C_{37}H_{66}N_2O_6$.
Molecular Weight : 634.94.
Mass Spectrometric Analysis: Calculated : 634.4920, Found : 634.4899.
Melting Point (° C.): Oil.
Specific Rotary Power: $[\alpha]^{29}_D$+22.0° (C=1.0, CHCl$_3$).
IR($\nu$neat, cm$^{-1}$) 3352, 2936, 2864, 1742, 1664.
NMR(δ, CDCl$_3$): 0.88 (3H,t,J=7Hz), 0.97 (3H,s), 1.04 (3H,s), 1.21-1.67 (32H,m), 1.42 (3H,s), 1.46 (3H,s), 15 1.91-2.13 (3H,m), 2.15 (2H,t,J=7Hz), 2.56 (2H,t,J=6Hz), 3.28 (1H,d,J=12Hz), 3.46-3.63 (2H,m), 3.68 (1H,d,J=12Hz), 4.07 (1H,s), 4.31 (1H,d,J=11Hz), 4.36 (1H,d,J=11Hz), 5.13 (1H,s), 5.28-5.42 (2H,m), 6.96 (1H,t,J=5Hz).

EXAMPLE 100

(S)-2-Oleoylamino-2-phenylethyl N-(2,2,5,5-tetramethyl-1,3-dioxane-4-carbonyl)aminopropionate
Molecular Formula : $C_{37}H_{60}N_2O_6$.
Molecular Weight : 628.90.
Mass Spectrometric Analysis: Calculated : 628.4451, Found 628.4440.
Melting Point (° C.): Oil.
Specific Rotary Power: $[\alpha]^{29}_D$+46.9° (C=1.0, CHCl$_3$).
IR($\nu$neat, cm$^{-1}$) 3320, 2932, 2864, 1760, 1662.
NMR(δ, CDCl$_3$): 0.88 (3H,t,J=7Hz), 1.04 (6H,s), 1.19-1.38 (20H,m), 1.43 (3H,s), 1.48 (3H,s), 1.51-1.69 (2H,m), 1.91-2.05 (4H,m), 2.24 (2H,t,J=7Hz), 3.30 (1H,d,J=12Hz), 3.69 (1H,d,J=12Hz), 3.98 (2H,d,J=5Hz), 4.09 (1H,s), 4.39 (1H,dd,J=11Hz,6Hz), 4.56 (1H,dd,J=11Hz,5Hz), 5.28-5.40 (3H,m), 6.25 (1H,d,J=8Hz), 7.00 (1H,t,J=5Hz), 7.26-7.39 (5H,m).

EXAMPLE 101

(S)-2-Oleoylamino-2-phenylethyl 4-N-(2,2,5,5-tetramethyl-1,3-dioxane-4-carbonyl)animo]butanoate
Molecular Formula : $C_{39}H_{64}N_2O_6$.
Molecular Weight : 656.95.
Mass Spectrometric Analysis: Calculated : 656.4764, Found : 656.4770.
Melting Point (° C.): Oil.
Specific Rotary Power: $[\alpha]^{30}_D$+41.4° (C=1.0, CHCl$_3$).
IR($\nu$neat, cm$^{-1}$): 3320, 2932, 2864, 1744, 1654.
NMR(δ, CDCl$_3$): 0.88 (3H,t,J=7Hz), 0.99 (6H,s), 1.06 (3H,s), 1.21-1.38 (20H,m), 1.44 (3H,s), 1.48 (3H,s), 1.56-2.07 (8H,m), 2.26 (2H,t,J=7Hz), 2.32 (2H,d,J=6Hz), 3.16-3.38 (2H,m), 3.30 (1H,d,J=12Hz), 3.70 (1H,d,J=12Hz), 4.09 (1H,s), 4.38 (1H,dd,J=11Hz,6Hz), 4.44 (1H,dd,J=11Hz,5Hz), 5.28-5.42 (3H,m), 6.64 (1H,d,J=5Hz), 6.76 (1H,t,J=8Hz), 7.26-7.38 (5H,m).

EXAMPLE 102

(S)-2-Oleoylamino-2-phenylethyl 5-[N-(2,2,5,5-tetramethyl-1,3-dioxane-4-carbonyl)amino]pentanoate
Molecular Formula : $C_{40}H_{66}N_2O_6$.
Molecular Weight : 670.98.
Mass Spectrometric Analysis: Calculated : 670.4920, Found : 670.4912.
Melting Point (° C.): Oil.
Specific Rotary Power: $[\alpha]^{30}_D$+40.6° (C=1.0, CHCl$_3$).
IR($\nu$neat, cm$^{-1}$) 3324, 2932, 2864, 1742, 1654.
NMR(δ, CDCl$_3$): 0.88 (3H,t,J=7Hz), 0.99 (3H,s), 1.05 (3H,s), 1.20-1.38 (20H,m), 1.43 (3H,s), 1.47 (3H,s), 1.47-1.70 (6H,m), 1.92-2.08 (4H,m), 2.22 (2H,t,J=7Hz), 2.33 (2H,d,J=6Hz), 3.12-3.30 (2H,m), 3.29 (1H,d,J=12Hz), 3.69 (1H,d,J=12Hz), 4.08 (1H,s), 4.28 (1H,dd,J=11Hz,5Hz), 4.43 (1H,dd,J=11Hz,6Hz), 5.28-5.40 (3H,m), 6.19 (1H,d,J=8Hz), 6.68 (1H,t,J=5Hz), 7.26-7.39 (5H,m).

EXAMPLE 103

(1S,2S)-2-(2,2,-Dimethylstearoryl)aminocyclohexane-1-yl 3-N-(2,2,5,5-tetramethyl-1,3-dioxane-4carbonyl)amino]propionate
Molecular Formula : $C_{38}H_{70}N_2O_6$.
Molecular Weight : 650.99.
Mass Spectrometric Analysis: Calculated : 650.5233, Found : 650.5244.
Melting Point (° C.): Oil.
Specific Rotary Power: $[\alpha]^{28}_D$+10.6° (C=1.0, CHCl$_3$).
IR($\nu$neat, cm$^{-1}$): 3380, 2932, 2860, 1734.
NMR(δ, CDCl$_3$): 0.88 (3H,t,J=7Hz), 0.96 (3H,s), 1.04 (3H,s), 1.09 (6H,s), 1.10-2.16 (38H,m), 1.43 (3H,s), 1.47 (3H,s), 2.42-2.62 (2H,m), 3.28 (1H,d,J=12Hz), 3.39-3.63 (2H,m), 3.69 (1H,d,J=12Hz), 3.81-3.93 (1H,m), 4.08 (1H,s), 4.73 (1H,ddd,J=11Hz,11Hz,4Hz), 5.80 (1H,d,J=8Hz), 6.92 (1H,t,J=5Hz).

EXAMPLE 104

(1S,2S)-2-(2,2,-Dimethyloleoyl)aminocyclohexane-1-yl 3-[N-(2,2,5,5-tetramethyl-1,3-dioxane-4-carbonyl)amino)propionate
Molecular Formula : $C_{38}H_{68}N_2O_6$,
Molecular Weight : 648.97.
Mass Spectrometric Analysis: Calculated : 648.5077, Found : 648.5063.

Melting Point (° C.): Oil.
Specific Rotary Power: $[\alpha]^{28}{}_D +10.9°$ (C=1.0, CHCl$_3$).
IR($\delta$neat, cm$^{-1}$) 3380, 2936, 2864, 1734, 1672.
NMR($\delta$, CDCl$_3$): 0.88 (3H,t,J=7Hz), 0.96 (3H,s), 1.00-2.18 (34H,m), 1.03 (3H,s), 1.08 (6H,s), 1.42 (3H,s), 1.47 (3H,s), 2.41-2.62 (2H,m), 3.28 (1H,d,J=12Hz), 3.38-3.62 (2H,m), 3.69 (1H,d,J=12Hz), 3.80-3.92 (1H,m), 4.07 (1H,s), 4.73 (1H,ddd,J=11Hz,11Hz,4Hz), 5.28-5.41 (2H,m), 5.79 (1H,d,J=8Hz), 6.92 (1H,t,J=5Hz).

EXAMPLE 105

(1S,2S)-2-(2-Methyloleoyl)aminocyclohexane-1-yl 3-[N-(2,2,5,5-tetramethyl-1,3-dioxane-4-carbonyl-)amino]
propionate
Molecular Formula : C$_{37}$H$_{66}$N$_2$O$_6$.
Molecular Weight : 634.94.
Mass Spectrometric Analysis: Calculated : 634.4920, Found : 634.4950.
Melting Point (° C.): Oil.
Specific Rotary Power: $[\alpha]^{28}{}_D +10.8°$ (C=1.0, CHCl$_3$).
IR($\nu$neat, cm$^{-1}$) 3324, 2936, 2864, 1734.
NMR($\delta$, CDCl$_3$): 0.88 (3H,t,J=7Hz), 0.96 (3H,s), 1.03 (3H,s), 1.06 (3/2H,d,J=7Hz), 1.08 (3/2H,d,J=7Hz), 1.09-2.18 (35H,m), 1.43 (3H,s), 1.47 (3H,s), 2.50 (2H,t,J=6Hz), 3.28 (1H,d,J=12Hz), 3.51 (2H,dt,J=6Hz,6Hz), 3.69 (1H,d,J=12Hz), 3.81-3.94 (1H,m), 4.08 (1H,s), 4.61-4.73 (1H,m), 5.28-5.42 (2H,m), 5.70-5.78 (1H,m), 6.91 (1H,t,J=6Hz).

EXAMPLE 106

(1S,2S)-2-(2-Methylpalmitoyl)aminocyclohexane-1-yl 3-[N-(2,2,5,5-tetramethyl-1,3-dioxane 4-carbonyl)-amino]propionate Molecular Formula: C$_{35}$H$_{64}$N$_2$O$_6$.
Molecular Weight: 608.91.
Mass Spectrometric Analysis:
Calculated: 608.4764, Found: 608.4754.
Melting Point (° C.): 77°-79° C. (benzene/hexane).
Specific Rotary Power: $[\alpha\ ^{28}{}_D +14.4°$ (C=1.0, CHCl$_3$).
IR($\nu$KBr, cm$^{-1}$) 3312, 2932, 2860, 1742, 1652.
NMR($\delta$, CDCl$_3$): 0.88 (3H,t,J=7Hz), 0.96 (3H,s), 1.03 (3H,s),
1.39 (3H,d,J=7Hz), 1.10-2.18 (35H,m), 1.43 (3H,s), 1.47 (3H,s), 2.43-2.58 (2H,m), 3.28 (1H=12Hz), 3.51 (2H,dt,J=6Hz,6Hz), 3.69 (1H,d,J=12Hz), 3.38-3.93 (1H,m), 4.08 (1H,s), 4.68 (1H,ddd,J=11 Hz,11 Hz,4Hz), 5.76 (1H,d,J=8Hz), 6.91 (1H,t,J=6Hz).

EXAMPLE 107

(1S,2S)-2-(2-Methylpalmitoyl)aminocyclohexane-1-yl 3-N-(2,2,5,5-tetramethyl-1,3-dioxane-4-carbonyl)-amino]propionate Molecular Formula: C$_{35}$H$_{64}$N$_2$O$_6$.
Molecular Weight: 608.91.
Mass Spectrometric Analysis: Calculated 608.4764. Found 608.4762.
Melting Point (° C.): 92°-94° C. (benzene/hexane).
Specific Rotary Power: $[\alpha]^{19} +6.7°$ (C=1.0, CHCl$_3$).
IR($\nu$KBr, cm$^{-1}$): 3284, 2928, 2860, 1736, 1652 .
NMR($\delta$, CDCl$_3$):
0.88 (3H,t,J=7Hz), 0.96 (3H,s), 1.03 (3H,s), 1.06 (3H,d,J=7Hz), 1.10-2.17 (35H,m), 1.43 (3H,s), 1.47 (3H,s), 2.50 (2H,t,J=6Hz), 3.28 (1H,d,J=12Hz), 3.51 (2H,dt,J=6Hz,6Hz), 3.69 (1H,d,J=12Hz), 3.82-3.95 (1H,m), 4.08 (1H,s), 4.67 (1H,ddd,J=11 Hz,11 Hz,4Hz), 5.73 (1H,d,J=8Hz), 6.92 (1H,t,J=6Hz).

EXAMPLE 108

(1S,2S)-2l-(2-Ethylmyristoyl)aminocyclohexane-1-yl 3-[N-(2,2,5,5-tetramethyl-1,3-dioxane-4-carbonyl-)amino]propionate Molecular Formula: C$_{34}$H$_{62}$N$_2$O$_6$.
Molecular Weight: 594.88.
Mass Spectrometric Analysis: Calculated 594.4607, Found 594.4621.
Melting Point (° C.): Oil.
Specific Rotary Power: $[\alpha]^{19}{}_D +10.1°$ (C=1.0, CHCl$_3$).
IR($\nu$neat, cm$^{-1}$) 3320, 2936, 2864, 1734, 1648.
NMR($\delta$, CDCl$_3$): 0.85 (3H,t,J=7Hz), 0.88 (3H,d,J=7Hz), 0.96 (3H,s), 1.04 (3H,s), 1.10-2.23 (33H,m), 1.43 (3H,s), 1.47 (3H,s), 2.42-2.59 (2H,m), 3.28 (1H,d,J=12Hz), 3.51 (2H,dt,J=6Hz,6Hz), 3.69 (1H,d,J=12Hz), 3.38-3.95 (1H,m), 4.08 (1H,s), 4.68 (1H,ddd,J=1Hz,1Hz,4Hz), 5.85 (1H,d,J=8Hz), 6.92 (1H,t,J=6Hz).

EXAMPLE 109

(1S,2S)-2-(2-Ethylmyristoyl)aminocyclohexane-1-yl 3-N-(2,2,5,5-tetramethyl-1,3-dioxane-4-carbonyl-)amino]propionate Molecular Formula: C$_{34}$H$_{62}$N$_2$O$_6$.
Molecular Weight: 594.88.
Mass Spectrometric Analysis: Calculated: 594.4607, Found: 594.4591.
Melting Point (° C.): Calomel ,
Specific Rotary Power: $[\alpha]^{20}{}_D +9.6°$ (C=1.0, CHCl$_3$).
IR($\nu$KBr, cm$^{-1}$): 3288, 2928, 2860, 1736, 1680, 1648.
NMR($\delta$, CDCl$_3$): 0.82 (3H,t,J=7Hz), 0.88 (3H,d,J=7Hz), 0.96 (3H,s), 1.03 (3H,s), 1.09-2.18 (33H,m), 1.43 (3H,s), 1.47 (3H,s), 2.41-2.58 (2H,m), 3.28 (1H,d,J=12Hz), 3.51 (2H,dd,J=6Hz,6Hz), 3.69 (1H,d,J=12Hz), 3.85-3.98 (1H,m), 4.08 (1H,s), 4.68 (1H,ddd,J=1Hz,1Hz,4Hz), 5.79 (1H,d,J=8Hz), 6.92 (1H,t,J=6Hz).

EXAMPLE 110

(1S,2S)-2-(2-Propylstearoyl)aminocyclohexane-1-yl 3-[N-(2,2,5,5-tetramethyl-1,3-dioxane-4-carbonyl-)amino]propionate Molecular Formula: C$_{39}$H$_{72}$N$_2$O$_6$.
Molecular Weight: 665.01.
Mass Spectrometric Analysis: Calculated: 664.5390, Found: 664.5395.
Melting Point (° C.): Calomel.
Specific Rotary Power: $[\alpha]^{19}{}_D +9.6°$ (C=1.0, CHCl$_3$).
IR($\nu$neat, cm$^{-1}$): 3288, 2932, 2860, 1730, 1670, 1644.
NMR($\delta$, CDCl$_3$): 0.87 (3H,t,J=7Hz), 0.88 (3H,d,J=7Hz), 0.96 (3H,s), 1.04 (3H,s), 1.12-2.23 (43H,m), 1.43 (3H,s), 1.47 (3H,s), 2.42-2.58 (2H,m), 3.28 (1H,d,J=12Hz), 3.51 (2H,dt,J=6Hz,6Hz), 3.69 (1H,d,J=12Hz), 3.83-3.95 (1H,m), 4.08 (1H,s), 4.68 (1H,ddd,J=1Hz,1Hz,4Hz), 5.82 (1H,d,J=8Hz), 6.92 (1H,t,J=6Hz).

EXAMPLE 111

(1S,2S)-2-(2-Propylstearoyl)aminocyclohexane-1-yl 3-[N-(2,5,5-tetramethyl-1,3-dioxane-4-carbonyl)amino]propionate Molecular Formula: $C_{39}H_{72}N_2O_6$.
Molecular Weight: 665.01.
Mass Spectrometric Analysis: Calculated: 664.5390, Found: 664.5390.
Melting Point (° C.): 103°–105° C. (benzene/hexane).
Specific Rotary Power: $[\alpha]^{20}_D + 8.0°$ (C=1.0, CHCl$_3$).
IR($\nu$KBr, cm$^{-1}$) 3288, 2928, 2860, 1730, 1666, 1644.
NMR($\delta$, CDCl$_3$): 0.86 (3H,t,J=7Hz), 0.88 (3H,t,J=7Hz), 0.96 (3H,s), 1.04 (3H,s), 1.11–2.21 (43H,m), 1.43 (3H,s), 1.47 (3H,s), 2.41–2.60 (2H,m), 3.28 (1H,d,J=12Hz), 3.51 (2H,dt,J=6Hz,6Hz), 3.69 (1H,d,J=12Hz), 3.83–3.97 (1H,m), 4.08 (1H,s), 4.68 (1H,ddd,J=1Hz,1Hz,4Hz), 5.77 (1H,d,J=8Hz), 6.92 (1H,t,J=6Hz).

EXAMPLE 112

(1S,2S)-2-(1-Laurylcyclopentanecarbonyl)aminocyclohexane-1-yl 3-[N-(2,2,5,5-tetramethyl-1,3-dioxane-4-carbonyl)amino]propionate Molecular Formula: $C_{36}H_{64}N_2O_6$.
Molecular Weight: 620.92.
Mass Spectrometric Analysis: Calculated: 620.4764, Found: 620.4775.
Melting Point (° C.): Oil.
Specific Rotary Power: $[\alpha]^{22}_D + 9.2°$ (C=1.0, CHCl$_3$).
IR($\nu$neat, cm$^{-1}$): 3360, 2932, 2864, 1732.
NMR($\delta$, CDCl$_3$): 0.88 (3H,t,J=7Hz), 0.96 (3H,s), 1.04 (3H,s), 1.11–2.18 (38H,m), 1.43 (3H,s), 1.47 (3H,s), 2.42–2.62 (2H,m), 3.28 (1H,d,J=12Hz), 3.38–3.42 (2H,m), 3.69 (1H,d,J=12Hz), 3.80–3.92 (1H,m), 4.08 (1H,s), 4.73 (1H,ddd,J=11Hz,1Hz,4Hz), 5.76 (1H,d,J=8Hz), 6.92 (1H,t,J=6Hz).

EXAMPLE 113

(1S,2S)-2-(1-Decylcyclobutanecarbonyl)aminocyclohexane-1-yl 3-[N-(2,2,5,5-tetramethyl-1,3-dioxane-4-carbonyl)amino]propionate Molecular Formula: $C_{33}H_{58}N_2O_6$.
Molecular Weight: 578.84.
Mass Spectrometric Analysis: Calculated: 578.4294, Found: 578.4285.
Melting Point (° C.): Oil.
Specific Rotary Power: $[\alpha]^{22}_D + 8.9°$ (C=1.0, CHCl$_3$).
IR($\nu$neat, cm$^{-1}$) 3336, 2936, 2864, 1734.
NMR($\delta$, CDCl$_3$): 0.88 (3H,t,J=7Hz), 0.96 (3H,s), 1.04 (3H,s), 1.06–1.40 (20H,m), 1.43 (3H,s), 1.47 (3H,s), 1.57–2.34 (12H,m), 2.43–2.62 (2H,m), 3.28 (1H,d,J=12Hz), 3.41–3.62 (2H,m), 3.69 (1H,d,J=12Hz), 3.81–3.94 (1H,m), 4.07 (1H,s), 4.71 (1H,ddd,J=1Hz,1Hz,5Hz), 5.59 (1H,d,J=8Hz), 7.92 (1H,t,J=5Hz).

EXAMPLE 114

(1S,2S)-2-(1-Oleylcyclopentanecarbonyl)aminocyclohexane-1-yl 3-N-(2,2,5,5-tetramethyl-1,3-dioxane-4-carbonyl)amino]propionate Molecular Formula: $C_{42}H_{74}N_2O_6$.
Molecular Weight: 701.05.
Mass Spectrometric Analysis: Calculated: 702.5546, Found: 702.5570.
Melting Point (° C.): Oil.
Specific Rotary Power: $[\alpha]^{22}_D 8.6°$ (=1.0, CHCl$_3$).
IR($\nu$neat, cm$^{-1}$): 3368, 2932, 2864, 1734.
NMR($\delta$, CDCl$_3$):
0.88 (3H,t,J=7Hz), 0.96 (3H,s), 1.04 (3H,s), 1.09–2.17 (46H,m), 1.43 (3H,s), 1.47 (3H,s), 2.41–2.61 (2H,m), 3.28 (1H,d,J=12Hz), 3.37–3.62 (2H,m), 3.69 (1H,d,J=12Hz), 3.81–3.93 (1H,m), 4.08 (1H,s), 4.73 (1H,ddd,J=1Hz,1Hz,4Hz), 5.28–5.40 (2H,m), 5.75 (1H,d,J=8Hz), 6.93 (1H,t,J=5Hz).,

EXAMPLE 115

(1S,2S)-2-(1-Methyl-8-heptadecenyl)carbamoyl]aminocyclohexane-1-yl 3-N-(2,2,5,5-tetramethyl-1,3-dioxane-4-carbonyl)amino]propionate Molecular Formula: $C_{37}H_{67}N_3O_6$.
Molecular Weight: 649.96.
Mass Spectrometric Analysis: Calculated: 649.5029, Found: 649.5029.
Melting Point (° C.): Oil.
Specific Rotary Power: $[\alpha]^{21}_D + 19.3°$ (C=1.0, CHCl$_3$).
IR($\nu$neat, cm$^{-1}$): 2864, 1734, 1682, 1644.
NMR($\delta$, CDCl$_3$): 0.88 (3H,t,J=7Hz), 0.96 (3H,s), 1.04 (3H,s), 1.08 (3/2H,d,J=6Hz), 1.09 (3/2H,d,J=6Hz), 1.14–1.50 (24H,m), 1.44 (3H,s), 1.47 (3H,s), 1.52–2.26 (1H,m), 2.37–2.59 (2H,m), 3.28–3.46 (1H,m), 3.58–3.80 (3H,m), 3.69 (1H,d,J=12Hz), 4.10 (1H,s), 4.55 (1H,ddd,J=1Hz,1Hz,4Hz), 5.28–5.42 (2H,m), 6.86–6.96 (1H,m).

EXAMPLE 116

(1S,2S)-2-(1-Methylpentadecanyl)carbamoyl]aminocyclohexane-1-yl 3-N-(2,2,5,5-tetramethyl-1,3-dioxane-4-carbonyl)amino]propionate Molecular Formula: $C_{35}H_{65}N_2O_6$.
Molecular Weight: 623.92.
Mass Spectrometric Analysis: Calculated: 623.4873, Found: 623.4852.
Melting Point (° C.): Oil.
Specific Rotary Power: $[\alpha]^{21}_D + 20.5°$ (C=1.0, CHCl$_3$).
IR($\nu$KBr, cm$^{-1}$) 3360, 2932, 2860, 1738, 1682, 1642.
NMR($\delta$, CDCl$_3$): 0.88 (3H,t,J=7Hz), 0.96 (3H,s), 1.04 (3H,s), 1.08 (3H,d,J=6Hz), 1.12–1.78 (32H,m), 1.44 (3H,s), 1.47 (3H,s), 1.94–2.58 (4H,m), 3.28 (1H,d,J=12Hz), 3.34–3.79 (4H,m), 3.69 (1H,d,J=12Hz), 4.10 (1H,s), 4.55 (1H,ddd,J=1Hz,1Hz,4Hz), 6.92 (1H,t,J=5Hz).

EXAMPLE 117

(1S,2S)-2-(1-Octylcyclobutanecarbonyl)aminocyclohexane-1-yl 3-N-(2,2,5,5-tetramethyl-1,3-dioxane-4-carbonyl)amino]propionate Molecular Formula: $C_{31}H_{54}N_2O_6$.
Molecular Weight: 550.78.
Mass Spectrometric Analysis: Calculated: 550.3981, Found: 550.4005.
Melting Point (° C.): Oil.
Specific Rotary Power: $[\alpha]^{30}_D + 13.1°$ (C=1.0, CHCl$_3$).
IR($\nu$neat, cm$^{-1}$): 3336, 2932, 2860, 1732.
NMR($\delta$, CDCl$_3$): 0.88 (3H,t,J=7Hz), 0.96 (3H,s), 1.04 (3H,s), 1.06–1.58 (16H,m), 1.43 (3H,s), 1.47 (3H,s), 1.60-2.36 (12H,m), 3.43-2.63 (2H,m), 3.28 (1H,d,J=12Hz), 3.39-3.63 (2H,m), 3.69 (1H,d,J=12Hz), 3.81-3.94 (1H,m), 4.08 (1H,s), 4.72 (1H,ddd,J=1Hz,1Hz,4Hz), 5.60 (1H,d,J=8Hz), 6.93 (1H,t,J=5Hz).

EXAMPLE 118

(1S,2S)-2-(1-Isopropyllauroyl)aminocyclohexane-1-yl 3-[N-(2,2,5,5-tetramethyl-1,3-dioxane-4-carbonyl)amino]propionate Molecular Formula: $C_{33}H_{60}N_2O_6$.
Molecular Weight: 580.85.
Mass Spectrometric Analysis: Calculated: 580.4451, Found: 580.4435.
Melting Point (° C.): wax.
Specific Rotary Power: $[\alpha]^{27}_D +11.9°$ (C=0.9, CHCl$_3$).
IR($\nu$KBr, cm$^{-1}$): 3288, 2932, 2860, 1730
NMR($\delta$, CDCl$_3$): 0.88 (3H,t,J=7Hz), 0.88 (3H,d,J=6Hz), 0.91 (3H,d,J=6Hz), 0.96 (3H,s), 1.04 (3H,s), 1.00-1.82 (26H,m), 1.43 (3H,s), 1.47 (3H,s), 1.93-2.04 (1H,m), 2.15-2.26 (1H,m), 2.41-2.58 (2H,m), 3.28 (1H,d,J=12Hz), 3.42-3.60 (2H,m), 3.69 (1H,d,J=12Hz), 3.82-3.94 (1H,m), 4.08 (1H,s), 4.67 (1H,ddd,J=1Hz,1Hz,4Hz), 5.87 (1H,d,J=8Hz), 6.91 (1H,t,J=5Hz).

EXAMPLE 119

(1S,2S)-2-(1-Isopropyllauroyl)aminocyclohexane-1-yl 3-N-(2,2,5,5-tetramethyl-1,3-dioxane-4-carbonyl)amino]propionate Molecular Formula: $C_{33}H_{60}N_2O_6$.
Molecular Weight: 580.85.
Mass Spectrometric Analysis: Calculated: 580.4451, Found: 580.4458.
Melting Point (° C.): Calomel.
Specific Rotary Power: $[\alpha]^{30}_D +10.6°$ (C=1.0, CHCl$_3$).
(IR($\delta$KBr, cm$^{-1}$): 3276, 2932, 2860, 1730.
NMR($\delta$, CDCl$_3$): 0.85 (3H,d,J=6Hz), 0.88 (3H,t,J=7Hz), 0.89 (3H,d,J=6Hz), 0.96 (3H,s), 1.04 (3H,s), 1.05-1.83 (26H,m), 1.43 (3H,s), 1.47 (3H,s), 1.92-2.04 (1H,m), 2.13-2.22 (1H,m), 2.40-2.58 (2H,m), 3.28 (1H,d,J=12Hz), 3.45-3.58 (2H,m), 3.69 (1H,d,J=12Hz), 3.85-3.97 (1H,m), 4.08 (1H,s), 4.68 (1H,ddd,J=1Hz,1Hz,4Hz), 5.78 (1H,d,J=8Hz), 6.90 (1H,t,J=5Hz).

EXAMPLE 120

(1S,2S)-2-(1-Hexylcyclobutanecarbonyl)aminocyclohexane-1-yl 3-[N-(2,2,5,5-tetramethyl-1,3-dioxane-4-carbonyl)amino]propionate Molecular Formula: $C_{29}H_{50}N_2O_6$.
Molecular Weight: 522.73.
Mass Spectrometric Analysis: Calculated: 522.3668, Found: 522.3668.
Melting Point (° C.): oil.
Specific Rotary Power: $[\alpha]^{30}_D +13.8°$ (C=1.0, CHCl$_3$).
IR($\delta$neat, cm$^{-1}$) 3336, 2936, 2864, 1732.
NMR($\delta$, CDCl$_3$): 0.87 (3H,t,J=7Hz), 0.96 (3H,s), 1.04 (3H,s), 1.07-1.58 (12H,m), 1.42 (3H,s), 1.47 (3H,s), 1.61-2.34 (12H,m), 2.43-2.62 (2H,m), 3.28 (1H,d,J=12Hz), 3.41-3.62 (2H,m), 3.69 (1H,d,J=12Hz), 3.82-3.93 (1H,m), 4.07 (1H,s), 4.71 (1H,ddd,J=1Hz,1Hz,4Hz), 5.60 (1H,d,J=8Hz), 6.92 (1H,t,J=5Hz).

EXAMPLE 121

(1S,2S)-2-(1-Butylcyclobutanecarbonyl)aminocyclohexane-1-yl 3-[N-(2,2,5,5-tetramethyl-1,3-dioxane-4-carbonyl)amino)propionate Molecular Formula: $C_{27}H_{46}N_2O_6$.
Molecular Weight: 494.67.
Mass Spectrometric Analysis: Calculated: 494.3355, Found: 494.3366.
Melting Point (° C.): Calomel.
Specific Rotary Power: $[\alpha]^{30}_D +15.2°$ (C=1.0, CHCl$_3$).
IR($\nu$KBr, cm$^{-1}$): 3348, 2940, 2868, 1732.
NMR($\delta$, CDCl$_3$): 0.88 (3H,t,J=7Hz), 0.96 (3H,s), 1.04 (3H,s), 1.05-1.58 (8H,m), 1.43 (3H,s), 1.47 (3H,s), 1.62-2.33 (12H,m), 2.44-2.61 (2H,m), 3.28 (1H,d,J=12Hz), 3.41-3.63 (2H,m), 3.69 (1H,d,J=12Hz), 3.81-3.94 (1H,m), 4.08 (1H,s), 4.72 (1H,ddd,J=1Hz,1Hz,4Hz), 5.61 (1H,d,J=8Hz), 6.93 (1H,t,J=5Hz).

EXAMPLE 122

(1S,2S)-2-(1-Decylcyclobutanecarbonyl)aminocyclohexane-1-yl 3-[N-(2,4-dihydroxy-3,3-diemthyl-1-oxobutyl)amino]propionate Molecular Formula: $C_{30}H_{54}N_2O_6$.
Molecular Weight: 538.77.
Mass Spectrometric Analysis: Calculated: 538.3981, Found: 538.3989.
Melting Point (° C.): oil.
Specific Rotary Power: $[\alpha]^{28}_D +10.6°$ (C=1.0, CHCl$_3$).
IR($\nu$neat, cm$^{-1}$): 2932, 2860, 1732.
NMR($\delta$, CDCl$_3$): 0.88 (3H,t,J=7Hz), 0.97 (3H,s), 1.05 (3H,s), 1.06-1.44 (20H,m), 1.46-2.28 (12H,m), 2.44-2.64 (2H,m), 2.77 (2H,brs), 3.46-3.68 (2H,m), 3.49 (1H,d,J=1Hz), 3.56 (1H,d,J=1Hz), 3.84-3.98 (1H,m), 4.05 (1H,s), 4.69 (1H,ddd,J=1Hz, 11Hz,4Hz), 5.53 (1H,d,J=9Hz), 7.37 (1H,t,J=5Hz).

EXAMPLE 123

(1S,2S)-2-(1-Methyllauroyl)aminocyclohexane-1-yl 3-[N-(2,2,5,5-tetramethyl-1,3-dioxane-4-carbonyl)amino]propionate Molecular Formula: $C_{31}H_{56}N_2O_6$.
Molecular Weight: 552.80.
Mass Spectrometric Analysis: Calculated: 552.4138, Found: 552.4127.
Melting Point (° C.): oil.
Specific Rotary Power: $[\alpha]^{31}_C +15.8°$ (C=1.0, CHCl$_3$).
IR($\nu$KBr, cm$^{-1}$): 3304, 2932, 2860, 1738.
NMR($\delta$, CDCl$_3$): 0.87 (3H,t,J=7Hz), 0.95 (3H,s), 1.03 (3H,s), 1.07 (3H,t,J=7Hz), 1.10-1.38 (20H,m), 1.42 (3H,s), 1.46 (3H,s), 1.48-2.19 (7H,m), 2.42-2.57 (2H,m), 3.28 (1H,d,J=12Hz), 3.51 (1H,dt,J=6Hz,6Hz), 3.69 (1H,d,J=12Hz), 3.81-3.94 (1H,m), 4.08 (1H,s), 4.68 (1H,ddd,J=4Hz), 5.76 (1H,d,J=8Hz), 6.92 (1H,t,J=6Hz).

EXAMPLE 124

(1S,2S)-2-(1-Methyllauroyl)aminocyclohexane-1-yl 3-N-(2,2,5,5-tetramethyl-1,3-dioxane-4-carbonyl)amino]propionate Molecular Formula: $C_{31}H_{56}N_2O_6$.
Molecular Weight: 552.80.
Mass Spectrometric Analysis: Calculated: 552.4138, Found: 552.4139.
Melting Point (° C.): wax.
Specific Rotary Power: $[\alpha]^{+}_D + 7.6°$ (C=1.0, CHCl$_3$).
IR($\nu$KBr, cm$^{-1}$): 3272, 2932, 2860, 1744.
NMR($\delta$, CDCl$_3$): 0.88 (3H,t,J=7Hz), 0.96 (3H,s), 1.03 (3H,s), 1.06 (3H,d,J=7Hz), 1.10–1.39 (20H,m), 1.43 (3H,s), 1.47 (3H,s), 1.49–2.16 (7H,m), 2.50 (2H,t,J=6Hz), 3.28 (1H,d,J=12Hz), 3.51 (1H,dt,J=6Hz,6Hz), 3.69 (1H,d,J=12Hz), 3.82–3.96 (1H,m), 4.08 (1H,s), 4.67 (1H,ddd,J=1Hz,1Hz,4Hz), 5.73 (1H,d,J=8Hz), 6.92 (1H,t,J=6Hz).

EXAMPLE 125

(1S,2S)-2-(2-Decyllauroyl)aminocyclohexane-1l-yl 3-[N-(2,2,5,5-tetramethyl-1,3-dioxane-4-carbonyl)amino]propionate Molecular Formula: $C_{40}H_{74}N_2O_6$.
Molecular Weight: 679.04.
Mass Spectrometric Analysis: Calculated: 678.5546, Found: 678.5535.
Melting Point (° C.): 70°–71° C. (hexane).
Specific Rotary Power: $[\alpha]^{28}_D + 10.3°$ (C=1.0, CHCl$_3$).
IR($\nu$KBr, cm$^{-1}$): 3288, 2928, 2856, 1732.
NMR($\delta$, CDCl$_3$): 0.88 (6H,t,J=7Hz), 0.96 (3H,s), 1.04 (3H,s), 1.08–2.22 (45H,m), 1.43 (3H,s), 1.47 (3H,s), 2.39–2.58 (2H,m), 3.28 (1H,d,J=12Hz), 3.51 (2H,dt,J=6Hz,6Hz), 3.69 (1H,d,J=12Hz), 3.83–3.96 (1H,m), 4.08 (1H,s), 4.68 (1H,ddd,J=1Hz, 11Hz,4Hz), 5.82 (1H,d,J=8Hz), 6.90 (1H,t,J=8Hz).

EXAMPLE 126

(1S,2S)-2-(N-Decyl-N-isopropylcarbamoyl)aminocyclohexane-1-yl 3-[N-(2,2,5,5-tetramethyl-1,3-dioxane-4-carbonyl)amino]propionate Molecular Formula: $C_{32}H_{59}N_3O_6$.
Molecular Weight: 581.84.
Mass Spectrometric Analysis: Calculated: 581.4403, Found: 581.4414.
Melting Point (° C.): oil.
Specific Rotary Power: $[\alpha]^{27}_D + 30.1°$ (C=0.5, CHCl$_3$).
IR($\nu$neat, cm$^{-1}$): 2932, 2860, 1732.
NMR($\delta$, CDCl$_3$): 0.88 (3H,t,J=7Hz), 0.96 (3H,s), 1.03 (3H,s), 1.10 (6H,d,J=7Hz), 1.15–2.21 (24H,m), 1.42 (3H,s), 1.47 (3H,s), 2.47–2.62 (2H,m), 2.93 (2H,t,J=7Hz), 3.28 (1H,d,J=12Hz), 3.34–3.64 (2H,m), 3.69 (1H,d,J=12Hz), 3.74–3.88 (1H,m), 4.08 (1H,s), 4.18–4.33 (1H,m), 4.38–4.46 (1H,m), 4.71 (1H,ddd,J=1Hz,1Hz,4Hz), 6.93 (1H,t,J=5Hz).

EXAMPLE 127

(1S,2S)-2-[N-(2,2-Dimethylpropyl)-N-nonylcarbamoyl)]aminocyclohexane-1-yl 3-[N-(2,2,5,5-tetramethyl-1,3-dioxane-4-carbonyl)amino)propionate Molecular Formula: $C_{33}H_{61}N_3O_6$.
Molecular Weight: 595.87.
NMR($\delta$, CDCl$_3$): 0.88 (3H,t,J=7Hz), 0.91 (9H,s), 0.96 (3H,s), 1.04 (3H,s), 1.05–2.21 (22H,m), 1.42 (3H,s), 1.47 (3H,s), 2.43–2.62 (2H,m), 2.91 (1H,d,J=15Hz), 2.97–3.10 (1H,m), 3.05 (1H,d,J=15Hz), 3.16–3.27 (1H,m), 3.28 (1H,d,J=12Hz), 3.37–3.64 (2H,m), 3.69 (1H,d,J=12Hz), 3.71–3.86 (1H,m), 4.08 (1H,s), 4.52 (1H,d,J=8Hz), 4.70 (1H,ddd,J=11Hz,1Hz,4Hz), 6.92 (1H,t,J=5Hz).

EXAMPLE 128

(1S,2S)-2-(2-Phenylmethycapryloyl)aminocyclohexane-1-yl 3-N-(2,2,5,5-tetramethyl-1,3-dioxane-4-carbonyl)amino]propionate Molecular Formula: $C_{34}H_{62}N_2O_6$.
Molecular Weight: 572.79.
Mass Spectrometric Analysis: Calculated: 572.3825, Found: 572.3841.
Melting Point (° C.): Calomel.
Specific Rotary Power: $[\alpha]^{21}_D - 5.8°$ (C=1.0, CHCl$_3$).
IR($\nu$KBr, cm$^{-1}$): 3304, 2936, 2864, 1734, 1662, 1646.
NMR($\delta$, CDCl$_3$): 0.87 (3H,t,J=7Hz), 0.95 (3H,s), 1.03 (3H,s), 1.05–1.95 (18H,m), 1.42 (3H,s), 1.46 (3H,s), 2.89–2.24 (1H,m), 2.37–2.54 (2H,m), 2.68 (1H,dd,J=13Hz,5Hz), 2.83 (1H,dd,J=13Hz,10Hz), 3.28 (1H,d,J=12Hz), 3.48 (2H,dt,J=6Hz,6Hz), 3.68 (1H,d,J=12Hz), 3.70–3.82 (1H,m), 4.07 (1H,s), 4.50 (1H,ddd,J=1Hz,1Hz,4Hz), 5.42 (1H,d,J=8Hz), 6.88 (1H,t,J=6Hz).

EXAMPLE 129

(1S,2S)-2-(2-Phenylmethycapryloyl)aminocyclohexane-1-yl 3-N-(2,2,5,5-tetramethyl-1,3-dioxane-4-7 carbonyl)amino]propionate Molecular Formula: $C_{33}H_{52}N_2O_6$.
Molecular Weight: 572.79.
Mass Spectrometric Analysis: Calculated: 572.3825, Found: 572.3812.
Melting Point (° C.): Calomel.
Specific Rotary Power: $[\alpha]^{21}_D + 26.1°$ (C=1.0, CHCl$_3$).
IR($\nu$KBr, cm$^{-1}$): 3320, 2940, 2864, 1734, 1652.
NMR($\delta$, CDCl$_3$): 0.87 (3H,t,J=7Hz), 0.95 (3H,s), 1.03 (3H,s), 1.05–1.47 (12H,m), 1.43 (3H,s), 1.47 (3H,s), 1.51–2.31 (9H,m), 2.61 (1H,dd,J=14Hz,5Hz), 2.94 (1H,dd,J=14Hz,9Hz), 3.22–3.28 (2H,m), 3.28 (1H,d,J=12Hz), 3.69 (1H,d,J=12Hz), 3.70–3.84 (1H,m), 4.07 (1H,s), 4.55 (1H,ddd,J=1Hz,1Hz, 4Hz), 5.93 (1H,d,J=8Hz), 6.81 (1H,t,J=5Hz), 7.12–7.30 (5H,m).

EXAMPLE 130

(1S,2S)-2-(2-Phenyllauroyl)aminocyclohexane-1-yl 3-N-(2,2,5,5-tetramethyl-1,3-dioxane-4-carbonyl)amino]propionate Molecular Formula: $C_{36}H_{58}N_2O_6$.
Molecular Weight: 614.87.

Mass Spectrometric Analysis: Calculated: 6144294, Found: 614.4310.
Melting Point (° C.): oil.
Specific Rotary Power: $[\alpha]^{30}_D+14.8°$ (C=0.9, CHCl$_3$).
IR($\nu$neat, cm$^{-1}$): 3312, 2932, 2860, 1734.
NMR($\delta$, CDCl$_3$): 0.87 (3H,t,J=7Hz), 0.97 (3H,s), 1.05 (3H,s), 1.11–1.39 (20H,m), 1.43 (3H,s), 1.48 (3H,s), 1.52–2.11 (6H,m), 2.32–2.51 (2H,m), 3.25 (1H,t,J=7Hz), 3.29 (1H,d,J=12Hz), 3.38–3.56 (2H,m), 3.70 (1H,d,J=12Hz), 3.77–3.89 (1H,m), 4.09 (1H,s), 4.59 (1H,ddd,J=1Hz,1Hz,4Hz), 5.68 (1H,d,J=8Hz), 6.89 (1H,t,J=5Hz), 7.21–7.36 (5H,m).

EXAMPLE 131

(1S,2S)-2-(2-Phenyllauroyl)aminocyclohexane-1-yl 3-N-(2,2,5,5-tetramethyl-1,3-dioxane-4-carbonyl)amino]propionate Molecular Formula: $C_{36}H_{58}N_2O_6$.
Molecular Weight: 614.87.
Mass Spectrometric Analysis: Calculated: 614.4294, Found: 614.4311.
Melting Point (° C.): wax.
Specific Rotary Power: $[\alpha]^{30}_D+34.4°$ (C=1.0, CHCl$_3$).
IR($\nu$KBr, cm$^{-1}$): 3308, 2932, 2860, 1730.
NMR($\delta$, CDCl$_3$): 0.87 (3H,t,J=7Hz), 0.94 (3H,s), 1.35 (3H,s), 1.09–1.42 (20H,m), 1.43 (3H,s), 1.48 (3H,s), 1.52–2.15 (8H,m), 3.20–3.21 (3H,m), 3.28 (1H,d,J=12Hz), 3.68 (1H,d,J=12Hz), 3.76–3.89 (1H,m), 4.06 (1H,s), 4.59 (1H,ddd,J=1Hz,1Hz,4Hz), 5.75 (1H,d,J=8Hz), 6.71 (1H,t,J=5Hz), 7.19–7.34 (5H,m).

EXAMPLE 132

(1S,2S)-2-(1-Benzylcyclopentanecarbonyl)aminocyclohexane-1-yl 3-N-(2,2,5,5-tetramethyl-1,3-dioxane--carbonyl)amino]propionate Molecular Formula: $C_{30}H_{44}N_2O_6$.
Molecular Weight: 528.69.
Mass Spectrometric Analysis: Calculated: 528.3199, Found: 528.3193.
Melting Point (° C.): Calomel.
Specific Rotary Power: $[\alpha]^{30}_D+11.9°$ (C=1.0, CHCl$_3$).
IR($\nu$KBr, cm$^{-1}$): 3356, 2944, 2868, 1732.
NMR($\delta$, CDCl$_3$): 0.84–1.55 (4H,m), 0.95 (3H,s), 1.03 (3H,s), 1.42 (3H,s), 1.46 (3H,s), 1.58–2.67 (12H,m), 3.00 (1H,d,J=14Hz), 3.03 (1H,d,J=14Hz), 3.28 (1H,d,J=12Hz), 3.27–3.52 (2H,m), 3.68 (1H,d,J=12Hz), 3.72–3.82 (1H,m), 4.06 (1H,s), 4.59 (1H,ddd,J=1Hz,1Hz,4Hz), 5.41 (1H,d,J=8Hz), 6.88 (1H,t,J=5Hz), 7.11–7.28 (5H,m).

EXAMPLE 133

(1S,2S)-2-(1-Furfurylcyclobutanecarbonyl)aminocyclohexane-1-yl 3-N-(2,2,5,5-tetramethyl-1,3-dioxane-4-carbonyl)amino]propionate Molecular Formula: $C_{28}H_{42}N_2O_7$.
Molecular Weight: 518.65.
Mass Spectrometric Analysis: Calculated: 518.2992, Found: 518.2969.
Melting Point (° C.): oil.

Specific Rotary Power: $[\alpha]^{30}_D+12.8°$ (C=0.5, CHCl$_3$).
IR($\nu$KBr, cm$^{-1}$): 3352, 2944, 2868, 1732.
NMR($\delta$, CDCl$_3$): 0.96 (3H,s), 1.03 (3H,s), 1.18–2.57 (16H,m), 1.42 (3H,s), 1.47 (3H,s), 3.03 (2H,s), 3.28 (1H,d,J=12Hz), 3.33–3.58 (2H,m), 3.69 (1H,d,J=12Hz), 3.67–3.90 (1H,m), 4.07 (1H,s), 4.63 (1H,ddd,J=1Hz,1Hz,4Hz), 5.49 (1H,d,J=8Hz), 6.03 (1H,d,J=3Hz), 6.26 (1H,dd,J=3Hz,1Hz), 6.92 (1H,t,J=5Hz), 7.29 (1H,d,J=1Hz).

EXAMPLE 134

(1S,2S)-2-(2-Benzyllauroyl)aminocyclohexane-1-yl 3-N-(2,2,5,5-tetramethyl-1,3-dioxane-4-carbonyl)amino]propionate Molecular Formula: $C_{37}H_{60}N_2O_6$.
Molecular Weight: 628.90.
Mass Spectrometric Analysis: Calculated: 628.4451, Found: 628.4442.
Melting Point (° C.): wax.
Specific Rotary Power: $[\alpha]^{29}_D-5.9°$ (C=1.0 CHCl$_3$).
IR($\nu$neat, cm$^{-1}$): 3320, 2932, 2860, 1732.
NMR($\delta$, CDCl$_3$): 0.62–1.50 (20H,m), 0.88 (3H,t,J=7Hz), 0.95 (3H,s), 1.03 (3H,s), 1.42 (3H,s), 1.46 (3H,s), 1.52–2.30 (7H,m), 2.38–2.55 (2H,m), 2.68 (1H,dd,J=15Hz,6Hz), 2.83 (1H,dd,J=15Hz,10Hz), 3.28 (1H,d,J=12Hz), 3.48 (2H,dt,J=6Hz,6Hz), 3.68 (1H,d,J=12Hz), 3.70–3.83 (1H,m), 4.07 (1H,s), 4.50 (1H,ddd,J=1Hz,1Hz,5Hz), 5.91 (1H,d,J=8Hz), 6.88 (1H,t,J=6Hz), 7.11–7.27 (5H,m).

EXAMPLE 135

(1S,2S)-2-(2-Benzyllauroyl)aminocyclohexane-1-yl 3-[N-(2,2,5,5-tetramethyl-1,3-dioxane-4-carbonyl)amino]-propionate Molecular Formula: $C_{74}H_{62}N_2O_6$.
Molecular Weight: 628.90.
Mass Spectrometric Analysis: Calculated: 628.4451, Found: 628.4478.
Melting Point (° C.): wax.
Specific Rotary Power : $[\alpha]^{27}_D+26.7°$ (C=1.0, CHCl$_3$).
IR($\nu$KBr, cm$^{-1}$): 3300, 2932, 2860, 1734.
NMR($\delta$, CDCl$_3$): 0.88 (3H,t,J=7Hz), 0.95 (3H,s), 1.03 (3H,s), 1.06–1.50 (20H,m), 1.43 (3H,s), 1.47 (3H,s), 1.52–2.30 (9H,m), 2.61 (1H,dd,J=15Hz,6Hz), 2.93 (1H,dd,J=15Hz,10Hz), 3.20–3.30 (2H,m), 3.28 (1H,d,J=12Hz), 3.69 (1H,d,J=12Hz), 3.71–3.83 (1H,m), 4.07 (1H,s), 4.55 (1H,ddd,J=11Hz,11Hz,4Hz), 5.91 (1H,d,J=7Hz), 6.81 (1H,t,J =5Hz), 7.31–7.28 (5H,m).

EXAMPLE 136

(1S,2S)-2-(1-Cinnamylcyclobutanecarbonyl)aminocyclohexane-1-yl 3-[N-(2,2,5,5-tetramethyl-1,3-dioxane-4-carbonyl)amino]propionate Molecular Formula: $C_{32}H_{46}N_2O_6$.
Molecular Weight: 554.73.
Mass Spectrometric Analysis: Calculated: 554.3355, Found: 554.3361.
Melting Point (° C.): Calomel.
Specific Rotary Power: $[\alpha]^9_D+14.9°$ (C=1.0, CHCl$_3$).
IR($\nu$KBr, cm$^{-1}$): 3340, 2944, 2868, 1732.

NMR(δ, CDCl₃): 0.89–1.57 (4H,m), 0.95 (3H,s), 1.03 (3H,s), 1.4](3H,s), 1.46 (3H,s), 1.58–2.67 (12H,m), 2.59 (2H,d,J=7Hz), 3.27 (1H,d,J=12Hz), 3.32–3.63 (2H,m), 3.68 (1H,d,J=12Hz), 3.82–3.95 (1H,m), 4.06 (1H,s), 4.68 (1H,ddd,J=1Hz,11Hz, 4Hz), 5.68 (1H,d,J=8Hz), 6.08 (1H,dt,J=16Hz, 7Hz), 6.44 (1H,d,J=16Hz), 6.88 (1H,t,J=5Hz), 7.17–7.38 (5H,m).

EXAMPLE 137

(1S,2S)-2-[1-(3-Phenylpropyl)cyclobutanecarbonyl-]aminocyclohexane-1-yl 3-[N-(2,2,5,5-tetramethyl-1,3-dioxane-4-carbonyl-)amino]propionate Molecular Formula: $C_{32}H_{48}N_2O_6$.
Molecular Weight: 556.74.
Mass Spectrometric Analysis: Calculated: 556.3512, Found: 556.3516.
Melting Point (° C.): Calomel.
Specific Rotary Power: $[\alpha]^9_D + 12.5°$ (C=1.0, CHCl₃).
IR(νKBr, cm⁻¹): 3352, 2940, 2868, 1732.
NMR(δ, CDCl₃): 0.95 (3H,s), 0.95–1.56 (6H,m), 1.03 (3H,s), 1.42 (3H,s), 1.46 (3H,s), 1.62–2.48 (14H,m), 2.51–2.66 (2H,m), 3.27 (1H,d,J=12Hz), 3.28–3.48 (2H,m), 3.68 (1H,d,J=12Hz), 3.79–3.92 (1H,m), 4.06 (1H,s), 4.67 (1H,ddd,J11Hz,11Hz,4Hz), 5.64 (1H,d,J=8Hz), 6.86 (1H,t,J=5Hz), 7.12–7.30 (5H,m).

EXAMPLE 138

(1S,2S)-2-(2,2-Diphenyllauroyl)aminocyclohexane-1-yl 3-[N-(2,2,5,5-tetramethyl-1,3-dioxane-4-carbonyl-)amino]propionate Molecular Formula: $C_{42}H_{62}N_2O_6$.
Molecular Weight: 690.97.
Mass Spectrometric Analysis: Calculated: 690,4607, Found: 690,4604.
Melting Point (° C.): oil.
Specific Rotary Power: $[\alpha]^9_D + 18.8°$ (C=1.0, CHCl₃).
IR(νneat, cm⁻¹): 2932, 2860, 1730.
NMR(δ, CDCl₃): 0.87 (3H,t,J=7Hz), 0.94 (3H,s), 1.00–1.49 (20H,m), 1.04 (3H,s), 1.42 (3H,s), 1.47 (3H,s), 1.52–2.38 (8H,m), 3.16–3.28 (1H,m), 3.28 (1H,d,J=12Hz), 3.36–3.48 (1H,m), 3.69 (1H,d,J=12Hz), 3.82–3.94 (1H,m), 4.07 (1H,s), 4.49 (1H,ddd,J=11Hz,1Hz,4Hz), 5.52 (1H,d,J=8Hz), 6.82 (1H,t,J=5Hz), 7.18–7.37 (10H,m).

EXAMPLE 139

(1S,2S)-2-(2,2-Benzylcapryloyl)aminocyclohexane-1-yl 3-[N-(2,2,5,5-tetramethyl-1,3-dioxane-4-carbonyl-)amino]propionate Molecular Formula: $C_{34}H_{62}N_2O_6$.
Molecular Weight: 532.72.
Mass Spectrometric Analysis: Calculated: 532.3512, Found: 532.3524.
Melting Point (° C.): Calomel.
Specific Rotary Power: $[\alpha]^9_D + 28.8°$ (C=1 0, CHCl₃).
IR(νneat, cm⁻¹): 2936, 2864, 1728.
NMR(δ, CDCl₃): 0.86 (3H,t,J=7Hz), 0.94 (3H,s), 1.02 (3H,s), 1.06–1.50 (12H,m), 1.52–2.35 (9H,m), 2.64 (1H,dd,J=14Hz,6Hz), 2.89 (1H,dd,J=14Hz,8Hz), 3.22–3.48 (2H,m), 3.48 (1H,d,J=11Hz), 3.51 (1H,d,J=11Hz), 3.72–3.87 (1H,m), 4.03 (1H,s), 4.54 (1H,ddd,J=11Hz,1Hz,4Hz), 5.88 (1H,brs), 7.12–7.29 (6H,m).

EXAMPLE 140

(1S,2S)-2-(N-Benzyl-N-hexylcarbamoyl)aminocyclohexane-1-yl 3-[N-(2,2,5,5-tetramethyl-1,3-dioxane-4-carbonyl-)amino]propionate Molecular Formula: $C_{32}H_{51}N_3O_6$.
Molecular Weight: 573.78.
Mass Spectrometric Analysis: Calculated: 573.3777, Found: 573.3752.
Melting Point (° C.): oil.
Specific Rotary Power: $[\alpha]^8_D + 33.2°$ (C=0.8, CHCl₃).
IR(νneat, cm⁻¹): 3384, 2936, 2864, 1732.
NMR(δ, CDCl₃): 0.87 (3H,t,J=7Hz), 0.96 (3H,s), 0.97–2.18 (16H,m), 1.03 (3H,s), 1.42 (3H,s), 1.46 (3H,s), 2.32–2.53 (2H,m), 3.18 (2H,t,J=7Hz), 3.26–3.39 (1H,m), 3.28 (1H,d,J=12Hz), 3.43–3.56 (1H,m), 3.69 (1H,d,J=12Hz), 3.72–3:85 (1H,m), 4.07 (1H,s), 4.36 (1H,d,J=17Hz), 4.46 (1H,d,J=17Hz), 4.50 (1H,d,J=6Hz), 4.62 (1H,ddd,J=1Hz,11Hz, 4Hz), 6.88 (1H,t,J=5Hz), 7.19–7.37 (5H,m).

EXAMPLE 141

(1S,2S)-2-(N-Benzyl-N-octylcarbamoyl)aminocyclohexane-1-yl 3-[N-(2,2,5,5-tetramethyl-1,3-dioxane-4-carbonyl-)amino]propionate Molecular Formula: $C_{34}H_{55}N_3O_6$.
Molecular Weight: 601.83.
Mass Spectrometric Analysis: Calculated: 601.4090, Found: 601.4113.
Melting Point (° C.): oil.
Specific Rotary Power: $[\alpha]^8_D + 29.7°$ (C=0.5, CHCl₃).
IR(νneat, cm⁻¹): 3368, 2932, 2864, 1732.
NMR(δ, CDCl₃): 0.87 (3H,t,J=7Hz), 0.96 (3H,s), 0.97–2.18 (20H,m), 1.03 (3H,s), 1.42 (3H,s), 1.46 (3H,s), 2.33–2.53 (2H,m), 3.18 (2H,t,J=7Hz), 3.26–3.39 (1H,m), 3.28 (1H,m), 3.43–3.56 (1H,m), 3.69 (1H,d,J=12Hz), 3.72–3.85 (1H,m), 4.07 (1H,s), 4.37 (1H,d,J=17Hz), 4.48 (1H,d,J=17Hz), 4.49 (1H,d,J=6Hz), 4.62 (1H,ddd,J=1Hz,1Hz,4Hz), 6.88 (1H,t,J=5Hz), 7.19–7.36 (5H,m).

EXAMPLE 142

(1S,2S)-2-(N-Benzyl-N-decylcarbamoyl)aminocyclohexane-1-yl 3-[N-(2,2,5,5-tetramethyl-1,3-dioxane-4-carbonyl-)amino]propionate Molecular Formula: $C_{36}H_{59}N_3O_6$.
Molecular Weight: 629.88.
Mass Spectrometric Analysis: Calculated: 629.4403, Found: 629.4388.
Melting Point (° C.): oil.
Specific Rotary Power: $[\alpha]^7_D + 26.1°$ (C=1.0, CHCl₃).
IR(νneat, cm⁻¹): 3384, 2932, 2860, 1732.
NMR(δ, CDCl₃): 0.88 (3H,t,J=7Hz), 0.96 (3H,s), 0.79–2.19 (24H,m), 1.03 (3H,s), 1.42 (3H,s), 1.46 (3H,s), 2.32–2.53 (2H,m), 2.18 (2H,t,J=7Hz), 3.23–3.38 (1H,m), 3.28 (1H,d,J=12Hz), 3.32–3.55 (1H,m), 3.69 (1H,d,J=12Hz), 3.70–3.85 (1H,m), 4.07 (1H,s), 4.36 (1H,d,J=17Hz), 4.47 (1H,d,J=17Hz), 4.48

EXAMPLE 143

(1S,2S)-2-(2-Benzylundecanoyl)aminocyclohexane-1-yl 3-[N-(2,2,5,5-tetramethyl 1,3-dioxane-4-carbonyl)amino]propionate Molecular Formula: $C_{34}H_{62}N_2O_6$.
Molecular Weight: 614.87.
Mass Spectrometric Analysis: Calculated: 614.4294, Found: 614.4295.
Melting Point (° C.): wax.
Specific Rotary Power : $[\alpha]^8_D -7.7°$ (C=1.0, CHCl$_3$).
IR($\nu$neat, cm$^{-1}$): 3320, 2932, 2860, 1732.
NMR($\delta$, CDCl$_3$): 0.62–1.49 (18H,m), 0.88 (3H,t,J=7Hz), 0.95 (3H,s), 1.03 (3H,s), 1.42 (3H,s), 1.46 (3H,s), 1.51–1.95 (6H,m), 2.08–2.19 (1H,m), 2.37–2.56 (2H,m), 2.68 (1H,dd,J=14Hz,6Hz), 2.83 (1H,dd,J=14Hz,9Hz), 3.28 (1H,d,J=12Hz), 3.44–3.52 (2H,m), 3.68 (1H,d,J=12Hz), 3.70–3.82 (1H,m), 4.07 (1H,s), 4.51 (1H,ddd,J=1Hz,1Hz,4Hz), 5.42 (1H,d,J=8Hz), 6.88 (1H,t,J=5Hz), 7.11–7.30 (5H,m).

EXAMPLE 144

(1S,2S)-2-(2-Benzylundecanoyl)aminocyclohexane-1-yl 3-[N-(2,2,5,5-tetramethyl-1,3-dioxane-4-carbonyl)amino]propionate Molecular Formula: $C_{36}H_{58}N_2O_7$.
Molecular Weight: 614.87.
Mass Spectrometric Analysis: Calculated: 614.4294, Found: 614.4276.
Melting Point (° C.): oil.
Specific Rotary Power : $[\alpha]^7_D +27.4°$ (C=1.0, CHCl$_3$).
IR($\nu$neat, cm$^{-1}$): 3304, 2932, 2860, 1734.
NMR($\delta$, CDCl$_3$): 0.88 (3H,t,J=7Hz), 0.95 (3H,s), 0.98–1.49 (18H,m), 1.03 (3H,s), 1.43 (3H,s), 1.47 (3H,s), 1.52–2.30 (9H,m), 2.61 (1H,dd,J=14Hz,6Hz), 2.94 (1H,dd,J=14Hz,9Hz), 3.22–3.29 (2H,m), 3.28 (1H,d,J=12Hz), 3.69 (1H,d,J=12Hz), 3.71–3.84 (1H,m), 4.07 (1H,s), 4.55 (1H,ddd,J=1Hz,1Hz, 4 Hz), 5.91 (1H,d,J=8Hz), 6.81 (1H,t,J=5Hz), 7.12–7.28 (5H,m).

EXAMPLE 145

(1S,2S)-2-(3-Hexyl-2-nonenoyl)aminocyclohexane-1-yl 3-[N-(2,2,5,5-tetramethyl-1,3-dioxane-4-carbonyl)amino]propionate Molecular Formula: $C_{33}H_{58}N_2O_6$.
Molecular Weight: 578.93.
IR($\nu$neat ,cm$^{-1}$): 1660, 1736.
NMR($\delta$, CDCl$_3$): 0.87 (3H,t,J=7Hz), 0.88 (3H,t,J=7Hz), 0.96 (3H,s), 1.04 (3H,s), 1.10–1.50 (16H,m), 1.43 (3H,s), 1.47 (3H,s), 1.57–1.88 (6H,m), 1.88–2.18 (4H,m), 2.43–2.64 (4H,m), 3.28 (1H,d,J=2Hz), 3.49 (2H,t,J=6Hz), 3.69 (1H,d,J=12Hz), 3.84–4.02 (1H,m), 4.08 (1H,s), 4.64 (1H,ddd,J =1Hz,1Hz,4Hz), 5.42 (1H,s), 5.67 (1H,d,J=8 Hz), 6.92 (1H,m).

EXAMPLE 146

(1S,2S)-2-(3-Phenylmethyl-4-phenyl-2-butenoyl)aminocyclohexane-1-yl 3-[N-(2,2,5,5-tetramethyl-1,3-dioxane-4-carbonyl)amino]propionate Molecular Formula: $C_{35}H_{46}N_2O_6$.
Molecular Weight: 590.83.
Melting Point (° C.): wax.
NMR($\delta$, CDCl$_3$): 0.95 (3H,s), 1.00 (3H,s), 0.90–2.12 (8H,m), 1.39 (3H,s), 1.45 (3H,s), 2.24–2.54 (2H,m), 3.07 (2H,dd,J=15Hz,3Hz), 3.26 (1H,d,J=12Hz), 3.20–3.64 (2H,m), 3.53 (2H,dd,J=15Hz,5Hz), 3.67 (1H,d,J=12Hz), 3.80–3.94 (1H,m), 4.04 (1H,s), 4.60 (1H,ddd,J=10Hz,10Hz,4Hz), 5.76 (1H,d,J=8Hz), 6.60 (1H,s), 6.84 (1H,t,J=5Hz), 7.16–7.42 (10H,m).

EXAMPLE 147

(1S,2S)-2-(3-Propyl-2-nonenoyl)aminocyclohexane-1-yl 3-[N-(2,2,5,5-tetramethyl-1,3-dioxane-4-carbonyl)amino]propionate Molecular Formula: $C_{30}H_{52}N_2O_6$.
Molecular Weight: 536.84.
Melting Point (° C.): wax.
NMR($\delta$, CDCl$_3$): 0.80–0.96 (6H,m), 0.97 (3H,s), 1.04 (3H,s), 1.06–2.21 (20H,m), 1.43 (3H,s), 1.47 (3H,s), 2.40–2.67 (4H,m), 3.28 (1H,d,J=12Hz), 3.49 (2H,td,J=6Hz,6Hz), 3.69 (1H,d,J=12Hz), 3.94 (1H,ddd,J=10Hz,8Hz,4Hz), 4.08 (1H,s), 4.64 (1H,ddd,J=10Hz,10Hz,4Hz), 5.42+5.44 (1H,s), 5.67+5.70 (1H,d,J=8Hz), 6.92 (1H,t,J=6Hz).

EXAMPLE 148

(1S,2S)-2-(3-Methyl-2-tridecenoyl)aminocyclohexane-1-yl 3-[N-(2,25,5-tetramethyl-1,3-dioxane-4-carbonyl)amino]propionate Molecular Formula: $C_{32}H_{56}N_2O_6$.
Molecular Weight: 564.80.
NMR($\delta$, CDCl$_3$): 0.88 (3H,t,J=6Hz), 0.97 (3H,s), 1.04 (3H,s), 1.10–2.21 (26H,m), 1.43 (3H,s), 1.47 (3H,s), 2.12 (3H,s), 2.50 (2H,t,J=5Hz), 3.28 (1H,t,J=12Hz), 3.41–3.57 (2H,m), 3.69 (1H,d,J=12Hz), 3.86–4.01 (1H,m), 4.09 (1H,s), 4.65 (1H,ddd,J=10Hz,10Hz,4Hz), 5.48 (1H,d,J=8Hz), 6.92 (1H,t,J =5Hz).

EXAMPLE 149

(1S,2S)-2-(2,3-Dimethyl-2-tridecenoyl)aminocyclohexane-1-yl 3-[N-(2,2,5,5-tetramethyl-1,3-dioxane-4-carbonyl)amino]propionate Molecular Formula: $C_{33}H_{58}N_2O_6$.
Molecular Weight: 578.93.
NMR($\delta$, CDCl$_3$): 0.88 (3H,t,J=6Hz), 0.96 (3H,s), 1.03 (3H,s), 1.07–2.21 (26H,m), 1.43 (3H,s), 1.46 (3H,s), 1.63 (3H,s), 1.75 (3H,s), 2.53 (2H,t,J=6Hz), 3.28 (1H,d,J=12Hz), 3.36–3.64 (2H,m), 3.69 (1H,d,J=12Hz), 3.88–4.04 (1H,m), 4.08 (1H,s), 4.68 (1H,ddd,J=10Hz,10Hz,4Hz), 5.23+5.58 (1H,d,J=9Hz), 6.92 (1H,t,J=5Hz).

EXAMPLE 150

(1S,2S)-2-(3-Hexylnonanoyl)aminocyclohexane-1-yl 3-[N-(2,2,5,5-tetramethyl-1,3-dioxane-4-carbonyl)amino]propionate Molecular Formula: $C_{33}H_{60}N_2O_6$.

Molecular Weight: 580.95.

NMR(δ, CDCl$_3$): 0.87 (6H,t,J=6Hz), 0.96 (3H,s), 1.04 (3H,s), 1.10-2.20 (31H,m), 1.43 (3H,s), 1.47 (3H,s), 2.50 (2H,t,J=6Hz), 3.28 (1H,d,J=12Hz), 3.36-3.60 (2H,m), 3.69 (1H,d,J=12Hz), 3.88 (1H,m), 4.09 (1H,s), 4.64 (1H,ddd,J=10Hz,10Hz,4Hz), 5.88 (1H,d,J=8Hz), 6.91 (1H,t,J=6Hz).

EXAMPLE 151

(1S,2S)-2-[(E)-3-Phenyl-2-dodecenoyl]aminocyclohexane-1-yl 3-[N-(2,2,5,5-tetramethyl-1,3-dioxane-4-carbonyl)amino]propionate Molecular Formula: C$_{36}$H$_{56}$N$_2$O$_6$.
Molecular Weight: 612.94.

NMR(δ, CDCl$_3$): 0.55-0.73 (1H,m), 0.87 (3H,t,J=6Hz), 0.96 (3H,s), 1.04 (3H,s), 1.08-2.84 (21H,m), 1.42 (3H,s), 1.47 (3H,s), 2.30-2.43 (2H,m), 2.48 (2H,t,J=6Hz), 3.28 (1H,d,J=12Hz), 3.33-3.62 (2H,m), 3.69 (1H,d,J=12Hz), 3.70-3.86 (1H,m), 4.08 (1H,s), 4.28 ((1H,ddd,J=10Hz,10Hz,4Hz), 5.06 (1H,d,J=9Hz), 5.85 (1H,s), 6.92 (1H,t,J=6Hz).

EXAMPLE 152

(1S,2S)-2-[(Z)-3-Phenyl-2-dodecenoyl]aminocyclohexane-1-yl 3-[N-(2,2,5,5-tetramethyl-1,3-dioxane-4-carbonyl)amino]propionate Molecular Formula: C$_{36}$H$_{56}$N$_2$O$_6$.
Molecular Weight: 612.94.

NMR(δ, CDCl$_3$): 0.86 (3H,t,J=7Hz), 0,90 (3H,s), 0.99 (3H,s), 1,03-2.28 (22H,m), 1.39 (3H,s), 1.44 (3H,s), 2.40-2.6 (2H,m), 2.90-3.20 (2H,m), 3.25 (1H,d,J=12Hz), 3.36-3.63 (2H,m), 3.66 (1H,d,J=12Hz), 3.91-4.02 (1H,m), 4.06 (1H,s), 4.65 (1H,ddd,J=10Hz,10Hz,4Hz), 5.82 (1H,s), 6.04 (1H,d,J=8Hz), 6.91 (1H,t,J=6Hz), 7.29-7.44 (5H,m).

EXAMPLE 153

(1S,2S)-2-[(Z)-3-Phenyl-2-nonenoyl]aminocyclohexane-1-yl
3-[N-(2,2,5,5-tetramethyl-1,3-dioxane-4-carbonyl)amino]propionate Molecular Formula: C$_{33}$H$_{50}$N$_2$O$_6$.
Molecular Weight: 570.85.

NMR(δ, CDCl$_3$): 0.83 (3H,t,J=7Hz), 0,90 (3H,s), 0.99 (3H,s), 1.08-2.60 (18H,m), 1.39 (3H,s), 1.44 (3H,s), 2.94-3.20 (2H,m), 3.25 (1H,d,J=12Hz), 3.38-3.61 (2H,m), 3.66 (1H,d,J=12Hz), 3.90-4.04 (1H,m), 4.06 (1H,s), 4.65 (1H,ddd,J=1Hz,1Hz,4Hz), 5.82 (1H,s), 6.01 (1H,d,J=6Hz), 6.91 (1H,t,J=6 Hz), 7.29-7.44 (5H,m).

EXAMPLE 154

(1S,2S)-2-[(E)-3-Phenyl-2-nonenoyl]aminocyclohexane-1-yl 3-[N-(2,2,5,5-tetramethyl-1,3dioxane-4-carbonyl)amino]propionate Molecular Formula: C$_{33}$H$_{50}$N$_2$O$_6$.
Molecular Weight: 570.85.

NMR(δ, CDCl$_3$): 0.55-0.72 (1H,m), 0.85 (3H,t,J=7Hz), 0,96 (3H,s), 1.04 (3H,s), 0.88-1.99 (15H,m), 1.42 (3H,s), 1.47 (3H,s), 2.29-2.34 (2H,m), 2.48 (2H,t,J=6Hz), 3.28 (1H,d,J=12Hz), 3.32-3.61 (2H,m), 3.69 (1H,d,J=12Hz), 3.71-3.84 (1H,m), 4.08 (1H,s), 4.28 (1H,ddd,J=10Hz,10Hz,4Hz), 5.07 (1H,d,J=9Hz), 5.85 (1H,s), 6.92 (1H,t,J=6Hz), 7.13-7.45 (5H,m).

EXAMPLE 155

(1S,2S)-2-(2-Hexylideneoctanyol)aminocyclohexane-1-yl
3-[N-(2,2,5,5-tetramethyl-1,3-dioxane-4-carbonyl)amino]propionate Molecular Formula: C$_{32}$H$_{50}$N$_2$O$_6$.
Molecular Weight: 564.90.

NMR(δ, CDCl$_3$): 0.87 (3H,t,J=8Hz), 0.88 (3H,t,J=7Hz), 0,96 (3H,s), 1.03 (3H,s), 1.07-2.26 (26H,m), 1.42 (3H,s), 1.46 (3H,s), 2.40-2.66 (2H,m), 3.28 (1H,d,J=12Hz), 3.37-3.64 (2H,m), 3.69 (1H,d,J=12Hz), 3.90-4.06 (1H,m), 4.07 (1H,s), 4.70 (1H,ddd,J=10Hz,10Hz,4Hz), 5.38 (1H,t,J=7Hz), 5.61 (1H,d,J=8Hz), 6.91 (1H,t,=6Hz).

EXAMPLE 156

(1S,2S)-2-(2-Hexylideneoctanyol)aminocyclohexane-1-yl
3-[N-(2,2,5,5-tetramethyl-1,3-dioxane-4-carbonyl)amino]propionate Molecular Formula: C$_{32}$H$_{56}$N$_2$O$_6$.
Molecular Weight: 564.90.

NMR(δ, CDCl$_3$): 0.88 (3H,t,J=7Hz), 0.89 (3H,t,J=7Hz), 0,96 (3H,s), 1.03 (3H,s), 1.06-2.33 (26H,m), 1.42 (3H,s), 1.47 (3H,s), 2.40-2.66 (2H,m), 3.28 (1H,d,J=12Hz), 3.32-3.62 (2H,m), 3.69 (1H,d,J=12Hz), 3.86-4.02 (1H,m), 4.07 (1H,s), 4.74 (1H,ddd,J=1Hz,1Hz,4Hz), 5.82 (1H,d,J=8Hz), 6.01 (1H,t,J=7Hz), 6.90 (1H,t,J=6Hz).

EXAMPLE 157

(1S,2S)-2-(N-Benzyl-N-nonylcarbamoyl)aminocyclohexane-1-yl
3-[N-(2,2,5,5-tetramethyl-1,3-dioxane-4-carbonyl)amino]propionate Molecular Formula: C$_{35}$H$_{57}$N$_3$O$_6$.
Molecular Weight: 615.86.
Melting Point (° C.): oil.

NMR(δ, CDCl$_3$): 0.88 (3H,t,J=7Hz), 0.96 (3H,s), 1.03 (3H,s), 0 1.05-2.23 (22H,m), 1.42 (3H,s), 1.46 (3H,s), 2.32-2.53 (2H,m), 3.17 (2H,t,J=7Hz), 3.25-3.39 (1H,m), 3.28 (1H,d,J=12Hz), 3.42-3.55 (1H,m), 3.68 (1H,d,J=12Hz), 3.71-3.83 (1H,m), 4.07 (1H,s), 4.36 (1H,d,J=16Hz), 4.46 (1H,d,J=16Hz), 4.47 (1H,d,J=8Hz), 4.62 (1H,ddd,J=1Hz,1Hz, 4Hz), 4.87 (1H,t,J=6Hz), 7.20-7.37 (5H,m).

EXAMPLE 158

(1S,2S)-2-(2-Benzylundecanoyl)aminocyclohexane-1-yl
3-[N-(2,2,5,5-tetramethyl-1,3-dioxane-4-carbonyl)-amino]propionate Molecular Formula: C$_{35}$H$_{56}$N$_2$O$_6$.
Molecular Weight: 600.84.
Melting Point (° C.): oil.

NMR(δ, CDCl$_3$): 0.88 (3H,t,J=7Hz), 1.02 (3H,s), 1.08 (3H,s), 1.12-2.24 (25H,m), 1.46 (3H,s), 1.54 (3H,s), 2.61 (1H,dd,J=13Hz,5Hz), 2.92 (1H,dd,J=13Hz, 9 Hz), 3.22 (1H,dd,J=18Hz,5Hz), 3.31 (1H,d,J=12 Hz), 3.70-3.84 (1H,m), 3.71 (1H,d,J=12Hz), 3.94 (1H,dd,J=18Hz,7Hz), 4.13 (1H,s), 4.62 (1H,ddd,J=1Hz,1Hz,4Hz), 5.51 (1H,d,J=8Hz), 6.64-6.72 (1H,m), 7.14-7.21 (3H,m), 7.23-7.32 (2H,m).

EXAMPLE 159

(1,2S)-2-(2-Heptylnonanoyl)aminocyclohexane -1-yl
3-[N-(2,2,5,5-tetramethyl-1,3-dioxane-4-carbonyl-
)amino]propionate Molecular Formula: $C_{34}H_{62}N_2O_6$.
Molecular Weight: 594.88.
Melting Point (° C.): wax.
NMR(δ, CDCl$_3$): 0.87 (6H,t,J=7Hz), 0.96 (3H,s), 1.04 (3H,s), 1.08-2.21 (33H,m), 1.43 (3H,s), 1.47 (3H,s), 2.41-2.58 (2H,m), 3.28 (1H,d,J=12Hz), 3.51 (2H,dt,J=6Hz,6Hz), 3.69 (1H,d,J=12Hz), 3.82-3.95 (1H,m), 4.08 (1H,s), 4.68 (1H,ddd,J=11 Hz, 11 Hz,4Hz), 5.80 (1H,d,J=8Hz), 6.91 (1H,t,J=6Hz).

EXAMPLE 160

(1,2S)-2-[(1-Heptyloctyl)carbamoyl]aminocyclohex-
ane-1-yl
3-[N-(2,2,5,5-tetramethyl-1,3-dioxane-4-carbonyl-
)amino]propionate Molecular Formula: $C_{34}H_{63}N_3O_6$.
Molecular Weight: 609.89.
Melting Point (° C.): wax.
NMR(δ, CDCl$_3$): 0.87 (6H,t,J=7Hz), 0.96 (3H,s), 1.03 (3H,s), 1.08-2.28 (32H,m), 1.44 (3H,s), 1.47 (3H,s), 2.38-2.57 (2H,m), 3.28 (1H,d,J=12Hz), 3.31-3.42 (1H,m), 3.54-3.82 (3H,m), 3.69 (1H,d,J=12Hz), 4.10 (1H,s), 4.48 (1H,brs), 4.55 (1H,ddd,J=11 Hz, 11 Hz,4Hz), 4.83 (1H,brs), 6.90 (1H,t,J=6Hz).

EXAMPLE 161

(1,2S)-2-(2-Benzyl-3-phenylpropanoyl)aminocyclohex-
ane-1-yl
3-[N-(2,2,5,5-tetramethyl-1,3-dioxane-4-carbonyl-
)amino]propionate Molecular Formula: $C_{34}H_{46}N_2O_6$.
Molecular Weight: 578.75.
Melting Point (° C.): calomel.
NMR(δ, CDCl$_3$): 0.94 (3H,s), 0.95-2.23 (10H,m), 1.03 (3H,s), 1.42 (3H,s), 1.46 (3H,s), 2.43-2.56 (1H,m), 2.68-3.09 (4H,m), 3.15-3.32 (2H,m), 3.27 (1H,d,J=12Hz), 3.59-3.69 (1H,m), 3.68 (1H,d,J=12Hz), 4.06 (1H,s), 4.35 (1H,ddd,J=11 Hz,11 Hz,4Hz), 5.38 (1H,d,J=8Hz), 6.77 (1H,t,J=6Hz), 7.12-7.28 (10H,m).

EXAMPLE 162

(1,2S)-2-[(4-Phenyl-2-(3-phenylpropyl)pentanoyl)-
]aminocyclohexane-1-yl
3-[N-(2,2,5,5-tetramethyl-1,3-dioxane-4-carbonyl-
)amino]propionate Molecular Formula: $C_{38}H_{54}N_2O_6$.
Molecular Weight: 634.86.
Melting Point (° C.): calomel.
NMR(δ, CDCl$_3$): 0.93 (3H,s), 0.98-2.27 (19H,m), 1.02 (3H,s), 1.41 (3H,s), 1.46 (3H,s), 2.48-2.64 (4H,m), 3.12-3.28 (2H,m), 3.27 (1H,d,J=12Hz), 3.67 (1H,d,J=12Hz), 3.78-3.91 (1H,m), 4.05 (1H,s), 4.59 (1H,ddd,J=11 Hz,11 Hz,4Hz), 5.87 (1H,d,J=8Hz), 6.75 (1H,t,J=6Hz), 7.11-7.30 (10H,m).

EXAMPLE 163

(1,2S)-2-[5-Phenyl-2-(4-phenylpropyl)pentanoyl-
]aminocyclohexane-1-yl
3-[N-(2,2,5,5-tetramethyl-1,3-dioxane-4-carbonyl-
)amino]propionate Molecular Formula: $C_{40}H_{58}N_2O_6$.
Molecular Weight: 662.91.
Melting Point (° C.): oil.
NMR(δ, CDCl$_3$): 0.84-2.14 (21H,m), 0.94 (3H,s), 1.01 (3H,s), 1.41 (3H,s), 1.45 (3H,s), 2.32-2.61 (6H,m), 3.27 (1H,d,J=8Hz), 3.37-3.53 (2H,m), 3.67 (1H,d,J=8Hz), 3.78-3.92 (1H,m), 4.06 (1H,s), 4.62 (1H,ddd,J=11 Hz,11 Hz,4Hz), 5.82 (1H,d,J=8 Hz), 6.86 (1H,t,J=6Hz), 7.11-7.29 (10H,m).

EXAMPLE 164

(1,2S)-2-[2-(p-tert-Butylbenzyl)-3-(4-tertbutylphenyl)-
propanoyl)aminocyclohexane-1-yl
3-[N-(2,2,5,5-tetramethyl-1,3-dioxane-4-carbonyl-
)amino]propionate Molecular Formula: $C_{42}H_{62}N_3O_6$.
Molecular Weight: 690.97.
Melting Point (° C.): calomel.
NMR(δ, CDCl$_3$): 0.94 (3H,s), 1.02 (3H,s), 1.05-1.84 (8H,m), 1.28 (9H,s), 1.29 (9H,s), 1.41 (3H,s), 1.46 (3H,s), 2.12-2.34 (2H,m), 2.48-2.58 (1H,m), 2.66-3.04 (4H,m), 3.27 (1H,d,J=12Hz), 3.33 (2H,dt,J=6Hz,6Hz), 3.61-3.73 (1H,m), 3.68 (1H,d,J=12Hz), 4.06 (1H,s), 4.38 (1H,ddd,J=11 Hz,11 Hz,4Hz), 5.32 (1H,d,J=8Hz), 6.83 (1H,t,J=6Hz), 7.06 (2H,d,J=8Hz), 7.11 (2H,d,J=8Hz), 7.26 (2H,d,J=8Hz), 7.28 (2H,d,J=8Hz).

EXAMPLE 165

Preparation of
(S)-2-Oleoylaminomethyl-1-(3-[N-(2,2,5,5-tetramethyl-
1,3-dioxane-4-carbonyl)amino)propanoyl)pyrrolidine 1-Ethyl-3-(3-dimethylaminopropyl)carbodiimide hydrochloride (530 m9) was added to a solution of 910 mg of (S)-2-oleylamino-methylpyrrolidine and 650 mg of 3-[N-(2,2,5,5-tetramethyl-1,3-dioxane-4-carbonyl-)amino]propionic acid in 10 ml of methylene chloride under ice cooling. The mixture was stirred at room temperature for 18 hours. The reaction mixture was washed with water and dried over anhydrous sodium sulfate, followed by removal of the solvent by vacuum evaporation. Then, the residue was purified by silica gel column chromatography to obtain 1.05 g of the title compound (yield: 59 %).
Property: oily.
Specific rotary power [α]$_D$: +5.2° (C=1.0, CHCl$_3$).
IR(cm$^{-1}$, neat): $v_{NH}$3336, $c_O$1656.
Mass Spectrometric Analysis Molecular Formula: $C_{35}H_{63}N_3O_5$, Calculated: 605.4746, Found: 605.4747.
NMR(δ, CDCl$_3$): 0.88 (3H,t,J=7Hz), 0.96 (3H,s), 1.04 (3H,s), 1.19-1.39 (20H,m), 1.42 (3H,s), 1.46 (3H,s), 1.53-1.82 (3H,m), 1.85-2.09 (7H,m), 2.16 (2H,t,J=7Hz), 2.44-2.62 (2H,m), 3.13-3.23 (1H,m), 3.28 (1H,d,J=12Hz), 3.39-3.60 (5H,m), 3.69 (1H,d,J=12Hz), 4.08 (1H,s), 4.21-4.28 (1H,m), 5.29-5.40 (2H,m), 7.09 (1H,t,J=6Hz), 7.24 (1H,brs).

EXAMPLE 166

Preparation of
(S)-2-(Oleoylamino)methyl-1-(3-N-(2,4-dihydroxy-3,3-dimethyl-1-oxobutyl)amino)propanoyl)pyrrolidine A solution of 500 mg of (S)-2-(Oleoylamino)methyl-1-(3-N-(2,2,5,5-tetramethyl-1,3-dioxane-4-carbonyl-)amino]propanoyl)pyrrolidine in a mixed solvent composed of 20 ml of acetic acid and 10 ml of water was stirred at room temperature for 16 hours. Then, 20 ml of ethyl acetate and 20 ml of water were added thereto, and the organic layer was separated. The organic layer was washed with water, and dried over anhydrous sodium sulfate. After removing the solvent by evaporation, the residue obtained was subjected to silica gel column chromatography for purification to obtain 397 mg of the title compound (yield: 85 %).

Property: oily.
Specific Rotary Power $[\alpha]_D$: $-5.8°$ (C=1.0, CHCl$_3$).
IR(cm$^{-1}$, neat): $\nu_{NH}$3324, $\nu_{CO}$1650.
Mass Spectrometric Analysis Molecular Formula: C$_{35}$H$_{63}$N$_3$O$_5$, Calculated: 565.4454, Found: 565.4449.
NMR($\delta$, CDCl$_3$): 0.88 (3H,t,J=7Hz), 0.92 (3H,s), 1.02 (3H,s), 1.21–1.39 (20H,m), 1.71–1.84 (1H,m), 1.53–1.67 (2H,m), 1.85–2.09 (7H,m), 2.17 (2H,t,J=7Hz), 2.45–2.87 (4H,m), 3.13–3.75 (8H,m), 3.99 (1H,s), 3.39–3.68 (5H,m), 3.68 (1H,d,J=12Hz), 4.08 (1H,s), 4.19–4.29 (1H,m), 5.29–5.40 (2H,m), 6.85–7.07 (1H,brs), 7.36–7.44 (1H,m).

EXAMPLE 167

Preparation of
(R)-2-Oleoylaminomethyl-1-(3-N-(2,2,5,5-tetramethyl-1,3-dioxane-4-carbonyl)amino)propanoyl)pyrrolidine (R)-2-Oleoylaminomethylpyrrolidine (910 mg) and 650 mg of 3-[N-(2,2,5,5-tetramethyl-1,3-dioxane-4-carbonyl)amino]propionic acid were reacted in the same manner as in Example 165 to obtain 1.24 g of the title compound (yield: 82 %).

Property: oily.
Specific rotary power: $[\alpha]_D$: $+41.5°$ (C=1.0, CHCl$_3$).
IR(cm$^{-1}$, $\nu$neat): $\nu_{NH}$3336, $\nu_{CO}$1654.
Mass Spectrometric analysis; Molecular Formula: C$_{35}$H$_{63}$N$_3$O$_5$, Calculated: 605.4747, Found: 605.4787.
NMR($\delta$, CDCl$_3$): 0.88 (3H,t,J=7Hz), 0.97 (3H,s), 1.04 (3H,s), 1.21–1.39 (20H,m), 1.43 (3H,s), 1.46 (3H,s), 1.55–1.82 (3H,m), 1.87–2.09 (7H,m), 2.17 (2H,t,J=7Hz), 2.53 (2H,t,J=6Hz), 3.12–3.21 (1H,m), 3.28 (1H,t,J=12Hz), 3.39–3.68 (5H,m), 3.68 (1H,t,J=12Hz), 4.08 (1H,s), 4.20–4.28 (1H,m), 5.28–5.40 (2H,m), 7.11 (1H,t,J=6Hz), 7.24 (1H,brs).

EXAMPLE 168

Preparation of
3-Oleoylamino-1-(3-N-(2,2,5,5-tetramethyl-1,3-dioxane-4-carbonyl)amino]propanoyl)piperidine 3-Oleoylaminopiperidine (1.02 g) and 0.78 g of 3-[N-(2,2,5,5-tetramethyl-1,3-dioxane-4-carbonyl)aminopropionic acid were reacted in the same manner as in Example 165 to obtain 1.61 g of the title compound (yield: 89 %).

Property: oil.
Specific Rotary Power $[\alpha]_D$: $+25.3°$ (C=1.0, CHCl$_3$).
IR(cm$^{-1}$, $\nu$neat): $\nu_{NH}$3316, $\nu_{CO}$1652.

Mass Spectrometric Analysis Molecular Formula: C$_{35}$H$_{63}$N$_3$O$_5$. Calculated: 605.4767, Found: 605.4749,
NMR($\delta$, CDCl$_3$): 0.88 (3H,t,J=7Hz), 0.98 (3H,s), 1.04 (3H,s), 1.18–1.39 (20H,m), 1.43 (3H,s), 1.47 (3H,s), 1.49–2.08 (10H,m), 2.16 (2H,t,J=7Hz), 2.56 (2H,t,J=6Hz), 3.01–3.15 (1H,m), 3.16–3.66 (4H,m), 3.28 (1H,d,J=12Hz), 3.68 (1H,d,J=12Hz), 3.69–4.08 (2H,m), 4.07 (1H,s), 5.29–5.40 (2H,m), 7.01–7.11 (1H,d,J=6Hz).

EXAMPLE 169

Preparation of
3-Oleoylamino-1-(3-N-(2,4-dihydroxy-3,3-dimethyl-1-oxobutyl)amino)propanoyl)piperidine 3-Oleoylamino-1-(3-[N-(2,2,5,5-tetramethyl-1,3-dioxane-4-carbonyl)amino]propanoyl)piperidine (1.61 g) was reacted in the same manner as in Example 166 to obtain 1.1 g of the title compound (yield: 73 %).

Property: oil.
Specific Rotary Power $[\alpha]_D$: $+10.4°$ (C=1.0, CHCl$_3$).
IR(cm$^{-1}$, neat): $\nu_{NH}$3316, $\nu_{CO}$1650
Mass Spectrometric Analysis Molecular Formula: C$_{35}$H$_{59}$N$_3$O$_5$Calculated: 565.4454 Found: 565.4446
NMR($\delta$, CDCl$_3$): 0.88 (3H,t,J=7Hz), 0.93–0.95 (3H,s), 1.03 (3H,s), 1.21–1.38 (20H,m), 1.48–2.09 (10H,m), 2.15 (2H,t,J=7Hz), 2.57 (2H,t,J=6Hz), 3.05–3.98 (7H,m), 3.47 (1H,d,J=12Hz), 3.51 (1H,d,J=12Hz), 3.95 (1H,m), 5.29–5.40 (2H,m), 5.61–5.86 (1H,brs), 7.23 (1H,brs).

EXAMPLE 170

Preparation of
1-Oleoylamino-3-(3-N-(2,4-dihydroxy-3,3-dimethyl-1-oxo-butyl)amino)propanoyl)aminopiperidines A and B Oleoyl chloride (945 mg) was added to a solution of 942 mg of 3-3-(2,4-dihydroxy-3,3-dimethyl-1-oxo-butylamino)propanyl)aminopiperidine and 1.06 g of sodium carbonate in a mixed solvent composed of 20 ml of water and 20 ml of ethyl acetate under ice cooling and the mixture was stirred for additional 30 minutes. Then the aqueous layer was removed. The organic layer was washed with brine and dried over anhydrous sodium sulfate. After removing the solvent by evaporation, the residue was purified by silica gel column chromatography to obtain two diastereomers A and B, respectively, the title compound, in amount of 390 mg (yield: 22 %) and 409 mg (yield: 23 %), respectively.

A
Property: oily.
Specific Rotary Power $[\alpha]_D$: $+22.5°$ (C=1.0, CHCl$_3$).
IR(cm$^{-1}$, neat): $\nu_{NH}$3324, $\nu_{CO}$1652.
Mass Spectrometric Analysis Molecular Formula: C$_{32}$H$_{59}$N$_3$O$_5$, Calculated: 565.4453, Found: 565.4433.
NMR($\delta$, CDCl$_3$): 0.88 (3H,t,J=7Hz), 0.91 (3H,s), 1.04 (3H,s), 1.22–1.38 (20H,m), 1.52–2.09 (10H,m), 2.25–2.53 (4H,m), 2.65–3.70 (9H,m), 3.98 (1H,brs), 4.04–4.31 (2H,m), 5.28–5.40 (2H,m), 5.94 (1H,brs), 7.50 (1H,brs).

B
Property: oil.
Specific Rotary Power $[\alpha]_D$: $+7.6°$ (C=1.0, CHCl$_3$).
IR(cm$^{-1}$, neat): $\nu_{NH}$3320, $\nu_{CO}$1652 Mass Spectrometric Analysis Molecular Formula: C$_{32}$H$_{59}$N$_3$O$_5$, Calculated: 565.4453, Found: 565.4461.

NMR(δ, CDCl₃): 0.88 (3H,t,J=7Hz), 0.97 (3H,s), 1.03 (3H,s), 1.22-1.38 (20H,m), 1.52-2.09 (10H,m), 2.25-2.80 (6H,m), 3.10-4.05 (1H,s), 5.29-5.40 (2H,m), 6.23 (1H,brs), 7.50 (1H,brs).

EXAMPLE 171

Preparation of
1-Oleoyl-3-3-(2,2,5,5-tetramethyl-1,3-dioxane-4-carbonylamino)propanoyl]aminopiperidine-A To a solution of 180 mg of 1-oleoylamino-3-[3-(2,4-dihydroxy-3,3-dimethyl-1-oxobutylamino)propanoyl)aminopiperidine-A obtained in Example 170 in 10 ml of acetone was added 10 mg of p-toluenesulfonic acid, and the mixture was stirred at room temperature for 10 hours. After adding a saturated aqueous solution of sodium hydrogen carbonate thereto, the reaction mixture was extracted with ethyl acetate. The organic layer was washed with brine and dried over anhydrous sodium sulfate, followed by removal of the solvent. The residue was subjected to silica gel column chromatography to obtain 176 mg of the title compound (yield: 91 %).

Property: oily.

Specific Rotary Power [α]$_D$: +30.6° (C=1.0, CHCl₃).

IR(cm⁻¹, neat): $v_{NH}$3312, $v_{CO}$1652, 1636.

Mass Spectrometric Analysis Molecular Formula: C₃₅H₆₃N₃O₅, Calculated: 605.4767. Found: 605.4789.

NMR(δ, CDCl₃): 0.88 (3H,t,J=7Hz), 0.96 (3H,s), 1.04 (3H,s), 1.21-1.38 (20H,m), 1.43 (3H,s), 1.47 (3H,s), 1.49-1.7 (5H,m), 1.81-2.08 (5H,m), 2.34 (2H,t,J=7Hz), 2.36-2.49 (2H,m), 2.98-3.16 (1H,m), 3.28 (1H,d,J=12Hz), 3.32-3.72 (4H,m), 3.70 (1H,d,J=12Hz), 3.78-4.04 (2H,m), 4.08 (1H,s), 5.29-5.40 (2H,m), 5.99-6.16 (1H,m), 7.02 (1H,brs).

EXAMPLE 172

Preparation of
1-Oleoyl-3-3-(2,2,5,5-tetramethyl-1,3-dioxane-4-carbonylamino]propanoylaminopiperidine-B 1-Oleoylamino-3-3-(2,4-dihydroxy-3,3-dimethyl-1-oxo-butylamino)propanoyl]aminopiperidine-B obtained in Example 170 (238 mg) was reacted in the same manner as in Example 171 to obtain 206 mg of the title compound.

Property: oily.

Specific Rotary Power [α]$_D$: +16.0° (C=1.0, CHCl₃).

IR(cm⁻¹, neat): $v_{NH}$3312, $v_{CO}$1654

Mass Spectrometric Analysis. Molecular Formula: C₃₅H₆₃N₃O₅, Calculated: 605.4767, Found: 605.4776.

NMR(δ, CDCl₃): 0.88 (3H,t,J=7Hz), 0.98 (3H,s), 1.05 (3H,s), 1.18-1.38 (20H,m), 1.42 (3H,s), 1.47 (3H,s), 1.49-2.08 (10H,m), 2.34 (2H,t,J=7Hz), 2.37-2.50 (2H,m), 2.90-3.07 (1H,m), 3.29 (1H,d,J=12Hz), 3.32-3.73 (4H,m), 3.69 (1H,d,J=12Hz), 3.76-4.11 (2H,m), 4.07 (1H,s), 5.29-5.41 (2H,m), 5.97-6.11 (1H,m), 7.02 (1H,brs).

EXAMPLE 173

Preparation of 1-Oleoyl-4-piperidinyl
3-N-(2,2,5,5-tetramethyl-1,3-dioxane-4-carbonylamino]-propionate A solution of 1.83 g of 1-oleoyl-4-hydroxypiperidine, 1.3 g of 3-[N-(2,2,5,5-tetramethyl-1,3-dioxane-4-carbonyl)amino]propionic acid, 1.03 g of dicyclohexylcarbodiimide and 0.61 g of 4-(N,N-dimethylamino)pyridine in 60 ml of toluene was heated under reflux for one night. After completion of the reaction, the reaction mixture was cooled and precipitates were removed. Then, the organic layer was washed sequentially with water, 1N hydrochloric acid and brine, and dried over anhydrous sodium sulfate. After removing the solvent by evaporation, the residue was subjected to silica gel column chromatography to obtain 1.95 g of the title compound (yield: 65 %).

Property: oily.

IR(cm⁻¹, neat): $v_{CO}$1740, 1660.

Mass Spectrometric Analysis Molecular Formula: C₃₅H₆₂N₂O₆, Calculated: 606.4606, Found: 606.4587.

NMR(δ, CDCl₃): 0.88 (3H,t,J=7Hz), 0.96 (3H,s), 1.04 (3H,s), 1.16-1.40 (19H,m), 1.43 (3H,s), 1.46 (3H,s), 1.50-1.77 (6H,m), 1.76-2.04 (6H,m), 3.32 (2H,t,J=6Hz), 2.58 (2H,t,J=6Hz), 3.29 (1H,d,J=12Hz), 3.26-3.70 (4H,m), 3.69 (1H,d,J=12Hz), 3.88-4.00 (1H,m), 4.08 (1H,s), 4.96-5.06 (1H,m), 5.30-5.42 (2H,m), 6.88-6.96 (1H,m).

EXAMPLE 174

Preparation of 1-Oleoyl-4-piperidinyl
3[N-(2,4-dihydroxy-3,3-dimethyl-1-oxobutyl)amino)-propionate 1-Oleoyl-4-piperidine 3-[N-(2,2,5,5-tetramethyl-1,3-dioxane-4-carbonyl)aminopropionate (1.51 g) was reacted in the same manner as in Example 166 to obtain 1.37 g of the title compound (yield: 97 %).

Property: oily.

IR(cm⁻¹, neat): $v_{NH}$3436, $v_{CO}$1740, 1658.

Mass Spectrometric Analysis: Molecular Formula: C₃₂H₅₈N₂O₆, Calculated: 566.4294, Found: 566.4318.

NMR(δ, CDCl₃): 0.88 (3H,t,J=7Hz), 0.92 (3H,s), 1.02 (3H,s), 1.02 (3H,s), 1.20-1.40 (21H,m), 1.56-1.72 (4H,m), 1.80-2.10 (5H,m), 2.32 (2H,t,J=7Hz), 2.59 (2H,t,J=6Hz), 3.20-4.10 (10H,m), 4.96-5.06 (1H,m), 4.96-5.06 (1H,m), 5.30-5.42 (2H,m), 7.14-7.24 (1H,m).

EXAMPLE 175

Preparation of 1-Oleoyl-4-piperidinyl
3-[N-(2,4-diacetoxy-3,3-dimethyl-1-oxobutyl)amino]-propionate Acetic anhydride (10 ml) was added to a solution of 530 mg of 1-oleoyl-4-piperidine 3-[N-(2,4-dihydroxy-3,3-dimethyl-1-oxo-butyl)amino]propionate in 5 ml of ypridine, and the mixture was stirred at room temperature for 15 hours. The reaction mixture was poured into ice water, and extracted with ethyl acetate. The organic layer was washed sequentially with a saturated aqueous sodium hydrogen carbonate solution, with water and then with brine, followed by drying over anhydrous sodium sulfate. After removing the solvent by vacuum evaporation, the residue was subjected to silica gel column chromatography to obtain 610 mg of the title compound.

Property: oily.

IR(cm⁻¹, neat): $v_{CO}$1746, 1642.

Mass Spectrometiric Analysis: Molecular Formula: C₃₆H₆₂N₂O₈, Calculated: 650.4505, Found: 650.4502.

NMR(δ, CDCl₃): 0.88 (3H,t,J=7 Hz), 1.02 (3H,s), 1.07 (3H,s), 1.20-1.40 (20H,m), 1.56-1.70 (5H,m), 1.80-2.08 1 (6H,m), 2.07 (3H,s), 2.15 (2H,t,J=6 Hz), 3.26-3.70 (6H,m), 3.83 (1H,d,J=11 Hz), 3.82-3.94 (1H,m), 4.04 (1H,d,J=11 Hz), 4.96 (1H,s), 4.93-5.02 (1H,m), 5.30 (2H,m), 6.52-6.60 (1H,m).

EXAMPLE 176

Preparation of 1-Oleoyl-3-piperidinyl 3-[N-(2,4-dihydroxy-3,3-dimethyl-1-oxobutyl)amino]-propionate 1-Oleoyl-3-hydroxypiperidine (3.30 g) and 2.33 g of 3-]N-(2,2,5,5-tetramethyl-1,3-dioxane-4-carbonyl-)amino]propionic acid were reacted in the same manner as in Example 173 to obtain crude 1-oleoyl-3-piperidinyl 3-[N-(2,2,5,5-tetramethyl-1,3-dioxane-4-carbonyl-)amino]propionate. This compound was reacted in the same manner as in Example 166 to obtain two disastereomers-A and -B of the title compound in amount of 1.25 g (45%) and 1.36 g (yield: 49%).

A

Property: oily.

Specific Rotary Power $[\alpha]_D$: +19.5° (C=1.0, CHCl$_3$).

IR(cm$^{-1}$, neat): $\nu_{NH}$3312, $\nu_{CO}$1740, 1652;

Mass Spectrometric Analysis: Molecular Formula: $C_{32}H_{58}N_2O_6$, Calculated: 566.4294, Found: 566.4297.

NMR($\delta$, CDCl$_3$): 0.88 (3H,t,J=7 Hz), 0.90 (3H,s), 1.07 (3H,s), 1.22–1.39 (20H,m), 1.45–2.09 (10H,m), 2.31 (2H,t,J=7 Hz), 2.33–3.18 (6H,m), 3.29–3.58 (3H,m), 3.70–3.89 (3H,m), 4.02 (1H,brs), 4.81–4.93 (2H,m), 5.29–5.41 (2H,m), 7.38 (1H,brs).

B

Property: oily.

Specific Rotary Power $[\alpha]_D$: +32.8° (C=1.0, CHCL$_3$).

IR(cm$^{-1}$, neat: $\nu_{NH}$3312, $\nu_{CO}$1740, 1650.

Mass Spectrometric Analysis Molecular Formula: $C_{32}H_{58}N_2O_6$, Calculated: 566.4294, Found: 566.4394.

NMR($\delta$, CDCl$_3$): 0.88 (3H,t,J=7 Hz), 1.00 (3H,s), 1.06 (3H,s), 1.22–1.38 (20H,m), 1.52–2.08 (10H,m), 2.15–2.63 (4H,m), 2.92–3.84 (7H,m), 4.00 (1H,s), 4.47–4.58 (1H,m), 4.96 (1H,brs), 5.29–5.40 (2H,m), 7.42 (1H,brs).

EXAMPLE 177

Preparation of 1-Oleoyl-3-piperidinyl 3[N-(2,2,5,5-tetramethyl-1,3-dioxane-4-carbonyl-)amino]propionate-A 1-Oleoyl-3-piperidinyl 3-N-(2,4-dihydroxy-3,3-dimethyl-1-oxo-butyl)amino]propionate-A (568 mg) was reacted in the same manner as in Example 171 to obtain mg of the title compound (yield: 79 %).

Property: oily.

Specific Rotary Power $[\alpha]_D$: +18.8° (C=1.0, CHCl$_3$).

IR(cm$^{-1}$, neat): $\nu_{NH}$3312, $\nu_{CO}$1740, 1678, 1650.

Mass Spectrometric Analysis: Molecular Formula: $C_{35}H_{62}N_2O_6$, Calculated: 606.4607, Found: 606.4635.

NMR($\delta$, CDCl$_3$): 0.88 (3H,t,J=7Hz), 0.90 (3H,s), 1.04 (3H,s), 1.21–1.38 (20H,m), 1.42 (3H,s), 1.46 (3H,s), 1.40–2.09 (10H,m), 2.30 (2H,t,J=7Hz), 2.45–2.63 (2H,m), 3.27 (1H,d,J=12Hz), 3.32–3.70 (6H,m), 3.66 (1H,d,J=12Hz), 4.07 (1H,s), 4.81 (1H,brs), 5.29–5.40 (2H,m), 6.79–7.02 (1H,brs).

EXAMPLE 178

Preparation of 1-Oleoyl-3-piperidinyl 3-N-(2,2,5,5-tetramethyl-1,3-dioxane-4-carbonyl-)amino)propionate-B 1-Oleoyl-3-piperidinyl 3-N-(2,4-dihydroxy-3,3-dimethyl-1-oxo-butyl)amino)propionate-B (567 mg) was reacted in the same manner as in Example 171 to obtain 490 mg of the title compound (yield: 81 %).

Property: oily.

Specific Rotary Power $[\alpha]_D$: +22.8° (C=1.0, CHCl$_3$).

IR(cm$^{-1}$, neat): $\nu_{NH}$3312, $\nu_{CO}$1740, 1680, 1652.

Mass Spectrometric Analysis: Molecular Formula: $C_{35}H_{62}N_2O_6$, Calculated: 606.4607, Found: 606.4607.

NMR($\delta$, CDCl$_3$): 0.88 (3H,t,J=7Hz), 0.98 (3H,s), 1.05 (3H,s), 1.21–1.38 (20H,m), 1.42 (3H,s), 1.45 (3H,s), 1.50–2.05 (10H,m), 2.30 (2H,t,J=7Hz), 2.54 (2H,t,J=6Hz), 3.24 (1H,d,J=12Hz), 3.32–3.72 (6H,m), 3.66 (1H,d,J=12Hz), 4.06 (1H,s), 4.75–4.85 (1H,m), 5.29–5.40 (2H,m), 7.81–7.93 (1H,m).

EXAMPLE 179

Preparation of 1-Oleoyl-2-(2S)-pyrrolidinylmethyl 3-N-(2,2,5,5-tetramethyl-1,3-dioxane-4-carbonyl-)amino)propionate (S)-1-Oleoyl-2-pyrrolidinemethanol (1.83 g) and 1.30 g of 3-N-(2,2,5,5-tetramethyl-1,3-dioxane-4-carbonyl-)amino]propionic acid were reacted in the same manner as in Example 173 to obtain 2.24 g of the title compound (yield: 74 %).

Property: oily.

Specific Rotary Power $[\alpha]_D$: +0.5° (C=1.0, CHCl$_3$).

IR(cm$^{-1}$, neat): $\nu_{NH}$3312, $\nu_{CO}$1740, 1680, 1652.

Mass Spectrometric Analysis: Molecular Formula: $C_{35}H_{62}N_2O_6$, Calculated: 606.4607, Found: 606.4589.

NMR($\delta$, CDCl$_3$): 0.88 (3H,t,J=7Hz), 0.90 (3H,s), 1.04 (3H,s), 1.20–1.40 (20H,m), 1.43 (3H,s), 1.46 (3H,s), 1.56–1.72 (2H,m), 1.75–2.09 (8H,m), 2.25 (2H,t,J=7Hz), 2.57 (2H,t,J=6Hz), 3.28 (1H,d,J=12Hz), 3.35–3.64 (4H,m), 3.68 (1H,d,J=12Hz), 4.05–4.28 (3H,m), 4.31–4.41 (1H,m), 5.29–5.41 (2H,m), 6.90–7.04 (1H,m).

EXAMPLE 180

Preparation of 1-Oleoyl-2-(2R)-pyrrolidinylmethyl 3-N-(2,2,5,5-tetramethyl-1,3-dioxane-4-carbonyl-)amino1propionate (R)-1-Oleoyl-2-pyrrolidinemethanol (1.46 g) and 1.04 g of 3-[N-(2,2,5,5-tetramethyl-1,3-dioxane-4-carbonyl-)amino]propionic acid were reacted in the same manner as in Example 173 to obtain 1.62 g of the title compound (yield: 67 %).

Property: oily.

Specific Rotary Power $[\alpha]_D$: +44.9° (C=1.0, CHCl$_3$).

IR(cm$^{-1}$, neat): $\nu_{NH}$3312, $\nu_{CO}$1742, 1682, 1652.

Mass Spectrometric Analysis: Molecular Formula: $C_{35}H_{62}N_2O_6$, Calculated: 606.4607, Found: 606.4605.

NMR($\delta$, CDCl$_3$): 0.88 (3H,t,J=7Hz), 1.97 (3H,s), 1.04 (3H,s), 1.19–1.39 (20H,m), 1.43 (3H,s), 1.46 (3H,s), 1.55–2.09 (10H,m), 2.26 (2H,t,J=7Hz), 2.57 (2H,t,J=6Hz), 3.22 (1H,d,J=12Hz), 3.36–3.70 (4H,m), 3.68 (1H,d,J=12Hz), 4.08 (1H,s), 4.09–4.24 (2H,m), 4.30–4.43 (1H,m), 5.29–5.40 (2H,m), 6.92–7.05 (1H,m).

EXAMPLE 181

Preparation of 1-Stearoyl-2-(2S)-pyrrolidinylmethyl -N-(2,2,5,5-tetramethyl-1,3-dioxane-4-carbonyl)amino)-propionate (S)-1-Stearoyl-2-pyrrolidinemethanol (367 mg) and 259 mg of 3-N-2,2,5,5-tetramethyl-1,3-dioxane-4-carbonyl)amino]propionic acid were reacted in the same manner as in Example 173 to obtain 470 mg of the title compound (yield: 77 %).

Property: oily.

Specific Rotary Power $[\alpha]_D$: $-5.10°$ (C=1.0, CHCl$_3$).

IR(cm$^{-1}$, neat): $\nu_{CO}$1742, 1650.

Mass Spectrometric Analysis: Molecular Formula: C$_{35}$H$_{64}$N$_2$O$_6$, Calculated: 608.4764, Found: 608.4760.

NMR($\delta$, CDCl$_3$): 0.88 (3H,t,J=7Hz), 0.97 (3H,s), 1.04 (3H,s), 1.18–1.37 (24H,m), 1.43 (3H,s), 1.46 (3H,s), 1.53–2.10 (10H,m), 2.25 (3H,t,J=7Hz), 2.56 (2H,t,J=6Hz), 3.28 (1H,d,J=12Hz), 3.35–3.62 (4H,m), 3.68 (1H,d,J=12Hz), 4.08 (1H,s), 4.12 (1H,dd,J=11 Hz,4Hz), 4.23 (1H,dd,J=11 Hz,4Hz), 4.32–4.40 (1H,m), 6.08 (1H,t,J=6Hz).

EXAMPLE 182

Preparation of 1-Linoleoyl-2-(2S)-pyrrolidinylmethyl N-(2,2,5,5-tetramethyl-1,3-dioxane-4-carbonyl)amino]-propionate (S)-1-Linoleoyl-2-pyrrolidinemethanol (363 mg) and 259 mg of 3-N-(2,2,5,5-tetramethyl-1,3-dioxane-4-carbonyl)amino]propionic acid were reacted in the same manner as in Example 173 to obtain 433 mg of the title compound (yield: 70 %).

Property: oily.

Specific Rotary Power $[\alpha]_D$: $+2.30°$ (C=1.0, CHCl$_3$).

IR(cm$^{-1}$, neat): $\nu_{NH}$3312, $\nu_{CO}$1680, 1652.

Mass Spectrometric Analysis: Molecular Formula: C$_{35}$H$_{60}$N$_2$O$_6$, Calculated: 604.4451, Found: 604.4452.

NMR($\delta$, CDCl$_3$): 0.89 (3H,t,J=7Hz), 0.97 (3H,s), 1.04 (3H,s), 1.41 (14H,m), 1.43 (3H,s), 1.46 (3H,s), 1.56–2.09 (10H,m), 2.25 (2H,t,J=7Hz), 2.56 (2H,t,J=6Hz), 2.77 (2H,t,J=6Hz), 3.28 (1H,d,J=12Hz), 3.37–3.63 (4H,m), 4.08 (1H,s), 4.11 (1H,dd,J=11 Hz,4Hz), 4.23 (1H,dd,J=11 Hz,4Hz), 4.31–4.40 (1H,m), 5.28–5.43 (4H,m), 6.98 (1H,t,J=6Hz).

EXAMPLE 183

Preparation of 1-Oleoyl-2-(2S)-pyrrolidinylmethyl 3-[N-2,4-dihydroxy-3,3-dimethyl-1-oxobutyl)amino]-propionate 1-Oleoyl-2-(2S)-pyrrolidinylmethyl 3-N-(2,2,5,5-tetramethyl-1,3-dioxane-4-carbonyl)amino]propionate (1.5 g) was reacted in the same manner as in Example 166 to obtain 1.27 g of the title compound (yield: 91 %).

Property: oily.

Specific Rotary Power $[\alpha]_D$: $+13.4°$ (C=1.0, CHCl$_3$).

IR(cm$^{-1}$, neat): $\nu_{NH}$3312, $\nu_{CO}$1742, 1650.

Mass Spectrometric Analysis: Molecular Formula: C$_{32}$H$_{58}$N$_2$O$_6$, Calculated: 566.4294, Found: 566.4301.

NMR($\delta$, CDCl$_3$): 0.88 (3H,t,J=7Hz), 0.94 (3H,s), 1.04 (3H,s), 1.21–1.40 (20H,m), 1.54–1.68 (2H,m), 1.69–1.86 (1H,m), 1.88–2.09 (7H,m), 2.10–2.38 (3H,m), 2.40–2.63 (2H,m), 3.33–3.71 (6H,m), 4.00 (1H,m), 4.03–4.15 (2H,m), 4.38–4.50 (1H,m), 5.28–5.40 (2H,m), 7.30–7.52 (1H,m).

EXAMPLE 184

Preparation of 1-Oleoyl-2-(2S)-pyrrolidinylmethyl 3-[N-(2,4-diacetoxy-3,3-dimethyl-1-oxobutyl)amino)-propionate 1-Oleoyl-2-(2S)-pyrrolidinylmethyl 3-N-(2,4-dihydroxy-3,3-dimethyl-1-oxobutylamino)amino]propionate (556 mg) was reacted int he same manner as in Example 175 to obtain 463 mg of the title compound (yield: 71 %).

Property: oily.

Specific Rotary Power $[\alpha]_D$: $-0.40°$ (C=1.0, CHCl$_3$).

IR(cm$^{-1}$, neat): $\nu_{NH}$, $\nu_{CO}$2748, 1646.

Mass Spectrometric Analysis: Molecular Formula: C$_{36}$H$_{62}$N$_2$O$_8$, Calculated: 650.4506, Found: 650.4500.

NMR($\delta$, CDCl$_3$): 0.88 (3H,t,J=7Hz), 1.02 (3H,s), 1.07 (3H,s), 1.22–1.38 (20H,m), 1.55–1.67 (2H,m), 1.70–1.85 (1H,m), 1.88–2.08 (7H,m), 2.07 (3H,m), 2.14 (3H,s), 2.26 (2H,t,J=7Hz), 2.43–2.59 (2H,m), 3.35–3.68 (4H,m), 3.84 (1H,d,J=12Hz), 4.04 (1H,d,J=12Hz), 4.15 (2H,d,J=6Hz), 4.37–4.45 (1H,m), 4.97 (1H,s), 5.28–5.40 (2H,m), 6.89–6.96 (1H,m).

EXAMPLE 185

Preparation of (DSD)-1-Oleoyl-2-{3-[N-(2,2,5,5l-tetramethyl-1,3-dioxane-4-carbonyl)amino-1-oxopropyl]aminomethyl}pyrrolidine Pyridine (1 ml) was added to a solution of 321 mg of (S)-2-{3-[N-(2,2,5,5-tetramethyl-1,3-dioxane-4-carbonyl)amino-1-oxopropyl]aminomethyl}pyrrolidine in 20 ml of methylene chloride. Under ice cooling, a solution of 271 mg of oleoyl chloride in 5 ml of methylene chloride was added portion-wise to the mixture, and the mixture thus formed was stirred for 3 hours as it was. After completion of the reaction, the reaction mixture was washed with water, and dried over anhydrous sodium sulfate. After removal of the solvent by evaporation, the residue was subjected to silica gel column chromatography to obtain 166 mg of the title compound (yield: 30%).

Property: oily.

Specific Rotary power $[\alpha]_D$: $+3.90°$ (C=1.0, CHCl$_3$).

IR(cm$^{-1}$, neat): $\nu_{NH}$3324, $\nu_{CO}$1676.

Mass Spectrometric Analysis: Molecular Formula: C$_{35}$H$_{63}$N$_3$O$_5$, Calculated: 605.4767, Found: 605.4778.

NMR($\delta$, CDCl$_3$): 0.88 (3H,t,J=7 Hz), 0.99 (3H,s), 1.04 (3H,s), 1.18–1.39 (20H,m), 1.42 (4H,s), 1.47 (3H,s), 1.57–1.80 (3H,m), 1.88–2.09 (7H,m), 2.27 (2H,t,J=7 Hz), 2.23–2.45 (2H,m), 3.13–3.23 (1H,m), 3.28 (1H,d,J=11 Hz)), 3.40–3.64 (5H,m), 3.68 (1H,d,J=11 Hz), 4.07 (1H,s), 4.23–4.31 (1H,m), 5.29–5.40 (2H,m), 7.12 (1H,t,J=6 Hz), 7.50–7.62 (1H,m).

EXAMPLE 186

Preparation of (R)-1-Oleoyl-2-(3-N-(2,2,5,5-tetramethyl-1,3-dioxane-4-carbonyl)amino-1-oxopropylaminomethyl)pyrrolidine Triethylamine (2 ml) was added to a solution of 821 mg of (R)-2-(3-N-(2,2,5,5-tetramethyl-1,3-dioxane-4-carbonyl)amino-1-oxopropyl]aminomethyl)pyrrolidine in 40 ml of methylene chloride. Under ice cooling, a solution of 697 mg of oleoyl chloride in 10 ml of methylene chloride was added portion-wise to the mixture, and the mixture thus formed was stirred for 3 hours at it was. After completion of the reaction, the reaction mixture was washed with water, and dried over anhydrous sodium sulfate. After removal of the solvent by evaporation, the residue was subjected to silica gel column chromatography to obtain 1.20 g of the title compound (yield: 87 %).

Property: oily.

Specific Rotary Power [α]$_D$: +40.7° (C=1.0, CHCl$_3$).

IR(cm$^{-1}$, neat): $\nu_{NH}$3328, $\nu_{CO}$1656.

Mass Spectrometric Analysis: Molecular Formula: C$_{35}$H$_{63}$N$_3$O$_5$, Calculated: 605.4767, Found: 606.4757.

NMR(δ, CDCl$_3$): 0.88 (3H,t,J=7Hz), 0.97 (3H,s), 1.04 (3H,s), 1.21–1.39 (20H,m), 1.42 (3H,s), 1.47 (3H,s), 1.56–1.80 (3H,m), 1.88–2.09 (7H,m), 2.27 (2H,t,J=7Hz), 2.40 (2H,t,J=6Hz), 3.12–3.20 (1H,m), 3.27 (1H,d,J=12Hz), 3.41–3.64 (5H,m), 3.68 (1H,d,J=12Hz), 4.07 (1H,s), 4.24–4.33 (1H,m), 5.29–5.40 (2H,m), 7.12 (1H,t,J=6Hz), 7.60 (1H,brs).

EXAMPLE 187

1-(2-Methyllauroyl)4-piperidinyl 3-[N-(2,2,5,5-tetramethyl-1,3-dioxane-4-carbonyl-)amino]propionate Molecular Formula: C$_{30}$H$_{54}$N$_2$O$_6$.
Molecular Weight: 538.77.
Mass Spectrometric Analysis Calculated: 538.398. Found: 538.3966.
Melting Point (° C.): oil.
Specific Rotary Power: [α]$^{28}$$_D$+25.7° (C=1.0, CHCl$_3$).

IR($\nu$neat, cm$^{-1}$): 2932, 2860, 1736.

NMR(δ, CDCl$_3$): 0.88 (3H,t,J=7Hz), 0.96 (3H,s), 1.04 (3H,s), 1.10 (3H,d,J=7Hz), 1.17–1.33 (16H,m), 1.43 (3H,s), 1.46 (3H,s), 1.52–1.97 (6H,m), 2.58 (2H,t,J=6Hz), 1.60–1.76 (1H,m). 3.28 (2H,d,J=12Hz), 3.31–4.03 (6H,m), 3.69 (1H,d,J=12Hz), 4.08 (1H,s), 4.98–5.08 (1H,m), 6.93 (1H,t,J=5Hz).

EXAMPLE 188

1-(1-Decylcyclobutanecarbonyl)-4-piperidinyl 3-[N-(2,2,5,5-tetramethyl-1,3-dioxane-4-carbonyl-)amino)propionate Molecular Formula: C$_{32}$H$_{56}$N$_2$O$_6$.
Molecular Weight: 564.81.
1.21–1.3.
Mass Spectrometric Analysis Calculated: 564.4138, Found: 564.4119.
Melting Point (° C.): oil.
Specific Rotary Power: [α]$^{28}$$_D$+23.7° (C=1.0, CHCl$_3$).

IR($\nu$neat, cm$^{-1}$) 2932, 2860, 1738.

NMR(δ, CDCl$_3$): 0.88 (3H,t,J=7Hz), 0.96 (3H,s), 1.04 (3H,s), 1.16–1.37 (16H,m), 1.42 (3H,s), 1.46 (3H,s) 1.52–1.98 (10H,m), 2.42–2.54 (2H,m), 2.58 (2H,t,J=6Hz), 3.11–3.98 (6H,m), 3.28 (1H,d,J=12Hz), 3.69 (1H,d,J=12Hz), 4.08 (1H,s), 4.96–5.05 (1H,m), 6.92 (1H,t,J=5Hz).

EXAMPLE 189

1-(1-Decylcyclobutanecarbonyl)-3-piperidinyl 3-[N-(2,2,5,5-tetramethyl-1,3-dioxane-4-carbonyl-)amino)propionate Molecular Formula: C$_{32}$H$_{56}$N$_2$O$_6$.
Molecular Weight: 564.81.
Mass Spectrometric Analysis Calculated: 564.4138, Found: 564.4153.
Specific Rotary Power: [α]$^{27}$$_D$+21.4° (C=1.0, CHCl$_3$).

IR($\nu$neat, cm$^{-1}$) 2932, 2860, 1740.

NMR(δ, CDCl$_3$): 0.88 (3H,t,J=7Hz), 0.97 (3H,s), 1.04 (3H,s), 1.12–1.35 (16H,m), 1.43 (3H,s), 1.46 (3H,s) 1.50–2.02 (10H,m), 2.39–2.60 (4H,m), 2.90–3.75 (6H,m), 3.28 (1H,d,J=12Hz), 3.69 (1H,d,J=12Hz), 4.08 (1H,s), 4.65–4.92 (1H,m), 6.92–7.08 (1H,m).

EXAMPLE 190

1-(2-Benzylundecanoyl)-4-piperidinyl 3-[N-(2,2,5,5-tetramethyl-1,3-dioxane-4-carbonyl-)amino]propionate Molecular Formula: C$_{35}$H$_{56}$N$_2$O$_6$.
Molecular Weight: 600.84.
Mass Spectrometric Analysis Calculated: 600,4138. Found: 600,4122.
Melting Point (° C.): oil.
Specific Rotary Power: [α]$^{28}$$_D$+22.6° (C=1.0, CHCl$_3$).

IR($\nu$neat, cm$^{-1}$) 2932, 2860, 1734.

NMR(δ, CDCl$_3$): 55° C. 0.88 (3H,t,J=7Hz), 0.95 (3H,s), 1.04 (3H,s), 1.19–1.85 (20H,m), 1.41 (3H,s), 1.44 (3H,s) 2.51 (2H,t,J=6Hz), 2.66–2.77 (1H,m), 2.85–3.64 (8H,m), 3.27 (1H,d,J=12Hz), 3.66 (1H,d,J=12Hz), 4.05 (1H,s), 4.78–4.88 (1H,m), 4.78–6.87 (1H,m), 7.13–7.28 (5H,m).

EXAMPLE 191

1-(1-Benzyldecyl)carbamoyl-4-piperazinyl 3-N-(2,2,5,5-tetramethyl-1,3-dioxane-4-carbonyl-)amino]propionate Molecular Formula: C$_{35}$H$_{57}$N$_3$O$_6$.
Molecular Weight: 615.86.
Mass Spectrometric Analysis Calculated: 615.4247, Found: 615,4222.
Melting Point (° C.): wax.
Specific Rotary Power: [α]$^{28}$$_D$+21.8° (C=1.0, CHCl$_3$).

IR($\nu$neat, cm$^{-1}$): 2932, 2860, 1734.

NMR(δ, CDCl$_3$): 0.88 (3H,t,J=7Hz), 0.96 (3H,s), 1.04 (3H,s), 1.16–1.38 (16H,m), 1.42 (3H,s), 1.46 (3H,s) 1.48–1.89 (4H,m), 2.57 (2H,t,J=6Hz), 2.72–2.87 (2H,m), 3.05–3.21 (2H,m), 3.28 (1H,d,J=12Hz), 3.41–3.66 (4H,m), 3.69 (1H,d,J=12Hz), 4.01–4.07 (1H,m), 4.08 (1H,s), 4.15–4.23 (1H,m), 4.91–4.99 (1H,m), 6.92 (1H,t,J=5Hz), 7.14–7.32 (5H,m).

EXAMPLE 192

Preparation of 1-Oleoyl-4-(1-oxo-3-[N-(1-oxo-2,4-diacetoxy-3,3-dimethylbutyl)amino]propyl)piperazine 1-Ethyl-3-(3-dimethylaminopropyl)carbodiimide hydrochloride (530 mg) was added to a solution of 980 mg of 1-oleylamino-piperazine and 836 mg of 3-[N-(2,4-dihydroxy-3,3-dimethyl-1-oxobutyl)amino]propionic acid in 10 ml of methylene chloride with stirring under ice cooling. The mixture was stirred at room temperature for 18 hours. The reaction mixture was washed with water and dried over anhydrous sodium sulfate, followed by removal of the solvent by vacuum evaporation. Then, the residue was purified by silica gel column chromatography to obtain 900 mg of the title compound (yield: 51 %).

Property: oily.
Specific Rotary Power [α]$_D$: +20.2° (C=1.0, CHCl$_3$).

IR(cm$^{-1}$, neat): $\nu_{NH}$3336, $\nu_{CO}$1748, 1644.

Mass Spectrometric Analysis: Molecular Formula: C$_{35}$H$_{61}$N$_3$O$_7$, Calculated: 635.4509, Found: 635.4517.

NMR(δ, CDCl$_3$): 0.88 (3H,t,J=7Hz), 1.03 (3H,s), 1.06 (3H,s), 1.23–1.38 (20H,m), ⁻1.58–1.68 (2H,m), 1.95-2.08 (4H,m), 2.05 (3H,s), 2.11 (3H,s), 2.31 (2H,t,J=7Hz), 2.42-2.59 (2H,m), 3.35-3.69 (10H,m), 3.83 (1H,d,J=12Hz), 4.02 (1H,d,J=12Hz), 4.88 (1H,s), 5.28-5.40 (2H,m), 6.73 (1H,t,J=6Hz).

EXAMPLE 193

Preparation of 1-Oleoyl-4-(1-oxo-3-N-(1-oxo-2,4-dihydroxy-3,3-dimethylbutyl)amino]propyl)piperazine An aqueous 1N NaOH solution (2 ml) was added to a solution of 635 mg of 1-Oleoyl-4-(1-oxo-3-N-(1-oxo-2,4-dihacetoxy-3,3-dimethylbutyl)amino)propyl)piperazine in 5 ml of methanol, and the mixture was stirred at room temperature for 30 minutes. After adding methylene chloride and water to the reaction mixture, the organic layer was separated, which then was washed with brine and dried over anhydrous sodium sulfate, followed by removal of the solvent. The residue was purified by silica gel column chromatography to obtain 482 mg of the title compound (yield: 87 %).

Property: oily.

Specific Rotary Power $[\alpha]_D$: +16.1° (C=1.0, CHCl$_3$).

IR(cm$^{-1}$, neat): $\nu_{NH}$, $\nu_{CO}$1646.

Mass Spectrometric Analysis: Molecular Formula: C$_{31}$H$_{57}$N$_3$O$_5$, Calculated: 605.4767, Found: 605.4787.

NMR($\delta$, CDCl$_3$): 0.88 (3H,t,J=7Hz), 0.92 (3H,s), 1.02 (3H,s), 1.22-1.41 (20H,m), 1.57-1.68 (2H,m), 1.92-2.08 (4H,m), 2.33 (2H,t,J=7Hz), 2.54 (2H,brs), 3.12-3.21 (1H,m), 2.59 (2H,t,J=6Hz), 3.41-3.68 (10H,m), 3.99 (1H,s), 5.28-5.40 (2H,m), 7.30-7.39 (1H,m).

EXAMPLE 194

Preparation of 1-Oleoyl-4-(1-oxo-3-N-(1-oxo-2,4-diacetoxy-3,3-dimethylbutyl)aminopropyl)tetrahydro-1,4-diazepine 1-Oleoylhomopiperazine (919 mg) and 755 mg of 3-[N-(1-oxo-2,4-diacetoxy-3,3-dimethylbutyl)amino]-propionic acid were reacted in the same manner as in Example 192 to obtain 930 mg of the title compound (yield: 57 %).

Property: oily.

Specific Rotary Power $[\alpha]_D$: +27.3° (C=1.0, CHCl$_3$).

IR(cm$^{-1}$, neat): $\nu_{NH}\nu_{CO}$1748, 1644.

Mass Spectrometric Analysis: Molecular Formula: C$_{36}$H$_{63}$N$_3$O$_7$. Calculated: 649.4665, Found: 649.4652.

NMR($\delta$, CDCl$_3$): 0.88 (3H,t,J=7Hz), 1.02 (3H,s), 1.06 (3H,s), 1.23-1.40 (20H,m), 1.56-1.70 (2H,m), 1.78-1.91 (2H,m), 1.92-2.06 (4H,m), 2.04 (3H,s), 2.11 (3H,s), 2.28 (2H,t,J=7Hz), 2.42-2.56 (2H,m), 3.35-3.76 (1H,m), 3,84 (1H,d,J=12Hz), 4.03 (1H,d,J=12Hz), 4.91 (1H,brs), 5.27-5.40 (2H,m), 6.74-6.83 (1H,m).

EXAMPLE 195

Preparation of 1-Oleoyl-4-(1-oxo-3-N-(1-oxo-2,4-dihydroxy-3,3-dimethylbutyl)amino]propyl)tetrahydro-1,4-diazepine 1-Oleoyl-4-(1-oxo-3-[N-(1-oxo-2,4-diacetoxy-3,3-dimethylbutyl)amino]propyl)tetrahydro-1,4-diazepine (649 mg) was reacted in the same manner as in Example 193 to obtain 515 mg of the title compound.

Property: oily.

Specific Rotary Power $[\alpha]_D$: +14.0° (C=1.0, CHCl$_3$).

Mass Spectrometric Analysis: Molecular Formula: C$_{32}$H$_{59}$N$_3$O$_5$, Calculated: 565.4454, Found: 565.4440.

NMR($\delta$, CDCl$_3$): 0.88 (3H,t,J=7Hz), 0.92 (3H,s), 1.02 (3H,s), 1.21-1.39 (20H,m), 1.55-1.68 (2H,m), 1.72-1.88 (2H,m), 1.92-2.08 (4H,m), 2.12-2.62 (6H,m), 3.25-3.85 (10H,m), 3.96 (1H,brs), 5.28-5.40 (2H,m), 7.12-7.22 (1H,m).

EXAMPLE 196

Preparation of 1-Stearoyl-4-[3-(2,2,5,5-tetramethyl-1,3-dioxane-4-carbonylamino)propanyl]piperazine Sodium carbonate (106 mg) was suspended in a solution of 326 mg of 1-3-(2,2,5,5-tetramethyl-1,3-dioxane-4-carbonylamino)propanyl]piperazine and 303 mg of stearoyl chloride in 20 ml of methylene chloride, and the mixture was allowed to react for 2 hours. After removing insoluble matters by filtration, the solvent was distilled off. The residue was subjected to silica gel column chromatography to obtain 498 mg of the title compound (yield: 84 %).

Property: oily.

Specific Rotary Power $[\alpha]_D$: +28.9° (C=1.0, CHCl$_3$).

IR(cm$^{-1}$, neat): $\nu_{NH}$3408, $\nu_{CO}$1656, 1638.

Mass Spectrometric Analysis: Molecular Formula: C$_{34}$H$_{63}$N$_3$O$_5$, Calculated: 593.4767, Found: 593.4776.

NMR($\delta$, CDCl$_3$): 0.88 (3H,t,J=7Hz), 0.96 (3H,s), 1.04 (3H,s), 1.19-1.39 (28H,m), 1.56-1.73 (2H,m), 2.33 (2H,t,J=7Hz), 2.56-2.66 (2H,m), 3.28 (1H,d,J=12Hz), 3.39-3.68 (5H,m), 3.37-3.71 (10H,m), 3.68 (1H,d,J=12Hz), 4.07 (1H,s), 7.05-7.14 (1H,m).

EXAMPLE 197

Preparation of 1-Linoleoyl-4-(3-N-(2,2,5,5-tetramethyl-1,3-dioxane-4-carbonyl)amino)propanyl)piperazine 1-(3-[N-(2,2,5,5-tetramethyl-1,3-dioxane-4-carbonyl)amino]propanoyl)piperazine (489 mg) and linoloyl chloride (421 mg) were reacted in the same manner as in Example 192 to obtain 496 mg of the title compound (yield: 56 %).

Property: oily.

Specific Rotary Power $[\alpha]_D$: +26.7° (C=1.0, CHCl$_3$).

IR(cm$^{-1}$, neat): $\nu_{CO}$1646.

Mass Spectrometric Analysis Molecular Formula: C$_{34}$H$_{59}$N$_3$O$_5$, Calculated: 589.4454, Found: 589.4431.

NMR($\delta$, CDCl$_3$): 0.89 (3H,t,J=7Hz), 0.96 (3H,s), 1.04 (3H,s), 1.22-1.42 (14H,m), 1.98-2.09 (2H,m), 2.33 (2H,t,J=7Hz), 2.52-2.63 (2H,m), 2.77 (2H,d,J=12Hz), 3.28 (1H,d,J=12Hz), 3.36-3.72 (10H,m), 3.68 (1H,d,J=12Hz), 4.07 (1H,s), 5.29-5.44 (4H,m), 7.05-7.13 (1H,m).

EXAMPLE 198

Preparation of 1-(8-Heptadecenyl)carbamoyl-4-(3-N-(2,2,5,5-tetramethyl-1,3-dioxane-4-carbonyl)amino]propanoyl)piperazine Heptadecenyl isocyanate (419 mg) was added to a solution of 489 mg of 1-(3-[N-(2,2,5,5-tetramethyl-1,3-dioxane-4-carbonyl)amino)propanoyl)piperazine (489 mg) in methylene chloride (30 ml) with stirring under ice cooling. Then the solvent was distilled off, and the residue obtained was subjected to silica gel column chromatography to obtain 900 mg of the title compound.

Property: oily.

Specific Rotary Power $[\alpha]_D$: +27.0° (C=1.0, CHCl$_3$).

IR(cm$^{-1}$, neat):$\nu_{CO}$1648.

Mass Spectrometric Analysis: Molecular Formula: C$_{34}$H$_{62}$N$_4$O$_5$, Calculated: 606.4820, Found: 606.4719.

NMR($\delta$, CDCl$_3$): 0.88 (3H,t,J=7Hz), 0.90 (3H,s), 1.04 (3H,s), 1.21-1.38 (20H,m), 1.40-1.57 (2H,m), 1.42 (3H,s), 1.46 (3H,s), 2.33 (2H,t,J=7Hz), 1.92-2.04 (4H,m), 2.49-2.65 (2H,m), 3.17-3.73 (14H,m), 4.07 (1H,s), 4.43 (1H,brs), 5.29-5.40 (2H,m), 7.08 (1H,t,J=6Hz).

EXAMPLE 199

1-(2-Methyllauroyl)4-(3-N-(2,2,5,5-tetramethyl-1,3-dioxane)amino]propanoyl)piperazine Molecular formula: C$_{29}$H$_{53}$N$_3$O$_5$.

Molecular weight: 523.76.

Mass Spectrometric Analysis: Calculated: 523.3985, Found: 523.3974.

Melting Point (° C.): oil.

Specific Rotary Power: $[\alpha]^{29}_D$+30.3° (C=1.0, CHCl$_3$).

IR($\nu$neat, cm$^{-1}$): 2928, 2860, 1646.

NMR($\delta$, CDCl$_3$): 0.88 (3H,t,J=7Hz), 0.96 (3H,s), 1.04 (3H,s), 1.11 (3H,d,J=7Hz), 1.15-1.34 (16H,m), 1.42 (3H,s), 1.46 (3H,s), 1.54-1.62 (2H,m), 2.54-2.72 (3H,m), 3.28 (1H,d,J=12Hz), 3.38-3.70 (10H,m), 3.68 (1H,d,J=12Hz), 4.07 (1H,s), 7.15-7.23 (1H,m).

EXAMPLE 200

1-(1-Decylcyclobutanecarbonyl)-4-(3-N(2,2,5,5-tetramethyl-1,3-dioxane-4-carbonyl)amino)propanoyl)piperazine Molecular Formula: C$_{31}$H$_{55}$N$_3$O$_5$.

Molecular Weight: 549.80.

Mass Spectrometric Analysis Calculated: 549.4141, Found: 549.4119.

Melting Point (° C.): oil.

Specific Rotary Power: $[\alpha]^{27}_D$+29.6° (C=1.0, CHCl$_3$).

IR($\nu$neat, cm$^{-1}$): 2932, 2860, 1642.

NMR($\delta$, CDCl$_3$): 0.88 (3H,t,J=7Hz), 0.96 (3H,s), 1.04 (3H,s), 1.16-1.35 (16H,m), 1.42 (3H,s), 1.46 (3H,s), 1.68-1.98 (6H,m), 2.42-2.60 (4H,m), 3.26-3.68 (10H,m), 3.28 (1H,d,J=12Hz), 3.68 (1H,d,J =12Hz), 4.07 (1H,s), 7.08 (1H,t,J=5Hz).

EXAMPLE 201

1-(2-Benzylundecanoyl)-4-(3-[N-(2,2,5,5-tetramethyl-1,3-dioxane-4-carbonyl)amino]propanoyl)piperazine Molecular Formula: C$_{34}$H$_{55}$N$_3$O$_5$.

Molecular Weight: 585.83.

Mass Spectrometric Analysis: Calculated: 585.41411, Found: 585.4130.

Melting Point (° C.): oil.

Specific Rotary Power: $[\alpha]^{27}_D$+25.0° (C=1.0, CHCl$_3$).

IR($\nu$, cm$^{-1}$): 2928, 2860, 1648.

NMR($\delta$, CDCl$_3$): 0.88 (3H,t,J=7Hz), 0.94 (3H,s), 1.03 (3H,s), 1.16-1.35 (14H,m), 1.41 (3H,s), 1.45 (3H,s), 1.49-1.78 (2H,m), 2.24-2.58 (3H,m), 2.27-3.93 (14H,m), 4.06 (1H,s), 7.03 (1H,t,J=5Hz), 7.13-7.29 (5H,m).

EXAMPLE 202

1-(1-Benzyldecyl)carbamoyl-4-(3-N-(2,2,5,5-tetramethyl-1,3-dioxane-4-carbonyl)amino]propanoyl)piperazine To a solution of 553 mg of 2-benzylundecanoic acid and 550 mg of diphenylphosphorylazide in 3 ml of anhydrous toluene was added portion-wise a solution of 223 mg of triethylamine in 3 ml of anhydrous toluene with stirring at room temperature. The reaction mixture was stirred at 80° C. for additional 2 hours. After completion of the reaction, the reaction mixture was cooled down to room temperature. Then, a solution of 655 mg of 1-{1-oxo-3-[N-(2,2,5,5-tetramethyl-1,3-dioxane-4-carbonyl)amino)propyl}piperazine in 2 ml of chloroform was added thereto. The resulting mixture was stirred at room temperature for 18 hours. After washing it with a saturated aqueous sodium hydrogen carbonate solution and then with brine, the reaction mixture was dried over anhydrous sodium sulfate, and the solvent was removed by evaporation. The residue was purified by silica gel column chromatography to obtain 599 mg of the title compound (yield: 50 %).

Molecular Formula: C$_{34}$H$_{56}$N$_4$O$_5$.

Molecular Weight: 600.85.

Mass Spectrometric Analysis: Calculated: 600.4250, Found: 600,4244.

Melting Point (° C.): oil.

Specific Rotary Power: $[\alpha]^{27}_D$+25.8° (C=1.0, CHCl$_3$).

IR($\nu$neat, cm$^{-1}$) 2932, 2860, 1636.

NMR($\delta$, CDCl$_3$): 0.88 (3H,t,J=7Hz), 0.96 (3H,s), 1.04 (3H,s), 1.17-1.40 (16H,m), 1.42 (3H,s), 1.46 (3H,s), 2.47-2.64 (2H,m), 2.72-2.88 (2H,m), 3.15-3.65 (11H,m), 3.28 (1H,d,J=12Hz), 3.68 (1H,d,J=12Hz), 4.07 (1H,s), 4.08-4.17 (1H,m), 7.18 (1H,t,J=5Hz), 7.12-7.33 (5H,m).

What is claimed is:

1. A compound of the formula $$\begin{array}{c} R^1O \quad OR^2 \\ | \quad \backslash \\ H_2C \quad *CH-CONH-(CH_2)_n-CO-Q-CO-R^3 \\ \backslash \quad / \\ C \\ / \quad \backslash \\ H_3C \quad CH_3 \end{array}$$

wherein

R$^1$ and R$^2$, which are the same or different, each represent a hydrogen atom or a protective group for a hydroxyl group or R$^1$ and R$^2$ together form a ylidene group;

R$^3$ represents (1) a saturated or unsaturated, linear, branched or cyclic, monovalent C$_5$–C$_{25}$-aliphatic hydrocarbon group any said cyclic group being of less than 10 carbon atoms, such hydrocarbon groups being unsubstituted or substituted by (a) an aromatic hydrocarbon group of 6 to 10 carbon atoms or (b) an aromatic heterocyclic group having 5 to 10 ring atoms of which 1 to 4 atoms are oxygen, sulfur or nitrogen, said groups (a) and (b) being unsubstituted or substituted by at least one member selected from the group consisting of halogen, lower alkyl, lower alkoxy, lower alkylthio, cyano, nitro, trichloromethyl, trifluoromethyl, hydroxy, phenyl and phenoxy, or (2) a group of the formula

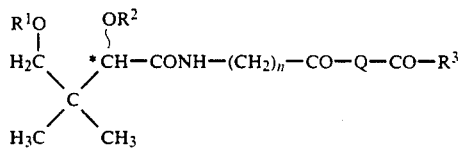 (I)

wherein

R[4] represents a saturated or unsaturated, linear, branched or cyclic, monovalent $C_5$–$C_{25}$-aliphatic hydrocarbon group any said cyclic group being of less than 10 carbon atoms, such hydrocarbon groups being unsubstituted or substituted by (a) an aromatic hydrocarbon group of 6 to 10 carbon atoms or (b) an aromatic heterocyclic group having 5 to 10 ring atoms of which 1 to 4 atoms are oxygen, sulfur or nitrogen, said groups (a) and (b) being unsubstituted or substituted by at least one member selected from the group consisting of halogen, lower alkyl, lower alkoxy, lower alkylthio, cyano, nitro, trichloromethyl, trifluoromethyl, hydroxy, phenyl and phenoxy, and R[5] represents a hydrogen atom, or a saturated or unsaturated, linear, branched or cyclic, monovalent $C_5$–$C_{25}$ aliphatic hydrocarbon group any said cyclic group being of less than 10 carbon atoms, such hydrocarbon groups being unsubstituted or substituted by (a) an aromatic hydrocarbon group of 6 to 10 carbon atoms or (b) an aromatic heterocyclic group having 5 to 10 ring atoms of which 1 to 4 atoms are oxygen, sulfur or nitrogen, said groups (a) and (b) being unsubstituted or substituted by at least one member selected from the group consisting of halogen, lower alkyl, lower alkoxy, lower alkylthio, cyano, nitro, trichloromethyl, trifluoromethyl, hydroxy, phenyl and phenoxy, Q represents (a) a group of formula —X[1]—A—Y[1]—, where A represents (1) a saturated or unsaturated, linear, branched or cyclic divalent $C_2$–$C_{16}$-aliphatic hydrocarbon group any said cyclic group being of up to 7 carbon atoms, such hydrocarbon group being unsubstituted or substituted by (a) an aromatic group of 6 to 10 carbon atoms, or (b) a heteroaryl group selected from furyl, thienyl, pyridyl or indolyl, (21) a divalent aromatic hydrocarbon group of 6 to 10 carbon atoms or (3) a divalent aromatic heterocyclic group of 5 to 10 ring atoms having one or two nitrogen, oxygen or sulfur ring atoms; one of X[1] and Y[1] represents

and the other represents —O—, —S— or

in which R[6] and R[7] each represent a hydrogen atom or a lower alkyl group;

(b) a group of formula —X[2]—(CH$_2$)$_2$—Y[2]—, where one of X[2] and Y[2] represents a group of formula

and the other represents —O—, —S— or —N— in which

represents a 4~7-membered, divalent nitrogen-containing aromatic heterocyclic group, and R[6] has the same meaning as defined above, and l is 0, 1 or 2; or (c) a group of formula

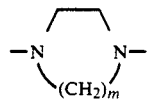

where m is 2 or 3;
n is an integer of from 1 to 4.

2. A compound according to claim 1, wherein R[1] and R[2], which are the same or different, each represent a hydrogen atom; a lower alkyl group; a benzyl group which may optionally be substituted with a halogen atom, a lower alkoxy group, a nitro group or a cyano group; a 5- or 6l-membered saturated heterocyclic group containing one hetero atom selected from N, S and O; or a carboxylic acid acyl group; or R[1] and R[2] combine to form a ylidene group selected from a 1-t-butylethylidene group, a 1-phenylethylidene group, an isopropylidene group, a butylidene group, a cyclopentylidene group, a cyclohexylidene group, a cycloheptylidene group, a benzylidene group, a p-methoxybenzylidene group, a 2,4l-dimethoxybenzylidene group, a p-dimethylaminobenzylidene group, and an o-nitrobenzylidene group.

3. A compound according to claim 1, wherein said saturated or unsaturated, linear, branched or cyclic, monovalent aliphatic hydrocarbon group represented by R[3], R[4] or R[5] is selected from the class consisting of an alkyl group, an alkenyl group, an alkynyl group, a cycloalkyl group, a cycloalkenyl group, a cycloalkylalkyl group, a cycloalkenylalkyl group, an alkylcycloalkyl group, an alkenylcycloalkyl group, an alkylcycloalkenyl group and alkynylcycloalkenyl group.

4. A compound according to claim 1, wherein said saturated or unsaturated, linear, branched or cyclic, monovalent aliphatic hydrocarbon group which is substituted with an aromatic group, represented by R[3], R[4] or R[5], is selected from the group consisting of an alkyl group, an alkenyl group, an alkynyl group, a cycloalkyl group, a cycloalkenyl group, a cycloalkylalkyl group, a cycloalkenylalkyl group, an alkylcycloalkyl group, an alkenylcycloalkyl group, an alkylcycloalkenyl group and alkenylcycloalkenyl group, each being substituted with an aromatic hydrocarbon or aromatic heterocyclic group as defined in claim 1.

5. A compound according to claim 1, wherein $R^3$ represents a $C_8$–$C_{22}$-monovalent aliphatic hydrocarbon group.

6. A compound according to claim 1, wherein $R^3$ represents a $C_8$–$C_{22}$-monovalent aliphatic hydrocarbon group substituted with an aromatic hydrocarbon or aromatic heterocyclic group as defined in claim 1.

7. A compound according to claim 1, wherein $R^3$ represents a $C_8$–$C_{22}$-monovalent aliphatic hydrocarbon group; a $R^5$ represents a hydrogen atom or a $C_1$–$C_{10}$-monovalent aliphatic hydrocarbon group.

8. A compound according to claim 5, wherein $R^4$ and $R^5$ have 5 to 25 carbon atoms in total.

9. A compound according to claim 1, wherein $R^3$ represents a group selected from the class consisting of a $C_5$–$C_{25}$-alkyl group which is linear or has a branched chain at the 1-position thereof; a $C_{12}$–$C_{18}$-alkenyl group which is linear or has a branched chain at the 1-position thereof, a $C_8$–$C_{18}$-alkyl-$C_4$–$C_6$-cycloalkyl group; a monosubstituted amino group substituted with a $C_8$–$C_{20}$-alkyl group or a $C_8$–$C_{20}$-alkenyl group; and an amino group which is substituted with an alkyl group or an alkenyl group and has from 8 to 20 carbon atoms in total.

10. A compound according to claim 1, wherein Q represents a group of formula: —$X^1$—A—$Y^1$— wherein $X^1$, $Y^1$ and A are as defined in claim 1.

11. A compound according to claim 10, wherein A represents a group selected from the class consisting of a $C_2$–$C_{10}$-alkenyl group which is linear or branched; a $C_5$–$C_7$-cycloalkyl-$C_2$–$C_5$-alkylene group; a $C_5$–$C_7$-cycloalkylene group; a $C_4$–$C_8$-alkenylene group; a $C_4$–$C_8$-alkynylene group; a $C_5$–$C_7$-cycloalkylene-$C_1$–$C_5$-alkylene group; a $C_2$–$C_5$-alkylene group substituted with an aryl group or a heteroaryl group as defined in claim 1; and a phenylene group.

12. A compound according to claim 10, wherein one of $X^1$ and $Y^1$ represents —NH— or

and another represents —O—, —S—, —NH— or

13. A compound according to claim 1, wherein Q represents a group of formula: —$X^2$—(CH$_2$)—$Y^2$— wherein $X^2$, $Y^2$— wherein $X^2$, $Y^2$ and are as defined in claim 1.

14. A compound according to claim 13, wherein one of $X^2$ and $Y^2$ represents a group of formula:

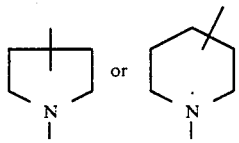

and the other represents —O—, —S— or

15. A compound according to claim 1, wherein Q represents a group of the formula

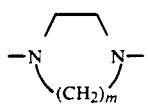

wherein m is as defined in claim 1.

16. A pharmaceutical composition for inhibiting ACAT comprising a therapeutically effective amount of at least one compound as defined in claim 1 as an active ingredient and a pharmaceutical adjuvant.

17. A method for treating or preventing hyperlipemia, arteriosclerosis, angina pectoris, myocardial infarction or thrombosis, comprising administering to a patient a therapeutically effective amount of at least one compound as defined in claim 1.

* * * * *

UNITED STATES PATENT AND TRADEMARK OFFICE
CERTIFICATE OF CORRECTION

PATENT NO. : 5,120,738
DATED : June 9, 1992
INVENTOR(S) : Hiroshi IKAWA et al.

It is certified that error appears in the above-identified patent and that said Letters Patent is hereby corrected as shown below:

Claim 1, in the patent column 155, lines 1-8, delete the formula in its entirety and insert the following formula

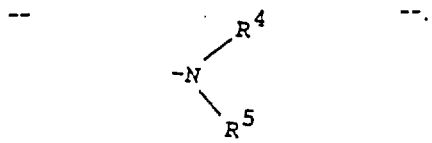

Claim 1, in the patent column 155, line 50, change "(21)" to -- (2) --;

Claim 1, in the patent column 156, line 1, change "—$X^2$—$(CH_2)_2$—$Y^2$—" to -- -$X^2$-$(CH_2)_l$-$Y^2$- --.

Claim 13, in the patent column 158, line 12, change "—$X^2$—$(CH_2)_2$—$Y^2$—" to -- -$X^2$-$(CH_2)_l$-$Y^2$- --.

Signed and Sealed this

Twenty-ninth Day of May, 2001

Attest:

NICHOLAS P. GODICI

Attesting Officer    Acting Director of the United States Patent and Trademark Office